(12) United States Patent
Moriarity et al.

(10) Patent No.: US 10,912,797 B2
(45) Date of Patent: Feb. 9, 2021

(54) TUMOR INFILTRATING LYMPHOCYTES AND METHODS OF THERAPY

(71) Applicants: REGENTS OF THE UNIVERSITY OF MINNESOTA, Minneapolis, MN (US); INTIMA BIOSCIENCE, INC., New York, NY (US); The United States of America, as Represented by the Secretary, Department of Health and Human Services, Bethesda, MD (US)

(72) Inventors: Branden Moriarity, Shoreview, MN (US); Beau Webber, Coon Rapids, MN (US); Modassir Choudhry, New York, NY (US); Steven A. Rosenberg, Potomac, MD (US); Douglas C. Palmer, North Bethesda, MD (US); Nicholas P. Restifo, Chevy Chase, MD (US)

(73) Assignees: INTIMA BIOSCIENCE, INC., New York, NY (US); REGENTS OF THE UNIVERSITY OF MINNESOTA, Minneapolis, MN (US); THE UNITED STATES OF AMERICA, AS REPRESENTED BY THE SECRETARY, DEPARTMENT OF HEALTH AND HUMAN SERVICES, OFFICE OF TECHNOLOGY TRANSFER, NATIONAL INSTITUTES OF HEALTH, Bethesda, MD (US)

( * ) Notice: Subject to any disclaimer, the term of this patent is extended or adjusted under 35 U.S.C. 154(b) by 0 days.

(21) Appl. No.: 15/947,688

(22) Filed: Apr. 6, 2018

(65) Prior Publication Data
US 2019/0008899 A1    Jan. 10, 2019

Related U.S. Application Data

(63) Continuation of application No. PCT/US2017/057228, filed on Oct. 18, 2017.

(60) Provisional application No. 62/452,244, filed on Jan. 30, 2017, provisional application No. 62/409,651, filed on Oct. 18, 2016.

(51) Int. Cl.
| | | |
|---|---|---|
| A61K 35/17 | (2015.01) |
| C12N 15/113 | (2010.01) |
| C07K 14/705 | (2006.01) |
| C07K 14/47 | (2006.01) |
| A61P 31/00 | (2006.01) |
| A61P 35/00 | (2006.01) |
| A61K 9/00 | (2006.01) |
| C07K 14/725 | (2006.01) |
| C07K 14/715 | (2006.01) |
| C12N 5/0783 | (2010.01) |
| C12N 9/22 | (2006.01) |
| C12N 15/79 | (2006.01) |
| C12N 15/90 | (2006.01) |
| A61K 45/06 | (2006.01) |

(52) U.S. Cl.
CPC ............ *A61K 35/17* (2013.01); *A61K 9/0019* (2013.01); *A61K 9/0053* (2013.01); *A61P 31/00* (2018.01); *A61P 35/00* (2018.01); *C07K 14/4703* (2013.01); *C07K 14/7051* (2013.01); *C07K 14/70503* (2013.01); *C07K 14/70521* (2013.01); *C07K 14/7158* (2013.01); *C12N 5/0636* (2013.01); *C12N 9/22* (2013.01); *C12N 15/113* (2013.01); *C12N 15/79* (2013.01); *C12N 15/902* (2013.01); *A61K 45/06* (2013.01); *A61K 2300/00* (2013.01); *C12N 2310/20* (2017.05); *C12N 2510/00* (2013.01)

(58) Field of Classification Search
None
See application file for complete search history.

(56) References Cited

U.S. PATENT DOCUMENTS

| | | |
|---|---|---|
| 5,830,755 A | 11/1998 | Nishimura et al. |
| 5,831,016 A | 11/1998 | Wang et al. |
| 5,840,526 A | 11/1998 | Casterman et al. |
| 5,906,936 A | 5/1999 | Eshhar et al. |
| 6,132,980 A | 10/2000 | Wang et al. |
| 6,187,306 B1 | 2/2001 | Pardoll et al. |

(Continued)

FOREIGN PATENT DOCUMENTS

| | | |
|---|---|---|
| CN | 103820454 B | 3/2016 |
| EP | 2258720 A1 | 12/2010 |

(Continued)

OTHER PUBLICATIONS

Palmer, Douglas C., et al. "Cish actively silences TCR signaling in CD8+ T cells to maintain tumor tolerance." Journal of Experimental Medicine 212.12 (2015): 2095-2113. (Year: 2015).*

(Continued)

*Primary Examiner* — Robert J Yamasaki
(74) *Attorney, Agent, or Firm* — Wilson Sonsini Goodrich & Rosati

(57) ABSTRACT

Genetically modified compositions, such as non-viral vectors and tumor infiltrating lymphocytes, for the treatment of gastrointestinal cancer are disclosed. Disclosed are methods of utilizing a CRISPR system to generate genetically modified compositions. Also disclosed are the methods of making and using the genetically modified compositions for the treatment of gastrointestinal cancer.

33 Claims, 52 Drawing Sheets
Specification includes a Sequence Listing.

(56) References Cited

U.S. PATENT DOCUMENTS

| | | |
|---|---|---|
| 6,207,147 B1 | 3/2001 | Hiserodt et al. |
| 7,070,995 B2 | 7/2006 | Jensen |
| 7,265,209 B2 | 9/2007 | Jensen |
| 7,446,190 B2 | 11/2008 | Sadelain et al. |
| 7,608,410 B2 | 10/2009 | Dunn et al. |
| 7,619,057 B2 | 11/2009 | Wang et al. |
| 7,723,111 B2 | 5/2010 | Hwu et al. |
| 7,741,465 B1 | 6/2010 | Eshhar et al. |
| 7,763,718 B2 | 7/2010 | Jakobsen et al. |
| 7,868,158 B2 | 1/2011 | Chen et al. |
| 8,211,422 B2 | 7/2012 | Eshhar et al. |
| 8,354,516 B2 | 1/2013 | Endl et al. |
| 8,367,804 B2 | 2/2013 | Boulter et al. |
| 8,389,282 B2 | 3/2013 | Sadelain et al. |
| 8,399,645 B2 | 3/2013 | Campana et al. |
| 8,486,694 B2 | 7/2013 | Schendel et al. |
| 8,541,204 B2 | 9/2013 | Endl et al. |
| 8,546,553 B2 | 10/2013 | Terns et al. |
| 8,697,359 B1 | 4/2014 | Zhang |
| 8,754,046 B2 | 6/2014 | Wang et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Zhang et al. |
| 8,889,356 B2 | 11/2014 | Zhang |
| 8,889,365 B2 | 11/2014 | Madura et al. |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,921,332 B2 | 12/2014 | Choulika et al. |
| 8,932,814 B2 | 1/2015 | Zhang et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,074,185 B2 * | 7/2015 | Dudley ............... A61K 31/675 |
| 9,131,589 B2 | 9/2015 | Hayashi et al. |
| 9,234,213 B2 | 1/2016 | Wu |
| 9,260,723 B2 | 2/2016 | Mali et al. |
| 9,260,752 B1 | 2/2016 | May et al. |
| 9,362,208 B2 | 6/2016 | Schwab et al. |
| 9,393,257 B2 | 7/2016 | Osborn et al. |
| 9,404,098 B2 | 8/2016 | Terns et al. |
| 9,410,198 B2 | 8/2016 | May et al. |
| 9,422,553 B2 | 8/2016 | Terns et al. |
| 9,458,439 B2 | 10/2016 | Choulika et al. |
| 9,570,114 B1 | 2/2017 | Sudo et al. |
| 2004/0023388 A1 | 2/2004 | Rozwadowski et al. |
| 2005/0250207 A1 | 11/2005 | Rozwadowski et al. |
| 2007/0274974 A1 | 11/2007 | Bonyhadi et al. |
| 2008/0009447 A1 | 1/2008 | Nash et al. |
| 2009/0197338 A1 | 8/2009 | Vandenberghe et al. |
| 2009/0220488 A1 | 9/2009 | Gardner |
| 2009/0220582 A1 | 9/2009 | Min |
| 2010/0076057 A1 | 3/2010 | Sontheimer et al. |
| 2010/0093617 A1 | 4/2010 | Barrangou et al. |
| 2010/0104556 A1 | 4/2010 | Blankenstein et al. |
| 2011/0136895 A1 | 6/2011 | Gregory et al. |
| 2011/0158957 A1 | 6/2011 | Bonini et al. |
| 2011/0189141 A1 | 8/2011 | Kieback et al. |
| 2011/0217739 A1 | 9/2011 | Terns et al. |
| 2012/0192298 A1 | 7/2012 | Weinstein et al. |
| 2013/0011828 A1 | 1/2013 | Barrangou et al. |
| 2013/0288237 A1 | 10/2013 | Robins et al. |
| 2013/0309258 A1 | 11/2013 | June et al. |
| 2013/0315884 A1 | 11/2013 | Galetto et al. |
| 2014/0004132 A1 | 1/2014 | Brenner et al. |
| 2014/0068797 A1 | 3/2014 | Doudna et al. |
| 2014/0106449 A1 | 4/2014 | June et al. |
| 2014/0113375 A1 | 4/2014 | Liu |
| 2014/0113376 A1 | 4/2014 | Sorek et al. |
| 2014/0120622 A1 | 5/2014 | Gregory et al. |
| 2014/0134142 A1 | 5/2014 | Smith et al. |
| 2014/0141026 A1 | 5/2014 | Schendel et al. |
| 2014/0179770 A1 | 6/2014 | Zhang et al. |
| 2014/0199334 A1 | 7/2014 | Sasikumar et al. |
| 2014/0199767 A1 | 7/2014 | Barrangou et al. |
| 2014/0227237 A1 | 8/2014 | June et al. |
| 2014/0242049 A1 | 8/2014 | Choi et al. |
| 2014/0242702 A1 | 8/2014 | Chen et al. |
| 2014/0273223 A1 | 9/2014 | Cho et al. |
| 2014/0273226 A1 | 9/2014 | Wu et al. |
| 2014/0273230 A1 | 9/2014 | Chen et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0302563 A1 | 10/2014 | Doudna et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2015/0011007 A1 | 1/2015 | Liu et al. |
| 2015/0017136 A1 | 1/2015 | Galetto et al. |
| 2015/0020223 A1 | 1/2015 | Zhang et al. |
| 2015/0020233 A1 | 1/2015 | Harriman et al. |
| 2015/0024499 A1 | 1/2015 | Brouns et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0059010 A1 | 2/2015 | Cigan et al. |
| 2015/0067898 A1 | 3/2015 | Fahrenkrug et al. |
| 2015/0079681 A1 | 3/2015 | Zhang |
| 2015/0082478 A1 | 3/2015 | Cigan et al. |
| 2015/0098954 A1 | 4/2015 | Hyde et al. |
| 2015/0140664 A1 | 5/2015 | Byrne et al. |
| 2015/0141347 A1 | 5/2015 | Parkhurst et al. |
| 2015/0152436 A1 | 6/2015 | Musunuru et al. |
| 2015/0158822 A1 | 6/2015 | Raghavan et al. |
| 2015/0166980 A1 | 6/2015 | Liu et al. |
| 2015/0176013 A1 | 6/2015 | Musunuru et al. |
| 2015/0184139 A1 | 7/2015 | Zhang et al. |
| 2015/0203872 A1 | 7/2015 | Zhang |
| 2015/0211023 A1 | 7/2015 | Shiboleth et al. |
| 2015/0232881 A1 | 8/2015 | Glucksmann et al. |
| 2015/0232883 A1 | 8/2015 | Dahlman et al. |
| 2015/0240261 A1 | 8/2015 | Siksnys et al. |
| 2015/0247150 A1 | 9/2015 | Zhang et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0306141 A1 | 10/2015 | Jensen et al. |
| 2015/0322457 A1 | 11/2015 | Kim et al. |
| 2015/0344912 A1 | 12/2015 | Kim et al. |
| 2015/0353917 A1 | 12/2015 | Miller |
| 2015/0356239 A1 | 12/2015 | Zhang et al. |
| 2016/0002670 A1 | 1/2016 | Church et al. |
| 2016/0007929 A1 | 1/2016 | Chuang et al. |
| 2016/0017366 A1 | 1/2016 | Chen et al. |
| 2016/0024523 A1 | 1/2016 | Joung et al. |
| 2016/0024524 A1 | 1/2016 | Joung et al. |
| 2016/0032274 A1 | 2/2016 | Church et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0060330 A1 | 3/2016 | Presta |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0120906 A1 | 5/2016 | Galetto et al. |
| 2016/0130609 A1 | 5/2016 | Doudna et al. |
| 2016/0138027 A1 | 5/2016 | Gan et al. |
| 2016/0138046 A1 | 5/2016 | Wu |
| 2016/0153004 A1 | 6/2016 | Zhang et al. |

(56) References Cited

U.S. PATENT DOCUMENTS

| | | |
|---|---|---|
| 2016/0153005 A1 | 6/2016 | Zhang et al. |
| 2016/0153006 A1 | 6/2016 | Zhang et al. |
| 2016/0160210 A1 | 6/2016 | Mali et al. |
| 2016/0168594 A1 | 6/2016 | Zhang et al. |
| 2016/0175462 A1 | 6/2016 | Zhang et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0208243 A1 | 7/2016 | Zhang et al. |
| 2016/0210905 A1 | 7/2016 | Lee et al. |
| 2016/0237455 A1 | 8/2016 | Glucksmann et al. |
| 2016/0251640 A1 | 9/2016 | May et al. |
| 2016/0272965 A1 | 9/2016 | Zhang et al. |
| 2016/0281072 A1 | 9/2016 | Zhang |
| 2016/0289675 A1 | 10/2016 | Ryan et al. |
| 2016/0298096 A1 | 10/2016 | Charpentier et al. |
| 2016/0304907 A1 | 10/2016 | Mali et al. |
| 2016/0319349 A1 | 11/2016 | May et al. |
| 2016/0348073 A1 | 12/2016 | Meissner et al. |
| 2016/0355816 A1 | 12/2016 | Terns et al. |
| 2017/0028082 A1 | 2/2017 | Wilson et al. |
| 2017/0037416 A1 | 2/2017 | Barrangou et al. |
| 2017/0051310 A1 | 2/2017 | Doudna et al. |
| 2017/0051312 A1 | 2/2017 | Jinek et al. |
| 2017/0065636 A1 | 3/2017 | Moriarity et al. |
| 2017/0067021 A1 | 3/2017 | Moriarity et al. |
| 2017/0073695 A1 | 3/2017 | Verruto et al. |
| 2017/0119820 A1 | 5/2017 | Moriarity et al. |
| 2017/0130200 A1 | 5/2017 | Moriarity et al. |
| 2017/0172936 A1 | 6/2017 | Okada et al. |
| 2017/0175128 A1 | 6/2017 | Welstead et al. |
| 2017/0175142 A1 | 6/2017 | Zhang et al. |
| 2018/0298101 A1 | 10/2018 | Huntington et al. |
| 2019/0054122 A1 | 2/2019 | Moriarity et al. |
| 2019/0060363 A1 | 2/2019 | Moriarity et al. |
| 2019/0060364 A1 | 2/2019 | Moriarity et al. |
| 2019/0298770 A1* | 10/2019 | Rabinovich ............ A61K 35/17 |

FOREIGN PATENT DOCUMENTS

| | | |
|---|---|---|
| EP | 3004337 B1 | 8/2017 |
| WO | WO-2007025097 A2 | 3/2007 |
| WO | WO-2007136815 A2 | 11/2007 |
| WO | WO-2010011961 A2 | 1/2010 |
| WO | WO-2010025177 | 3/2010 |
| WO | WO-2010054108 A2 | 5/2010 |
| WO | WO-2010093784 A2 | 8/2010 |
| WO | WO-2011117258 A2 | 9/2011 |
| WO | WO-2012078540 A1 | 6/2012 |
| WO | WO-2012112079 A1 | 8/2012 |
| WO | WO-2012129514 | 9/2012 |
| WO | WO-2012164565 A1 | 12/2012 |
| WO | WO-2013049330 A1 | 4/2013 |
| WO | WO-2013074916 A1 | 5/2013 |
| WO | WO-2013088446 A1 | 6/2013 |
| WO | WO-2013098244 A1 | 7/2013 |
| WO | WO-2013141680 A1 | 9/2013 |
| WO | WO-2013176772 A1 | 11/2013 |
| WO | WO-2013176915 A1 | 11/2013 |
| WO | WO-2014018423 A2 | 1/2014 |
| WO | WO-2014022702 A2 | 2/2014 |
| WO | WO-2014059173 A2 | 4/2014 |
| WO | WO-2014065596 A1 | 5/2014 |
| WO | WO-2014/093661 | 6/2014 |
| WO | WO-2014083173 A1 | 6/2014 |
| WO | WO-2014089290 | 6/2014 |
| WO | WO-2014089290 A1 | 6/2014 |
| WO | WO-2014093595 | 6/2014 |
| WO | WO-2014093595 A1 | 6/2014 |
| WO | WO-2014093622 A2 | 6/2014 |
| WO | WO-2014093655 A2 | 6/2014 |
| WO | WO-2014093661 A2 | 6/2014 |
| WO | WO-2014093709 A1 | 6/2014 |
| WO | WO-2014093712 A1 | 6/2014 |
| WO | WO-2014093718 | 6/2014 |
| WO | WO-2014099744 A1 | 6/2014 |
| WO | WO-2014099750 A2 | 6/2014 |
| WO | WO-2014127287 | 8/2014 |
| WO | WO-2014130955 A1 | 8/2014 |
| WO | WO-2014134165 A1 | 9/2014 |
| WO | WO-2014150624 A1 | 9/2014 |
| WO | WO-2014165825 A2 | 10/2014 |
| WO | WO-2014184741 A1 | 11/2014 |
| WO | WO-2014184744 | 11/2014 |
| WO | WO-2014184744 A1 | 11/2014 |
| WO | WO-2014186585 | 11/2014 |
| WO | WO-2014186585 A2 | 11/2014 |
| WO | WO-2014191128 | 12/2014 |
| WO | WO-2014191128 A1 | 12/2014 |
| WO | WO-2014191518 A1 | 12/2014 |
| WO | WO-2014204723 A1 | 12/2014 |
| WO | WO-2014204725 A1 | 12/2014 |
| WO | WO-2014204726 A1 | 12/2014 |
| WO | WO-2014204727 A1 | 12/2014 |
| WO | WO-2014204728 A1 | 12/2014 |
| WO | WO-2014204729 A1 | 12/2014 |
| WO | WO-2015006294 A2 | 1/2015 |
| WO | WO-2015026887 A1 | 2/2015 |
| WO | WO-2015035917 A1 | 3/2015 |
| WO | WO-2015048577 A2 | 4/2015 |
| WO | WO-2015048690 A1 | 4/2015 |
| WO | WO-2015052133 A1 | 4/2015 |
| WO | WO-2015053995 A1 | 4/2015 |
| WO | WO-2015054253 A1 | 4/2015 |
| WO | WO-2015070083 A1 | 5/2015 |
| WO | WO-2015071474 A2 | 5/2015 |
| WO | WO-2015079056 A1 | 6/2015 |
| WO | WO-2015084897 A2 | 6/2015 |
| WO | WO-2015089419 A2 | 6/2015 |
| WO | WO-2015136001 | 9/2015 |
| WO | WO-2015142675 A2 | 9/2015 |
| WO | WO-2015143328 A1 | 9/2015 |
| WO | WO-2015155686 A2 | 10/2015 |
| WO | WO-2015157534 A1 | 10/2015 |
| WO | WO-2015164675 A1 | 10/2015 |
| WO | WO-2015188228 | 12/2015 |
| WO | WO-2015191693 | 12/2015 |
| WO | WO-2016011210 | 1/2016 |
| WO | WO-2016053338 A1 | 4/2016 |
| WO | WO-2016054326 A1 | 4/2016 |
| WO | WO-2016057821 A2 | 4/2016 |
| WO | WO-2016057835 A2 | 4/2016 |
| WO | WO-2016057961 A1 | 4/2016 |
| WO | WO-2016/069283 | 5/2016 |
| WO | WO-2016089433 | 6/2016 |
| WO | WO-2016112351 | 7/2016 |
| WO | WO-2016115326 | 7/2016 |
| WO | WO-2016183345 A1 | 11/2016 |
| WO | WO-2017011519 A1 | 1/2017 |
| WO | WO-2017023801 A1 | 2/2017 |
| WO | WO-2017023803 A1 | 2/2017 |
| WO | WO-2017139264 A1 | 8/2017 |
| WO | WO-2018081470 A1 | 5/2018 |
| WO | WO-2018081476 A2 | 5/2018 |
| WO | WO-2019/006418 | 1/2019 |
| WO | WO-2019/051278 A1 | 3/2019 |

OTHER PUBLICATIONS

Dudley, Mark E., et al. "Adoptive cell transfer therapy following non-myeloablative but lymphodepleting chemotherapy for the treatment of patients with refractory metastatic melanoma." Journal of clinical oncology: official journal of the American Society of Clinical Oncology 23.10 (2005): 2346. (Year: 2005).*

Ahmadi, et al. CD3 limits the efficacy of TCR gene therapy in vivo. Blood. Sep. 29, 2011;118(13):3528-37. doi: 10.1182/blood-2011-04-346338. Epub Jul. 12, 2011.

Arap, et al. Cancer treatment by targeted drug delivery to tumor vasculature in a mouse model. Science. Jan. 16, 1998;279(5349):377-80.

Baumgaertner, et al. Ex vivo detectable human CD8 T-cell responses to cancer-testis antigens. Cancer Res. Feb. 15, 2006;66(4):1912-6.

(56) References Cited

OTHER PUBLICATIONS

Beane, et al. Clinical Scale Zinc Finger Nuclease-mediated Gene Editing of PD-1 in Tumor Infiltrating Lymphocytes for the Treatment of Metastatic Melanoma. Mol Ther. Aug. 2015;23(8):1380-90. doi: 10.1038/mt.2015.71. Epub May 5, 2015.
Chacon, et al. Continuous 4-1BB co-stimulatory signals for the optimal expansion of tumor-infiltrating lymphocytes for adoptive T-cell therapy. Oncoimmunology. Sep. 1, 2013;2(9):e25581. Epub Jul. 3, 2013.
Chacon, et al. Co-stimulation through 4-1BB/CD137 improves the expansion and function of CD8(+) melanoma tumor-infiltrating lymphocytes for adoptive T-cell therapy. PLoS One. 2013;8(4):e60031. doi: 10.1371/journal.pone.0060031. Epub Apr. 1, 2013.
Chan, et al. Viral evasion of intracellular DNA and RNA sensing. Nat Rev Microbiol. Jun. 2016;14(6):360-73. doi: 10.1038/nrmicro.2016.45. Epub May 13, 2016.
Chen, et al. Molecular mechanism for silencing virally transduced genes involves histone deacetylation and chromatin condensation. Proc Natl Acad Sci U S A. Jan. 4, 2000;97(1):377-82.
Chen, et al. Reactivation of silenced, virally transduced genes by inhibitors of histone deacetylase. Proc Natl Acad Sci U S A. May 27, 1997;94(11):5798-803.
Chikuma, et al. Suppressors of cytokine signaling: Potential immune checkpoint molecules for cancer immunotherapy: Cancer Sci 108 (2017) 574-580.
Chu, et al. Increasing the efficiency of homology-directed repair for CRISPR-Cas9-induced precise gene editing in mammalian cells. Nat Biotechnol. May 2015;33(5):543-8. doi: 10.1038/nbt.3198. Epub Mar. 24, 2015.
CLR, RLR, & CDS Signaling Pathways. InvivoGen. Poster. 2016. www.invivogen.com/docs/2016-Poster_CLR-RLR-CDS-invivogen.pdf.
Cong et al. Multiplex genome engineering using CRISPR/Cas systems. Science 339(6121):819-823 (2013).
Co-pending U.S. Appl. No. 15/100,105, filed May 27, 2016.
Co-pending U.S. Appl. No. 15/302,655, filed Oct. 7, 2016.
Feoktistova, et al. Programmed necrosis and necroptosis signalling. FEBS J. Jan. 2015;282(1):19-31. doi: 10.1111/febs.13120. Epub Nov. 11, 2014. Review.
Fu, et al. High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Gao, et al. Structure-function analysis of STING activation by c[G(2',5')pA(3',5')p] and targeting by antiviral DMXAA. Cell. Aug. 15, 2013;154(4):748-62. doi: 10.1016/j.cell.2013.07.023. Epub Aug. 1, 2013.
Guschin, et al. A rapid and general assay for monitoring endogenous gene modification. Methods Mol Biol. 2010;649:247-56. doi: 10.1007/978-1-60761-753-2_15.
Gwiazda, et al. High Efficiency CRISPR/Cas9-mediated Gene Editing in Primary Human T-cells Using Mutant Adenoviral E4orf6/E1b55k "Helper" Proteins. Mol Ther. Jun. 28, 2016. doi: 10.1038/mt.2016.105.
Hamid, et al. Safety and tumor responses with lambrolizumab (anti-PD-1) in melanoma. N Engl J Med. Jul. 11, 2013;369(2):134-44. doi: 10.1056/NEJMoa1305133. Epub Jun. 2, 2013.
Harrison. Competitive repopulation: a new assay for long-term stem cell functional capacity. Blood. Jan. 1980;55(1):77-81.
Hendel, et al. Chemically modified guide RNAs enhance CRISPR-Cas genome editing in human primary cells. Nat Biotechnol. Sep. 2015;33(9):985-9. doi: 10.1038/nbt.3290. Epub Jun. 29, 2015.
*Homo sapiens* cytokine inducible SH2 containing protein (CISH), RefSeqGene on chromosome 3 NCBI Reference Sequence: NG_023194.1 pp. 1-5; downloaded May 31, 2017.
Hsu, et al. Development and applications of CRISPR-Cas9 for genome engineering. Cell. Jun. 5, 2014;157(6):1262-78. doi: 10.1016/j.cell.2014.05.010.
Hunder, et al. Treatment of metastatic melanoma with autologous CD4+ T cells against NY-ESO-1. N Engl J Med. Jun. 19, 2008;358(25):2698-703. doi: 10.1056/NEJMoa0800251.

Idorn, et al. Transfection of Tumor-Infiltrating T Cells with mRNA Encoding CXCR2. Methods Mol Biol. 2016;1428:261-76. doi: 10.1007/978-1-4939-3625-0_17.
International Search Report and Written Opinion dated Jan. 12, 2018 for International PCT Patent Application No. PCT/US2017/058605.
International Search Report and Written Opinion dated Oct. 17, 2016 for International PCT Patent Application No. PCT/US2016/044856.
International Search Report and Written Opinion dated Nov. 16, 2016 for International PCT Patent Application No. PCT/US2016/044858.
Invitrogen. Neon Transfer System: For transfecting mammalian cells, including primary and stem cells, with high transfection efficiency. User Guide. Life Technologies. Jul. 11, 2014. 52 pages.
InvivoGen Insight. Cytosolic DNA Sensors (CDSs): a sting in the tail. InvivoGen. Fall 2012. 8 pages.
Izmiryan et al. Efficient gene targeting mediated by a lentiviral vector-associated meganuclease. Nucleic Acids Res. Sep. 2011;39(17):7610-19.
Jin, et al. Simplified method of the growth of human tumor infiltrating lymphocytes in gas-permeable flasks to numbers needed for patient treatment. J Immunother. Apr. 2012;35(3):283-92. doi: 10.1097/CJI.0b013e31824e801f.
Jinek, et al. A programmable dual-RNA-guided DNA endonuclease in adaptive bacterial immunity. Science. Aug. 17, 2012;337(6096):816-21. doi: 10.1126/science.1225829. Epub Jun. 28, 2012.
Keir, et al. PD-1 and its ligands in tolerance and immunity. Annu Rev Immunol. 2008;26:677-704. doi: 10.1146/annurev.immunol.26.021607.090331.
Klebanoff et al. Prospects for gene-engineered T cell immunotherapy for solid cancers. Nat Med 22(1):26-36 (2016).
Letai. BH3 domains as BCL-2 inhibitors: prototype cancer therapeutics. Expert Opin Biol Ther. Apr. 2003;3(2):293-304.
Li, et al. HomeRun Vector Assembly System: a flexible and standardized cloning system for assembly of multi-modular DNA constructs. PLoS One. Jun. 24, 2014;9(6):e100948. doi: 10.1371/journal.pone.0100948. eCollection 2014.
Love, et al. ITAM-mediated signaling by the T-cell antigen receptor. Cold Spring Harb Perspect Biol. Jun. 2010;2(6):a002485. doi: 10.1101/cshperspect.a002485. Epub Apr. 28, 2010.
Makarova et al. An updated evolutionary classification of CRISPR-Cas systems. Nat Rev Microbiol 13:722-736 (2015).
Mali, et al. RNA-Guided Human Genome Engineering via Cas9. Science. Feb. 15, 2013; 339(6121): 823-826. Published online Jan. 3, 2013. doi: 10.1126/science.1232033.
Menger, et al.TALEN-Mediated Inactivation of PD-1 in Tumor-Reactive Lymphocytes Promotes Intratumoral T-cell Persistence and Rejection of Established Tumors. Cancer Res. Apr. 15, 2016;76(8):2087-93. doi: 10.1158/0008-5472.CAN-15-3352.
Milone et al. Chimeric receptors containing CD137 signal transduction domains mediate enhanced survival of T cells and increased antileukemic efficacy in vivo. Mol Ther 17(8):1453-1464 (2009).
Moriarty, et al. Simple and efficient methods for enrichment and isolation of endonuclease modified cells. PLoS One. May 5, 2014;9(5):e96114. doi: 10.1371/journal.pone.0096114. eCollection 2014.
Natsume, et al. Rapid Protein Depletion in Human Cells by Auxin-Inducible Degron Tagging with Short Homology Donors. Cell Rep. Apr. 5, 2016;15(1):210-8. doi: 10.1016/j.celrep.2016.03.001. Epub Mar. 24, 2016.
Neon Transfection System Protocols and Cell line data. ThermoFisher Scientific, p. 1; downloaded on May 30, 2017.
Ochi, et al. Novel adoptive T-cell immunotherapy using a WT1-specific TCR vector encoding silencers for endogenous TCRs shows marked antileukemia reactivity and safety. Blood. Aug. 11, 2011;118(6):1495-503. doi: 10.1182/blood-2011-02-337089. Epub Jun. 14, 2011.
Odunsi, et al. Epigenetic potentiation of NY-ESO-1 vaccine therapy in human ovarian cancer. Cancer Immunol Res. Jan. 2014;2(1):37-49. doi: 10.1158/2326-6066.CIR-13-0126.
Office Action dated Mar. 23, 2017 for U.S. Appl. No. 15/256,086.
Office Action dated Jun. 5, 2017 for U.S. Appl. No. 15/250,514.

(56) References Cited

OTHER PUBLICATIONS

Office Action dated Sep. 19, 2017 for U.S. Appl. No. 15/224,159.
Office Action dated Dec. 5, 2017 for U.S. Appl. No. 15/224,151.
Office Action dated Dec. 14, 2017 for U.S. Appl. No. 15/256,086.
Osborn, et al. Evaluation of TCR Gene Editing Achieved by TALENs, CRISPR/Cas9, and megaTAL Nucleases. Mol Ther. Mar. 2016;24(3):570-81. doi: 10.1038/mt.2015.197. Epub Oct. 27, 2015.
Palmer, et al. Cish actively silences TCR signaling in CD8+ T cells to maintain tumor tolerance. J Exp Med. Nov. 16, 2015;212(12):2095-113. doi: 10.1084/jem.20150304. Epub Nov. 2, 2015.
Palmer, et al. Cish attenuates proximal TCR-signaling and CD8+ T cell immunity. J Immunother Cancer. 2014; 2(Suppl 3): P32. Published online Nov. 6, 2014. doi: 10.1186/2051-1426-2-S3-P32.
Palmer, et al. Suppressors of cytokine signaling (SOCS) in T cell differentiation, maturation, and function. Trends Immunol. Dec. 2009;30(12):592-602. doi: 10.1016/j.it.2009.09.009. Epub Oct. 30, 2009.
Pauken, et al. Epigenetic stability of exhausted T cells limits durability of reinvigoration by PD-1 blockade. Science Oct. 27, 2016. 10 pages. DOI: 10.1126/science.aaf2807.
PCT/US2017/057228 International Search Report dated Mar. 22, 2018.
Poirot, et al. Multiplex Genome-Edited T-cell Manufacturing Platform for "Off-the-Shelf" Adoptive T-cell Immunotherapies. Cancer Res. Sep. 15, 2015;75(18):3853-64. doi: 10.1158/0008-5472.CAN-14-3321. Epub Jul. 16, 2015.
Postow, et al. Immune Checkpoint Blockade in Cancer Therapy. J Clin Oncol. Jun. 10, 2015;33(17):1974-82. doi: 10.1200/JCO.2014.59.4358. Epub Jan. 20, 2015.
Rahdar, et al. Synthetic CRISPR RNA-Cas9-guided genome editing in human cells. Proc Natl Acad Sci U S A. Dec. 22, 2015;112(51):E7110-7. doi: 10.1073/pnas.1520883112. Epub Nov. 16, 2015.
Rapoport, et al. NY-ESO-1-specific TCR-engineered T cells mediate sustained antigen-specific antitumor effects in myeloma. Nat Med. Aug. 2015;21(8):914-21. doi: 10.1038/nm.3910. Epub Jul. 20, 2015.
Robbins, et al. Tumor regression in patients with metastatic synovial cell sarcoma and melanoma using genetically engineered lymphocytes reactive with NY-ESO-1. J Clin Oncol. Mar. 1, 2011;29(7):917-24. doi: 10.1200/JCO.2010.32.2537. Epub Jan. 31, 2011.
Rosenberg, et al. A new approach to the adoptive immunotherapy of cancer with tumor-infiltrating lymphocytes. Science Sep. 1986;233 (4770): 1318-21.
Rosenberg et al. Adoptive cell transfer as personalized immunotherapy for human cancer. Science 348(6230):62-68 (2015).
Rosenberg, et al. Durable complete responses in heavily pretreated patients with metastatic melanoma using T-cell transfer immunotherapy. Clin Cancer Res. Jul. 1, 2011;17(13):4550-7. doi: 10.1158/1078-0432.CCR-11-0116. Epub Apr. 15, 2011.
Safa, et al. Roles of c-FLIP in Apoptosis, Necroptosis, and Autophagy. J Carcinog Mutagen. 2013;Suppl 6. pii: 003.
Samoylova, et al. Peptide phage display: opportunities for development of personalized anti-cancer strategies. Anticancer Agents Med Chem. Jan. 2006;6(1):9-17.
Sander et al. CRISPR-Cas systems for editing, regulating and targeting genomes. Nat. Biotechnol 32:347-355 (2014).
Savoldo, et al. CD28 costimulation improves expansion and persistence of chimeric antigen receptor-modified T cells in lymphoma patients. J Clin Invest. May 2011;121(5):1822-6. doi: 10.1172/JCI46110. Epub Apr. 11, 2011.
Scheffel, et al. Efficacy of Adoptive T-cell Therapy Is Improved by Treatment with the Antioxidant N-Acetyl Cysteine, Which Limits Activation-Induced T-cell Death. Cancer Res. Oct. 15, 2016;76(20):6006-6016.
Schietinger, et al. Tolerance and exhaustion: defining mechanisms of T cell dysfunction. Trends Immunol. Feb. 2014;35(2):51-60. doi: 10.1016/j.it.2013.10.001. Epub Nov. 6, 2013.
Schmid, et al. Evidence for a TCR affinity threshold delimiting maximal CD8 T cell function. J Immunol. May 1, 2010;184(9):4936-46. doi: 10.4049/jimmunol.1000173. Epub Mar. 29, 2010.

Schumann, et al. Generation of knock-in primary human T cells using Cas9 ribonucleoproteins. Proc Natl Acad Sci U S A. Aug. 18, 2015;112(33):10437-42. doi: 10.1073/pnas.1512503112. Epub Jul. 27, 2015.
Scott, et al. Structural requirements for the biosynthesis of backbone cyclic peptide libraries. Chem Biol. Aug. 2001;8(8):801-15.
Sen, et al. The epigenetic landscape of T cell exhaustion. Science Oct. 27, 2016. 10 pages. DOI: 10.1126/science.aae0491.
Shmakov et al. Discovery and Functional Characterization of Diverse Class 2 CRISPR-Cas Systems. Mol Cell 60(3):385-397 (2015).
Silas, et al. Direct CRISPR spacer acquisition from RNA by a natural reverse transcriptase-Cas1 fusion protein. Science. Feb. 26, 2016;351(6276):aad4234. doi: 10.1126/science.aad4234.
Smith, et al. Gene transfer properties and structural modeling of human stem cell-derived AAV. Mol Ther. Sep. 2014;22(9):1625-34. doi: 10.1038/mt.2014.107. Epub Jun. 13, 2014.
Stanislawski, et al. Circumventing tolerance to a human MDM2-derived tumor antigen by TCR gene transfer. Nat Immunol. Oct. 2001;2(10):962-70.
Su, et al. CRISPR-Cas9 mediated efficient PD-1 disruption on human primary T cells from cancer patients. Sci Rep. Jan. 28, 2016;6:20070. doi: 10.1038/srep20070.
Tebas, et al. Gene editing of CCR5 in autologous CD4 T cells of persons infected with HIV. N Engl J Med. Mar. 6, 2014;370(10):901-10. doi: 10.1056/NEJMoa1300662.
Torikai et al. A foundation for universal T-cell based immunotherapy: T cells engineered to express a CD19-specific chimeric-antigen-receptor and eliminate expression of endogenous TCR. Blood 119(24):5697-5705 (2012).
Trabattoni, et al. Costimulatory pathways in multiple sclerosis: distinctive expression of PD1 and PD-L1 in patients with different patterns of disease. J Immunol. Oct. 15, 2009;183(8):4984-93. doi: 10.4049/jimmunol.0901038. Epub Sep. 30, 2009.
Tran et al. Cancer Immunotherapy Based on Mutation-Specific CD4+ T Cells in a Patient with Epithelial Cancer. Science 9:641-645 (2014).
Tran, et al. Immunogenicity of somatic mutations in human gastrointestinal cancers. Science. Dec. 11, 2015;350(6266):1387-90. doi: 10.1126/science.aad1253. Epub Oct. 29, 2015.
Tsai, et al. GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Tuschl, et al. Nucleic Acid Sensing Pathways: Innate Immunity, Immunobiology and Therapeutics. Keystone Symposia 2016 Conference. May 8-12, 2016. 3 pages.
Tyrakis, et al. S-2-hydroxyglutarate regulates CD8+ T-lymphocyte fate. (Accelerated Article Preview). Nature (2016). Published online: Oct. 26, 2016. 22 pages. DOI:10.1038/nature20165.
U.S. Appl. No. 15/250,514 Office Action dated Oct. 12, 2017.
Van Loenen, et al. Mixed T cell receptor dimers harbor potentially harmful neoreactivity. Proc Natl Acad Sci U S A. Jun. 15, 2010;107(24):10972-7. doi: 10.1073/pnas.1005802107. Epub Jun. 1, 2010.
Wang, et al. Highly efficient homology-driven genome editing in human T cells by combining zinc-finger nuclease mRNA and AAV6 donor delivery. Nucleic Acids Res. Feb. 18, 2016;44(3):e30. doi: 10.1093/nar/gkv1121. Epub Nov. 2, 2015.
Whiteside, et al. Regulatory T cell subsets in human cancer: are they regulating for or against tumor progression? Cancer Immunol Immunother (2014) 63:67-72.
Wiedenheft, et al. RNA-guided genetic silencing systems in bacteria and archaea. Nature. Feb. 15, 2012;482(7385):331-8. doi: 10.1038/nature10886.
Yuan, et al. CTLA-4 blockade enhances polyfunctional NY-ESO-1 specific T cell responses in metastatic melanoma patients with clinical benefit. Proc Natl Acad Sci U S A. Dec. 23, 2008;105(51):20410-5. doi: 10.1073/pnas.0810114105. Epub Dec. 12, 2008.
Zhang et al. A novel RNA motif mediates the strict nuclear localization of a long noncoding RNA. Mol Cell Biol. Jun. 2014;34(12):2318-29.
Zon. Intrinsic and extrinsic control of haematopoietic stem-cell self-renewal. Nature. May 15, 2008;453(7193):306-13. doi: 10.1038/nature07038.

(56) References Cited

OTHER PUBLICATIONS

Cho et al. Analysis of off-target effects of CRISPR/Cas-derived RNA-guided endonucleases and nickases. Genome Res. Jan. 2014;24(1):132-141. doi: 10.1101/gr.162339.113. Epub Nov. 19, 2013.
Goff et al. Randomized, Prospective Evaluation Comparing Intensity of Lymphodepletion Before Adoptive Transfer of Tumor-Infiltrating Lymphocytes for Patients With Metastatic Melanoma. J Clin Oncol. Jul. 10, 2016;34(20):2389-97.
Johnson et al. Gene transfer of tumor-reactive TCR confers both high avidity and tumor reactivity to nonreactive peripheral blood mononuclear cells and tumor-infiltrating lymphocytes. J Immunol. Nov. 1, 2006;177(9):6548-59.
Li et al. Heritable gene targeting in the mouse and rat using a CRISPR-Cas system. Nat Biotechnol. Aug. 2013;31(8):681-3.
Lu et al. Efficient identification of mutated cancer antigens recognized by T cells associated with durable tumor regressions. Clin Cancer Res. Jul. 1, 2014; 20(13): 3401-3410. Manuscript; Jul. 1, 2015.
Palmer et al. Effective tumor treatment targeting a melanoma/melanocyte-associated antigen triggers severe ocular autoimmunity. Proc Natl Acad Sci U S A. Jun. 10, 2008;105(23):8061-6.
Ran et al. Genome engineering using the CRISPR-Cas9 system. Nature Protocols 8:2281-2308 (2013).
Rao et al. Inhibition of histone lysine methylation enhances cancer-testis antigen expression in lung cancer cells: implications for adoptive immunotherapy of cancer. Cancer Res. Jun. 15, 2011;71(12):4192-204.
Robbins et al. Mining Exomic Sequencing Data to Identify Mutated Antigens Recognized by Adoptively Transferred Tumor-reactive T cells. Nat Med. Jun. 2013; 19(6): 747-752. Nat Med. Manuscript; Dec. 1, 2013.
Rosati et al. A novel murine T-cell receptor targeting NY-ESO-1. J Immunother. Apr. 2014;37(3):135-46.
Xiao et al. CasOT: a genome-wide Cas9/gRNA off-target searching tool. Bioinformatics. Apr. 15, 2015;30(8):1180-1182.
Yang et al. One-step generation of mice carrying reporter and conditional alleles by CRISPR/Cas-mediated genome engineering. Cell. Sep. 12, 2013;154(6):1370-9.
Yang et al. The signaling suppressor CIS controls proallergic T cell development and allergic airway inflammation. Nat Immunol. Jul. 2013; 14(7): 732-740. Manuscript; Jul. 7, 2014.
Chen et al. Silencing of episomal transgene expression by plasmid bacterial DNA elements in vivo. Gene Ther. May 2004;11(10):856-64.
clinicaltrials.gov: Archive: NC100501995 on Oct. 9, 2016 [online]. U.S. National Institute of Health. Oct. 9, 2016 [retrieved on Jan. 10, 2018]. Retrieved from the internet< https://clinicaltrials.gov/archive/NCT00501995/2016_10_09>.
Hirata et al. Targeted transgene insertion into human chromosomes by adeno-associated virus vectors. Nature Biotechnology 20 (2002): 735-738.
Hu et al. MicroRNA-98 and let-7 Confer Cholangiocyte Expression of Cytokine-Inducible Src Homology 2-Containing Protein in Response to Microbial Challenge. J Immunol. Aug. 1, 2009; 183(3): 1617-1624.
Roth et al. Reprogramming human T cell function and specificity with non-viral genome targeting. bioRxiv; 183418. Aug. 31, 2017. doi: https://doi.org/10.1101/183418.
Sather et al. Efficient modification of CCR5 in primary human hematopoietic cells using a megaTAL nuclease and AAV donor template. Sci Transl Med. Sep. 30, 2015;7(307):307ra156.
Shi et al. Silenced suppressor of cytokine signaling 1 (SOCS1) enhances the maturation and antifungal immunity of dendritic cells in response to Candida albicans in vitro. Immunol Res. 2015; 61(3): 206-218.
Komor, et al., CRISPR-Based technologies for the manipulation of Eukaryotic genomes. Cell 168; Jan. 12, 2017: p. 20-36.
PCT/US2017/058615 International Search Report dated Apr. 24, 2018.

U.S. Appl. No. 15/224,159 Office Action dated May 15, 2018.
Examiner's Summary Action dated Jul. 18, 2019 for U.S. Appl. No. 16/182,189.
Luo, et al., Comparative analysis of chimeric ZFP-, TALE- and Cas9-piggyBac transposases for integration into single locus in human cells. Nucleic Acids Res. Aug. 21, 2017; 45(14): 8411-8422.
Maurer, et al., The assembly-activating protein promotes stability and interactions between AAV's viral proteins to nuclete capsid assembly. Cell Reports, 2018;23:1817-1830.
Non-Final Office Action dated Jul. 25, 2019 for U.S. Appl. No. 16/182,189.
Ren, Jiantao, Zhao, Yangbing, (2017) Advancing chimeric antigen receptor T cell therapy with CRISPR/Cas9,Protein & Cell, Sep. 2017, vol. 8, Issue 9, pp. 634-643.
Voigt, et al., Retargeting Sleeping Beauty Transposon Insertions by Engineered Zinc Finger DNA-binding Domains. Mol Ther. Oct. 2012; 20(10): 1852-1862.
Wierson, Wesley et al., (2018), GeneWeld, a method for efficient targeted integration directed by short homology, epub: Oct. 3, 2018; doi:http://dx.doi.org/10.1101/431627.
Wu, et al. Single amino acid changes can influence titer, heparin binding, and tissue tropism in different adeno-associated virus serotypes. J Virol. Nov. 2006;80(22):11393-7. Epub Aug. 30, 2006.
Yao, Xuan et al., (2017) Homology-mediated end joining-based targeted integration using CRISPR/Cas9, Cell Research, Jun. 2017:27(6):801-814.
Aronovich, E.L, et al., "The Sleeping Beauty transposon system: a non-viral vector for gene therapy," Human Molecular Genetics, vol. 20, Review Issue 1, R14-R20, Apr. 1, 2011.
Bennett, A. et al., Original Article Thermal Stability as a Determinant of AAV Stereotype Identity, Molecular Therapy: Methods & Clinical Development, Jul. 24, 2017, vol. 6; pp. 171-182.
Delconte, et al., CIS is a potent checkpoint in NK cell-mediated tumor immunity. Nat Immunol, Jul. 2016; 17(7):816-24.
Donia, et al., (2013), Methods to Improve Adoptive T-Cell Therapy for Melanoma: IFN-g Enhances Anticancer Responses of Cell Products for Infusion. Journal of Investigative Dermatology, 133:545-552.
Dudley et al. Adoptive Cell Transfer Therapy Following Non-Myeloablative but Lymphodepleting Chemotherapy for the Treatment of Patients with Refractory Metastatic Melanoma. J Clin Oncol. 23(10):2346-2357 (2005).
Extended European Search Report for EP 16833645.1 dated Nov. 9, 2018.
Final Rejection for U.S. Appl. No. 15/256,086 dated May 15, 2019.
Fu et al. Improving CRISPR-Cas nuclease specificity using truncated guide RNAs. Nat Biotechnol 32(3):279-284 (2013).
Herrmann, Ann-Kathrin et al. Impact of the Assembly-Activating Protein on Molecular Evolution of Synthetic Adeno-Associated Virus Capsids, Human Gene Therapy, vol. 30, No. 1, pp. 21-35, 2019 by Mary Ann Liebert, Inc., DOI: 10.1089/hum.2018.085.
Hilton, et al., Twenty proteins containing a C-terminal SOCS box form five structural classes. Proc. Natl. Acad. Sci. Jan. 1998; 95:114-119.
International Search Report and Written Opinion dated Jan. 11, 2019 for PCT/US18/040480.
International Search Report and Written Opinion dated Feb. 1, 2019 for PCT/US2018/050029.
International Search Report and Written Opinion dated Apr. 24, 2018 for PCT/US17/058615.
Jiang, Chunling et al., (2000) Cloning and Characterization of CIS 1b (Cytokine Inducible SH2-Containing Protein 1b), an Alternative Splicing Form of CIS 1 Gene, DNA Sequence, vol. 11(1-2), pp. 149-154.
Krupovic, Mart et al., Capsosons: a new superfamily of self-synthesizing DNA transposons at the origin of prokaryotic CRISPR-Cas immunity, BMC Biology 2014, Received Apr. 18, 2014, A12:36; doi.org/10.1186/1741-7007-12-36.
Li, Shenglan et al., One-Step piggyBac Transposon-Based CRISR/Cas9 Activation of Multiple Genes, Molecular Therapy Nucleic Acids, vol. 8, p. 64-76, Sep. 15, 2017, DOI:https://doi.org/10.1016/j.omtn.2017.06.007.

(56) References Cited

OTHER PUBLICATIONS

Non-Final Office Action dated Jan. 24, 2019 for U.S. Appl. No. 16/182,146.
Non-Final Office Action dated Dec. 5, 2018 for U.S. Appl. No. 15/224,159.
Non-Final Office Action dated Jun. 3, 2019 for U.S. Appl. No. 16/180,867.
Office Action dated Nov. 9, 2018 for U.S. Appl. No. 15/250,214.
Overwijk et al. Tumor regression and autoimmunity after reversal of a functionally tolerant state of self-reactive CD8+ T cells. J Exp Med 198:569-580 (2003).
Cho, S et al Producing conjugate linoleic acid useful for preparing fermented milk used in dairy products for lowering blood cholesterol and treating cancer, involves culturing Bifidobacterium breve in culture medium, WPI / Thomson, vol. 2012, No. 42, Dec. 27, 2010 (Dec. 27, 2010), XP002711389, cf. WPI.
Peters, Joseph E. et al., Recruitment of CRISPR-Cas systems by Tn7-like transponsons, Proc Natl Acad Sci, 114(35); Aug. 29, 2017, PMC5584455.
Pre-Interview Office Action dated May 31, 2019 for U.S. Appl. No. 15/947,688.
De Witte, M. A., et al., Targeting self-antigens through allogeneic TCR gene transfer, Blood 108, 870-877, Jul. 22, 2006.
Radhar, M., et al., Synthetic CRISPR RNA-Cas9-guided genome editing in human cells, Proc Natl Acad Sci USA, v. 1112(51); Dec. 22, 2015, PMC4697396.
Restifo, et al., Acquired resistance to immunotherapy and future challenges. Nature Reviews Cancer, Feb. 2011;16:121-126.
Restifo, N.P., M.E. Dudley, and S.A. Rosenberg, Adoptive immunotherapy for cancer: harnessing the T cell response. Nature Reviews Immunology, Apr. 2012, pp. 269-281, vol. 12, No. 4.
Shifrut, et al., Genome-wide CRISPR screens in primary human T cells reveal key regulators of immune function. BioRxiv 384776, Aug. 2018; doi: https://doi.org/10.1101/384776.
International Search Report Written Opinion dated Apr. 24, 2018 for PCT/US17/057228.
Carosella, Edgardo D. et al., A Systematic Review of Immunotherapy in Urologic Cancer: Evolving Roles for Targeting of CTLA-4, PD-1/PD-L1, and HLA-G, Eur. Urol Aug. 2015;68(2):267-79.
Examiner-Initiated Interview Summary dated for U.S. Appl. No. 16/182,146 dated Jan. 24, 2019.
Hermann, A.K., et al., Impact of the Assembly-Activating Protein on Molecular Evolution of Synthetic Adeno-Associated Virus Capsids, Hum Gene Ther. Jan. 30, 2019(1):21-35.
Hinrichs, C.S., et al., Human effector CD8+ T cells derived from naive rather than memory subsets possess superior traits for adoptive immunotherapy, Blood, 117(3):808-814, Jan. 20, 2011.
Pre-Interview Action dated Feb. 25, 2019 for U.S. Appl. No. 16/180,867.
Pre-Interview Examiner first action, dated Mar. 21, 2019 for U.S. Appl. No. 16/182,189.
Twyman-Saint Victor, Christina et al., Radiation and Dual Checkpoint Blockage Activates Non-Redundant Immune Mechanism in Cancer, Nature Apr. 16, 2015: 520(7547): 373-377.
(University of Iowa Carver College of Medicine) Storage and Transduction instructions for AAV Vectors. Webpage [online]. Jul. 4, 2017 [date verified by web.archive.org; retrieved on May 21, 2019). Retrieved from the internet:< URL:https://medicine.uiowa.edu/vectorcore/sites/medicine.uiowa.edu.vectorcore/files/wysiwyg_uploads/Store/%20and%2020Transduction%20instructions%20AAV.pdf>;page, 5th paragraph</URL:<a>.
U.S. Appl. No. 15/224,151 Notice of Allowance dated Aug. 27, 2018.
U.S. Appl. No. 15/224,151 Notice of Allowance dated Oct. 3, 2018.
U.S. Appl. No. 15/224,151 Notice of Allowance dated Sep. 19, 2018.
U.S. Appl. No. 15/224,159 Non-Final Office Action dated Dec. 5, 2018.
U.S. Appl. No. 15/250,514 Office Action dated Sep. 11, 2018.
U.S. Appl. No. Office Action 15/256,086 dated Oct. 5, 2018.
Yan, Z., et al., Distinct transduction difference between adeno-associated virus type 1 and type 6 vectors in human polarized airway epithelia, Gene Therapy, Mar. 2013, Epub Jun. 14, 2012, vol. 20, No. 3, pp. 328-337.
Yoshimura, Akihiko et al., A novel cytokine-inducible gene CIS encodes an SH2-containing protein that binds to tyrosine-phosphorylated interleukin 3 and erythropoietin receptors, The EMBO Journal, vol. 14, No. 12, pp. 2816-2826, 1995.
Moriarity, Branden S., Modular assembly of transposon integratable multigene vectors using RecWay assembly, Nucleic Acids Research, 2013, vol. 41, No. 8, e92.
International Search Report and Written Opinion dated Jan. 12, 2018 for PCT/US17/058605.
Blast result (NCBI, 2019, web based at https://blast.nlm.nih.gov, pp. 1-16 (Year: 2019).
Brinkman et al., Easy quantitative assessment of genome editing by sequence trace decomposition, Nucleic Acids Research, 42(22): e168 (Dec. 16, 2014).
CISH probe http://www.ncbi.nlm.nih.gov/probe pp. 1-4 downloaded Feb. 7, 2019.
Crome, et al. A distinct innate lymphoid cell population regulates tumor-associated T cells. Nat Med, Mar. 23(3):368-375 (2017); Epub Feb. 6, 2017. doi: 10.1038/nm.4278.
Final Office Action dated Jun. 25, 2019, for U.S. Appl. No. 15/224,159.
Final Office Action dated Oct. 11, 2019, for U.S. Appl. No. 16/180,867.
Final Office Action dated Oct. 29, 2019, for U.S. Appl. No. 16/182,146.
Non-Final Office Action dated Nov. 4, 2019, for U.S. Appl. No. 15/256,086.
GenBank NCBI Ref Seq AF132297.2 Submitted Mar. 2, 2000.
Hardy et al., Costimulated tumor-infiltrating lymphocytes are a feasible and safe alternative donor cell therapy for relapse after allogeneic stem cell transplantation, Blood, 119:2956-2959 (2012).
Hashimoto et al., Coordinated Changes in DNA Methylation in Antigen-specific Memory CD4 T Cells, J. Immunol, 190:4076-4091 (2013).
*Homo sapiens* chromosome 3, GRCh38.p12 Primary Assembly NCBI Reference Sequence: NC_000003.12 pp. 1-5, downloaded Feb. 7, 2019.
Kochenderfer et al., Eradication of B-lineage cells and regression of lymphoma in a patient treated with autologous T cells genetically engineered to recognize CD19, Blood, 116:4099-4102 (2010).
Overwijk, Willem W. et al., B16 as a Mouse Model for Human Melanoma, Curr Protoc Immunol., May 2001, Chapter 20.1 (Available in PMC Oct. 19, 2009).
Jiang, F., et al., CRISPR—Cas9 Structures and Mechanisms, Annual Reviews Biophys., (2017), 46:505-529.
Gough, et al., Assignment of Homology to Genome Sequences using a Library of Hidden Markov Models that Represent all Proteins of Known Structure, J. Mol. Bio. (2001) 313, 903-919.
"Sasi, et al. "The Role of Suppressors of Cytokine Signaling in Human Neoplasms" Molecular Biology International, (2014) p. 1-24".
"Badalamenti, et al., "Role of tumor-infiltrating lymphocytes in patients with solid tumors: Can a drop dig a stone?", Cellular Immunology 343 (2019) p. 1-8".
"Extended European Search Report in corresponding European Patent Application 17861792.4 dated May 4, 2020".
"National Cancer Institute "Study of People with Metastatic Gastrointestinal Epithelial Cancer Administering Tumor-Infiltrating Lymphocytes in Which the Gene Encoding CISH was Inactivated Using the CRISPR/Cas9 System" (2018)".

* cited by examiner

FIG. 1
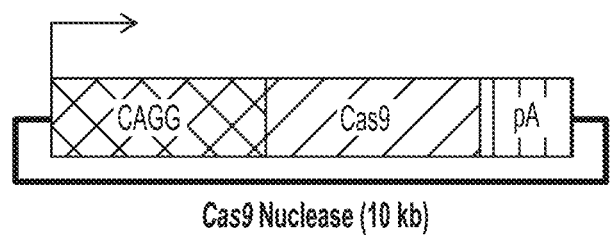
Cas9 Nuclease (10 kb)
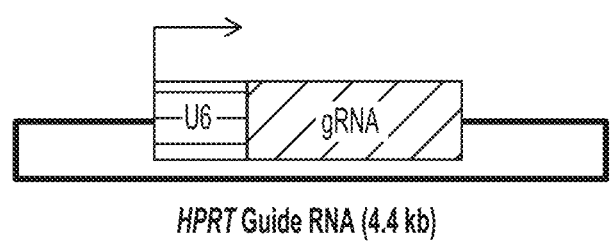
HPRT Guide RNA (4.4 kb)
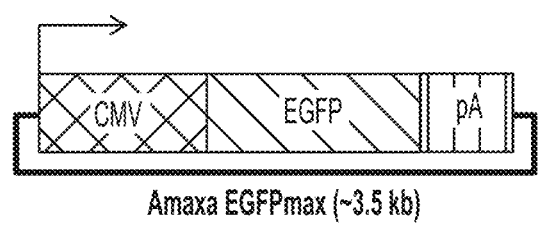
Amaxa EGFPmax (~3.5 kb)
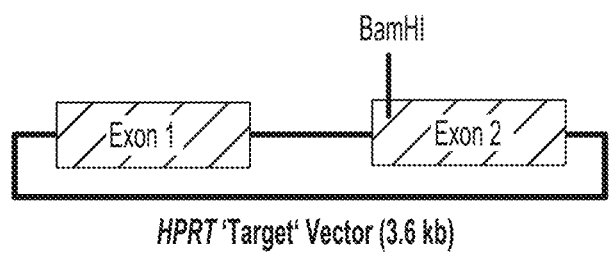
HPRT 'Target' Vector (3.6 kb)

|  | HPRT | AAVS1 | CCR5 | PD1 | CTLA4 |
|---|---|---|---|---|---|
| gRNA#1 | 27.85% | 32.99% | 21.47% | 10.83% | 40.96% |
| gRNA#2 | 30.04% | 27.10% | >60% | >60% | 56.10% |
| gRNA#3 | <1% | 39.82% | 55.98% | 37.42% | 39.33% |
| gRNA#4 | <5% | 25.93% | 45.99% | 20.87% | 40.13% |
| gRNA#5 | <1% | 27.55% | 36.07% | 30.60% | 15.90% |
| gRNA#6 | <5% | 39.62% | 33.17% | 25.91% | 36.93% |

| % Gene "Modification" |
|---|
| 0/10% |
| 10/20% |
| 20/30% |
| 30/40% |
| 40/50% |
| 50/60% |
| >60% |

FIG. 2

Lane 1: Ladder
Lane2: Cas9+gRNA
Lane3: Cas9+gRNA
Lane4: Cas9 alone Control

CTLA4 KO

PD1 KO

* Samples with 2 guides per gene are incompatible with TIDE analysis.

FIG. 22

PD-1 gRNA #2 Modified RNA Oligo
GCCUGCUCGUGGUGACCGAAGGUUUUAGAGCUAGAAAUAGCAAGUUAAAAUAAGGCUAGUCCGUUAUCAACUUGAAAAAGUGGCACCGAGUCGGUGCUUUU CTLA4 gRNA #3 Modified RNA Oligo
GCUAGAUGAUUCCAUCUGCACGUUUUAGAGCUAGAAAUAGCAAGUUAAAAUAAGGCUAGUCCGUUAUCAACUUGAAAAAGUGGCACCGAGUCGGUGCUUUU CISH gRNA #2 Modified RNA Oligo
GGGUUCCAUUACGGCCAGCGGUUUUAGAGCUAGAAAUAGCAAGUUAAAAUAAGGCUAGUCCGUUAUCAACUUGAAAAAGUGGCACCGAGUCGGUGCUUUU AAVS1 gRNA modified oligo
GUCACCAAUCCUGUCCCUAGGUUUUAGAGCUAGAAAUAGCAAGUUAAAAUAAGGCUAGUCCGUUAUCAACUUGAAAAAGUGGCACCGAGUCGGUGCUUUU PD-1 gRNA #2 Modified RNA Oligo
GCCUGCUCGUGGUGACCGAAGGUUUUAGAGCUAGAAAUAGCAAGUUAAAAUAAGGCUAGUCCGUUAUCAACUUGAAAAAGUGGGACCGAGUCGGUGCUUUU CTLA4 gRNA #3    Modified RNA Oligo
GCUAGAUGAUUCCAUCUGCACGUUUUAGAGCUAGAAAUAGCAAGUUAAAAUAAGGCUAGUCCGUUAUCAACUUGAAAAAGUGGCACCGAGUCGGUGCUUUU CISH gRNA #2 Modified RNA Oligo
GGGUUCCAUUACGGCCAGCGGUUUUAGAGCUAGAAAUAGCAAGUUAAAAUAAGGCUAGUCCGUUAUCAACUUGAAAAAGUGGCACCGAGUCGGUGCUUUU AAVS1 gRNA modified oligo
GUCACCAAUCCUGUCCCUAGGUUUUAGAGCUAGAAAUAGCAAGUUAAAAUAAGGCUAGUCCGUUAUCAACUUGAAAAAGUGGCACCGAGUCGGUGCUUUU PD-1 gRNA #2 Modified RNA Oligo
GCCUGCUCGUGGUGACCGAAGGUUUUAGAGCUAGAAAUAGCAAGUUAAAAUAAGGCUAGUCCGUUAUCAACUUGAAAAAGUGGCACCGAGUCGGUGCUUUU CTLA4 gRNA #3 Modified RNA Oligo
GCUAGAUGAUUCCAUCUGCACGUUUUAGAGCUAGAAAUAGCAAGUUAAAAUAAGGCUAGUCCGUUAUCAACUUGAAAAAGUGGCACCGAGUCGGUCGUUUU CISH gRNA #2 Modified RNA Oligo
GGGUUCCAUUACGGCCAGCGGUUUUAGAGCUAGAAAUAGCAAGUUAAAAUAAGGCUAGUCCGUUAUCAACUUGAAAAAGUGGCACCGAGUCGGUGCUUUU AAVS1 gRNA modified oligo
GUCACCAAUCCUGUCCCUAGGUUUUAGAGCUAGAAAUAGCAAGUUAAAAUAAGGCUAGUCCGUUAUCAACUUGAAAAAGUGGCACCGAGUCGGUGCUUUU

TARGET SITE
BACKBONE
2-O-METHYL 3PHOSPHOROTHIATE (MS)

| Sample | % PD1+ve | % expression compared with Cas9 only | % KO compared with Cas9 only |
|---|---|---|---|
| Non-stained | 0.018 | 0.5 | 99.5 |
| 3 | 3.77 | 100.0 | 0.0 |
| 4 | 0.278 | 7.4 | 92.6 |
| 5 | 0.94 | 24.9 | 75.1 |
| 6 | 0.322 | 8.5 | 91.5 |
| 7 | 3.56 | 94.4 | 5.6 |
| 8 | 4.16 | 110.3 | -10.3 |
| 9 | 3.7 | 98.1 | 1.9 |
| 10 | 0.637 | 16.9 | 83.1 |
| 11 | 0.744 | 19.7 | 80.3 |
| 12 | 1.55 | 41.1 | 58.9 |
| 13 | 1.59 | 42.2 | 57.8 |
| 14 | 0.568 | 15.1 | 84.9 |

| | | Cas9 mRNA | PD-1 gRNA2 | PD-1 gRNA6 | CTLA4 gRNA2 | CTLA4 gRNA3 |
|---|---|---|---|---|---|---|
| 1 | Pulsed | | | | | |
| 2 | GFP mRNA | | | | | |
| 3 | Cas9 only | Y | | | | |
| 4 | PD-1 | Y | P2 | | | |
| 5 | ↓ | Y | | P6 | | |
| 6 | ↓ | Y | P2 | P6 | | |
| 7 | CTLA4 | Y | | | C2 | |
| 8 | | Y | | | | C3 |
| 9 | ↓ | Y | | | C2 | C3 |
| 10 | PD-1+ CTLA4 | Y | P2 | | C2 | |
| 11 | ↓ | Y | P2 | | | C3 |
| 12 | | Y | | P6 | | C3 |
| 13 | ↓ | Y | | P6 | C2 | |
| 14 | ↓ | Y | P2 | P6 | C2 | C3 |

FIG. 32
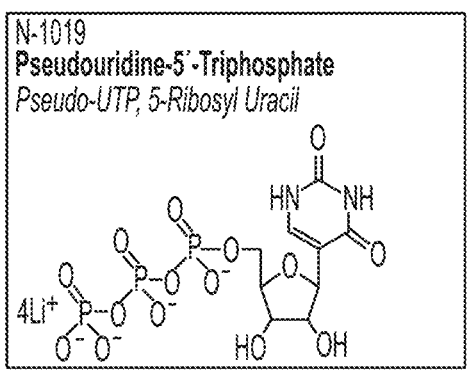 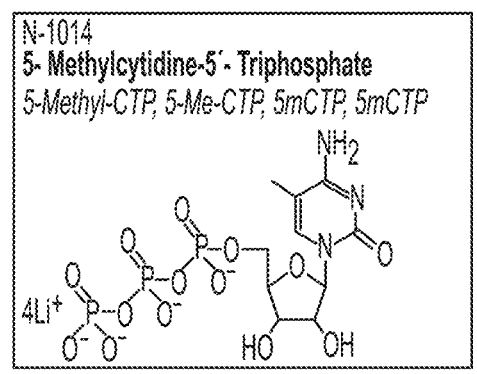

FIG. 41 A
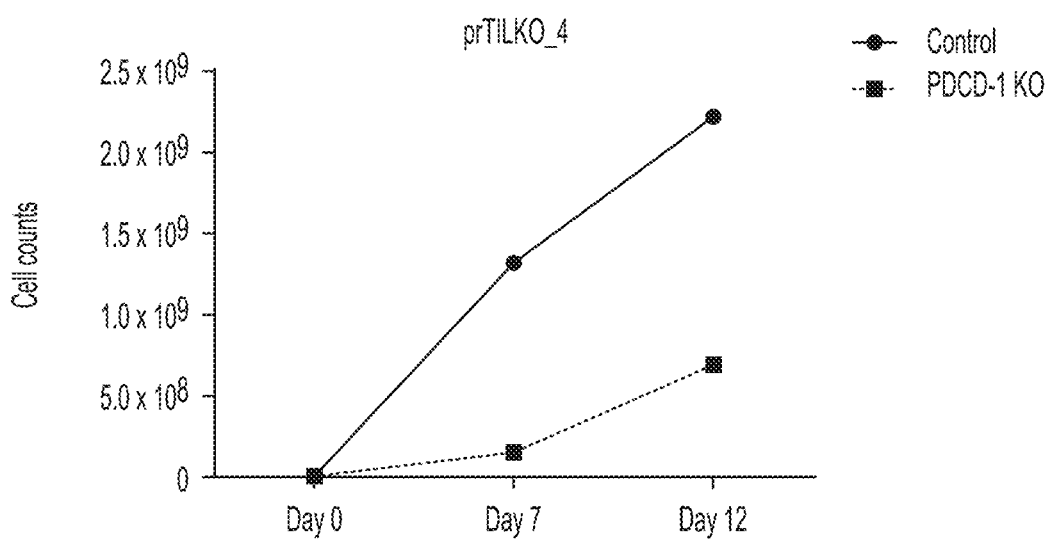
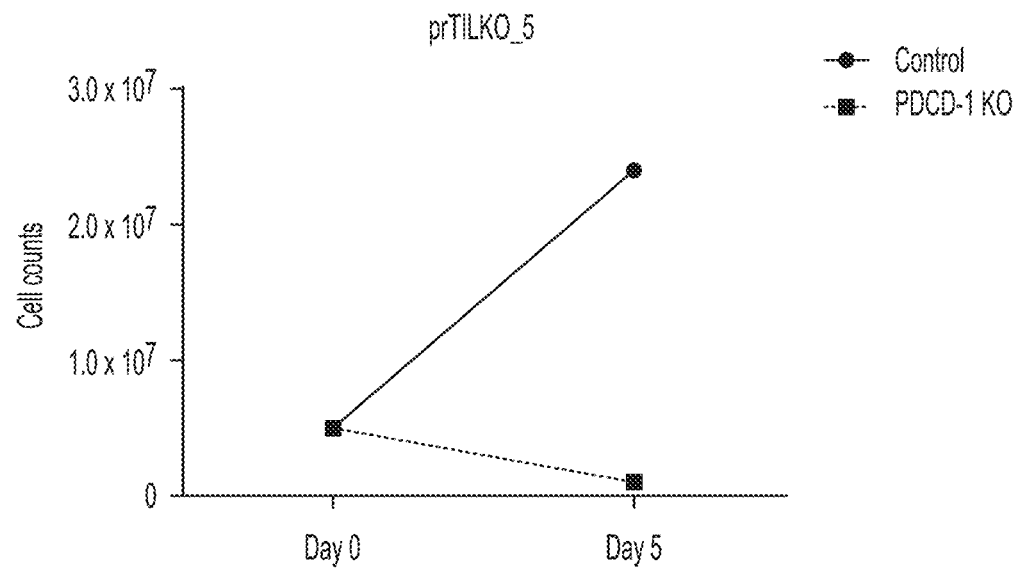
FIG. 41 B

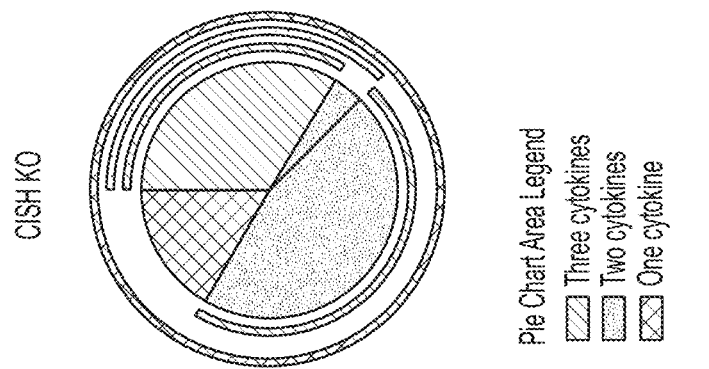
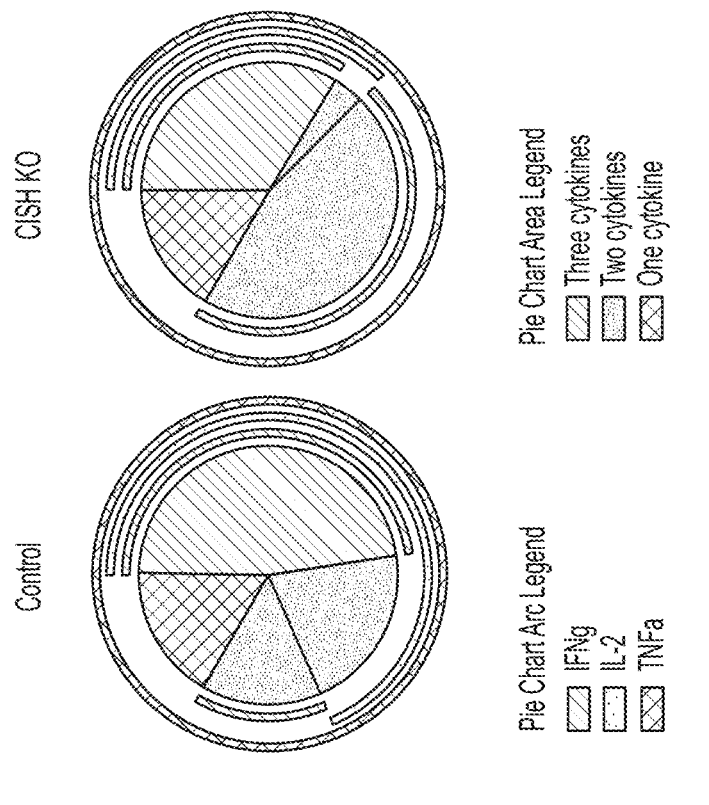
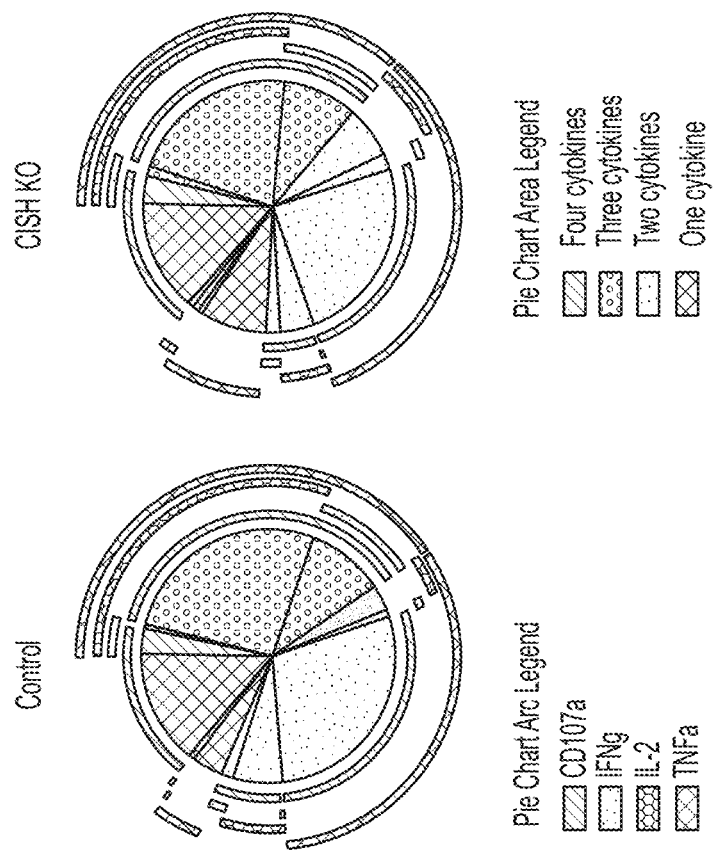
FIG. 47A
FIG. 47B

FIG. 48A
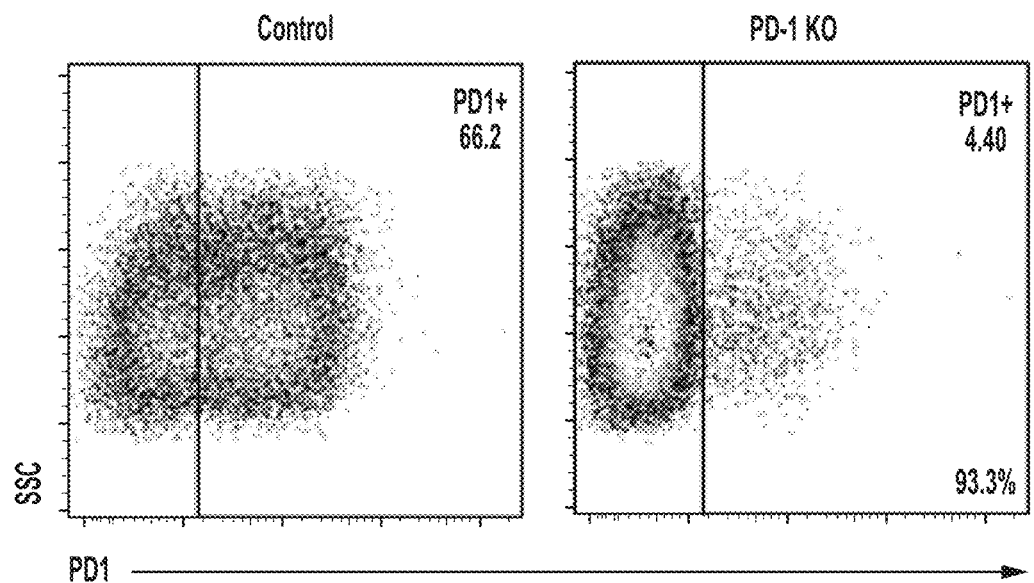
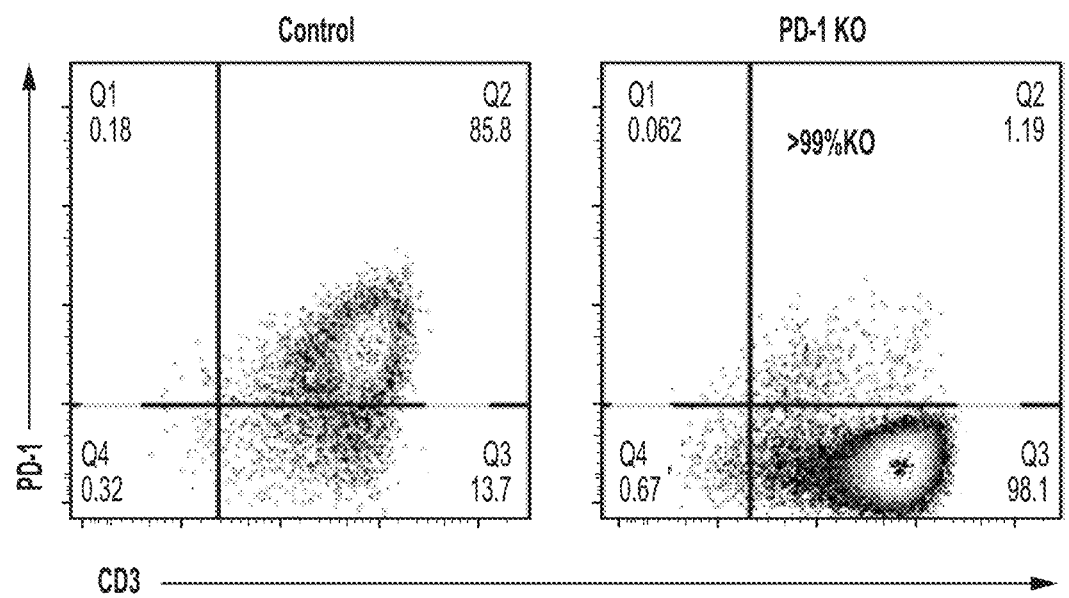
FIG. 48B

FIG. 51 A

```
 1            10              20   23
 G N T G T N G T G T G A N G A A G N G G   Reads
 . . . . . . . . . . . . . . . . . . . .   5926
 G . . . N . A . . . . . . . A . . . . .   1796
```

FIG. 51 B

```
 1            10              20   23
 G G T N C A T A G G N A G N G N G G   Reads
 . . . . . . . . . . . . . . . . . .   3248
```

SEQUENCE LISTING

<160> NUMBER OF SEQ ID NOS: 292

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

-continued

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23

```
<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34
```

000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

```
<210> SEQ ID NO 46
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000
```

<210> SEQ ID NO 57
<400> SEQUENCE: 57

000

<210> SEQ ID NO 58
<400> SEQUENCE: 58

000

<210> SEQ ID NO 59
<400> SEQUENCE: 59

000

<210> SEQ ID NO 60
<400> SEQUENCE: 60

000

<210> SEQ ID NO 61
<400> SEQUENCE: 61

000

<210> SEQ ID NO 62
<211> LENGTH: 187
<212> TYPE: DNA
<213> ORGANISM: Streptococcus pyogenes

<400> SEQUENCE: 62

```
atggactata aggaccacga cggagactac aaggatcatg atattgatta caaagacgat      60
gacgataaga tggccccaaa gaagaagcgg aaggtcggta tccacggagt cccagcagcc     120
gacaagaagt acagcatcgg cctggacatc ggcaccaact ctgtgggctg ggccgtgatc     180
accgacg                                                               187
```

<210> SEQ ID NO 63
<211> LENGTH: 4478
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
ggaaataaga gagaaaagaa gagtaagaag aaatataaga gccaccatgg ccccaaagaa      60
gaagcggaag gtcggtatcc acggagtccc agcagccgac aagaagtaca gcatcggcct     120
ggacatcggc accaactctg tgggctgggc cgtgatcacc gacgagtaca aggtgcccag     180
caagaaattc aaggtgctgg gcaacaccga ccggcacagc atcaagaaga acctgatcgg     240 agcccctgctg ttcgacagcg gcgaaacagc cgaggccacc cggctgaaga gaaccgccag     300
aagaagatac accagacgga gaaccggat ctgctatctg caagagatct tcagcaacga     360
gatggccaag gtggacgaca gcttcttcca cagactggaa gagtccttcc tggtggaaga     420
ggacaagaag cacgagagac accccatctt cggcaacatc gtggacgagg tggcctacca     480
cgagaagtac cccaccatct accacctgag aaagaaactg gtggacagca ccgacaaggc     540
```

-continued

| | |
|---|---|
| cgacctgaga ctgatctacc tggccctggc ccacatgatc aagttcagag gccacttcct | 600 |
| gatcgagggc gacctgaacc ccgacaacag cgacgtggac aagctgttca tccagctggt | 660 |
| gcagacctac aaccagctgt tcgaggaaaa ccccatcaac gccagcggcg tggacgccaa | 720 |
| ggctatcctg tctgccagac tgagcaagag cagaaggctg aaaatctga tcgcccagct | 780 |
| gcccggcgag aagaagaacg gcctgttcgg caacctgatt gccctgagcc tgggcctgac | 840 |
| ccccaacttc aagagcaact tcgacctggc cgaggatgcc aaactgcagc tgagcaagga | 900 |
| cacctacgac gacgacctgg acaacctgct ggcccagatc ggcgaccagt acgccgacct | 960 |
| gttcctggcc gccaagaacc tgtctgacgc catcctgctg agcgacatcc tgagagtgaa | 1020 |
| caccgagatc accaaggccc ccctgagcgc ctctatgatc aagagatacg acgagcacca | 1080 |
| ccaggacctg accctgctga agctctcgt gcggcagcag ctgcctgaga agtacaaaga | 1140 |
| aatcttcttc gaccagagca gaacggcta cgccggctac atcgatggcg gcgctagcca | 1200 |
| ggaagagttc tacaagttca tcaagcccat cctggaaaag atggacggca ccgaggaact | 1260 |
| gctcgtgaag ctgaacagag aggacctgct gagaaagcag agaaccttcg acaacggcag | 1320 |
| catcccccac cagatccacc tgggagagct gcacgctatc ctgagaaggc aggaagattt | 1380 |
| ttacccattc ctgaaggaca accgggaaaa gatcgagaag atcctgacct tcaggatccc | 1440 |
| ctactacgtg gggccccctgg ccagaggcaa cagcagattc gcctggatga ccagaaagag | 1500 |
| cgaggaaacc atcaccccct ggaacttcga ggaagtggtg gacaagggcg ccagcgccca | 1560 |
| gagcttcatc gagagaatga caaacttcga taagaacctg cccaacgaga aggtgctgcc | 1620 |
| caagcacagc ctgctgtacg agtacttcac cgtgtacaac gagctgacca aagtgaaata | 1680 |
| cgtgaccgag ggaatgagaa agcccgcctt cctgagcggc gagcagaaaa aggccatcgt | 1740 |
| ggacctgctg ttcaagacca acagaaaagt gaccgtgaag cagctgaaag aggactactt | 1800 |
| caagaaaatc gagtgcttcg actccgtgga aatctccggc gtggaagata gattcaacgc | 1860 |
| ctccctgggc acataccacg atctgctgaa aattatcaag gacaaggact tcctggataa | 1920 |
| cgaagagaac gaggacattc tggaagatat cgtgctgacc ctgacactgt ttgaggaccg | 1980 |
| cgagatgatc gaggaaggc tgaaaaccta cgctcacctg ttcgacgaca agtgatgaa | 2040 |
| gcagctgaag agaaggcggt acaccggctg gggcaggctg agcagaaagc tgatcaacgg | 2100 |
| catcagagac aagcagagcg gcaagacaat cctggattc ctgaagtccg acggcttcgc | 2160 |
| caaccggaac ttcatgcagc tgatccacga cgacagcctg acattcaaag aggacatcca | 2220 |
| gaaagcccag gtgtccggcc agggcgactc tctgcacgag catatcgcta acctggccgg | 2280 |
| cagccccgct atcaagaagg gcatcctgca gacagtgaag gtggtggacg agctcgtgaa | 2340 |
| agtgatgggc agacacaagc ccgagaacat cgtgatcgag atggctagag agaaccagac | 2400 |
| cacccagaag ggacagaaga actcccgcga gaggatgaag agaatcgaag agggcatcaa | 2460 |
| agagctgggc agccagatcc tgaaagaaca ccccgtggaa aacacccagc tgcagaacga | 2520 |
| gaagctgtac ctgtactacc tgcagaatgg ccgggatatg tacgtggacc aggaactgga | 2580 |
| catcaacaga ctgtccgact acgatgtgga ccatatcgtg cctcagagct ttctgaagga | 2640 |
| cgactccatc gataacaaag tgctgactcg gagcgacaag aacagaggca agagcgacaa | 2700 |
| cgtgccctcc gaagaggtcg tgaagaagat gaagaactac tggcgacagc tgctgaacgc | 2760 |
| caagctgatt acccagagga agttcgataa cctgaccaag gccgagagag cggcctgag | 2820 |
| cgagctggat aaggccggct tcatcaagag gcagctggtg gaaaccagac agatcacaaa | 2880 |
| gcacgtggca cagatcctgg actcccggat gaacactaag tacgacgaaa acgataagct | 2940 |

-continued

```
gatccgggaa gtgaaagtga tcaccctgaa gtccaagctg gtgtccgatt tccggaagga    3000
tttccagttt tacaaagtgc gcgagatcaa caactaccac cacgcccacg acgcctacct    3060
gaacgccgtc gtgggaaccg ccctgatcaa aaagtaccct aagctggaaa gcgagttcgt    3120
gtacggcgac tacaaggtgt acgacgtgcg gaagatgatc gccaagagcg agcaggaaat    3180
cggcaaggct accgccaagt acttcttcta cagcaacatc atgaactttt tcaagaccga    3240
aatcaccctg gccaacggcg agatcagaaa gcgccctctg atcgagacaa acggcgaaac    3300
cggggagatc gtgtgggata agggcagaga cttcgccaca gtgcgaaagg tgctgagcat    3360
gccccaagtg aatatcgtga aaaagaccga ggtgcagaca ggcggcttca gcaaagagtc    3420
tatcctgccc aagaggaaca gcgacaagct gatcgccaga aagaaggact gggacccaa     3480 gaagtacggc ggcttcgaca gccctaccgt ggcctactct gtgctggtgg tggctaaggt    3540
ggaaaagggc aagtccaaga aactgaagag tgtgaaagag ctgctgggga tcaccatcat    3600 ggaagaagc agctttgaga agaaccctat cgactttctg gaagccaagg gctacaaaga     3660
agtgaaaaag gacctgatca tcaagctgcc taagtactcc ctgttcgagc tggaaaacgg    3720
cagaaagaga atgctggcct ctgccggcga actgcagaag ggaaacgagc tggccctgcc    3780
tagcaaatat gtgaacttcc tgtacctggc ctcccactat gagaagctga agggcagccc    3840
tgaggacaac gaacagaaac agctgtttgt ggaacagcat aagcactacc tggacgagat    3900
catcgagcag atcagcgagt ctccaagag agtgatcctg gccgacgcca atctggacaa     3960
ggtgctgtct gcctacaaca gcacaggga caagcctatc agagagcagg ccgagaatat     4020
catccacctg ttcaccctga caaacctggg cgctcctgcc gccttcaagt actttgacac    4080
caccatcgac cggaagaggt acaccagcac caaagaggtg ctggacgcca ccctgatcca    4140
ccagagcatc accggcctgt acgagacaag aatcgacctg tctcagctgg aggcgacaa     4200 gagacctgcc gccactaaga aggccggaca ggccaaaaag aagaagtgag cggccgctta    4260
attaagctgc cttctgcggg gcttgccttc tggccatgcc cttcttctct cccttgcacc    4320
tgtacctctt ggtctttgaa taagcctga gtaggaagaa aaaaaaaaa aaaaaaaaa      4380 aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaa                             4478
```

```
<210> SEQ ID NO 64
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 64
ccugcucgug gugaccgaag guuuuagagc uagaaauagc aaguuaaaau aaggcuaguc    60
cguuaucaac uugaaaaagu ggcaccgagu cggugcuuuu                         100

<210> SEQ ID NO 65
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 65
```

```
acggaagcgg caguccuggc guuuuagagc uagaaauagc aaguuaaaau aaggcuaguc    60
cguuaucaac uugaaaaagu ggcaccgagu cggugcuuuu                         100
```

<210> SEQ ID NO 66
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 66

```
cuagaugauu ccaucugcac guuuuagagc uagaaauagc aaguuaaaau aaggcuaguc    60
cguuaucaac uugaaaaagu ggcaccgagu cggugcuuuu                         100
```

<210> SEQ ID NO 67
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 67

```
gugcggcaac cuacaugaug guuuuagagc uagaaauagc aaguuaaaau aaggcuaguc    60
cguuaucaac uugaaaaagu ggcaccgagu cggugcuuuu                         100
```

<210> SEQ ID NO 68
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 68

```
ggguuccauu acggccagcg guuuuagagc uagaaauagc aaguuaaaau aaggcuaguc    60
cguuaucaac uugaaaaagu ggcaccgagu cggugcuuuu                         100
```

<210> SEQ ID NO 69
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 69

```
gucaccaauc cugucccuag guuuuagagc uagaaauagc aaguuaaaau aaggcuaguc    60
cguuaucaac uugaaaaagu ggcaccgagu cggugcuuuu                         100
```

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70

```
ttgctggctg tggagcggac                                                20
```

<210> SEQ ID NO 71

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gactggcttg ggcagttcca                                                   20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgctggggcc ttcctcgagg                                                   20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ccgaaggtag gagaaggtct                                                   20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atgcacagca gatcctcctc                                                   20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agagagtgag ccaaaggtgc                                                   20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ggcatactca atgcgtacat                                                   20

<210> SEQ ID NO 77
<211> LENGTH: 20
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gggttccatt acggccagcg                                            20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaggctgacc acatccggaa                                            20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tgccgactcc agcttccgtc                                            20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ctgtcagtga aaaccactcg                                            20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cgtactaaga acgtgccttc                                            20

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
caccgcacgt gtgaaccaac ccgcc                                      25

<210> SEQ ID NO 83
<211> LENGTH: 25
<212> TYPE: DNA

<213> ORGANISM: Artificial Sequence
<220> FEATURE:
<223> OTHER INFORMATION: Description of Artificial Sequence: Synthetic primer

<400> SEQUENCE: 83
aaacggcggg ttggttcaca cgtgc    25

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
caccgaaaca acaggccggg cgggt    25

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
aaacacccgc ccggcctgtt gtttc    25

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
caccgacaaa aaaattagcc gggtg    25

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
aaaccacccg gctaattttt ttgt    24

<210> SEQ ID NO 88
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
caccgtaaat ttctctgata gacta    25

<210> SEQ ID NO 89
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 89
aaactagtct atcagagaaa tttac                                           25

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
caccgtgttt caatgagagc attac                                           25

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aaacgtaatg ctctcattga aacac                                           25

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
caccggtctc gaactcctga gctc                                            24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
aaacgagctc aggagttcga gacc                                            24

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
agtgaagtgg cgcattcttg                                                 20

<210> SEQ ID NO 95
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 95 cacccttttcc aaatcctcag c                                              21

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
caccgtgggg gttagaccca atatc                                           25

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
aaacgatatt gggtctaacc cccac                                           25

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
caccgacccc acagtggggc cacta                                           25

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
aaactagtgg ccccactgtg gggtc                                           25

<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
caccgagggc cggttaatgt ggctc                                           25

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 101
aaacgagcca cattaaccgg ccctc                                          25

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
caccgtcacc aatcctgtcc ctag                                           24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
aaacctaggg acaggattgg tgac                                           24

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
caccgccggc cctgggaata taagg                                          25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
aaacccttat attcccaggg ccggc                                          25

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
caccgcgggc ccctatgtcc acttc                                          25

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
aaacgaagtg gacatagggg cccgc    25

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
actcctttca tttgggcagc    20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ggttctggca aggagagaga    20

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
caccgcggag agcttcgtgc taaac    25

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aaacgtttag cacgaagctc tccgc    25

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
caccgcctgc tcgtggtgac cgaag    25

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 113
aaaccttcgg tcaccacgag caggc                                          25

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
caccgcagca accagacgga caagc                                          25

<210> SEQ ID NO 115
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaacgcttgt ccgtctggtt gctgc                                          25

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
caccgaggcg gccagcttgt ccgtc                                          25

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
aaacgacgga caagctggcc gcctc                                          25

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
caccgcgttg ggcagttgtg tgaca                                          25

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
```
aaactgtcac acaactgccc aacgc 25

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
caccgacgga agcggcagtc ctggc 25

<210> SEQ ID NO 121
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aaacgccagg actgccgctt ccgtc 25

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
agaaggaaga ggctctgcag 20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ctctttgatc tgcgccttgg 20

<210> SEQ ID NO 124
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
caccgccggg tgacagtgct tcggc 25

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
aaacgccgaa gcactgtcac ccggc                                          25

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
caccgtgcgg caacctacat gatg                                           24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aaaccatcat gtaggttgcc gcac                                           24

<210> SEQ ID NO 128
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
caccgctaga tgattccatc tgcac                                          25

<210> SEQ ID NO 129
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
aaacgtgcag atggaatcat ctagc                                          25

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
caccgaggtt cacttgattt ccac                                           24

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
aaacgtggaa atcaagtgaa cctc                                           24

<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
caccgccgca cagacttcag tcacc                                         25

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 133
aaacggtgac tgaagtctgt gcggc                                         25

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
caccgctggc gatgcctcgg ctgc                                          24

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
aaacgcagcc gaggcatcgc cagc                                          24

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
tggggatgaa gctagaaggc                                               20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
aatctgggtt ccgttgccta                                               20

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
caccgacaat gtgtcaactc ttgac           25

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
aaacgtcaag agttgacaca ttgtc           25

<210> SEQ ID NO 140
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
caccgtcatc ctcctgacaa tcgat           25

<210> SEQ ID NO 141
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
aaacatcgat tgtcaggagg atgac           25

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
caccggtgac aagtgtgatc actt           24

<210> SEQ ID NO 143
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
aaacaagtga tcacacttgt cacc           24

<210> SEQ ID NO 144
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
caccgacaca gcatggacga cagcc                               25

<210> SEQ ID NO 145
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
aaacggctgt cgtccatgct gtgtc                               25

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
caccgatctg gtaaagatga ttcc                                24

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
aaacggaatc atctttacca gatc                                24

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
caccgttgta tttccaaagt cccac                               25

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
aaacgtggga ctttggaaat acaac                               25

<210> SEQ ID NO 150

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ctcaacctgg ccatctctga                                            20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
cccgagtagc agatgaccat                                            20

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cctcctcctg gtgaccggag agg                                        23
```

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cttgctggtg gtgacagaag agg                                              23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
actgcttgtt gtgaccgatg ggg                                              23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ccagcacatg gtgaccaaag gag                                              23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cctgcttgtg gtgacctaat aag                                              23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ccaggtggtg gtgagcgaag agg                                              23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
cctaatcgtg gtcaccgaaa gag                                              23

-continued

```
<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
cctgctggtg gtgacctatg agg                                              23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cctgctactg gtgtccgaag tgg                                              23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gcagctcgag gtgacggaag agg                                              23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
catgctccta gtgacagaag ggg                                              23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
cccgctggtg ggaaccgaag gag                                              23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cctgggcgta gtgagcgaag cgg                                              23

<210> SEQ ID NO 171
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cctggccgcg gtgaccgagg cgg                                                23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cctgcccaag gttaccgaag tgg                                                23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cctgctccag ttgaccaaag agg                                                23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
actgcacgtg gtgaaccaag agg                                                23

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gctgcccatg gtgacagaag ggg                                                23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
actgctggtg gtgaacgaaa ggg                                                23

<210> SEQ ID NO 177
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gctgctagtg gtgacggaaa gag                                        23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tctgctattg gtgtccgaag tgg                                        23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cgagctcgtg gttacagaag ggg                                        23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ccagctcgtc gggacagaag agg                                        23

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ccacctcggg gtggccgaag cgg                                        23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ccagctagtg ttgactgaag ggg                                        23

<210> SEQ ID NO 183
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 183
cctggctgtg gtgacagaag ggg                                          23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cctgcacgtg atgacctaac agg                                          23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cctgctcgtg ctgtccgcag cag                                          23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cctgctggtg gtgacggcag cag                                          23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gctgctggtg gtgcccgatg ggg                                          23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cctgctcgtg gtgatatgag ggg                                          23

<210> SEQ ID NO 189
<211> LENGTH: 23
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 189
ccagctggtg gtgactcaag gag                                              23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ccttctcgtg gagacagatg agg                                              23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ccttctcgtg gtgcctggag tgg                                              23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ccttctcatg gtggcggaag gag                                              23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ccttctcatg gtgacagtag agg                                              23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
cctggtcgtg ttgagtgaag ggg                                              23

<210> SEQ ID NO 195
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 195
cctggtagtg gtgaccacag tgg                                              23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cctggtggtg gtgaccatag agg                                              23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cctgcccgtg gtaatcgaac cgg                                              23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cctgcccgtg gtgaacgctg tgg                                              23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
cctgcacgtg gtgacagcat ggg                                              23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cctgcgtgtg gaggccgaag ggg                                              23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 201
cctgccggtg gtgacctatg tgg                                        23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
cctgctggtg ctgcctgaag ggg                                        23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cctgctggtg ctggccgatg ggg                                        23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
cctgctagtg gaaaccgcag ggg                                        23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
cctgctggtg gtaccagaag agg                                        23

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
cctgctggtg gtaccagaag agg                                        23

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 207
cctgctggtg gtggcagcag tgg                                              23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
cctgctagtg gtggcagtag tgg                                              23

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
cctgcttatg gggactgaag ggg                                              23

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cctgcttctg gtgtcagaag tgg                                              23

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
cctgctgctg gtggccgacg tgg                                              23

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
cctgctgttg gtgactcaag gag                                              23

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 213
cctgctgttg gtgactcaag gag                                              23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
cctgcttggg ctgaccgtag ggg                                              23

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
cctgctaggg gagacagaag agg                                              23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
cctgctcctg ctgcacgaag tgg                                              23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
cctgctcttg gggactgaat tgg                                              23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
cctgctcctg gttcccaaag agg                                              23

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
```

```
cctgctcttg gtcactgcag agg                                              23
```

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220

```
cctgctcctg gtgcaagaag ggg                                              23
```

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221

```
cctgctcctg gtgcaagaag ggg                                              23
```

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222

```
cctgctcttg gtggaagaag tgg                                              23
```

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223

```
cctgctcctg gtgtgggaag agg                                              23
```

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224

```
cctgctcttg gtgaacacag gag                                              23
```

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225

```
cctgctcaag gagacagaag tgg                                              23
```

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226

```
cctgctccag gtgaatgaag agg                                              23
```

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227

```
cctgctctgg gtgacggagg gag                                              23
```

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228

```
cctgctcgcg gtgggctaag ggg                                              23
```

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229

```
cagttccatt accgccagcg ggg                                              23
```

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230

```
ggtttccatt cctgccagcg ggg                                              23
```

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231

```
gtgtcccgtt acggccagct cgg                                              23
```

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
agcttccctt agggccagcg aag                                           23

<210> SEQ ID NO 233
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ggggtcccta agggccagcg agg                                           23

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gcgtcgcact acggccagcg agg                                           23

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gcgtgccact acggccagct aag                                           23

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gggtccccat agggccagcg agg                                           23

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ggctcccatt gcagccagcg tgg                                           23

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ttgttccatt atggccagag aag                                              23

<210> SEQ ID NO 239
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ttgttccatt atggccagag aag                                              23

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ggataccaat acggccaacg agg                                              23

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggtttccttt actgccggcg agg                                              23

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gggtgccagt ggggccagcg agg                                              23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gggttccttc agggccagag agg                                              23

```
<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gggctccatc acagccagca ggg                                              23

<210> SEQ ID NO 245
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
aggttccagt tcggccagtg aag                                              23

<210> SEQ ID NO 246
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
gtgttccatt ccggcccgcc agg                                              23

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ggcttccaat aaggccaacg agg                                              23

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gggttccagt gtggccagca agg                                              23

<210> SEQ ID NO 249
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gggttccttt tctgccagct tgg                                              23

<210> SEQ ID NO 250
```

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gggttccttt tctgccagct tgg                                               23

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gggttccttt tctgccagct tgg                                               23

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gggttccttt agggccagga tgg                                               23

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gggttctatt ccagccagct tgg                                               23

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gggtttcagt aaggccaggg tgg                                               23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255 gggcccatt acagccatcg tgg                                                23

<210> SEQ ID NO 256
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ggggtccatg acagacagcg tgg                                              23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
ggggtccatt cccgccagag tgg                                              23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gggttacatc aaggccaccg agg                                              23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gggttcaatt acggaaaggg agg                                              23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gggttccact ccttccagcg agg                                              23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gggttccatt atgacaagca tgg                                              23

<210> SEQ ID NO 262
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 262
gggttccatt ctggcaaggg tgg                                           23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gggttccatt gctggcagag tgg                                           23

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gggttccatg aaggccaaag ggg                                           23

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gggttccaat ccggccactg tgg                                           23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gggttccact actgcctgct tgg                                           23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gggttccgtt ccggccactg ggg                                           23

<210> SEQ ID NO 268
<211> LENGTH: 23
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 268
gggtttcatt ggagccagcg tgg                                          23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gggtttcatt acgctcagct aag                                          23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gggttacctt acgacctgcg tgg                                          23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gggctccatt ccggccatgg tgg                                          23

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gtcaccaatc ctgtccctag                                              20

<210> SEQ ID NO 273
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
caggccctgg aaccccccca ccttctcccc agccctgctc gtggtgaccg aggactgccg    60
cttccgtgtc acacaactgc ccaacgggcg tgactt                              96

<210> SEQ ID NO 274
<211> LENGTH: 119
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 274
cggcaggctg acagccaggt gactgaagtc tgtgcggcaa cctacatgat ggggaatgag    60
ttgaccttcc tagatgattc catctgcacg ggcacctcca gtggaaatca agtgaacct   119

<210> SEQ ID NO 275
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
cggcaggctg acagccaggt gactgaagtc tgtgcggcaa cctacatgca cgggcacctc    60
cagtggaaat caagtgaacc t                                              81

<210> SEQ ID NO 276
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
gcctgctcgt ggtgaccgaa gguuuuagag cuagaaauag caaguuaaaa uaaggcuagu    60
ccguuaucaa cuugaaaaag uggcaccgag ucggugcuuu u                       101

<210> SEQ ID NO 277
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
gctagatgat tccatctgca cguuuuagag cuagaaauag caaguuaaaa uaaggcuagu    60
ccguuaucaa cuugaaaaag uggcaccgag ucggugcuuu u                       101

<210> SEQ ID NO 278
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278 ggggttccatt acggccagcg guuuuagagc uagaaauagc aaguuaaaau aaggcuaguc    60
cguuaucaac uugaaaaagu ggcaccgagu cggugcuuuu                         100

```
<210> SEQ ID NO 279
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
gtcaccaatc ctgtccctag guuuuagagc uagaaauagc aaguuaaaau aaggcuaguc    60
cguuaucaac uugaaaaagu ggcaccgagu cggugcuuuu                         100

<210> SEQ ID NO 280
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
gcctgctcgt ggtgaccgaa gguuuuagag cuagaaauag caaguuaaaa uaaggcuagu    60
ccguuaucaa cuugaaaaag uggcaccgag ucggugcuuu u                       101

<210> SEQ ID NO 281
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
gctagatgat tccatctgca cguuuuagag cuagaaauag caaguuaaaa uaaggcuagu    60
ccguuaucaa cuugaaaaag uggcaccgag ucggugcuuu u                       101

<210> SEQ ID NO 282
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
gggttccatt acggccagcg guuuuagagc uagaaauagc aaguuaaaau aaggcuaguc    60
cguuaucaac uugaaaaagu ggcaccgagu cggugcuuuu                         100

<210> SEQ ID NO 283
<211> LENGTH: 100
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
gtcaccaatc ctgtccctag guuuuagagc uagaaauagc aaguuaaaau aaggcuaguc     60
cguuaucaac uugaaaaagu ggcaccgagu cggugcuuuu                         100

<210> SEQ ID NO 284
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
gcctgctcgt ggtgaccgaa gguuuuagag cuagaaauag caaguuaaaa uaaggcuagu     60
ccguuaucaa cuugaaaaag uggcaccgag ucggugcuuu u                        101

<210> SEQ ID NO 285
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
gctagatgat tccatctgca cguuuuagag cuagaaauag caaguuaaaa uaaggcuagu     60
ccguuaucaa cuugaaaaag uggcaccgag ucggugcuuu u                        101

<210> SEQ ID NO 286
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
gggttccatt acggccagcg guuuuagagc uagaaauagc aaguuaaaau aaggcuaguc     60
cguuaucaac uugaaaaagu ggcaccgagu cggugcuuuu                         100

<210> SEQ ID NO 287
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
```
gtcaccaatc ctgtccctag guuuuagagc uagaaauagc aaguuaaaau aaggcuaguc    60
cguuaucaac uugaaaaagu ggcaccgagu cggugcuuuu                         100

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 288
cctgctcgtg gtgaccgaag ngg                                            23

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 289
gctgcccatg gtgacagaag ngg                                            23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 290
gggttccatt acggccagcg ngg                                            23

<210> SEQ ID NO 291
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 291
ggguuccauu acggccagcg guuuuagagc uagaaauagc aaguuaaaau aaggcuaguc    60
cguuaucaac uugaaaaagu ggcaccgagu cggugcuuuu                         100

<210> SEQ ID NO 292
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 292
gtttaattga gttgtcatat gttaataacg gtat                               34
```

US 10,912,797 B2

TUMOR INFILTRATING LYMPHOCYTES AND METHODS OF THERAPY

CROSS-REFERENCE

This application is a continuation of International Application No. PCT/US17/57228, filed Oct. 18, 2017 which claims priority to U.S. Provisional Patent Application No. 62/409,651, filed Oct. 18, 2016, and U.S. Provisional Patent Application No. 62/452,244, filed Jan. 30, 2017, each of which is entirely incorporated herein by reference for all purposes.

GOVERNMENT INTEREST STATEMENT

This invention was made with government support under project numbers Z01BC010985 and Z01BC010763 by the National Institutes of Health, National Cancer Institute. The government has certain rights in the invention.

SEQUENCE LISTING

The instant application contains a Sequence Listing which has been submitted electronically in ASCII format and is hereby incorporated by reference in its entirety. Said ASCII copy, created on Apr. 5, 2018, is named 47533-719_301_SL.txt and is 64,225 bytes in size.

BACKGROUND

The adoptive transfer of tumor infiltrating lymphocytes (TIL) has achieved considerable success in mediating durable regression of metastatic melanoma. In spite of these successes, the use of TIL therapy in the setting of other solid tumors has been challenging. This is likely due to the suppressive effects exerted by the tumor microenvironment and T-cell intrinsic impairments in receptor signaling and acquisition of effector functions. Monoclonal antibody-based immune-checkpoint inhibitors targeting programmed cell death protein 1 (PD-1) and cytotoxic T lymphocyte-associated protein (CTLA-4) function can sometimes relieve T-cell extrinsic suppressive effects, but carry risk of potentially lethal autoimmune side-effects resulting from their systemic activity on non-tumor reactive T-cells. Recently there have been significant advances in the genetic engineering of lymphocytes to recognize molecular targets on tumors in vivo, resulting in remarkable cases of remission of the targeted tumor. However, these successes have been limited largely to hematologic tumors, and more broad application to solid tumors is limited by the lack of an identifiable molecule that is expressed by cells in a particular tumor, and lack of a molecule that can be used to specifically bind to the tumor target in order to mediate tumor destruction. Some recent advances have focused on identifying tumor-specific mutations that in some cases trigger an anti-tumor T cell response. For example, these endogenous mutations can be identified using a whole-exomic-sequencing approach. Tran E, et al., "Cancer immunotherapy based on mutation-specific CD4+ T cells in a patient with epithelial cancer," Science 344: 641-644 (2014).

SUMMARY OF THE INVENTION

Disclosed herein is a method of treatment, comprising: administering to a subject in need thereof a preparative regime that comprises administration of at least one immunosuppressant to the subject in an amount sufficient to reduce an immune response in the subject; a pharmaceutical composition that comprises an antifungal agent in an amount sufficient to inhibit a fungal infection in the subject; and a pharmaceutical composition that comprises a plurality of tumor infiltrating lymphocytes (TILs) that comprise a disruption of at least a portion of a cytokine inducible SH2-containing protein (CISH) gene. In some cases, a method can further comprise administering an antibiotic.

Disclosed herein is a method of treatment, comprising: administering to a subject in need thereof a preparative regime that comprises administration of at least one immunosuppressant to the subject in an amount sufficient to suppress an immune response in the subject; a pharmaceutical composition that comprises an antibiotic in an amount sufficient to inhibit a bacterial infection in the subject; and a pharmaceutical composition that comprises a plurality of tumor infiltrating lymphocytes (TILs) that comprise a disruption of at least a portion of a cytokine inducible SH2-containing protein (CISH) gene. In some cases, a method can further comprise administering an antifungal agent.

Disclosed herein is a method of treatment, comprising: administering to a subject in need thereof: a pharmaceutical composition that comprises cyclophosphamide and fludarabine in an amount sufficient to reduce an immune response in the subject; a pharmaceutical composition that comprises fluconazole in an amount sufficient to inhibit a fungal infection in the subject; and a pharmaceutical composition that comprises a plurality of tumor infiltrating lymphocytes (TILs) that comprise a disruption of at least a portion of a cytokine inducible SH2-containing protein (CISH) gene. In some cases, a method can further comprise administering a pharmaceutical composition that comprises trimethoprim and sulfamethoxazole in an amount sufficient to inhibit a bacterial infection in the subject.

Disclosed herein is a method of treatment, comprising: administering to a subject in need thereof a pharmaceutical composition that comprises cyclophosphamide and fludarabine in an amount sufficient to reduce an immune response in the subject; a pharmaceutical composition that comprises trimethoprim and sulfamethoxazole in an amount sufficient to inhibit a bacterial infection in said subject; and a pharmaceutical composition that comprises a plurality of tumor infiltrating lymphocytes (TILs) that comprise a disruption of at least a portion of a cytokine inducible SH2-containing protein (CISH) gene. In some cases, a method can further comprise administering a pharmaceutical composition that comprises fluconazole in an amount sufficient to inhibit a fungal infection in the subject.

Disclosed herein is a method for treating cancer, comprising: administering to a subject in need thereof a therapeutically effective amount of ex vivo engineered tumor infiltrating lymphocytes (TILs), wherein the ex vivo engineered TILs comprise: a disruption in a Cytokine Inducible SH2 Containing Protein (CISH) gene that results in suppression of CISH protein function in the ex vivo engineered TILs, wherein the disruption is at a sequence that is bound by a guiding polynucleic acid of SEQ ID NO: 68. In some cases, a preparative regime comprises administration of an immunosuppressant from about 14 days to about 24 hours before administering TILs. In some cases, a preparative regime comprises administration of an immunosuppressant from about 10 days to about 24 hours before administering TILs. A preparative regime can comprise administration of an immunosuppressant from about 7 days to about 24 hours before administering TILs. In some cases, an immunosuppressant comprises a radiotherapeutic agent, a biologic agent, or a chemical agent. An immunosuppressant can comprise a chemical agent. A chemical agent can comprise at least one member selected from the group consisting of: cyclophosphamide, mechlorethamine, chlorambucil, melphalan, ifosfamide, thiotepa, hexamethylmelamine, busulfan, fludarabine, nitrosoureas, platinum, methotrexate, azathioprine, mercaptopurine, procarbazine, dacarbazine, temozolomide, carmustine, lomustine, streptozocin, fluorouracil, dactinomycin, anthracycline, mitomycin C, bleomycin, and mithramycin. A chemical agent can comprise cyclophosphamide A chemical agent can be fludarabine. Cyclophosphamide can be administered from about 40 mg/kg to about 50 mg/kg of a subject. Cyclophosphamide can be administered to a subject over at least about 2 days to about 5 days. In some cases, a cyclophosphamide can be administered from about 10 mg/kg to about 15 mg/kg of a subject. In some cases, cyclophosphamide can be administered to a subject over at least about 7 days to about 10 days. In some cases, cyclophosphamide can be administered from about 3 mg per kg to about 5 mg per kg of a subject. In some cases, cyclophosphamide can be administered from about 50 mg per kg to about 80 mg/kg of a subject. In some cases, cyclophosphamide can be administered in excess of 50 mg per kg. In some cases, cyclophosphamide can be administered at about 60 mg per kg. In some cases, fludarabine can be administered from about 20 mg/m$^2$ to about 30 mg/m$^2$ of body surface area of a subject. In some cases, fludarabine can be administered at about 25 mg/m$^2$ of body surface area of a subject. In some cases, a preparative regime comprises partial or complete immunosuppression. An antifungal can be selected from a group consisting of: polyene, azole, allylamine, and echinocandin. An antifungal can be an azole. An azole can be selected from the group consisting of: bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, and voriconazole. An antifungal that is an azole can be fluconazole. In some cases, fluconazole can be administered from about 100 mg to about 800 mg. Fluconazole can be administered at 400 mg. An antifungal can be administered concurrent or sequential to TILs. An antifungal can be administered from about day 0 to about day 4 after TILs. In some cases, an antibiotic comprises least one of: a bacterial wall targeting agent, a cell membrane targeting agent, a bacterial enzyme interfering agent, a bactericidal agent, a protein synthesis inhibitor, or a bacteriostatic agent. In some cases, an antibiotic comprises a bactericidal agent. A bactericidal agent can be cephalosporin or quinolone. In some cases, an antibiotic comprises a bacteriostatic agent. A bacteriostatic agent can be administered prophylactically. In some cases, a bacteriostatic agent can be trimethoprim, sulfamethoxazole, or pentamidine Trimethoprim, sulfamethoxazole, or pentamidine can be administered from about 100 mg to about 1000 mg. In some cases, trimethoprim can be administered at 160 mg. In some cases, sulfamethoxazole can be administered at 800 mg. In some cases, pentamidine can be administered at 300 mg. A bacteriostatic agent can be administered prior to TILs, concurrent with TILs, or after TILs. A bacteriostatic agent can be administered from about 14 days prior to administration of TILs to about 6 months after administration of TILs. In some cases, a bacteriostatic agent can be administered from about 8 days prior to said TILs to at least 4 days after TILs.

In some cases, administering comprises intravenous, oral, intramuscular, intraperitoneal, or intrapleural administration. In some cases, an immunosuppressant can be administered by infusion. In some cases, cyclophosphamide can be at a dose of about 60 mg/kg and is diluted in 250 ml 5% dextrose in water and infused over one hour. In some cases, fludarabine can be at a dose of 25 mg/m$^2$ in 100 ml 0.9% sodium chloride, USP and infused over about 15 to about 30 minutes. A method can further comprise administering a pharmaceutical composition that comprises an immunostimulant in an amount sufficient to activate TILs in a subject. An immunostimulant can comprise at least one member selected from the group consisting of: vaccines, colony stimulating agents, interferons, interleukins, viruses, antigens, co-stimulatory agents, immunogenicity agents, immunomodulators, or immunotherapeutic agents. An immunostimulant can comprise an interleukin. An interleukin can be aldesleukin and can be administered at a dose from about 550,000 to about 800,000 IU/kg. In some cases, aldesleukin can be administered at a dose of about 720,000 IU/kg. In some cases, a method can further comprise administering a pharmaceutical composition that comprises an infection prophylaxis agent in an amount sufficient to prevent an infection in a subject. In some cases, an infection prophylaxis agent can be a herpes virus prophylactic agent. In some cases, a subject can be HSV positive. In some cases, a herpes virus prophylactic agent can be valacyclovir or acyclovir. In some cases, a disruption can be induced by a system selected from the group consisting of CRISPR, Zinc Finger, TALEN, and any combination thereof. A system can be a CRISPR system. A CRISPR system can comprise an endonuclease selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Cpf1, c2c1, c2c3, and Cas9HiFi. An endonuclease can be Cas9. In some cases, an endonuclease performs a disruption. A disruption can comprise an exon or an intron of a gene. A disruption can be in an exon of a gene. A disruption can be within about 20 base pairs of a protospacer adjacent motif (PAM). A disruption can be within about 10 base pairs of a protospacer adjacent motif (PAM). A disruption can be within about 5 base pairs of a protospacer adjacent motif (PAM). A disruption can be 3 base pairs from a protospacer adjacent motif (PAM). In some cases, a disruption is in an exon or intron of SEQ ID NO: 13. A disruption can be in an exon of SEQ ID NO: 13. In some cases, a CRISPR system comprises a guiding polynucleic acid. A guiding polynucleic can comprise at least about 60% homology to SEQ ID NO: 68. In some cases, a disruption comprises a double strand break. A double strand break can occur at SEQ ID NO: 71 or SEQ ID NO: 77. In some cases, TILs can be administered at a dose from about $1\times10^9$ cells, $3\times10^9$ cells, $1\times10^{10}$ cells, $3\times10^{10}$ cells, and to about $1\times10^{11}$ cells. In some cases, TILs can be administered over about 30 minutes. In some cases, TILs can be administered intravenously. Intravenous administration can comprise an infusion.

In some cases, a method can further comprise performing a pre-infusion testing on TILs. A pre-infusion testing can comprise at least one of: phenotypic testing, potency testing, microbiological testing, endotoxin testing, viability testing, and tumor cell testing. In some cases, a phenotypic testing comprises detecting a presence of CD3 on TILs. In some cases, a potency testing comprises detecting a level of IFNγ upon anti-CD3 stimulation of TILs. In some cases, a microbiological testing comprises detecting growth of an aerobic culture, anaerobic culture, gram status, fungal status, or mycoplasma status. An endotoxin testing can comprise performing a limulus assay. In some cases, a viability testing comprises performing a trypan blue exclusion assay. In some cases, a tumor cell testing comprises a cytopathology assay. In some cases, TILs can be administered when a pre-infusion testing can be negative for a microbiological testing. In some cases, TILs can be administered when a pre-infusion testing is over at least about 70% viable cells for said viability testing. In some cases, TILs can be administered when a pre-infusion testing is at least about 80% CD3 positive for a phenotypic testing. In some cases, TILs can be administered when a pre-infusion testing is at least about 200 pg/mL per $10^5$ cells of IFNγ upon anti-CD3 stimulation of TILs in a potency testing. In some cases, TILs can be administered when a pre-infusion testing can be negative for tumor cells per at least about 200 TILs examined in a cytopathology testing.

Disclosed herein is a therapeutic product that comprises a dosage form of a plurality of tumor infiltrating lymphocytes (TILs) that comprise a disruption of at least a portion of a cytokine inducible SH2-containing protein (CISH) gene; and a dosage form of an antifungal agent.

Disclosed herein is a therapeutic product that comprises a dosage form of a folate synthesis inhibitor or a nucleic acid cross-linking agent in an amount sufficient to inhibit a fungal infection in a subject; and a dosage form of a plurality of tumor infiltrating lymphocytes (TILs) that comprise a disruption of at least a portion of a cytokine inducible SH2-containing protein (CISH) gene.

Disclosed herein is a therapeutic product that comprises a dosage form of an anti-fungal agent selected from a polyene, azole, allylamine, or echinocandins; and a dosage form of a plurality of tumor infiltrating lymphocytes (TILs) that comprise a disruption of at least a portion of a cytokine inducible SH2-containing protein (CISH) gene.

Disclosed herein is a therapeutic product that comprises a dosage form of a plurality of tumor infiltrating lymphocytes (TILs) that comprise a disruption of at least a portion of a cytokine inducible SH2-containing protein (CISH) gene wherein the TILs are cryopreserved at a freeze density from about $7.0 \times 10^7$ cells/mL to about $2.0 \times 10^8$ cells/mL.

Disclosed herein is a therapeutic product that comprises: a dosage form of an anti-fungal agent; a dosage form of an immunosuppressant; a dosage form of an antibiotic; and a dosage form of a plurality of tumor infiltrating lymphocytes (TILs) that comprise a disruption of at least a portion of a cytokine inducible SH2-containing protein (CISH) gene. In some cases, a therapeutic product can further comprise a dosage form of an immunosuppressant. An immunosuppressant can be formulated for administration to a subject from about 14 days to about 24 hours before an administration of TILs. In some cases, an immunosuppressant can be formulated for administration to a subject from about 10 days to about 24 hours before an administration of TILs. In some cases, an immunosuppressant can be formulated for administration to a subject from about 7 days to about 24 hours before an administration of TILs. In some cases, an immunosuppressant comprises a radiotherapeutic agent, a biologic agent, or a chemical agent. In some cases, an immunosuppressant comprises a chemical agent. In some cases, a chemical agent comprises at least one member selected from the group consisting of: cyclophosphamide, mechlorethamine, chlorambucil, melphalan, ifosfamide, thiotepa, hexamethylmelamine, busulfan, fludarabine, nitrosoureas, platinum, methotrexate, azathioprine, mercaptopurine, procarbazine, dacarbazine, temozolomide, carmustine, lomustine, streptozocin, fluorouracil, dactinomycin, anthracycline, mitomycin C, bleomycin, and mithramycin. In some cases, a chemical agent comprises cyclophosphamide. In some cases, a chemical agent comprises fludarabine. In some cases, cyclophosphamide can be administered from about 40 mg/kg to about 50 mg/kg of a subject. In some cases, cyclophosphamide can be administered to a subject over at least about 2 days to about 5 days. In some cases, cyclophosphamide can be administered from about 10 mg/kg to about 15 mg/kg of a subject. In some cases, cyclophosphamide can be administered to a subject over at least about 7 days to about 10 days. In some cases, cyclophosphamide can be administered from about 3 mg per kg to about 5 mg per kg of a subject. In some cases, cyclophosphamide can be administered from about 50 mg per kg to about 80 mg/kg of a subject. In some cases, cyclophosphamide can be administered in excess of 50 mg per kg. In some cases, cyclophosphamide can be administered at about 60 mg per kg. In some cases, fludarabine can be administered from about 20 mg/m² to about 30 mg/m² of body surface area of a subject. In some cases, fludarabine can be administered at about 25 mg/m² of body surface area of a subject. In some cases, an immunosuppressant produces a partial or complete immunosuppression. In some cases, a dosage form of an antifungal agent can be selected from a group consisting of: polyene, azole, allylamine, and echinocandin. In some cases, an antifungal agent can be an azole. An azole can be selected from the group consisting of: bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, and, voriconazole. In some cases, an azole can be fluconazole. In some cases, fluconazole can be present in an amount from about 100 mg to about 800 mg. In some cases, fluconazole can be present in an amount of 400 mg. In some cases, a dosage form of an antifungal can be administered concurrent or sequential to TILs. A dosage form of an antifungal can be administered from about day 0 to about day 4 after TILs. In some cases, a therapeutic product can further comprise a dosage form of an antibiotic. An antibiotic can comprise at least one of: a bacterial wall targeting agent, a cell membrane targeting agent, a bacterial enzyme interfering agent, a bactericidal agent, a protein synthesis inhibitor, and bacteriostatic agent. In some cases, an antibiotic comprises a bactericidal agent. A bactericidal agent can be cephalosporin or quinolone. In some cases, a dosage form of an antibiotic can be a bacteriostatic agent. A bacteriostatic agent can be formulated for prophylactic administration. In some cases, a bacteriostatic agent can be trimethoprim, sulfamethoxazole, or pentamidine. In some cases, trimethoprim, sulfamethoxazole, or pentamidine can be present in an amount of from about 100 mg to about 1000 mg. In some cases, trimethoprim can be present in an amount of 160 mg. In some cases, sulfamethoxazole can be present in an amount of 800 mg. In some cases, pentamidine can be present in an amount of 300 mg. In some cases, a bacteriostatic agent can be administered prior to TILs, concurrent with TILs, or after TILs. In some cases, a bacteriostatic agent can be administered from about 14 days prior to said administration of said TILs to about 6 months after said administration of said TILs. In some cases, a bacteriostatic agent can be administered from about 8 days prior to said TILs to at least 4 days after said TILs. A therapeutic product can further comprise administering a dosage form.

A therapeutic product can be formulated for administered by intravenous, oral, intramuscular, intraperitoneal, or intrapleural administration. In some cases, a dosage form of an immunosuppressant can be formulated for administration by infusion. In some cases, cyclophosphamide can be administered at a dose of about 60 mg/kg and is diluted in 250 ml 5% dextrose in water and infused over one hour. In some cases, fludarabine can be administered at a dose of 25 mg/m$^2$ in 100 ml 0.9% sodium chloride, USP and infused over about 15 to about 30 minutes. In some cases, an immunostimulant can be present in an amount sufficient to activate TILs in a subject. An immunostimulant comprises at least one member selected from the group consisting of: vaccines, colony stimulating agents, interferons, interleukins, viruses, antigens, co-stimulatory agents, immunogenicity agents, immunomodulators, and immunotherapeutic agents. In some cases, a dosage form of an immunostimulant comprises an interleukin. An interleukin can be aldesleukin and can be administered at a dose from about 550,000 to about 800,000 IU/kg. In some cases, aldesleukin can be administered at a dose of about 720,000 IU/kg. In some cases, a therapeutic product can further comprise a dosage form of an infection prophylaxis agent in an amount sufficient to prevent an infection in a subject. An infection prophylaxis agent can be a herpes virus prophylactic agent. A herpes virus prophylactic agent can be present in an amount effect to treat an HSV positive subject. In some cases, a herpes virus prophylactic agent can be valacyclovir or acyclovir. In some cases, a disruption can be induced by a system selected from the group consisting of CRISPR, Zinc Finger, TALEN, and any combination thereof. A system can be a CRISPR system. A CRISPR system can comprise an endonuclease selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Cpf1, c2c1, c2c3, and Cas9HiFi. In some cases, an endonuclease can be Cas9. An endonuclease can perform a disruption. A disruption can comprise an exon or an intron of a gene. In some cases, a disruption can be in an exon of a gene. In some cases, a disruption can be within about 20 base pairs of a protospacer adjacent motif (PAM). In some cases, a disruption can be within about 10 base pairs of a protospacer adjacent motif (PAM). In some cases, a disruption can be within about 5 base pairs of a protospacer adjacent motif (PAM). In some cases, a disruption can be 3 base pairs from a protospacer adjacent motif (PAM). In some cases, a disruption can be in an exon or intron of SEQ ID NO: 13. In some cases, a disruption can be in an exon of SEQ ID NO: 13. In some cases, a CRISPR system comprises a guiding polynucleic acid. A guiding polynucleic can comprise at least about 60% homology to SEQ ID NO: 68. A disruption can comprise a double strand break. In some cases, a double strand break occurs at SEQ ID NO: 71 or SEQ ID NO: 77. In some cases, TILs can be present in an amount from about 1×10$^9$ cells, 3×10$^9$ cells, 1×10$^{10}$ cells, 3×10$^{10}$ cells, and to about 1×10$^{11}$ cells. In some cases, TILs can be administered over about 30 minutes. In some cases, TILs can be administered intravenously. An intravenous administration can comprise an infusion. In some cases, a therapeutic product can further comprise performing a pre-infusion testing on TILs. In some cases, pre-infusion testing comprises at least one of: phenotypic testing, potency testing, microbiological testing, endotoxin testing, viability testing, and tumor cell testing. In some cases, phenotypic testing comprises detecting a presence of CD3 on said TILs. In some cases, potency testing comprises detecting a level of IFNγ upon anti-CD3 stimulation of TILs. In some cases, microbiological testing comprises detecting growth of an aerobic culture, anaerobic culture, gram status, fungal status, or mycoplasma status. In some cases, endotoxin testing comprises performing a limulus assay. In some cases, a viability testing comprises performing a trypan blue exclusion assay. In some cases, a tumor cell testing comprises a cytopathology assay. In some cases, TILs can be administered when a pre-infusion testing is negative for said microbiological testing. In some cases, TILs can be administered when a pre-infusion testing has over at least about 70% viable cells for a viability testing. In some cases, TILs can be administered when a pre-infusion testing is at least about 80% CD3 positive for a phenotypic testing. TILs can be administered when a pre-infusion testing is at least about 200 pg/mL per 10$^5$ cells of IFNγ upon anti-CD3 stimulation of TILs in a potency testing. In some cases, TILs can be administered when a pre-infusion testing can be negative for tumor cells per at least about 200 TILs examined in a cytopathology testing.

Disclosed herein is a nucleic acid composition that comprises at least 60% sequence homology to any one of SEQ ID NO: 64 to SEQ ID NO: 69. In some cases, a sequence homology can be at least about 65%, 70%, 75%, 80%, 85%, 90%, 95%, 96%, 97%, 98%, 99%, or up to about 100%.

Disclosed herein is a method of treating a condition such as cancer comprising obtaining tumor infiltrating lymphocytes (TIL) from a tumor sample, identifying a mutation reactive TIL, and disrupting an endogenous gene or portion thereof with a CRISPR nuclease. In some cases, a tumor sample can be subjected to sequencing analysis. In some cases, sequencing analysis identifies a mutation in a tumor sample and not in a non-tumor sample. In some cases, sequencing analysis can comprise whole exomic sequencing, transcriptome sequencing, or a combination thereof. Sequencing analysis can be whole exomic sequencing.

In some cases, identifying can comprise introducing a TIL to an antigen presenting cell (APC) expressing a peptide comprising a mutation. In some cases, identifying can further comprise detecting a presence of interferon γ (IFNγ) secreted by a TIL introduced to an APC expressing a peptide comprising a mutation. A peptide can comprise a length from about 15mer up to about 30mer. A peptide can comprise a length of 25mers. In some cases, identifying can comprise introducing a TIL to an antigen presenting cell (APC) electroporated with a polynucleic acid comprising a mutation.

In some cases, identifying can further comprise detecting a presence of interferon γ (IFNγ) secreted by a TIL introduced to an APC. Disrupting can comprise a double strand break in a genome of a TIL. A double strand break can be performed by a CRISPR nuclease. In some cases, a CRISPR nuclease can be selected from the group consisting of Cast, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Cpf1, c2c1, c2c3, and Cas9HiFi. A CRISPR nuclease can be Cas9.

In some cases, a method can further comprise expanding a TIL. A TIL can be human A method can further comprise administering an anti-fungal to a subject. A method can further comprise administering an antibiotic to a subject.

Disclosed herein is a method of treating gastrointestinal cancer in a subject in need thereof comprising obtaining tumor infiltrating lymphocytes (TIL) from a gastrointestinal tumor sample of a subject in need thereof, identifying a mutation reactive TIL, disrupting a CISH gene with a CRISPR nuclease in said mutation reactive TIL and expanding said TIL to a dose of $1\times10^9$ to about $2\times10^{11}$; wherein said gastrointestinal tumor sample is exomically sequenced to identify a mutation present in said tumor sample and not in a healthy tissue sample and wherein said identifying comprises presenting said mutation on a surface of an antigen presenting cell (APC) and culturing said APC with said TIL to detect a level of IFN-γ. In some cases, presenting can comprise culturing an antigen presenting cell (APC) electroporated with a polynucleic acid comprising a mutation with a TIL. In some cases, presenting can comprise culturing an antigen presenting cell (APC) pulsed with a peptide comprising a mutation with a TIL. A cytokine can be detected in a mutation reactive TIL and not detected in a non-mutation reactive TIL. A cytokine can be detected in a mutation reactive TIL at a higher level than in a non-mutation reactive TIL. A CRISPR nuclease can be Cas9. A TIL can be a T cell.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 demonstrates the structures of four plasmids, including Cas9 nuclease plasmid, HPRT gRNA plasmid, Amaxa EGFPmax plasmid and HPRT target vector.

FIG. 2 shows % gene modification occurring by CRISPR gRNAs at potential target sites.

FIG. 7A. shows percent CTLA-4 knock out in T cells treated with CTLA-4 guides #2, #3, #2 and #3, PD-1 guide #2 and CTLA-4 guide #2, PD-1 guide #6 and CTLA-4 guide #3, as compared to Zap only, Cas9 only, and an all guide RNA control. FIG. 7B. shows percent PD-1 knock out in T cells treated with PD-1 guide #2, PD-1 guide #6, PD-1 guides #2 and #6, PD-1 guide #2 and CTLA-4 guide #2, PD-1 guide #6 and CTLA-4 guide #3, as compared to Zap only, Cas9 only, and an all guide RNA control.

FIG. 22 depicts modified sgRNA for CISH, PD-1, CTLA4 and AAVS1.

Figure 3:
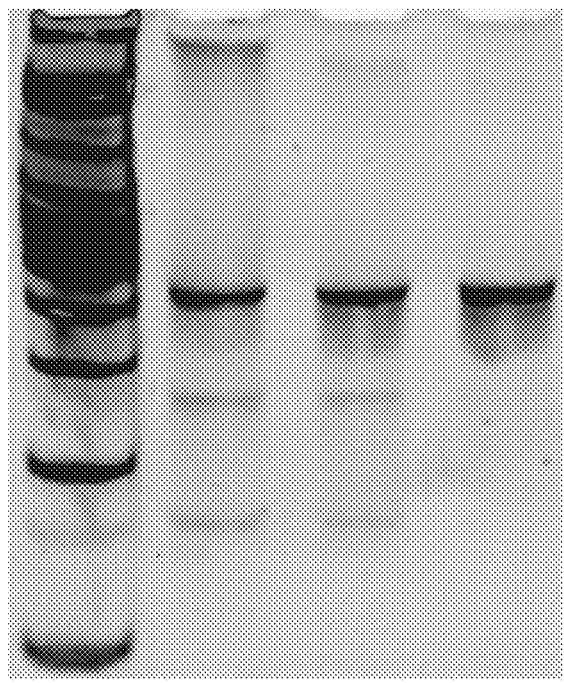
FIG. 3 demonstrates CRISPR-induced DSBs in stimulated T cells.
Figure 4:
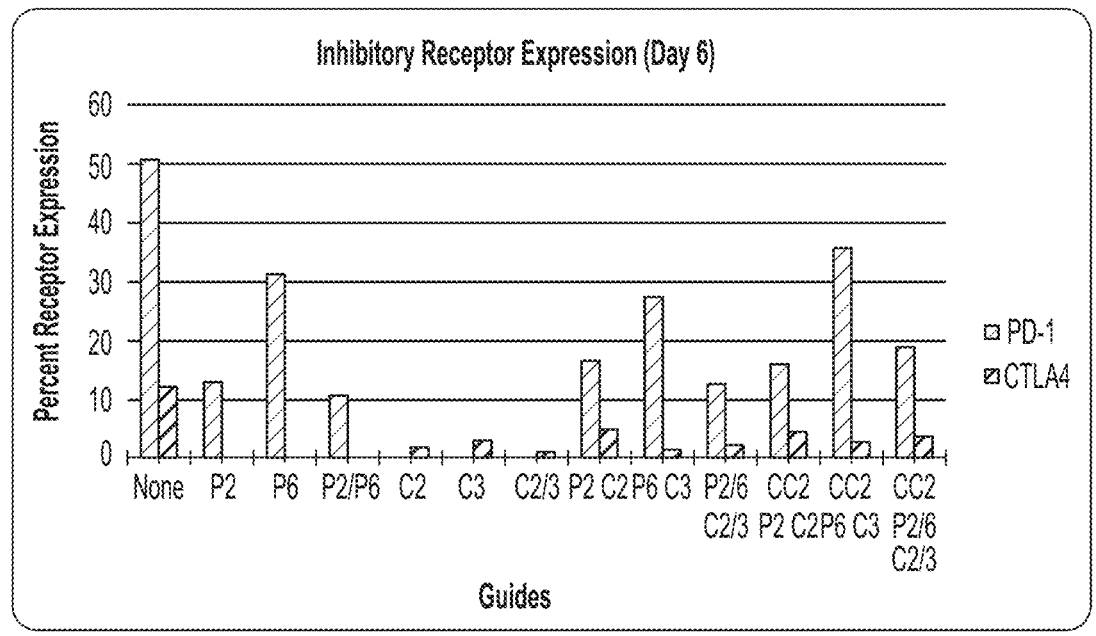
FIG. 4A and FIG. 4B show PD-1, CTLA-4, PD-1 and CTLA-2, or CCR5, PD-1, and CTLA-4 expression on day 6 post transfection with guide RNAs. Representative guides: PD-1 (P2, P6, P2/6), CTLA-4 (C2, C3, C2/3), or CCR5 (CC2). A. shows percent inhibitory receptor expression. B. shows normalized inhibitory receptor expression to a control guide RNA.
Figure 4:
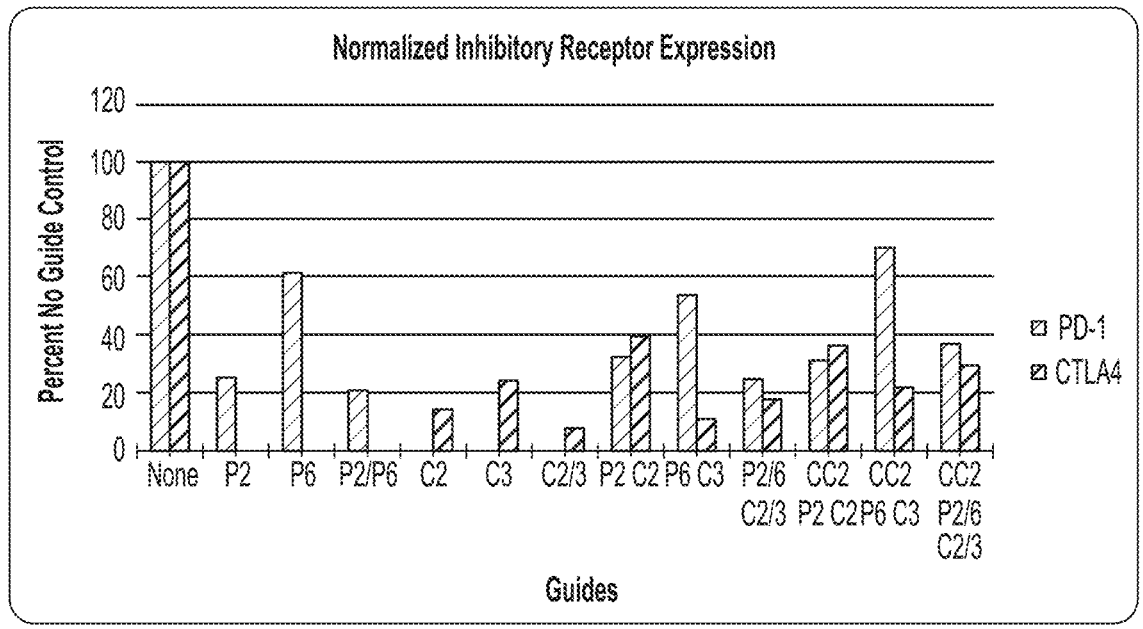
Figure 5:
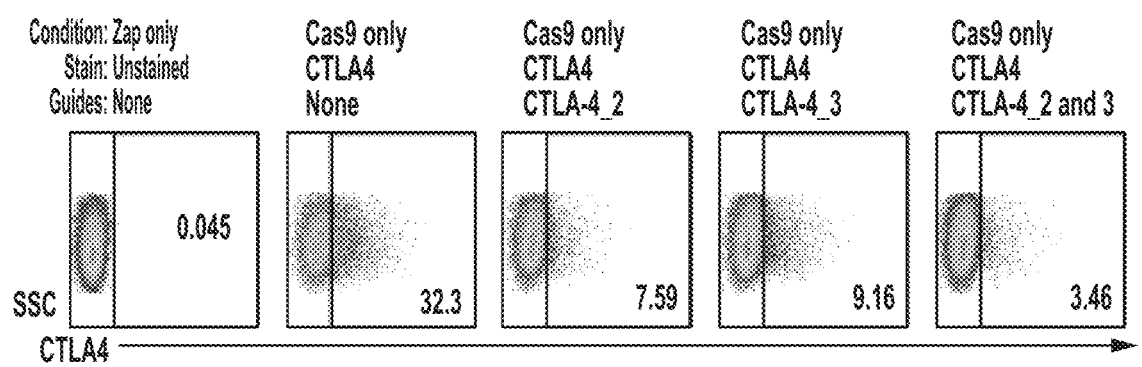
FIG. 5A show CTLA-4 expression in primary human T cells after electroporation with CRISPR and CTLA-4 specific guide RNAs, guides #2 and #3, as compared to unstained and a no guide control.
FIG. 5B. shows PD-1 expression in primary human T cells after electroporation with CRISPR and PD-1 specific guide RNAs, guides #2 and #6, as compared to unstained and a no guide control.
Figure 5:
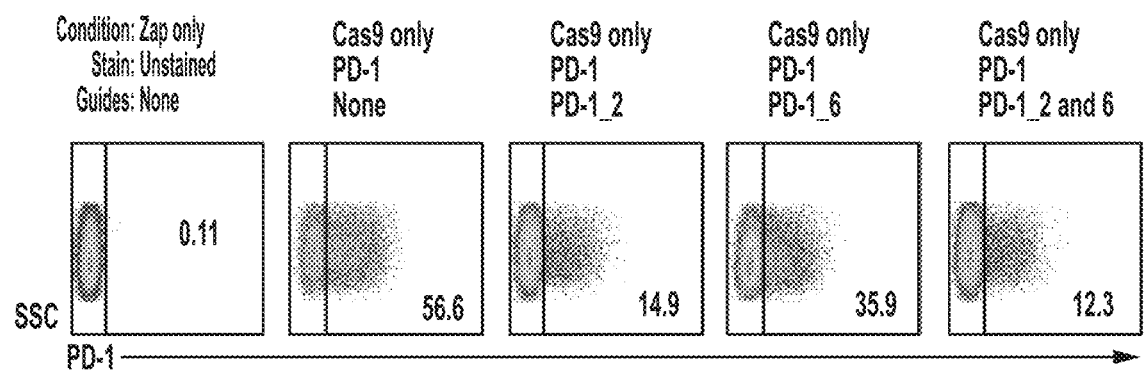
Figure 6:
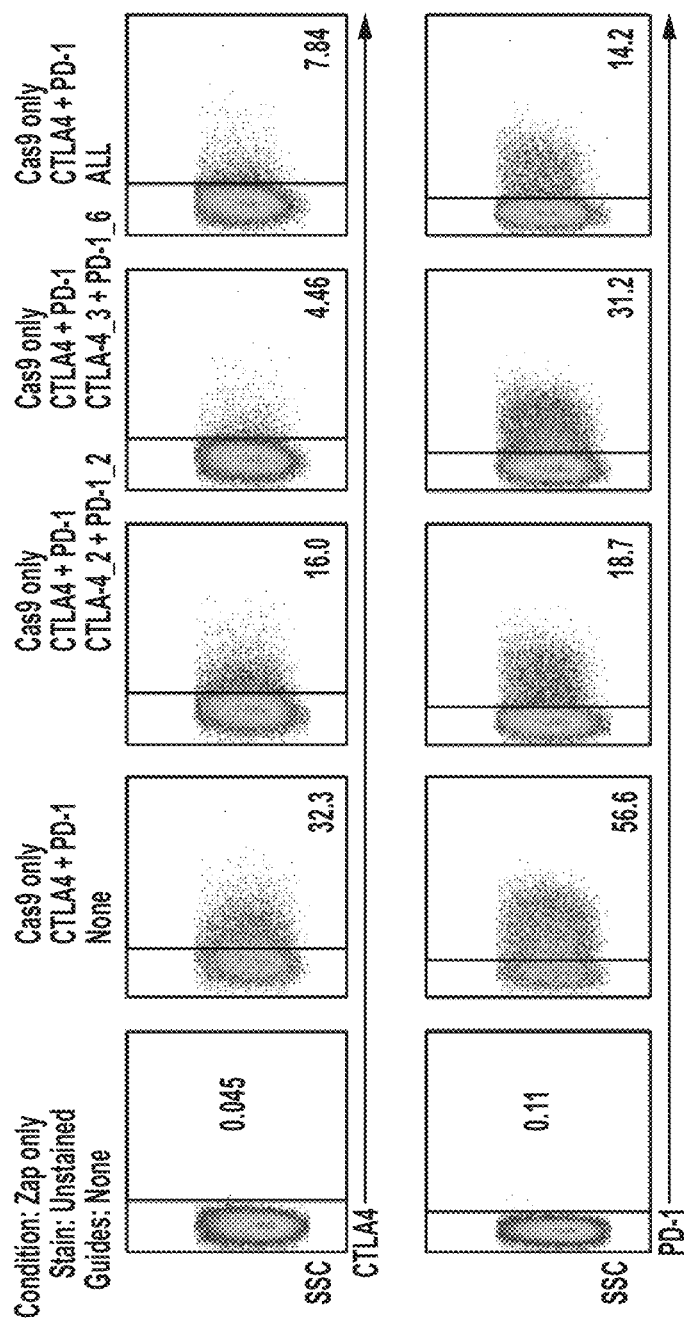
FIG. 6 shows FACs results of CTLA-4 and PD-1 expression in primary human T cells after electroporation with CRISPR and multiplexed CTLA-4 and PD-1 guide RNAs.
Figure 7:
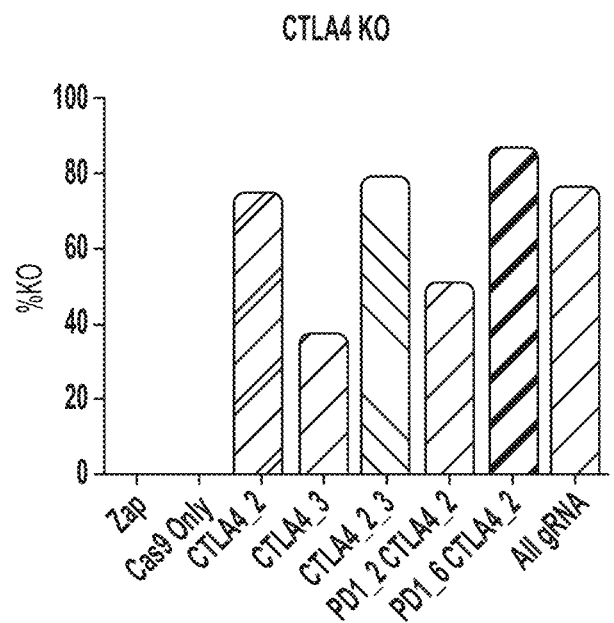
FIG. 7 A and FIG. 7 B show percent double knock out in primary human T cells post treatment with CRISPR.
Figure 7:
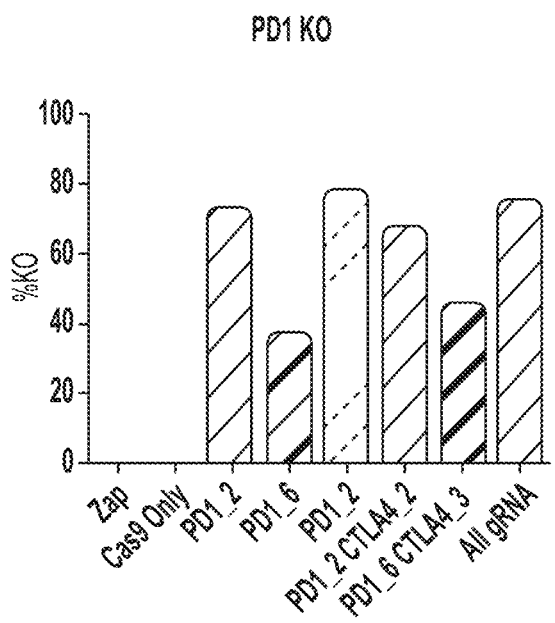
Figure 8:
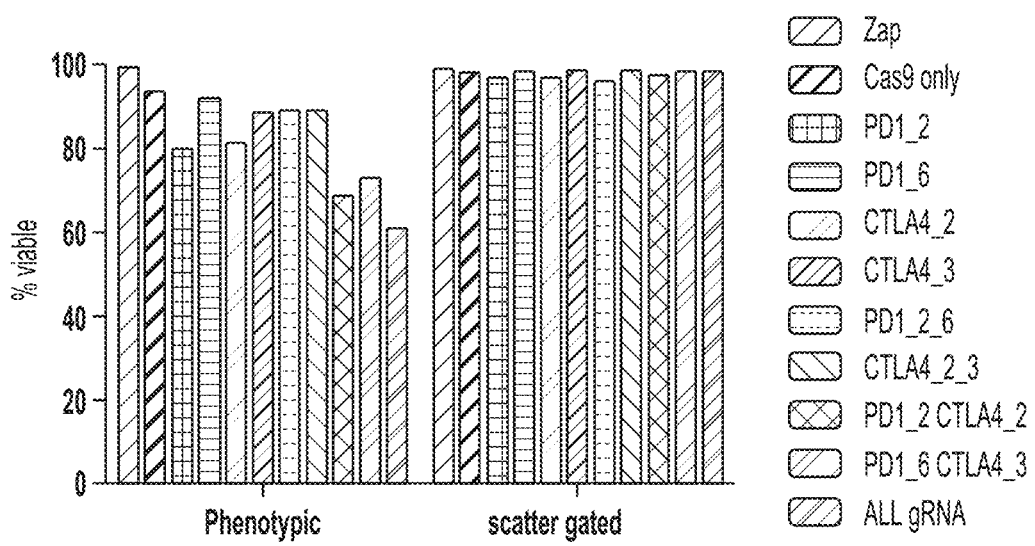
FIG. 8 shows T cell viability post electroporation with CRISPR and guide RNAs specific to CTLA-4, PD-1, or combinations.
Figure 9:
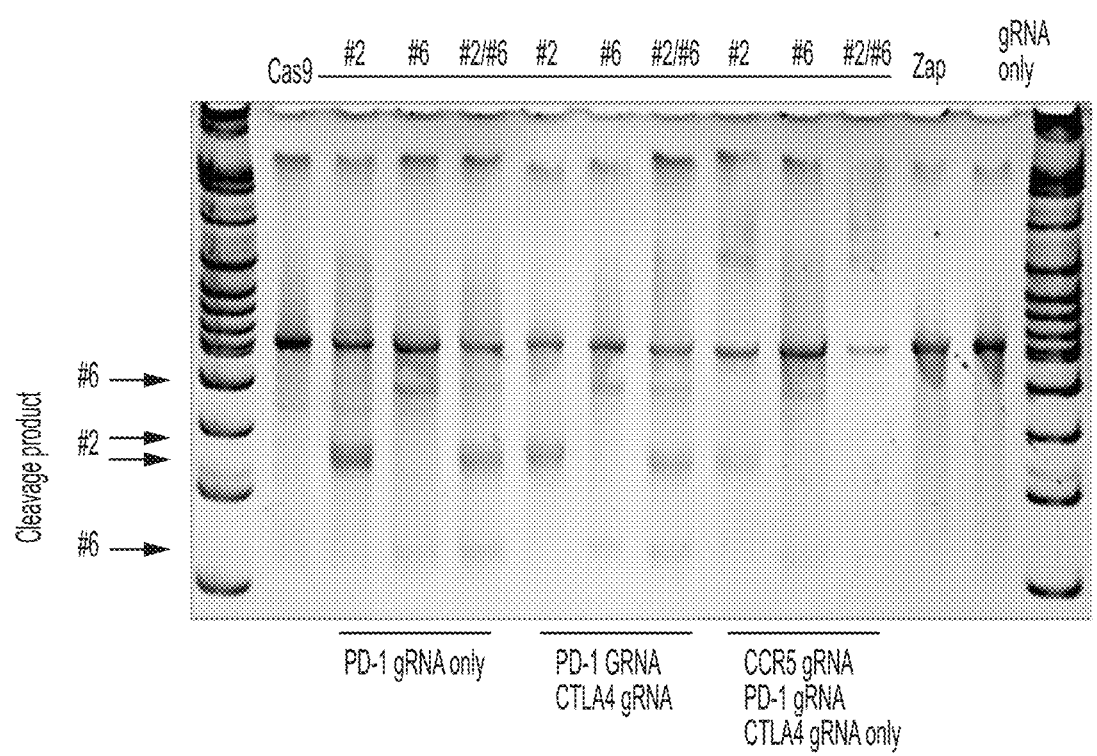
FIG. 9 results of a CEL-I assay showing cutting by PD-1 guide RNAs #2, #6, #2 and #6, under conditions where only PD-1 guide RNA is introduced, PD-1 and CTLA-4 guide RNAs are introduced or CCR5, PD-1, and CLTA-4 guide RNAs, Zap only, or gRNA only controls.
Figure 10:
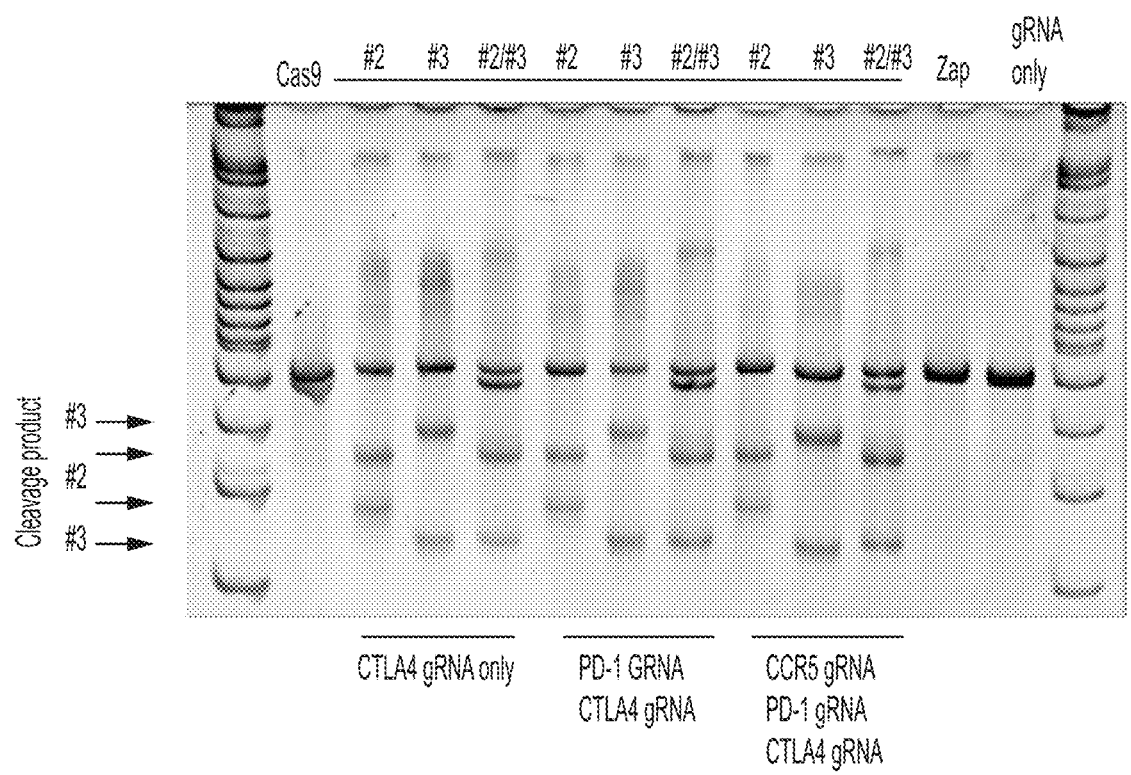
FIG. 10 results of a CEL-I assay showing cutting by CTLA-4 guide RNAs #2, #3, #2 and #3, under conditions where only CLTA-4 guide RNA is introduced, PD-1 and CTLA-4 guide RNAs are introduced or CCR5, PD-1, and CLTA-4 guide RNAs, Zap only, or gRNA only controls.
Figure 11:
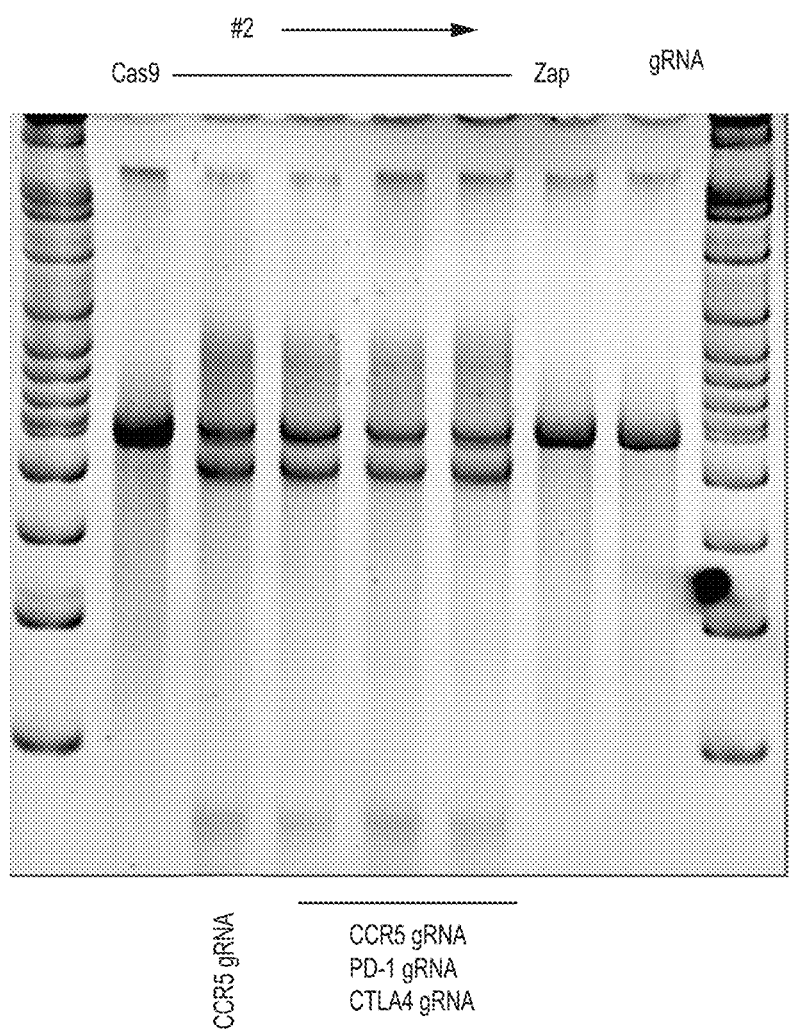
FIG. 11 results of a CEL-I assay showing cutting by CCR5 guide RNA #2 in conditions where CCR5 guide RNA is introduced, CCR5 guide RNA, PD-1 guide RNA, or CTLA-4 guide RNA, as compared to Zap only, Cas 9 only, or guide RNA only controls.
Figure 12:
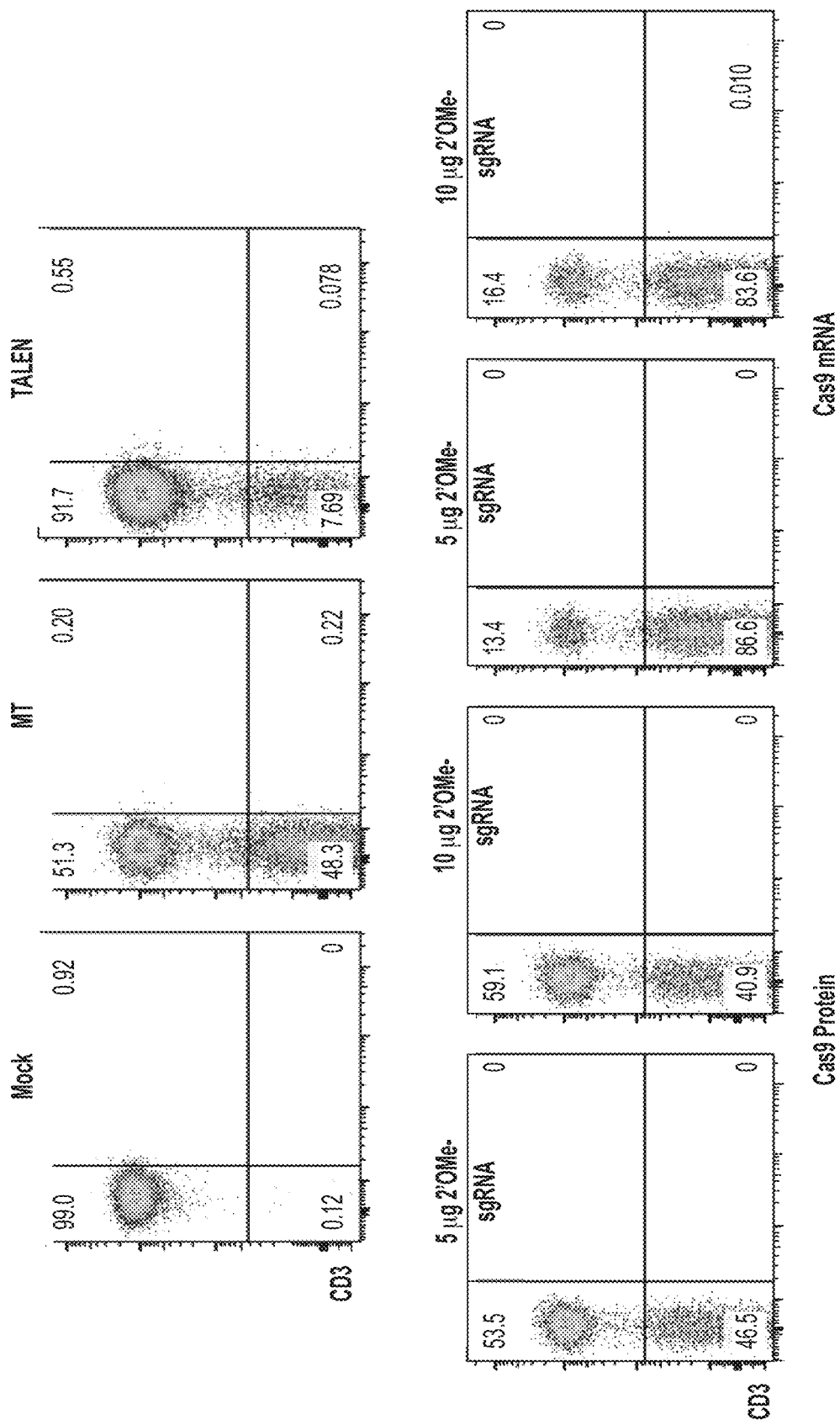
FIG. 12 shows knockout of TCR alpha, as measured by CD3 FACs expression, in primary human T cells utilizing optimized CRISPR guide RNAs with 2' 0-Methyl RNA modification at 5 micrograms and 10 micrograms.
Figure 13:
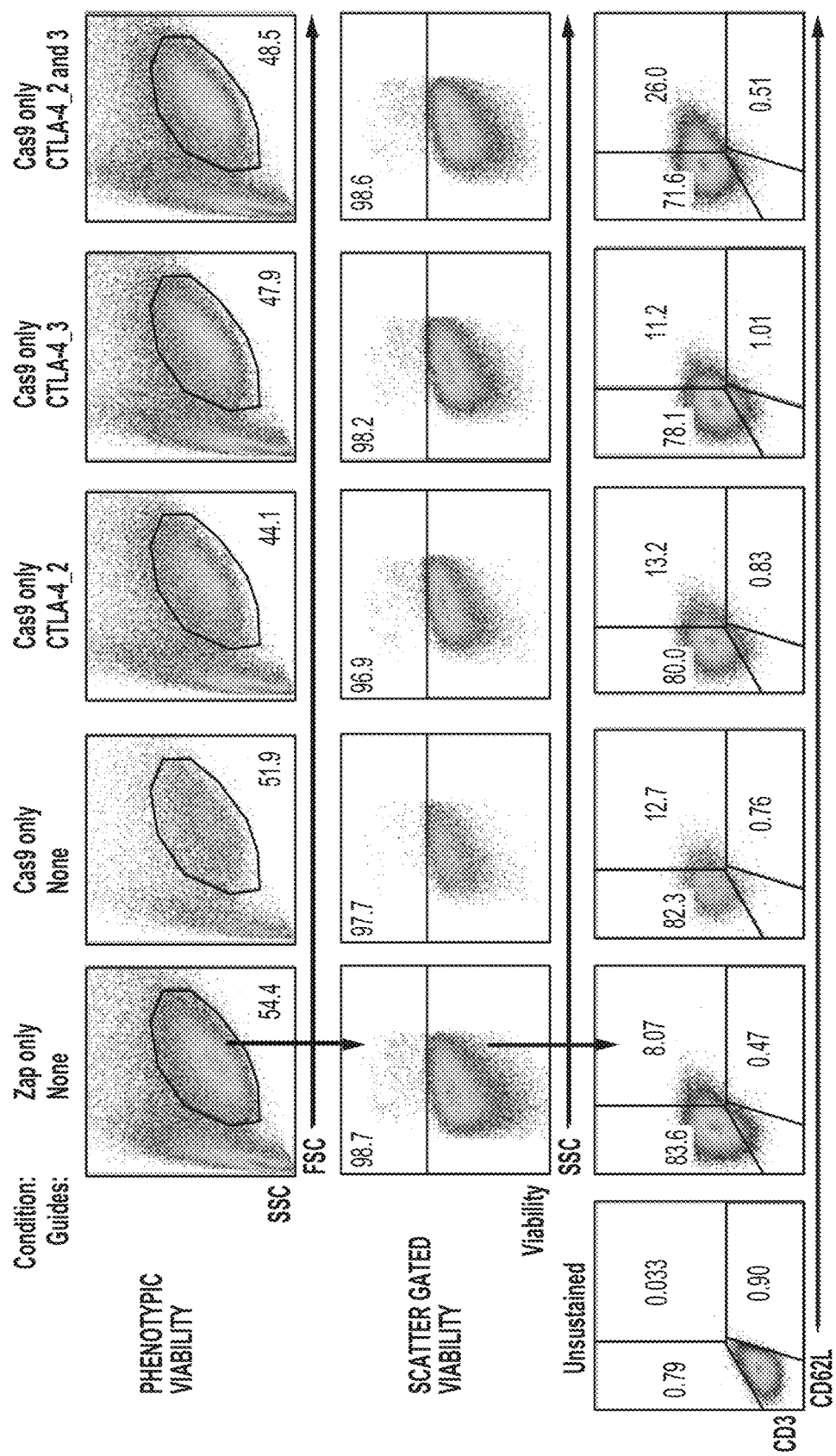
FIG. 13 depicts a method of measuring T cell viability and phenotype post treatment with CRISPR and guide RNAs to CTLA-4. Phenotype was measured by quantifying the frequency of treated cells exhibiting a normal FSC/SSC profile normalized to frequency of electroporation alone control. Viability was also measured by exclusion of viability dye by cells within the FSC/SSC gated population. T cell phenotype is measured by CD3 and CD62L.
Figure 14:
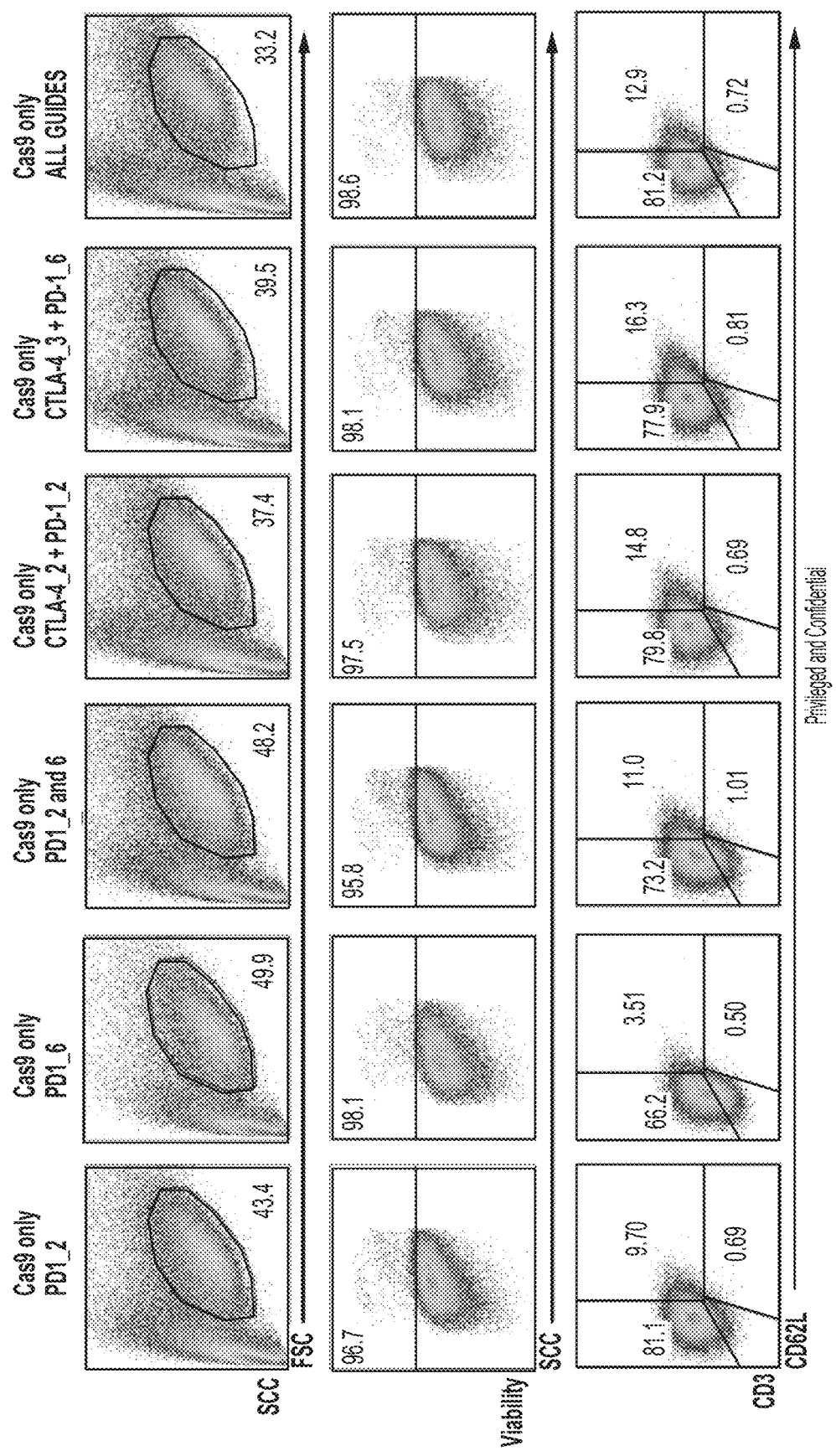
FIG. 14 shows method of measuring T cell viability and phenotype post treatment with CRISPR and guide RNAs to PD-1, and PD-1 and CTLA-4. Phenotype was measured by quantifying the frequency of treated cells exhibiting a normal FSC/SSC profile normalized to frequency of electroporation alone control. Viability was also measured by exclusion of viability dye by cells within the FSC/SSC gated population. T cell phenotype is measured by CD3 and CD62L.
Figure 15:
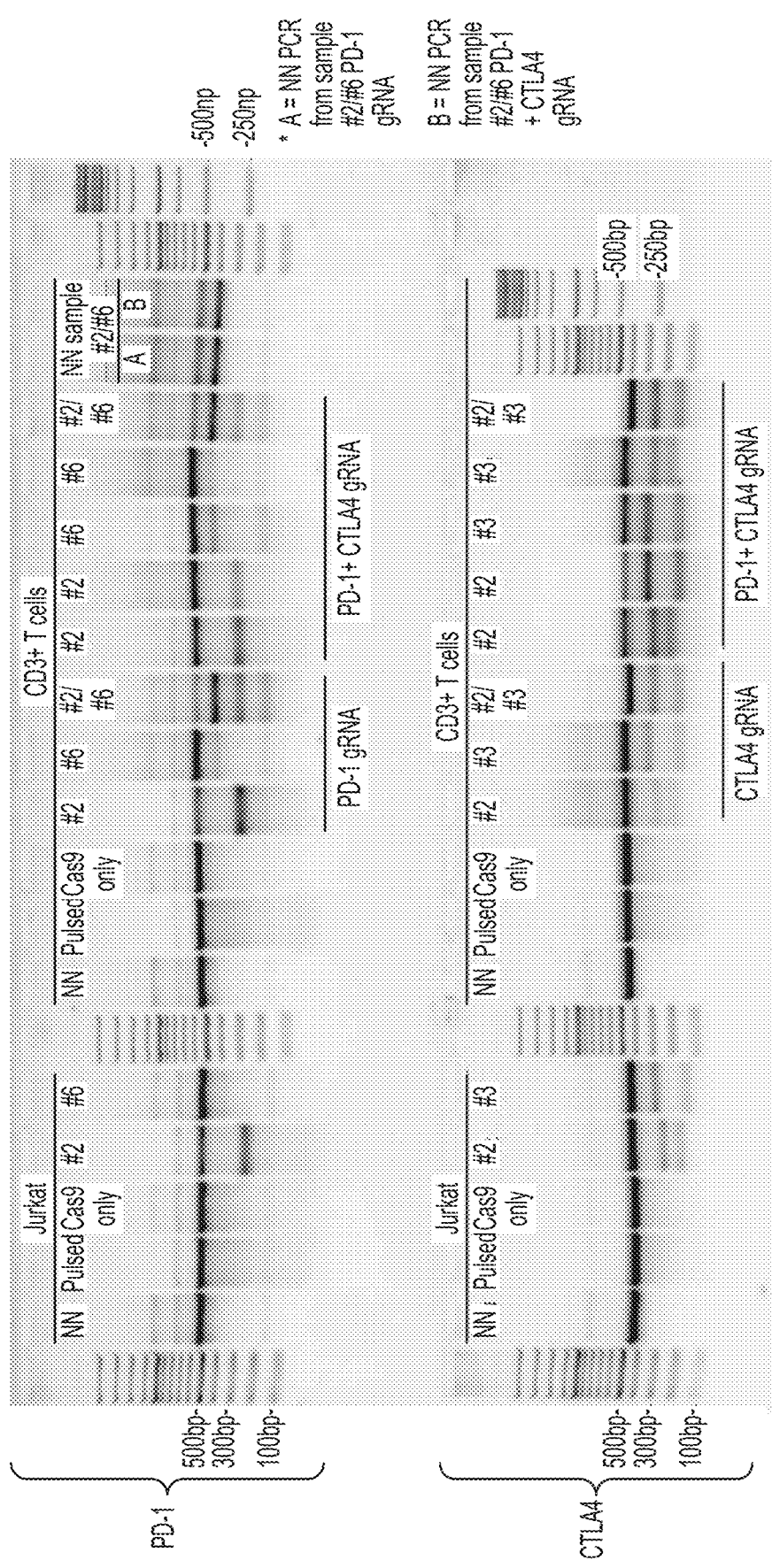
FIG. 15 shows results of a T7E1 assay to detect CRISPR gene editing on day 4 post transfection with PD-1 or CTLA-4 guide RNA of primary human T cells and Jurkat control. NN is a no T7E1 nuclease control.
Figure 16:
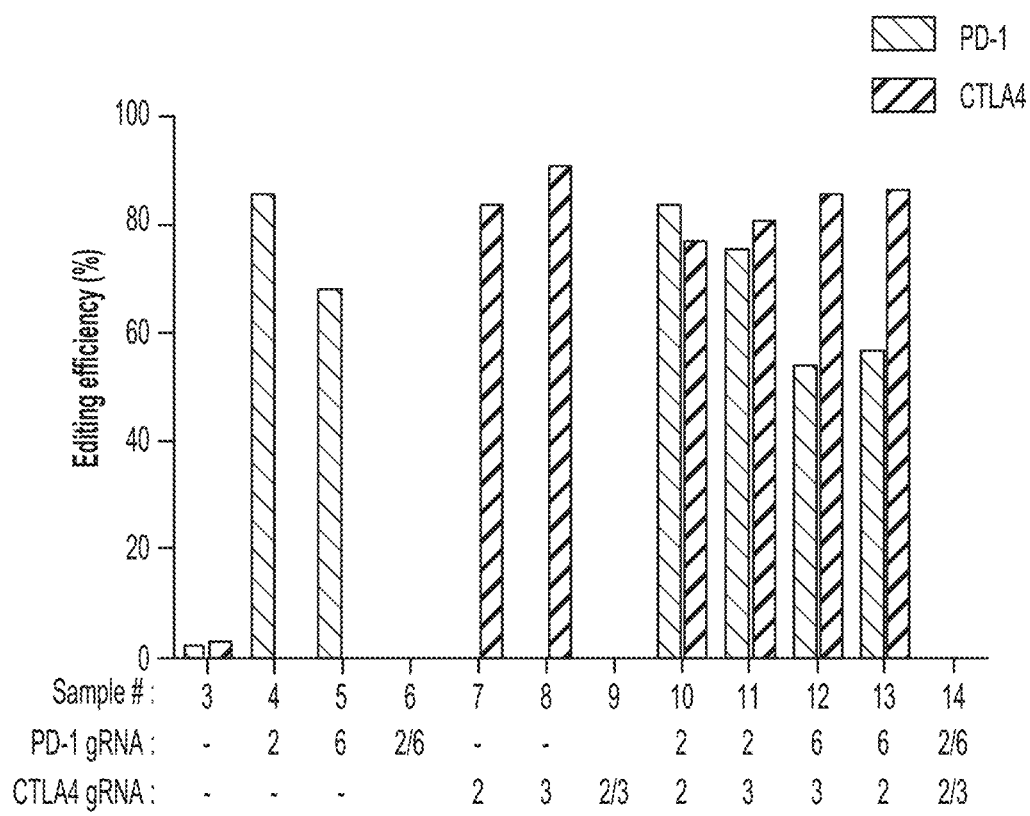
FIG. 16 shows results of a tracking of indels by decomposition (TIDE) analysis. Percent gene editing efficiency as shows to PD-1 and CTLA-4 guide RNAs.
Figure 17:
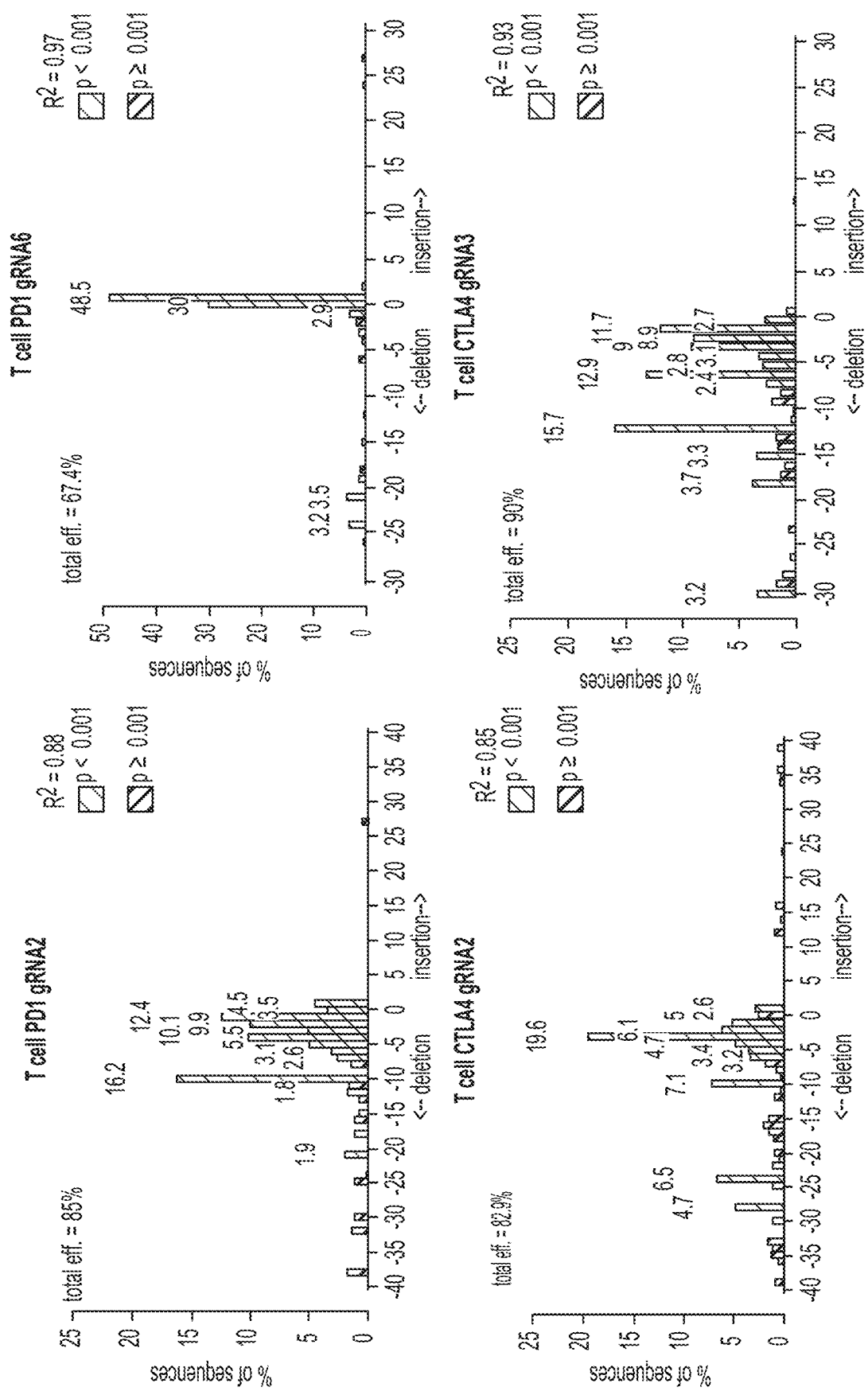
FIG. 17 shows results of a tracking of indels by decomposition (TIDE) analysis for single guide transfections. Percent of sequences with either deletions or insertions are shown for primary human T cells transfected with PD-1 or CTLA-1 guide RNAs and CRISPR.
Figure 18:
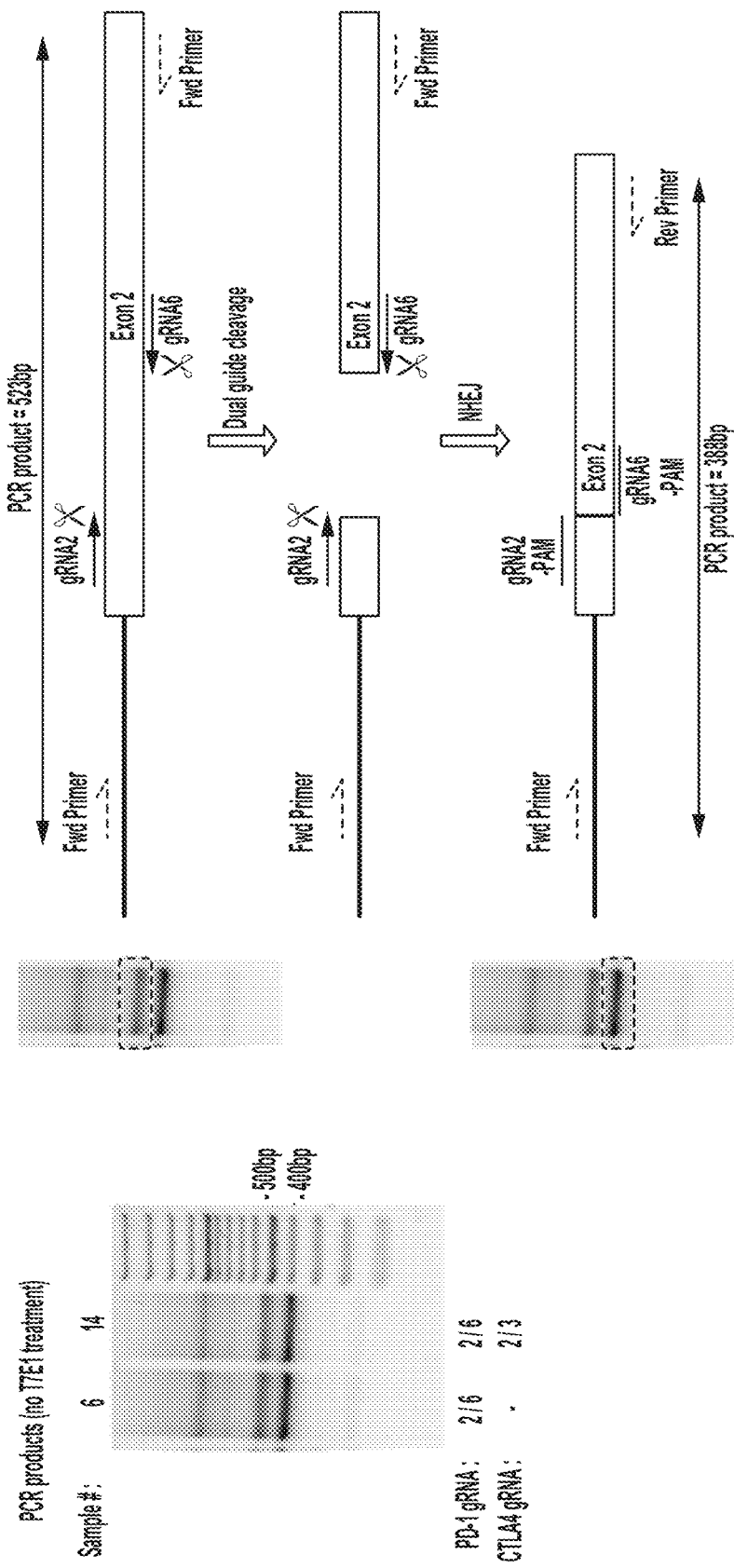
FIG. 18 shows PD-1 sequence deletion with dual targeting.
Figure 19:
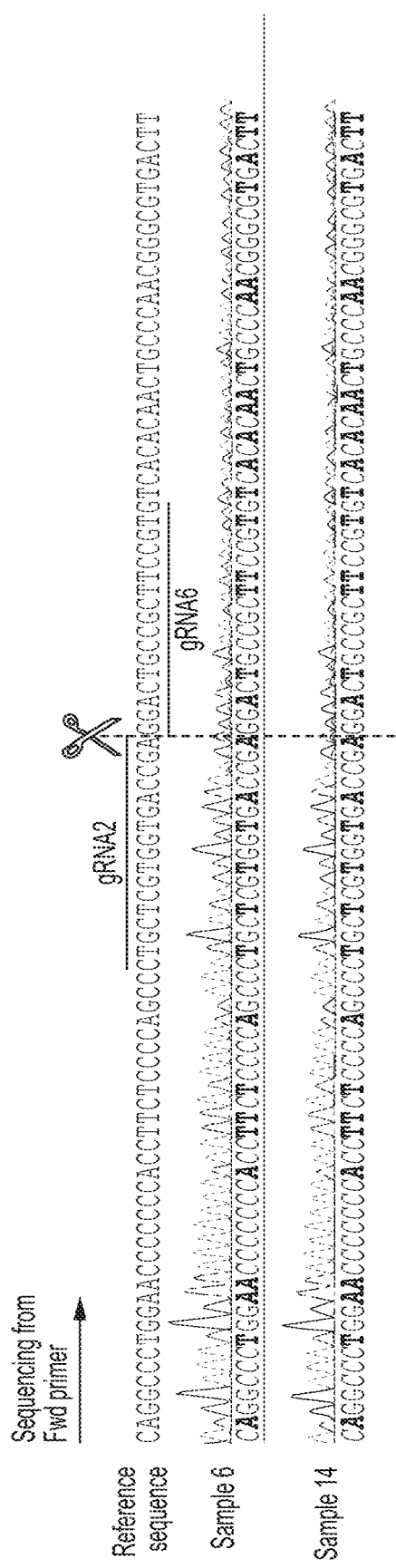
FIG. 19 shows sequencing results of PCR products of PD-1 sequence deletion with dual targeting. Samples 6 and 14 are shown with a fusion of the two gRNA sequences with the intervening 135 bp excised.
Figure 20:
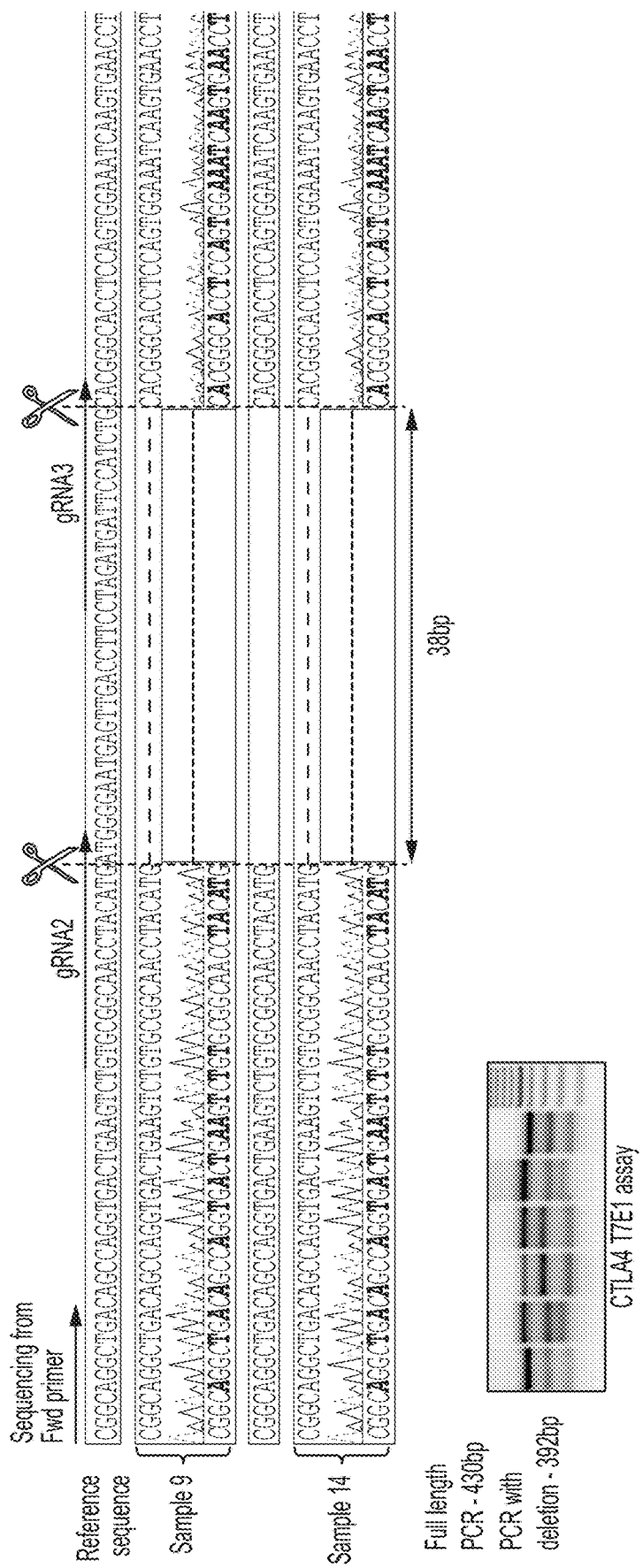
FIG. 20 shows dual targeting sequence deletion of CTLA-4. Deletion between the two guide RNA sequences is also present in the sequencing of dual guide targeted CTLA-4 (samples 9 and 14). A T7E1 Assay confirms the deletion by PCR.
Figure 21A:
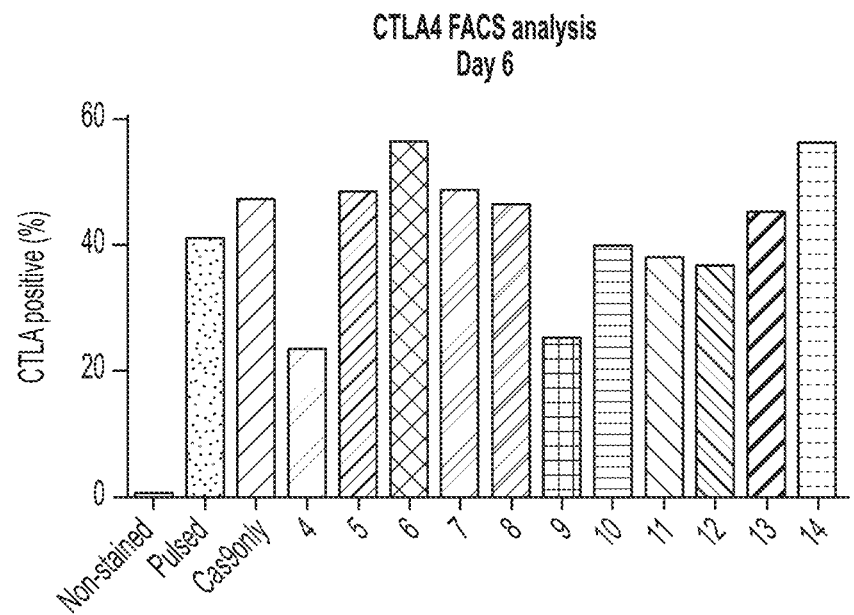
FIG. 21 A and FIG. 21 B show CTLA-4 FACs analysis of CTLA-4 positive human T cells post transfection with anti-CTLA-4 guide RNAs and CRISPR. B. shows CTLA-4 knock out efficiency relative to a pulsed control in human T cells post transfection with anti-CTLA-4 guide RNAs and CRISPR.
Figure 21B:
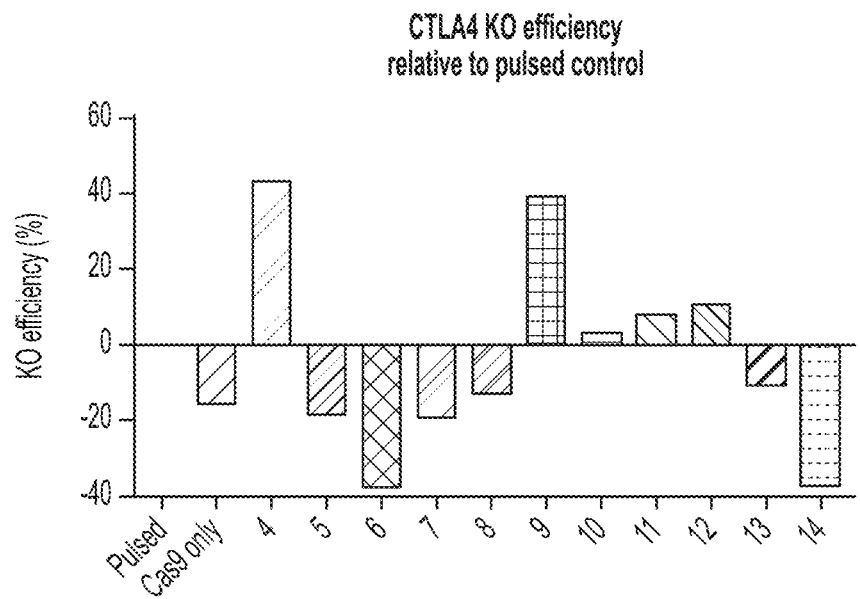
Figure 23A:
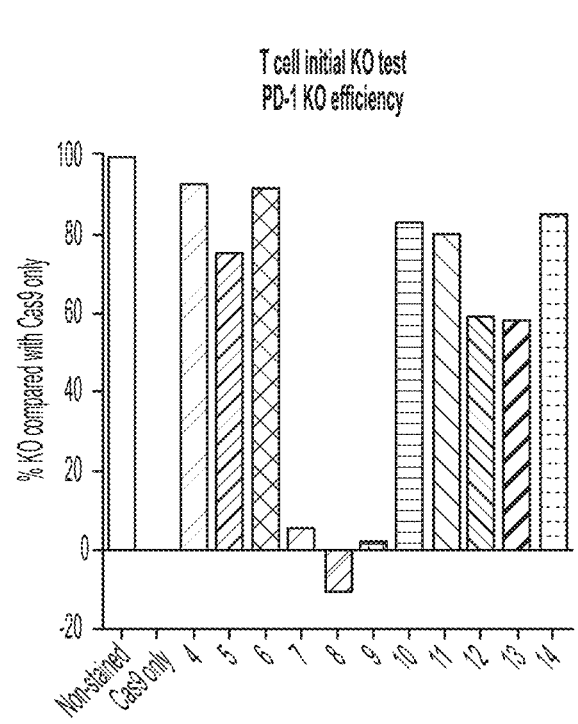

FIG. 23A shows percent PD-1 expression post transfection with an anti-PD-1 CRISPR system.

Figure 23B:
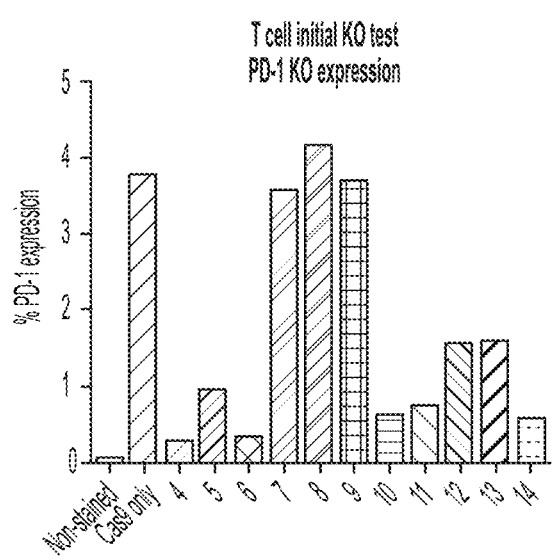

FIG. 23B. shows percent PD-1 knock out efficiency as compared to Cas9 only control.

Figure 24:
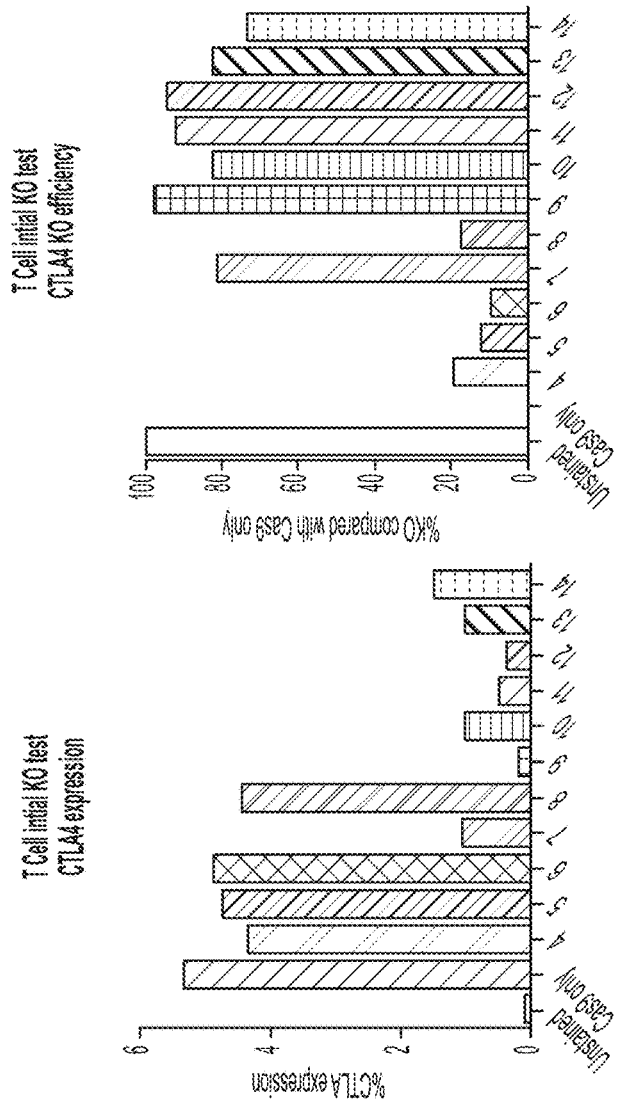

FIG. 24 depicts quantification data from a FACs analysis of CTLA-4 stained human T cells transfected with CRISPR and anti-CTLA-4 guide RNAs. Day 6 post transfection data is shown of percent CTLA-4 expression and percent knock out.

Figure 25:
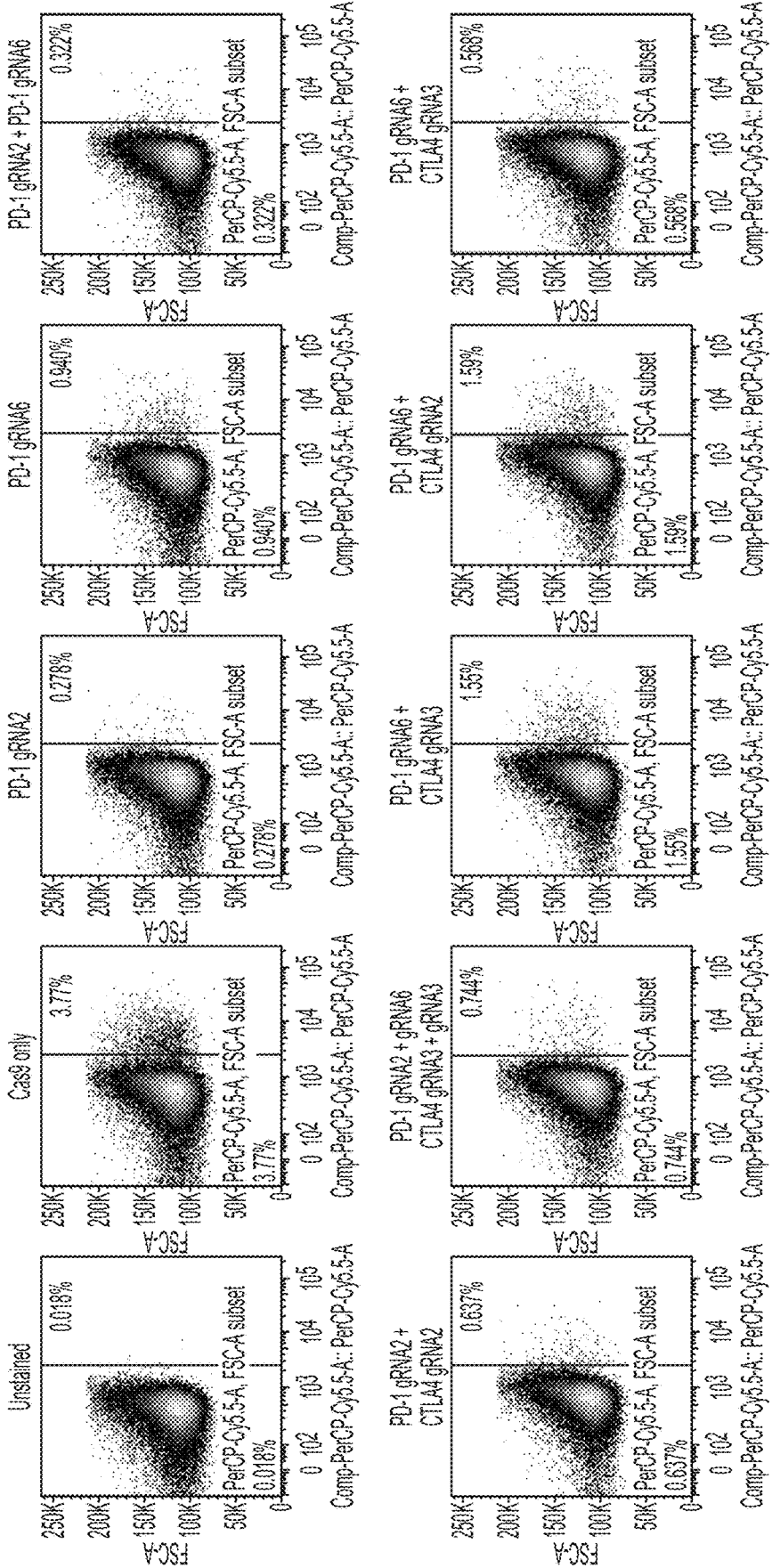

FIG. 25 shows FACs analysis of PD-1 stained human T cells transfected with CRISPR and anti-PD-1 guide RNAs. Day 14 post transfection data is shown of PD-1 expression (anti-human CD279 PerCP-Cy5.5)

Figure 26:
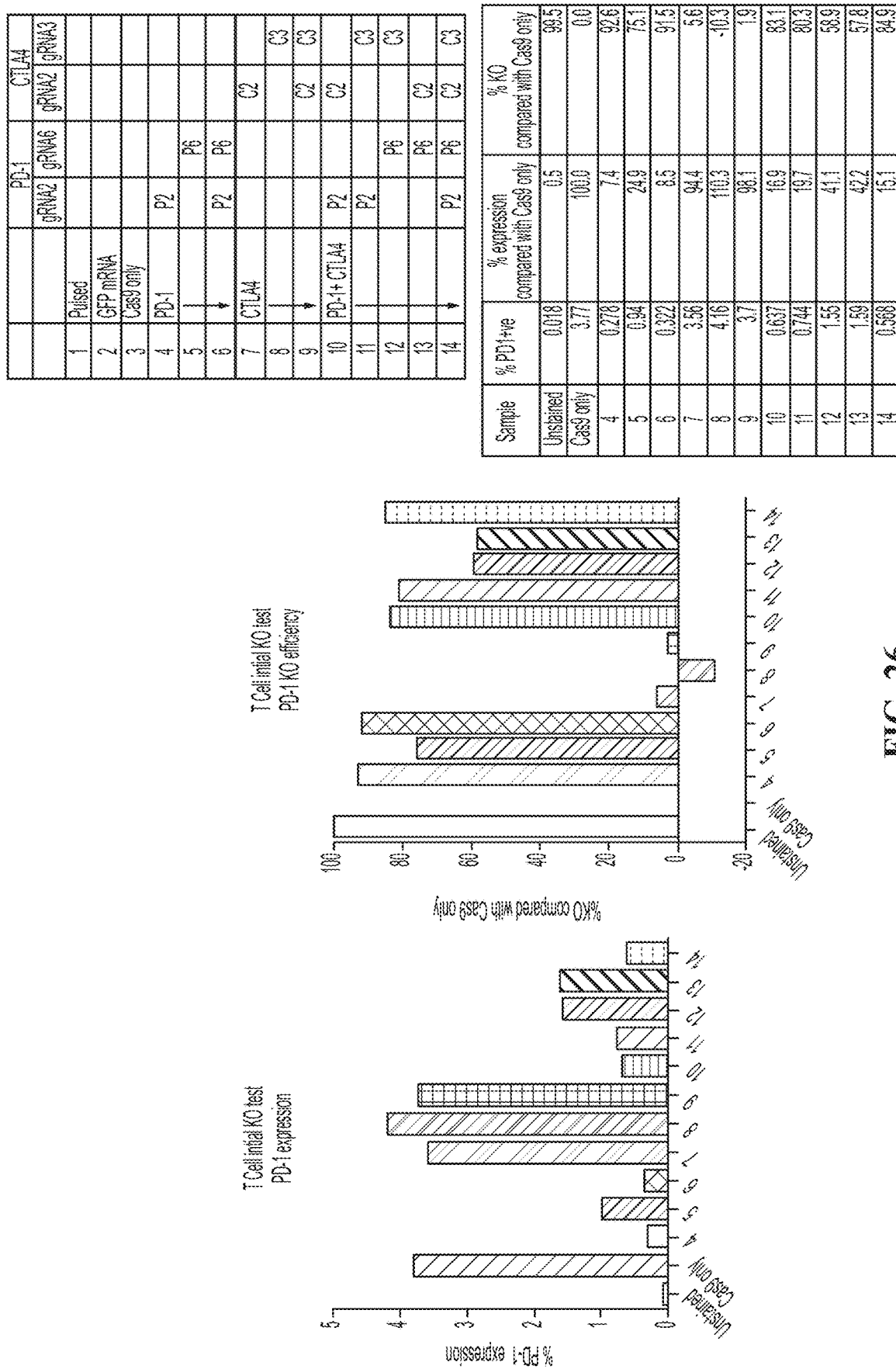

FIG. 26 shows percent PD-1 expression and percent knock out of PD-1 compared to Cas9 only control of human T cells transfected with CRISPR and anti-PD-1 guide RNAs.

Figure 27:
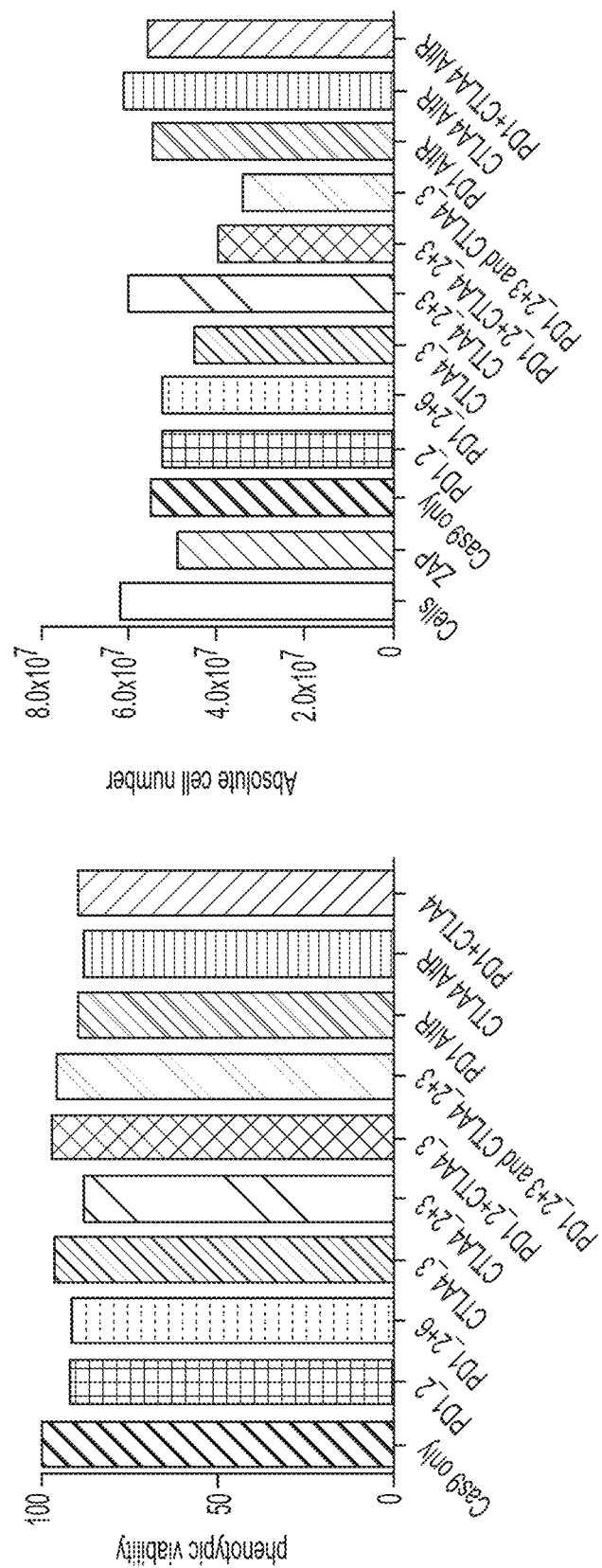

FIG. 27 shows day 14 cell count and viability of transfected human T cells with CRISPR, anti-CTLA-4, and anti-PD-1 guide RNAs.

Figure 28:
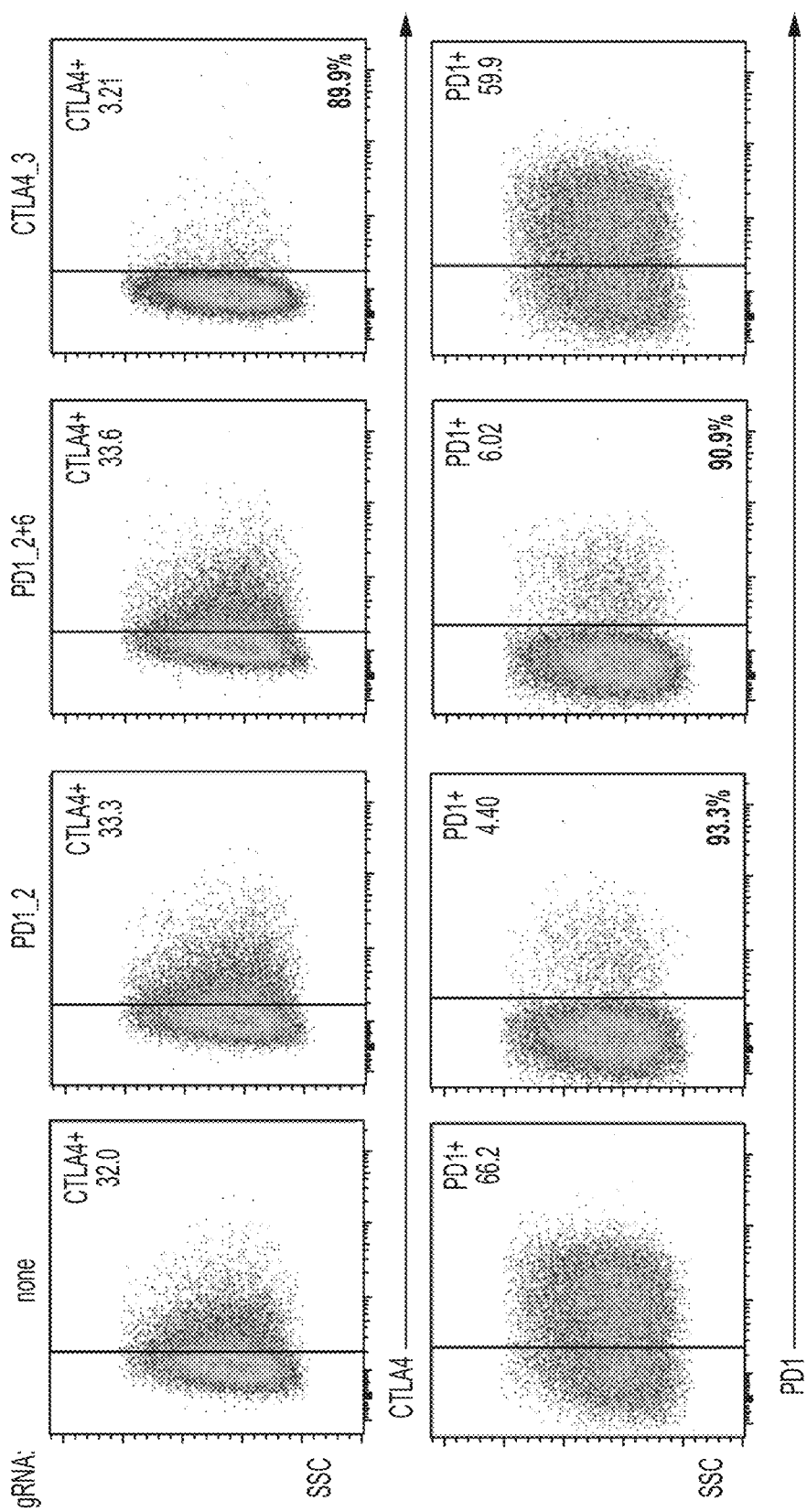

FIG. 28 shows FACs data for human T cells on day 14 post electroporation with CRISPR, and anti-PD-1 guide #2 alone, anti-PD-1 guide #2 and #6, or anti-CTLA-4 guide #3 alone. The engineered T cells were re-stimulated for 48 hours to assess expression of CTLA-4 and PD-1 and compared to control cells electroporated with no guide RNA.

Figure 29:
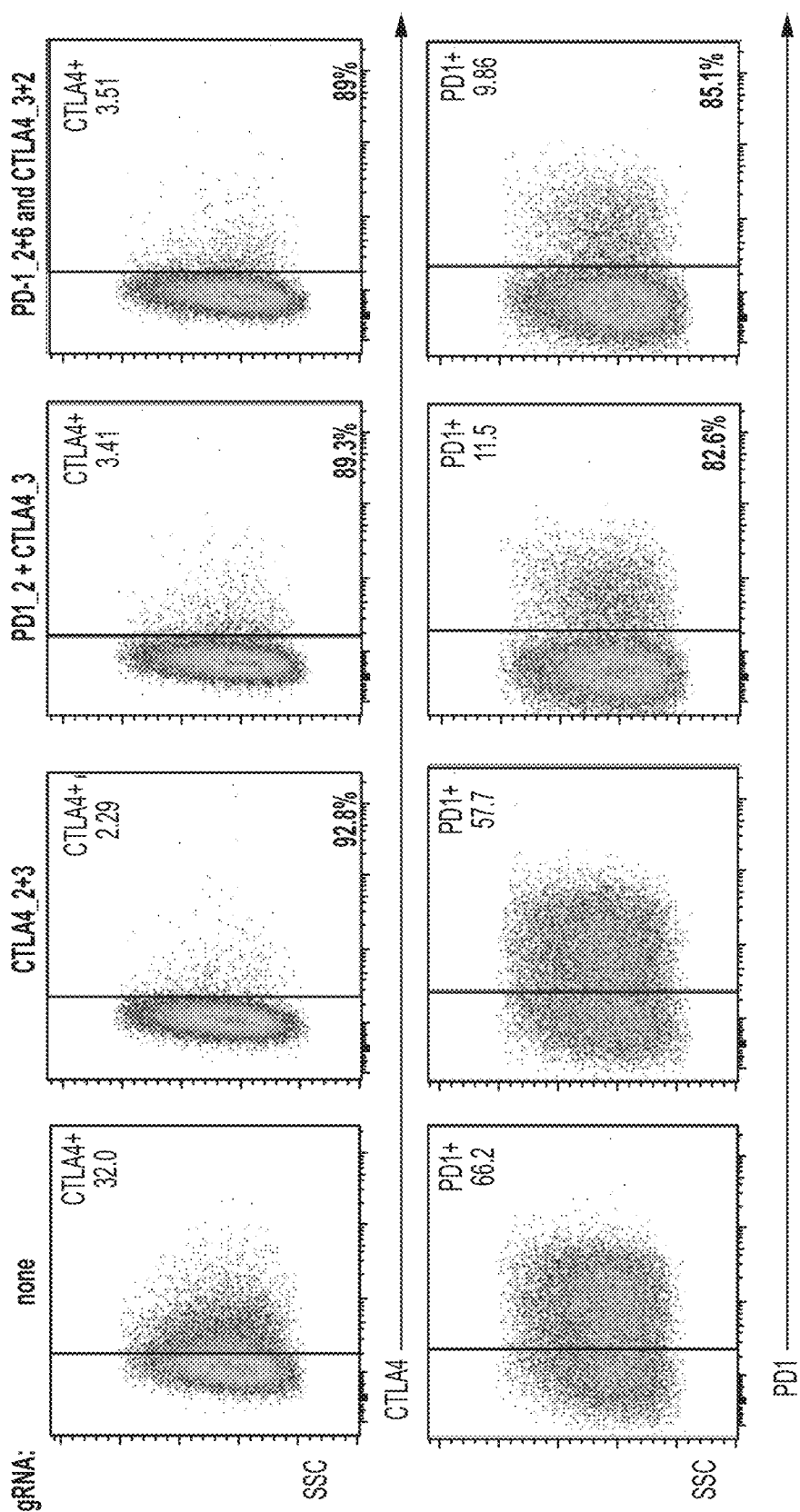

FIG. 29 shows FACs data for human T cells on day 14 post electroporation with CRISPR, and anti-CTLA-4 guide #2 and #3, anti-PD-1 guide #2 and anti-CTLA-4 guide #3, or anti-PD-1 guide #2 and #6, anti-CTLA-4 guide #3 and #2. The engineered T cells were re-stimulated for 48 hours to assess expression of CTLA-4 and PD-1 and compared to control cells electroporated with no guide RNA.

Figure 30:
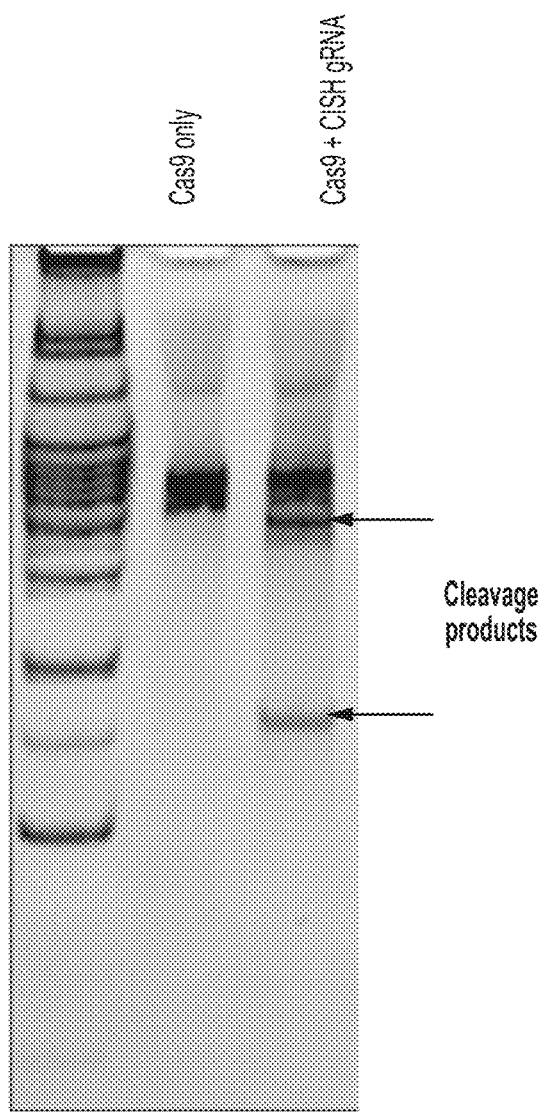

FIG. 30 depicts results of a surveyor assay for CRISPR mediated gene-modification of the CISH locus in primary human T cells.

Figure 31:
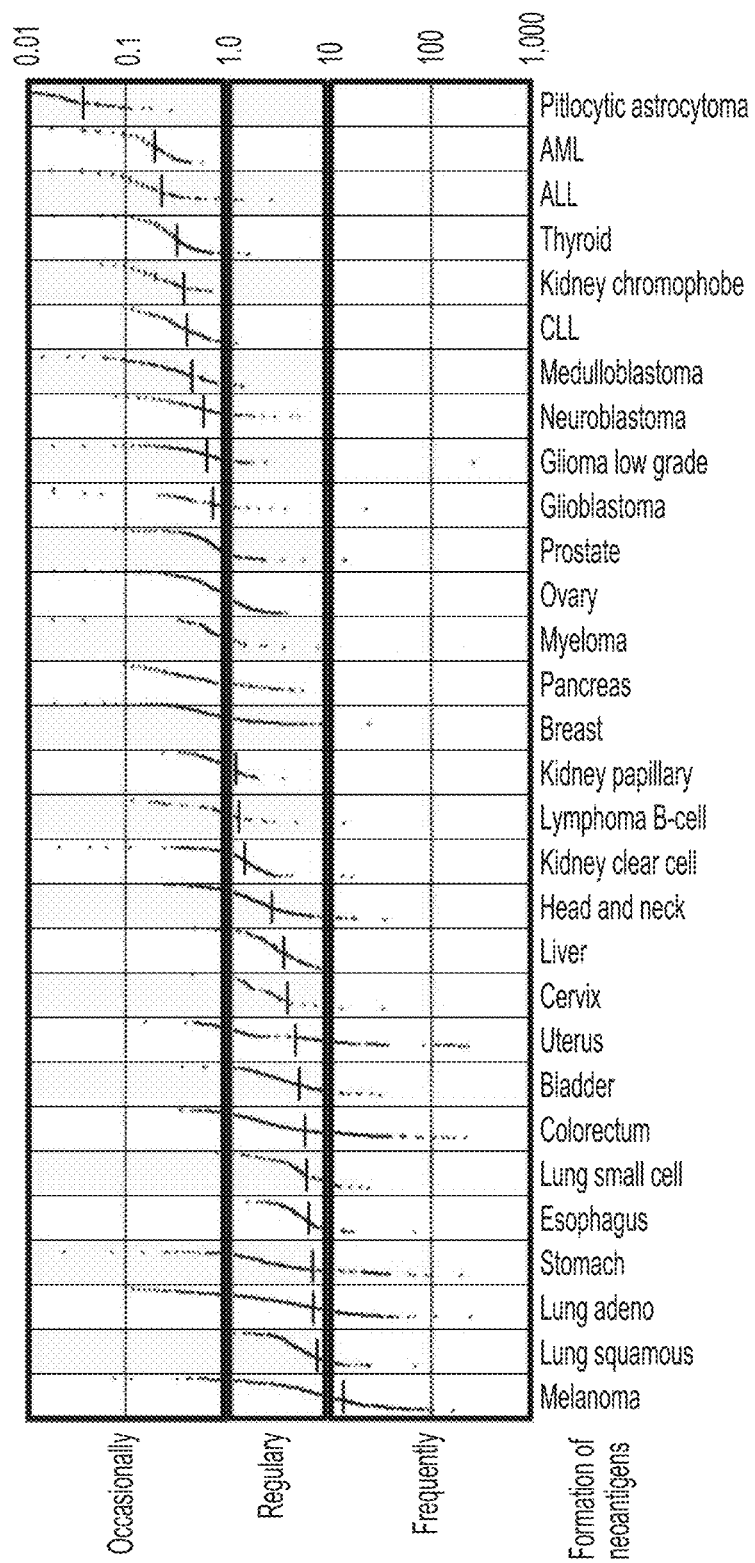

FIG. 31 shows that somatic mutational burden varies among tumor type. Tumor-specific neo-antigen generation and presentation is theoretically directly proportional to mutational burden.

FIG. 32 shows pseudouridine-5'-Triphosphate and 5-Methylcytidine-5-Triphosphate modifications that can be made to nucleic acid.

Figure 33:
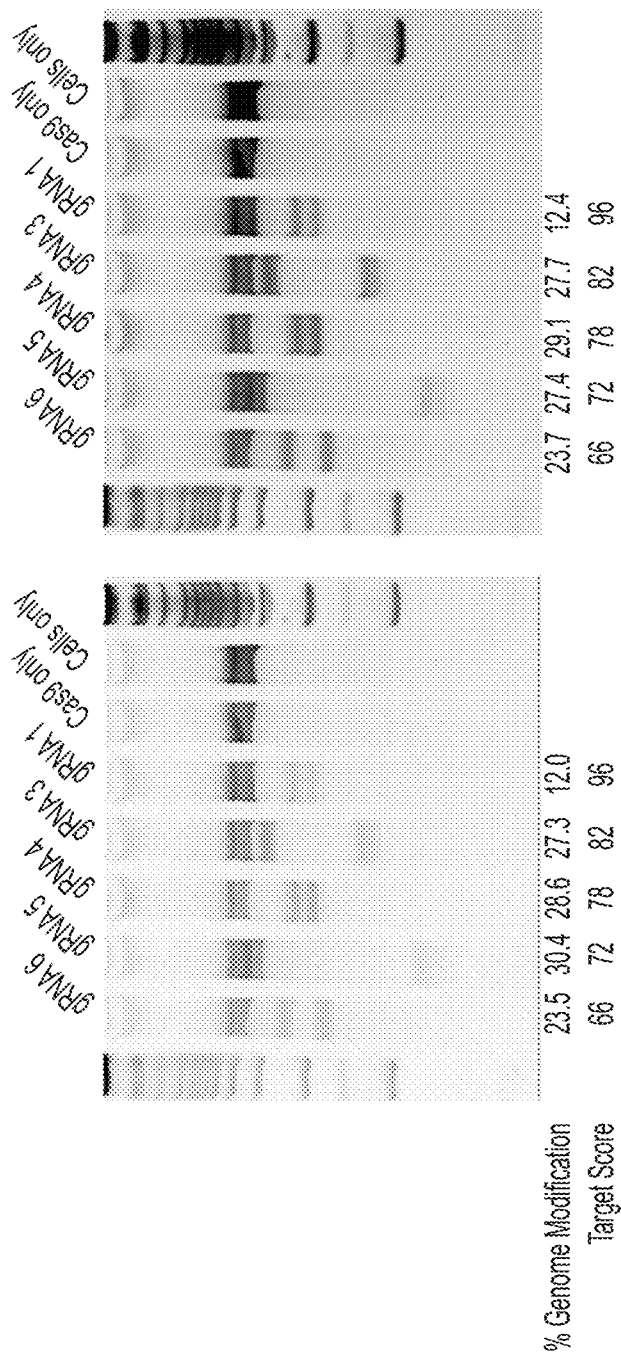

FIG. 33 depicts duplicate experiments of densitometry analysis for 293T cells transfected with CRISPR and CISH gRNAs 1,3,4,5 or 6.

Figure 34:
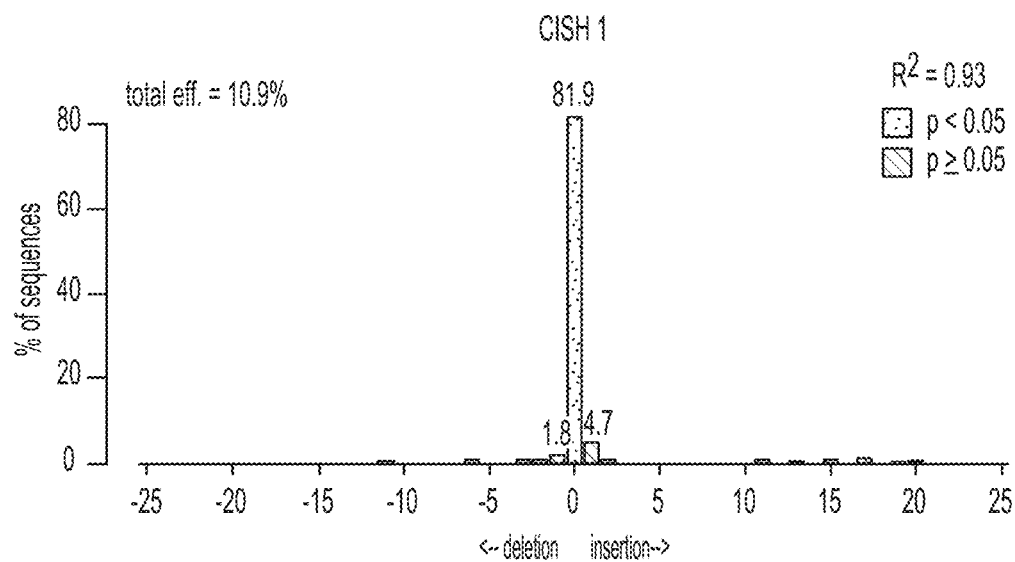
Figure 34B:
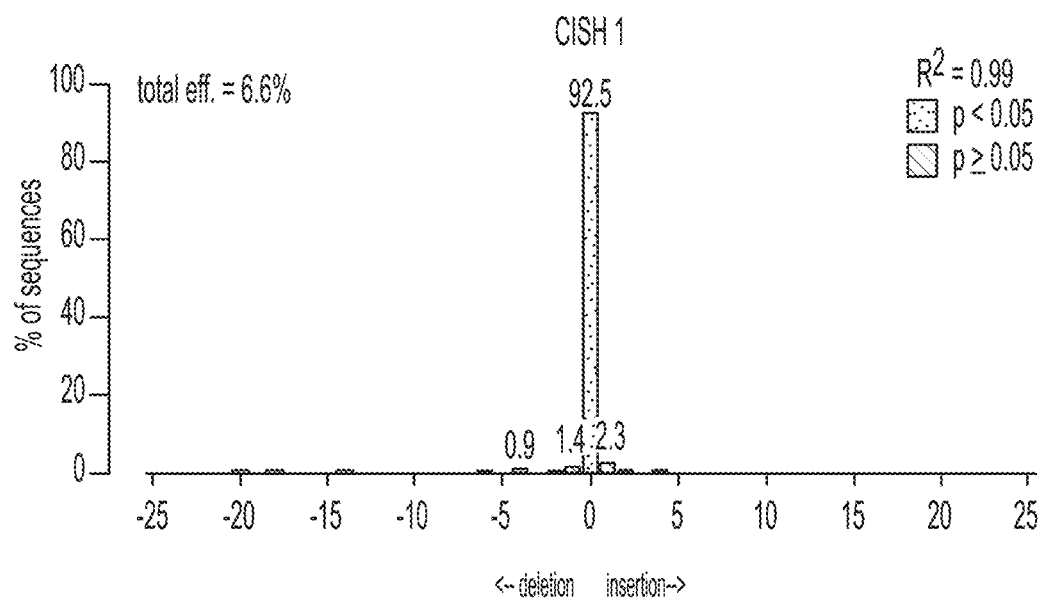

FIG. 34A and FIG. 34B show duplicate TIDE analysis of CISH gRNA 1.

Figure 35:
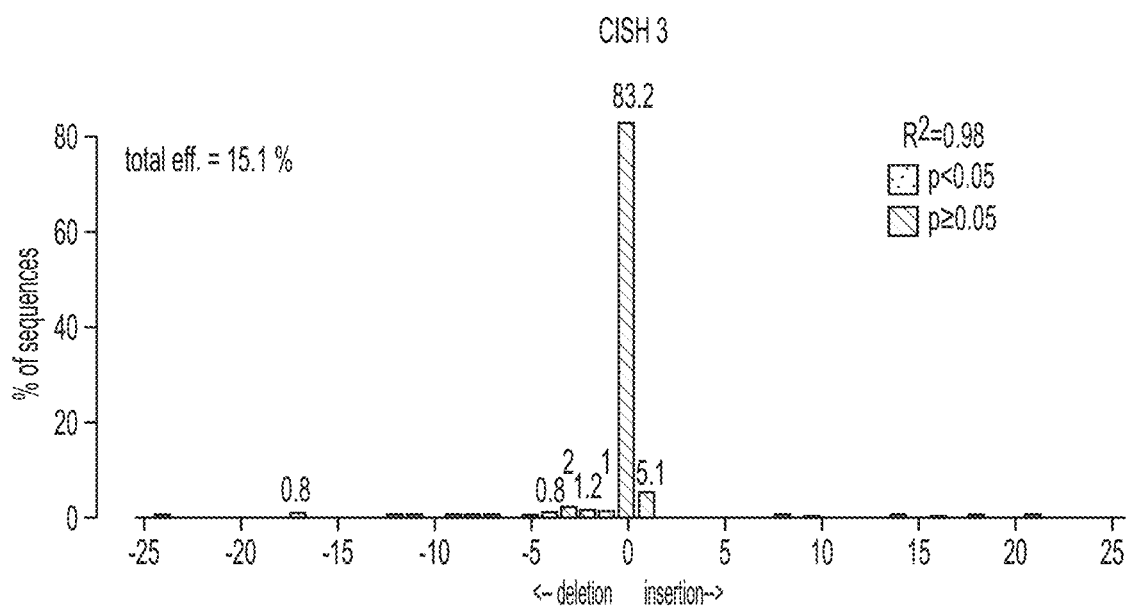
Figure 35:
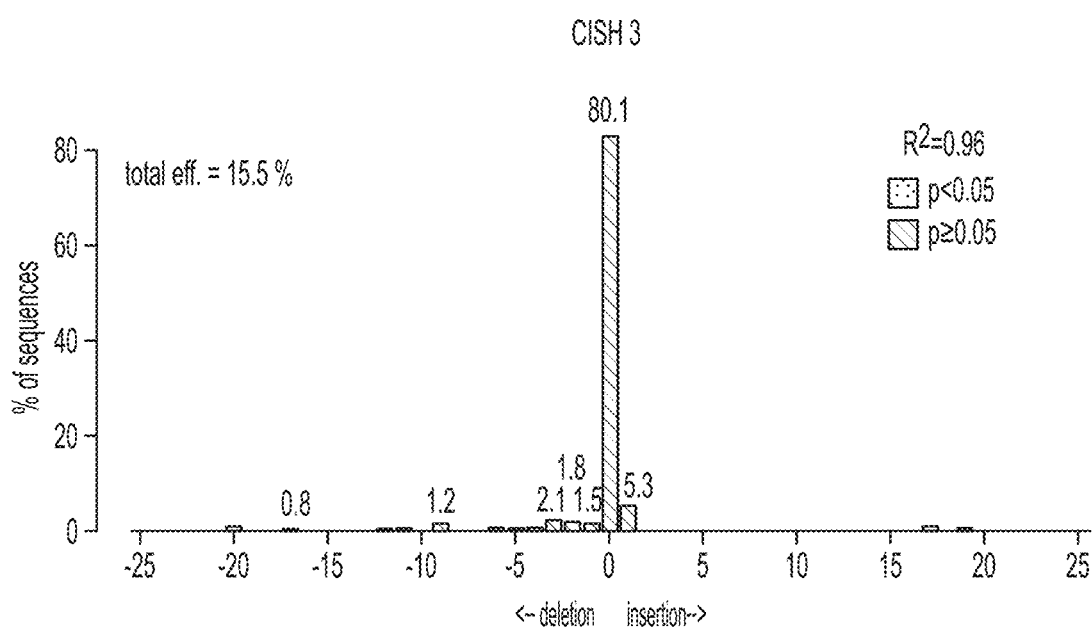

FIG. 35A and FIG. 35B show duplicate TIDE analysis of CISH gRNA 3.

Figure 36A:
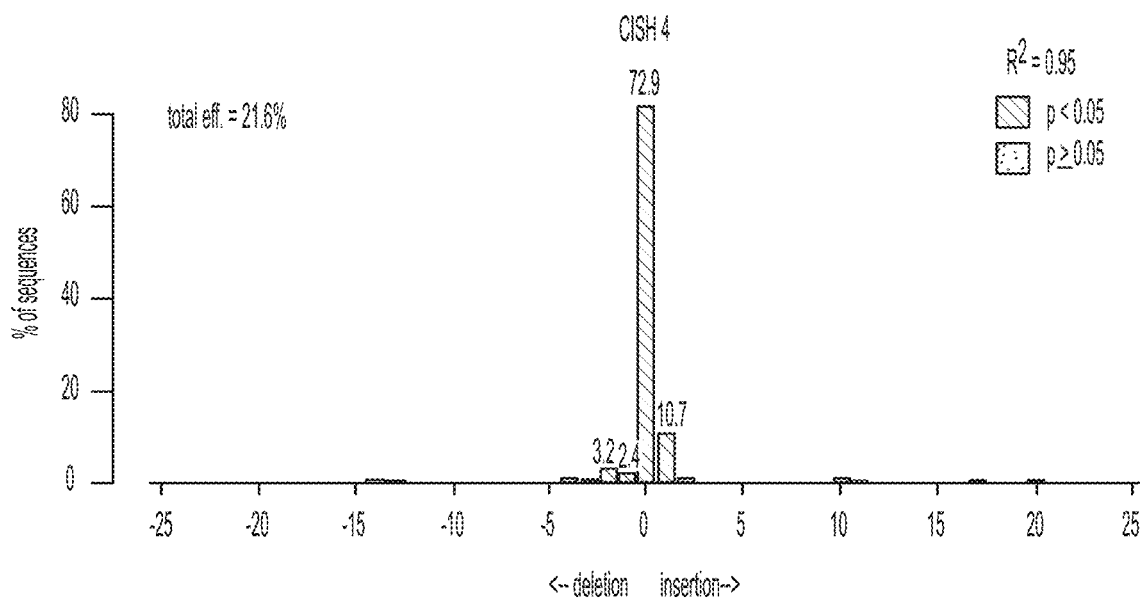
Figure 36:
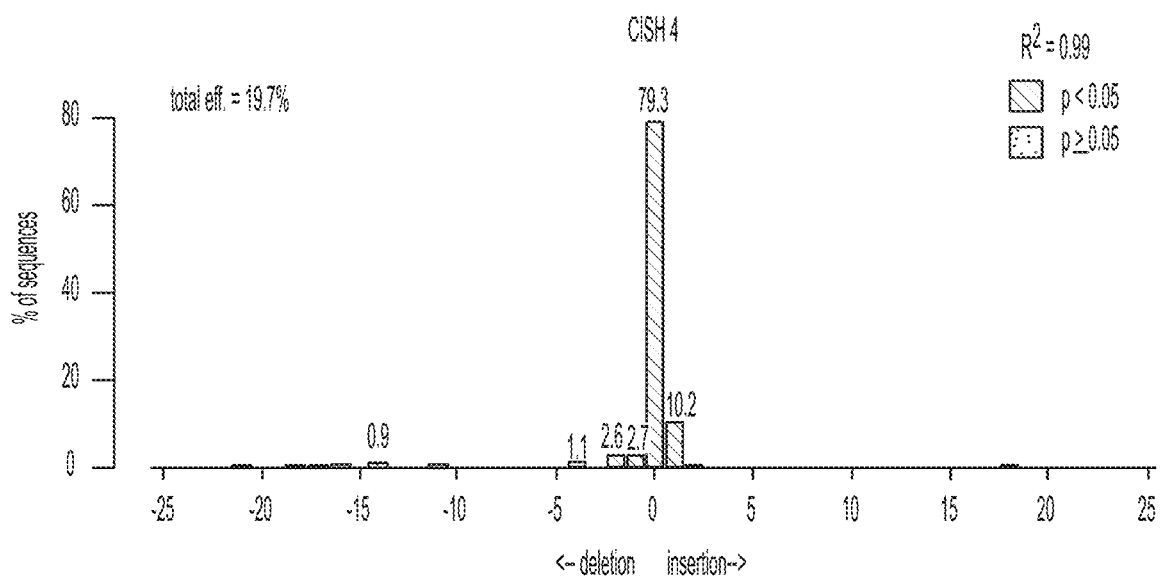

FIG. 36A and FIG. 36B show duplicate TIDE analysis of CISH gRNA 4.

Figure 37:
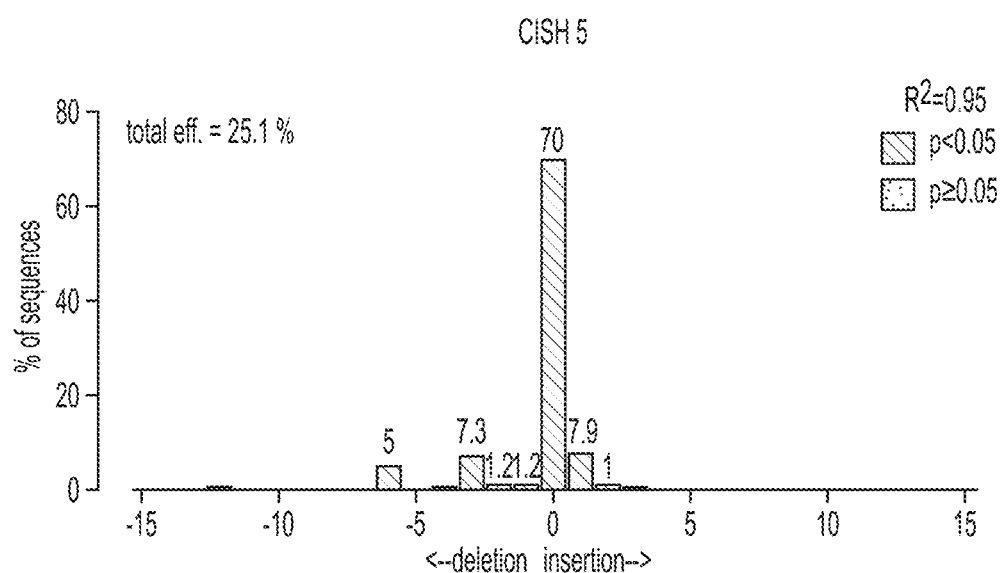
Figure 37:
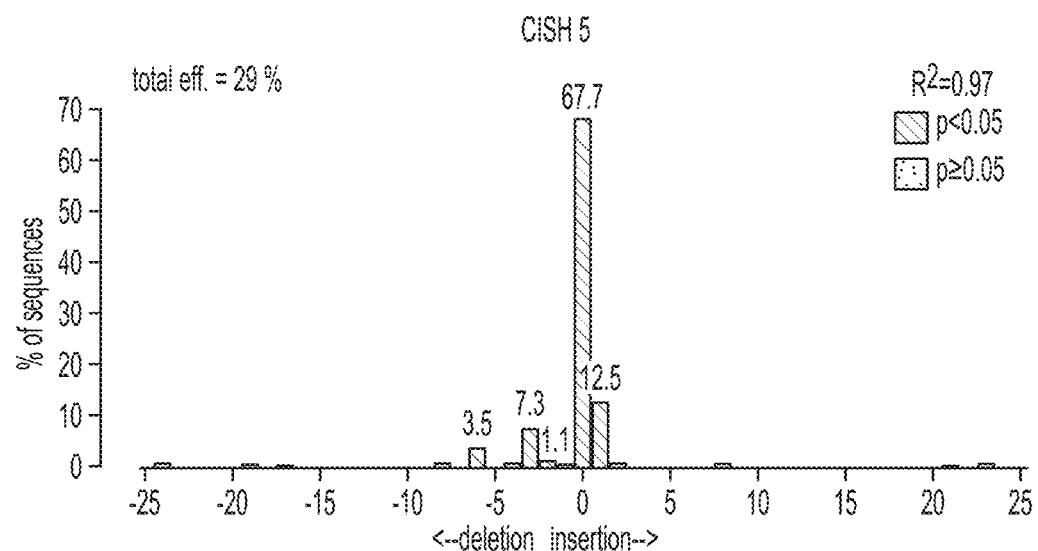

FIG. 37A and FIG. 37B show duplicate TIDE analysis of CISH gRNA 5.

Figure 38:
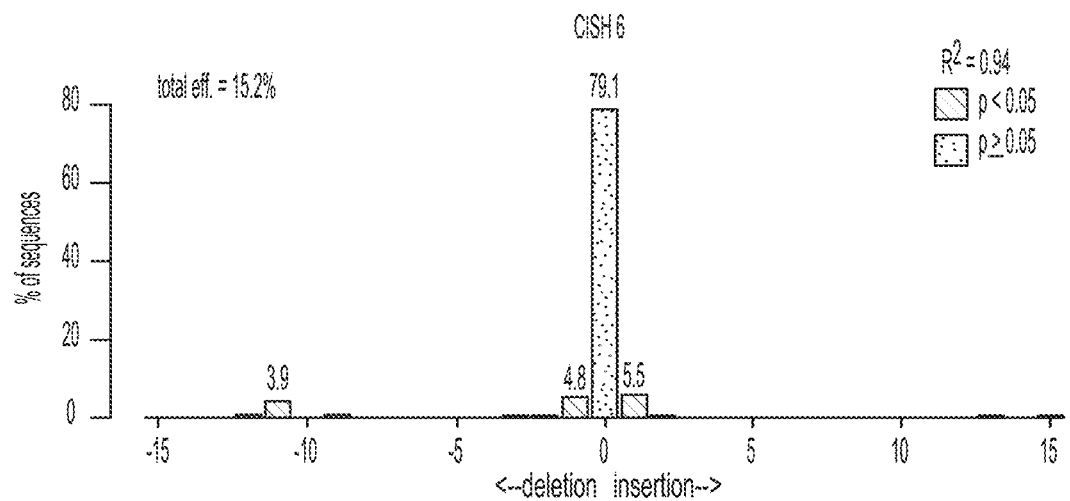
Figure 38:
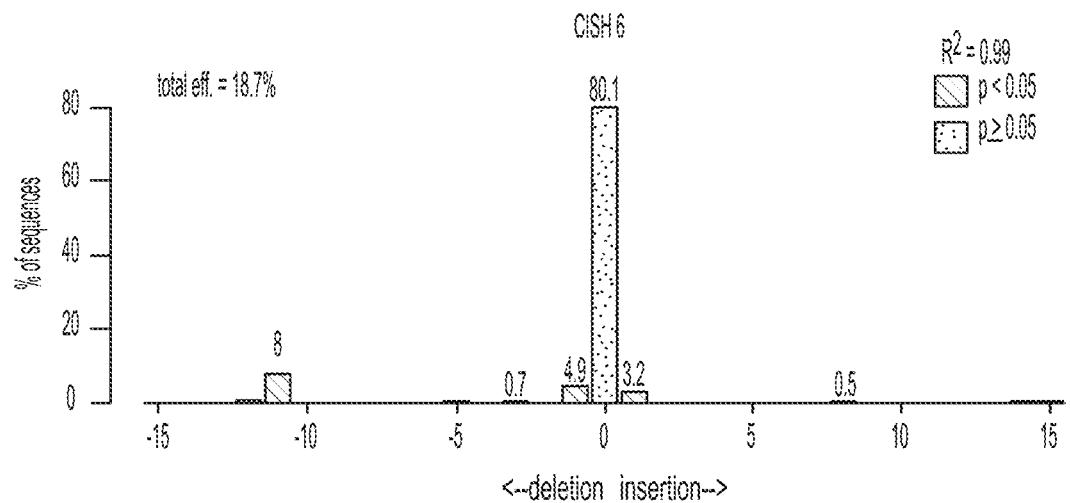

FIG. 38A and FIG. 38B show duplicate TIDE analysis of CISH gRNA 6.

Figure 39:
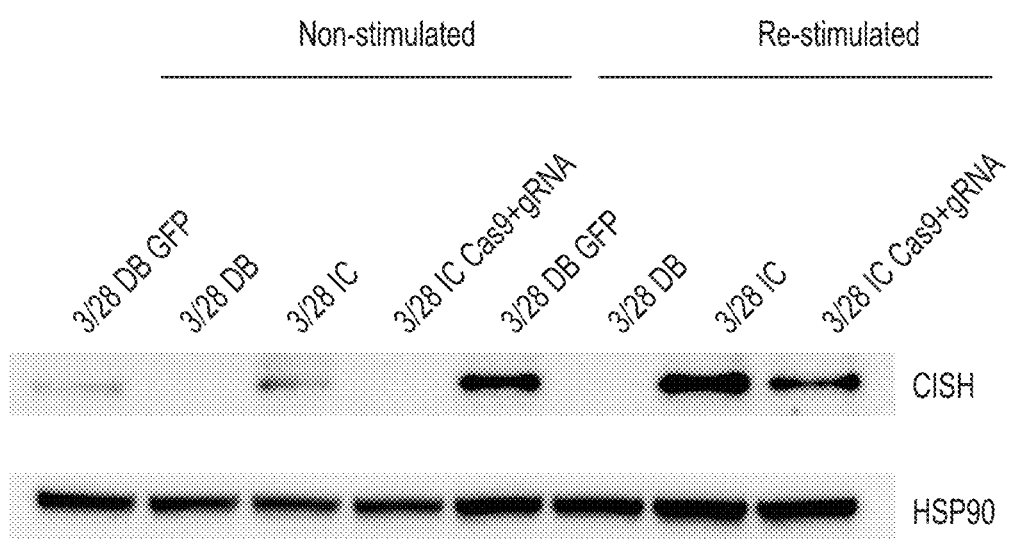

FIG. 39 shows a western blot showing loss of CISH protein after CRISPR knock out in primary T cells.

Figure 40:
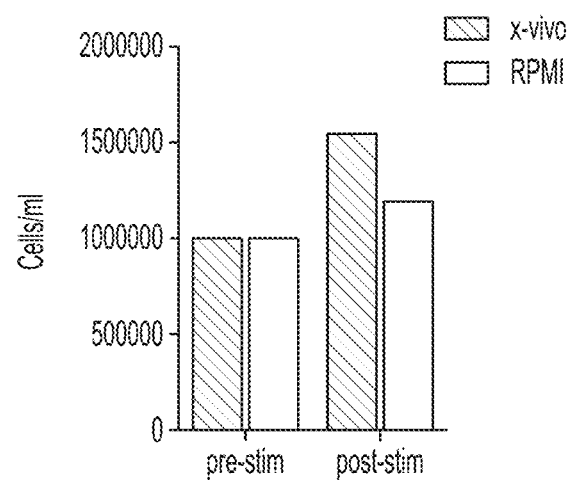
Figure 40:
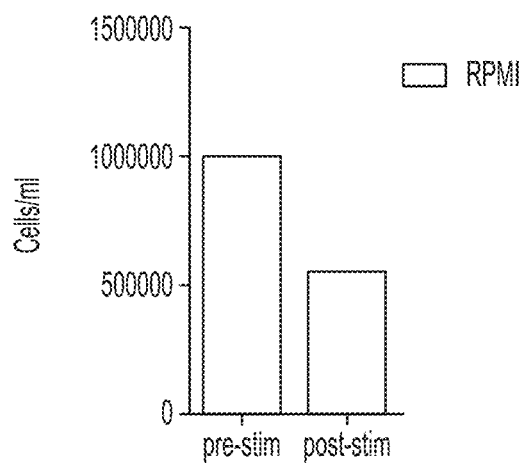

FIG. 40A and FIG. 40B show absolute cell count pre and post stimulation of human TILs. FIG. 40A. shows a first donor's cell count pre- and post-stimulation cultured in either RPMI media or ex vivo media. FIG. 40B. shows a second donor's cell count pre- and post-stimulation cultured in RPMI media.

FIG. 41A and FIG. 41B show cellular expansion of human tumor infiltrating lymphocytes (TILs) electroporated with a CRISPR system targeting PD-1 locus or controls cells FIG. 41A shows expansion with the addition of autologous feeders or FIG. 41B shows expansion without the addition of autologous feeders.

Figure 42:
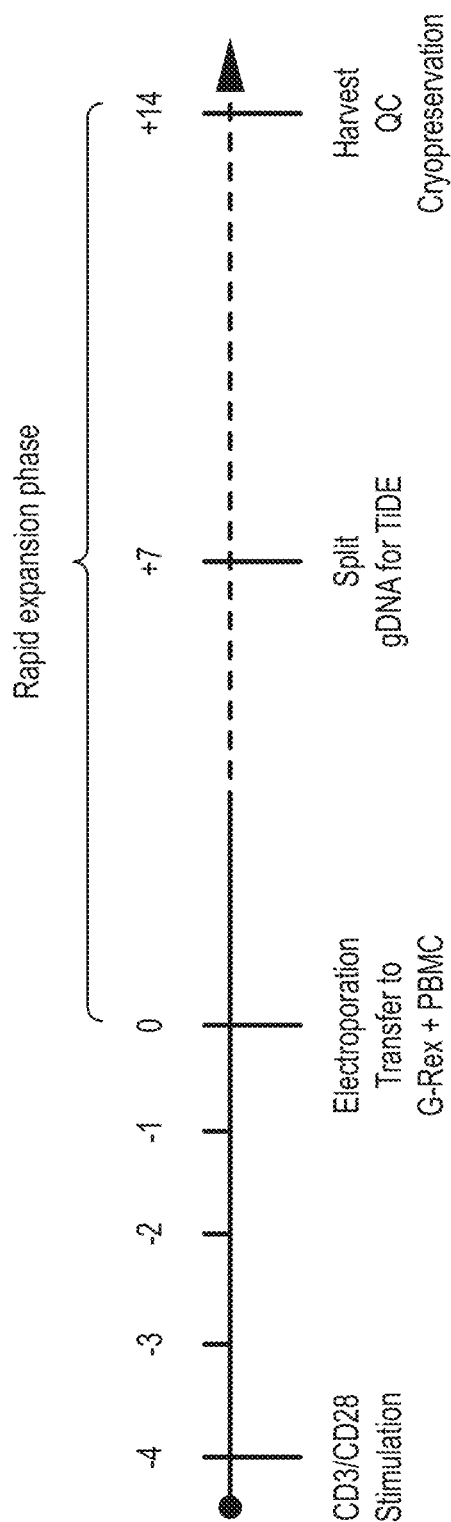

FIG. 42 depicts production of CISH KO TIL Interleukin-2 expanded TILs are stimulated by incubation with immobilized anti-CD3 and soluble anti-CD28 for four days. On day 0, TILs are collected and CRISPR/Cas9 reagents targeting CISH are delivered by electroporation. Following electroporation, the modified TILs are transferred to G-Rex flasks in the presence of irradiated peripheral blood mononuclear cell feeders and IL-2 for subsequent rapid expansion. During the first cell count and upon subculture at day (+)7, a small aliquot of cells is collected to determine insertion/deletion (indel) frequency by sequencing. TILs are subsequently harvested at day (+) 14 at which point samples are taken for quality control assessment and are subsequently cryopreserved within infusion-ready bags.

Figure 43:
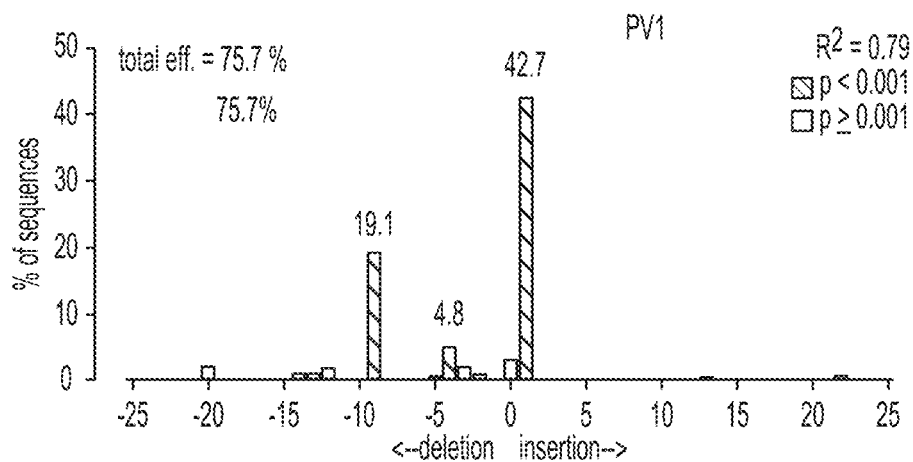
Figure 43:
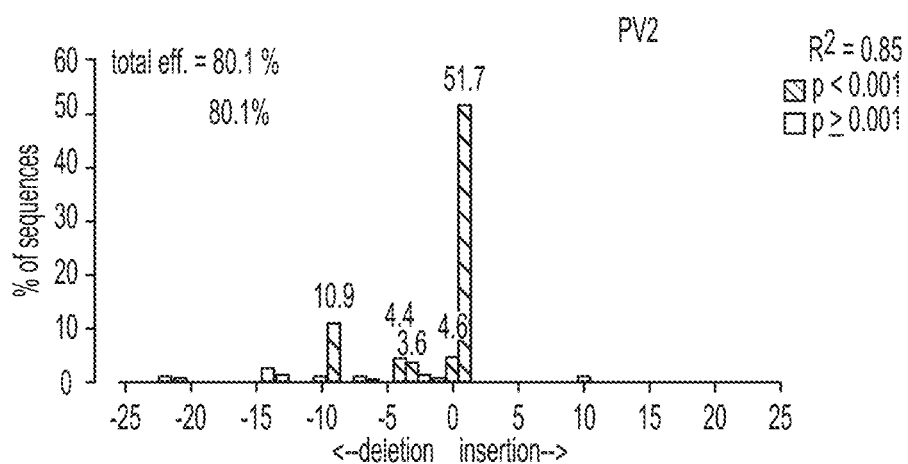
Figure 43:
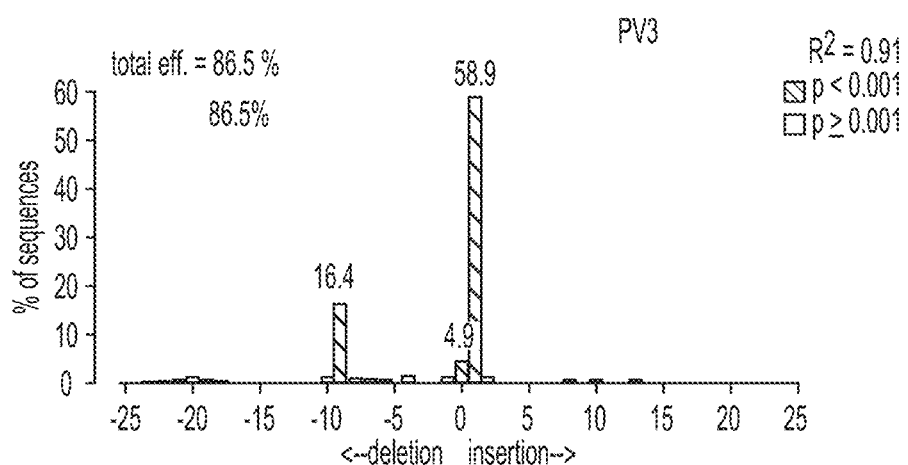

FIG. 43A, FIG. 43B, and FIG. 43C depict TiDE analysis of CISH loci after CRISPR/Cas9 editing. After 14 days of rapid expansion, genomic DNA was isolated and PCR was run across the CRISPR target region within PDCD1 and CISH. PCR amplicons were subjected to TiDE analysis. Plots indicate the total frequency of indels, and the distribution of insertions and deletions based on their size in base pairs lost or gained for subjects PV1, PV2, and PV3.

Figure 44:
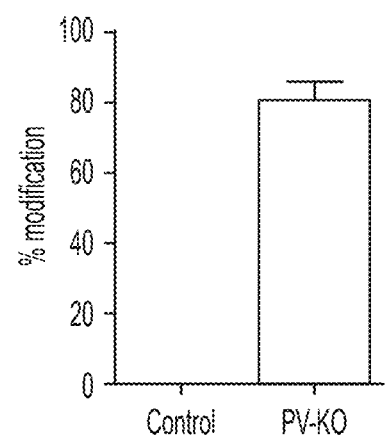

FIG. 44 depicts a summary of TiDE analysis of CISH loci after CRISPR/Cas9 editing for subjects PV1, PV2, and PV3.

FIG. 45A and FIG. 45B show loss of CISH protein expression after CRISPR/Cas9 editing. Fourteen days after electroporation, PB T-cells and TILs were re-stimulated or not re-stimulated for 48 hours to induce CISH expression. Control indicates that cells received no CRISPR/Cas9 components. Cas9+gRNA indicates cells that received Cas9 mRNA and a gRNA designed to target exon 3 of the CISH locus.

Figure 46A:
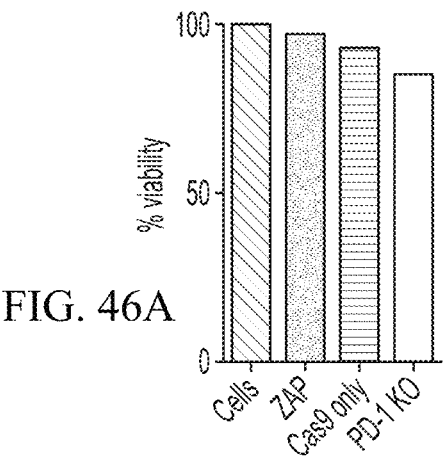
Figure 46B:
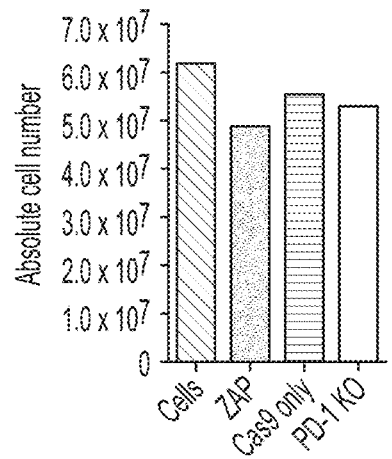
Figure 46C:
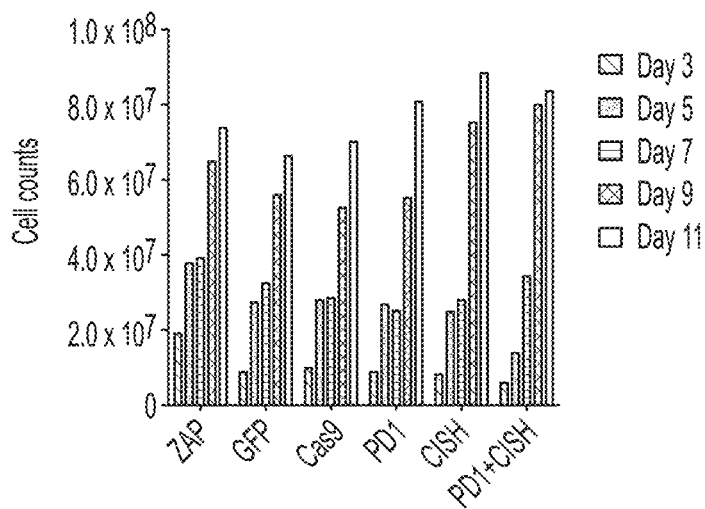

FIG. 46A, FIG. 46B, and FIG. 46C show growth and viability of T-cells after CRISPR editing. FIG. 46A shows viability at day 6 post-electroporation. FIG. 46B shows total cell numbers at day 12 post electroporation beginning with $3 \times 10^6$ cells. Cells=no manipulation; ZAP=electroporation only. FIG. 46C shows total cell numbers of TIL over 11 days in standard tissue culture flasks beginning with $3 \times 10^6$ cells for each condition.

FIG. 47A and FIG. 47B show SPICE plot of cytokine production in CRISPR/Cas9 edited T-cells and TILs. Fourteen days after electroporation, T-cells and TILs were re-stimulated using plate-bound anti-CD3 and soluble anti-CD28 antibody and assayed for cytokine production by intracellular staining and flow cytometry.

FIG. 48A depicts loss of PD-1 protein expression after CRISPR/Cas9 editing. Fourteen days after electroporation, peripheral blood T-cells or TILs were re-stimulated for 72 hours to induce PD-1 expression. PD-1 expression in re-stimulated T-cells. FIG. 48B shows PD-1 expression in re-stimulated TILs. Percent loss is indicated in red.

Figure 49:
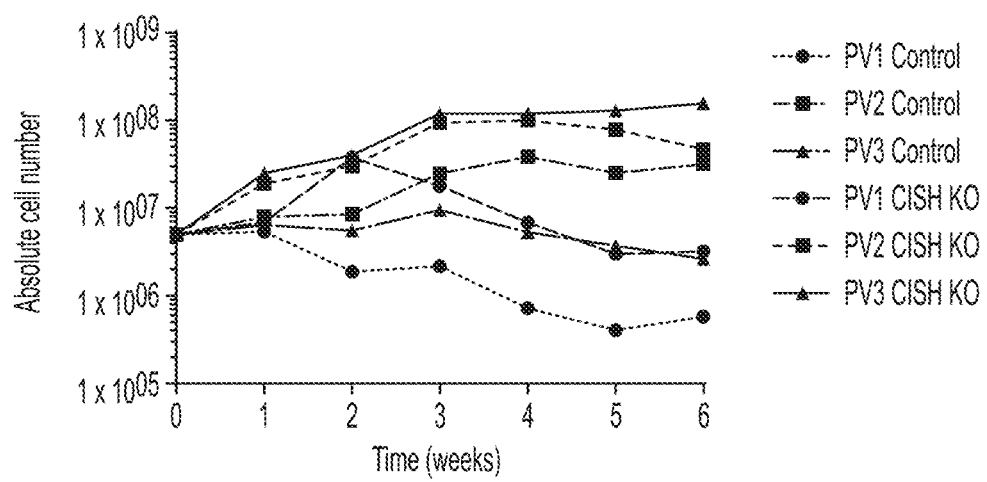

FIG. 49 shows absolute cell number of control and CISH-modified tumor infiltrating lymphocytes.

Figure 50:
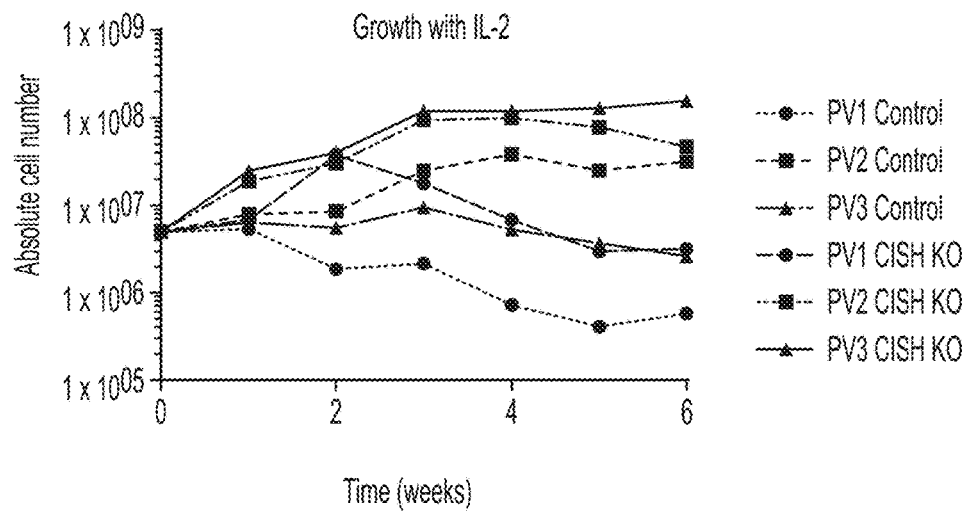
Figure 50:
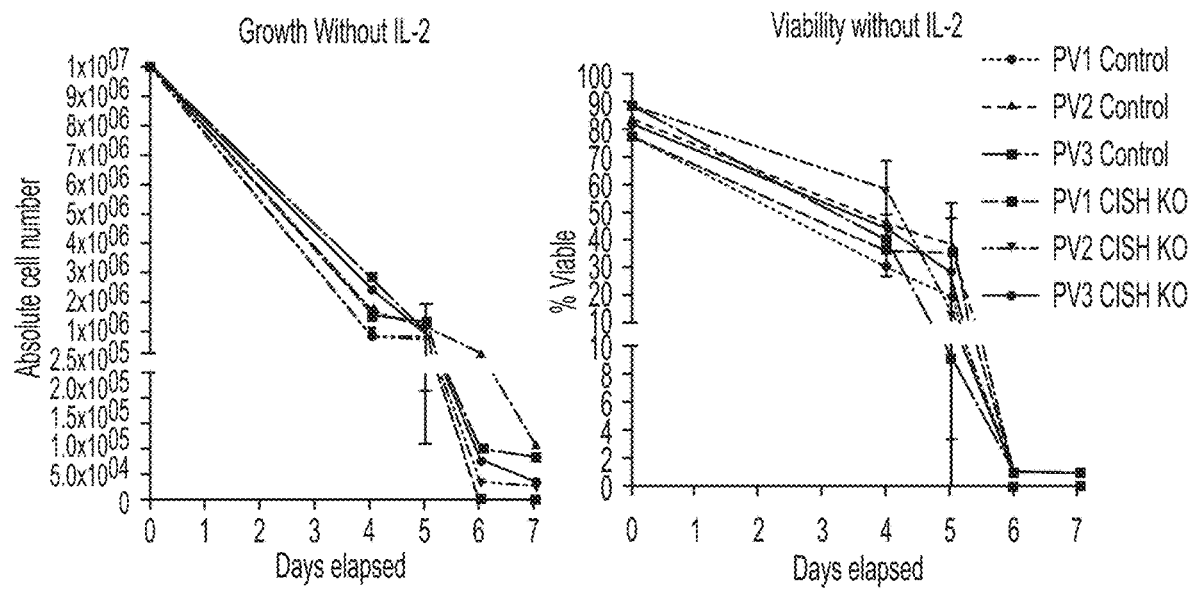

FIG. 50A shows control and CISH knockout TIL cultured in the presence of IL-2 at day 7. FIG. 50B shows control and CISH knockout TIL cultured in the absence of IL-2 at day 7.

FIG. 51A shows off-target sites for PDCD1. FIG. 51B shows CISH gRNA identified by GUIDE-Seq.

Figure 52:
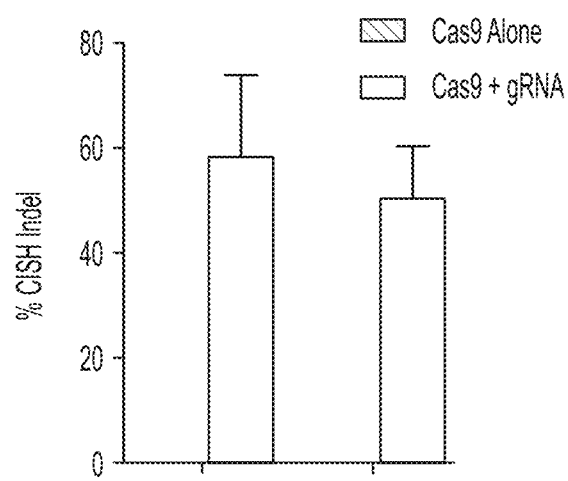

FIG. 52 shows frequency of targeted indels at the CISH locus across the GUIDE-Seq and GMP PQ manufacturing runs (ns, P=0.93).

DETAILED DESCRIPTION OF THE DISCLOSURE

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

Definitions

The term "about" and its grammatical equivalents in relation to a reference numerical value and its grammatical equivalents as used herein can include a range of values plus or minus 10% from that value. For example, the amount "about 10" includes amounts from 9 to 11. The term "about" in relation to a reference numerical value can also include a range of values plus or minus 10%, 9%, 8%, 7%, 6%, 5%, 4%, 3%, 2%, or 1% from that value.

The term "activation" and its grammatical equivalents as used herein can refer to a process whereby a cell transitions from a resting state to an active state. This process can comprise a response to an antigen, migration, and/or a phenotypic or genetic change to a functionally active state. For example, the term "activation" can refer to the stepwise process of T cell activation. For example, a T cell can require at least two signals to become fully activated. The first signal can occur after engagement of a TCR by the antigen-MHC complex, and the second signal can occur by engagement of co-stimulatory molecules. Anti-CD3 can mimic the first signal and anti-CD28 can mimic the second signal in vitro.

The term "adjacent" and its grammatical equivalents as used herein can refer to right next to the object of reference. For example, the term adjacent in the context of a nucleotide sequence can mean without any nucleotides in between. For instance, polynucleotide A adjacent to polynucleotide B can mean AB without any nucleotides in between A and B.

The term "antigen" and its grammatical equivalents as used herein can refer to a molecule that contains one or more epitopes capable of being bound by one or more receptors. For example, an antigen can stimulate a host's immune system to make a cellular antigen-specific immune response when the antigen is presented, or a humoral antibody response. An antigen can also have the ability to elicit a cellular and/or humoral response by itself or when present in combination with another molecule. For example, a tumor cell antigen can be recognized by a TCR. An antigen, such as a Neoantigen, can be associated with tumors of high mutational burden, FIG. 31.

The term "epitope" and its grammatical equivalents as used herein can refer to a part of an antigen that can be recognized by antibodies, B cells, T cells or engineered cells. For example, an epitope can be a cancer epitope that is recognized by a TCR. Multiple epitopes within an antigen can also be recognized. The epitope can also be mutated.

The term "autologous" and its grammatical equivalents as used herein can refer to as originating from the same being. For example, a sample (e.g., cells) can be removed, processed, and given back to the same subject (e.g., patient) at a later time. An autologous process is distinguished from an allogenic process where the donor and the recipient are different subjects.

The term "cancer" and its grammatical equivalents as used herein can refer to a hyperproliferation of cells whose unique trait—loss of normal controls—results in unregulated growth, lack of differentiation, local tissue invasion, and metastasis. With respect to the inventive methods, the cancer can be any cancer, including any of acute lymphocytic cancer, acute myeloid leukemia, alveolar rhabdomyosarcoma, bladder cancer, bone cancer, brain cancer, breast cancer, cancer of the anus, anal canal, rectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal cancer, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and/or urinary bladder cancer. As used herein, the term "tumor" refers to an abnormal growth of cells or tissues, e.g., of malignant type or benign type.

The term "cancer neo-antigen" or "neo-antigen" or "neo-epitope" and its grammatical equivalents as used herein can refer to antigens that are not encoded in a normal, non-mutated host genome. A "neo-antigen" can in some instances represent either oncogenic viral proteins or abnormal proteins that arise as a consequence of somatic mutations. For example, a neo-antigen can arise by the disruption of cellular mechanisms through the activity of viral proteins. Another example can be an exposure of a carcinogenic compound, which in some cases can lead to a somatic mutation. This somatic mutation can ultimately lead to the formation of a tumor/cancer.

The term "cytotoxicity" as used in this specification, refers to an unintended or undesirable alteration in the normal state of a cell. The normal state of a cell may refer to a state that is manifested or exists prior to the cell's exposure to a cytotoxic composition, agent and/or condition. Generally, a cell that is in a normal state is one that is in homeostasis. An unintended or undesirable alteration in the normal state of a cell can be manifested in the form of, for example, cell death (e.g., programmed cell death), a decrease in replicative potential, a decrease in cellular integrity such as membrane integrity, a decrease in metabolic activity, a decrease in developmental capability, or any of the cytotoxic effects disclosed in the present application.

The phrase "reducing cytotoxicity" or "reduce cytotoxicity" refers to a reduction in degree or frequency of unintended or undesirable alterations in the normal state of a cell upon exposure to a cytotoxic composition, agent and/or condition. The phrase can refer to reducing the degree of cytotoxicity in an individual cell that is exposed to a cytotoxic composition, agent and/or condition, or to reducing the number of cells of a population that exhibit cytotoxicity when the population of cells is exposed to a cytotoxic composition, agent and/or condition.

The term "engineered" and its grammatical equivalents as used herein can refer to one or more alterations of a nucleic acid, e.g., the nucleic acid within an organism's genome. The term "engineered" can refer to alterations, additions, and/or deletion of genes. An engineered cell can also refer to a cell with an added, deleted and/or altered gene.

The term "cell" or "engineered cell" and their grammatical equivalents as used herein can refer to a cell of human or non-human animal origin.

The term "checkpoint gene" and its grammatical equivalents as used herein can refer to any gene that is involved in an inhibitory process (e.g., feedback loop) that acts to regulate the amplitude of an immune response, for example, an immune inhibitory feedback loop that mitigates uncontrolled propagation of harmful responses. These responses can include contributing to a molecular shield that protects against collateral tissue damage that might occur during immune responses to infections and/or maintenance of peripheral self-tolerance. Non-limiting examples of checkpoint genes can include members of the extended CD28 family of receptors and their ligands as well as genes involved in co-inhibitory pathways (e.g., CTLA-4 and PD-1). The term "checkpoint gene" can also refer to an immune checkpoint gene.

A "CRISPR," "CRISPR system," or "CRISPR nuclease system" and their grammatical equivalents can include a non-coding RNA molecule (e.g., guide RNA) that binds to DNA and Cas proteins (e.g., Cas9) with nuclease functionality (e.g., two nuclease domains). See, e.g., Sander, J. D., et al., "CRISPR-Cas systems for editing, regulating and targeting genomes," Nature Biotechnology, 32:347-355 (2014); see also e.g., Hsu, P. D., et al., "Development and applications of CRISPR-Cas9 for genome engineering," Cell 157(6):1262-1278 (2014).

The term "disrupting" and its grammatical equivalents as used herein can refer to a process of modifying or altering a gene, e.g., by cleavage, deletion, insertion, mutation, rearrangement, or any combination thereof. A disruption can result in the knockout or knockdown of protein expression. A knockout can be a complete or partial knockout. For example, a gene can be disrupted by knockout or knockdown. Disrupting a gene can partially reduce or completely suppress expression of a protein encoded by the gene. Disrupting a gene can also cause activation of a different gene, for example, a downstream gene. In some embodiments, the term "disrupting" can be used interchangeably with terms such as suppressing, interrupting, or engineering.

The term "function" and its grammatical equivalents as used herein can refer to the capability of operating, having, or serving an intended purpose. Functional can comprise any percent from baseline to 100% of normal function. For example, functional can comprise or comprise about 5, 10, 15, 20, 25, 30, 35, 40, 45, 50, 55, 60, 65, 70, 75, 80, 85, 90, 95, and/or 100% of normal function. In some cases, the term functional can mean over or over about 100% of normal function, for example, 125, 150, 175, 200, 250, 300% and/or above normal function.

The term "gene editing" and its grammatical equivalents as used herein can refer to genetic engineering in which one or more nucleotides are inserted, replaced, or removed from a genome. Gene editing can be performed using a nuclease (e.g., a natural-existing nuclease or an artificially engineered nuclease).

The term "mutation" and its grammatical equivalents as used herein can include the substitution, deletion, and insertion of one or more nucleotides in a polynucleotide. For example, up to 1, 2, 3, 4, 5, 6, 7, 8, 9, 10, 11, 12, 13, 14, 15, 20, 25, 30, 40, 50, or more nucleotides/amino acids in a polynucleotide (cDNA, gene) or a polypeptide sequence can be substituted, deleted, and/or inserted. A mutation can affect the coding sequence of a gene or its regulatory sequence. A mutation can also affect the structure of the genomic sequence or the structure/stability of the encoded mRNA.

The term "non-human animal" and its grammatical equivalents as used herein can include all animal species other than humans, including non-human mammals, which can be a native animal or a genetically modified non-human animal. The terms "nucleic acid," "polynucleotide," "polynucleic acid," and "oligonucleotide" and their grammatical equivalents can be used interchangeably and can refer to a deoxyribonucleotide or ribonucleotide polymer, in linear or circular conformation, and in either single- or double-stranded form. For the purposes of the present disclosure, these terms should not to be construed as limiting with respect to length. The terms can also encompass analogues of natural nucleotides, as well as nucleotides that are modified in the base, sugar and/or phosphate moieties (e.g., phosphorothioate backbones). Modifications of the terms can also encompass demethylation, addition of CpG methylation, removal of bacterial methylation, and/or addition of mammalian methylation. In general, an analogue of a particular nucleotide can have the same base-pairing specificity, i.e., an analogue of A can base-pair with T.

The term "peripheral blood lymphocytes" (PBL) and its grammatical equivalents as used herein can refer to lymphocytes that circulate in the blood (e.g., peripheral blood). Peripheral blood lymphocytes can refer to lymphocytes that are not localized to organs. Peripheral blood lymphocytes can comprise T cells, NK cells, B cell, or any combinations thereof.

The term "phenotype" and its grammatical equivalents as used herein can refer to a composite of an organism's observable characteristics or traits, such as its morphology, development, biochemical or physiological properties, phenology, behavior, and products of behavior. Depending on the context, the term "phenotype" can sometimes refer to a composite of a population's observable characteristics or traits.

The term "protospacer" and its grammatical equivalents as used herein can refer to a PAM-adjacent nucleic acid sequence capable to hybridizing to a portion of a guide RNA, such as the spacer sequence or engineered targeting portion of the guide RNA. A protospacer can be a nucleotide sequence within gene, genome, or chromosome that is targeted by a guide RNA. In the native state, a protospacer is adjacent to a PAM (protospacer adjacent motif). The site of cleavage by an RNA-guided nuclease is within a protospacer sequence. For example, when a guide RNA targets a specific protospacer, the Cas protein will generate a double strand break within the protospacer sequence, thereby cleaving the protospacer. Following cleavage, disruption of the protospacer can result though non-homologous end joining (NHEJ) or homology-directed repair (HDR). Disruption of the protospacer can result in the deletion of the protospacer. Additionally or alternatively, disruption of the protospacer can result in an exogenous nucleic acid sequence being inserted into or replacing the protospacer.

The term "recipient" and their grammatical equivalents as used herein can refer to a human or non-human animal. The recipient can also be in need thereof.

The term "recombination" and its grammatical equivalents as used herein can refer to a process of exchange of genetic information between two polynucleic acids. For the purposes of this disclosure, "homologous recombination" or "HR" can refer to a specialized form of such genetic exchange that can take place, for example, during repair of double-strand breaks. This process can require nucleotide sequence homology, for example, using a donor molecule to template repair of a target molecule (e.g., a molecule that experienced the double-strand break), and is sometimes known as non-crossover gene conversion or short tract gene conversion. Such transfer can also involve mismatch correction of heteroduplex DNA that forms between the broken target and the donor, and/or synthesis-dependent strand annealing, in which the donor can be used to resynthesize genetic information that can become part of the target, and/or related processes. Such specialized HR can often result in an alteration of the sequence of the target molecule such that part or all of the sequence of the donor polynucleotide can be incorporated into the target polynucleotide. In some cases, the terms "recombination arms" and "homology arms" can be used interchangeably.

The terms "target vector" and "targeting vector" are used interchangeably herein.

The term "T cell" and its grammatical equivalents as used herein can refer to a T cell from any origin. For example, a T cell can be a primary T cell, e.g., an autologous T cell, a cell line, etc. The T cell can also be human or non-human.

The term "TIL" or tumor infiltrating lymphocyte and its grammatical equivalents as used herein can refer to a cell isolated from a tumor. For example, a TIL can be a cell that has migrated to a tumor. A TIL can also be a cell that has infiltrated a tumor. A TIL can be any cell found within a tumor. For example, a TIL can be a T cell, B cell, monocyte, natural killer (NK) cell, or any combination thereof. A TIL can be a mixed population of cells. A population of TILs can comprise cells of different phenotypes, cells of different degrees of differentiation, cells of different lineages, or any combination thereof.

A "therapeutic effect" may occur if there is a change in the condition being treated. The change may be positive or negative. For example, a 'positive effect' may correspond to an increase in the number of activated T-cells in a subject. In another example, a 'negative effect' may correspond to a decrease in the amount or size of a tumor in a subject. There is a "change" in the condition being treated if there is at least 10% improvement, preferably at least 25%, more preferably at least 50%, even more preferably at least 75%, and most preferably 100%. The change can be based on improvements in the severity of the treated condition in an individual, or on a difference in the frequency of improved conditions in populations of individuals with and without treatment with the therapeutic compositions with which the compositions of the present invention are administered in combination. Similarly, a method of the present disclosure may comprise administering to a subject an amount of cells that is "therapeutically effective". The term "therapeutically effective" should be understood to have a definition corresponding to 'having a therapeutic effect'.

The term "safe harbor" and "immune safe harbor", and their grammatical equivalents as used herein can refer to a location within a genome that can be used for integrating exogenous nucleic acids wherein the integration does not cause any significant effect on the growth of the host cell by the addition of the nucleic acid alone. Non-limiting examples of safe harbors can include HPRT, AAVS SITE (E.G. AAVS1, AAVS2, ETC.), CCR5, or Rosa26.

The term "sequence" and its grammatical equivalents as used herein can refer to a nucleotide sequence, which can be DNA or RNA; can be linear, circular or branched; and can be either single-stranded or double stranded. A sequence can be mutated. A sequence can be of any length, for example, between 2 and 1,000,000 or more nucleotides in length (or any integer value there between or there above), e.g., between about 100 and about 10,000 nucleotides or between about 200 and about 500 nucleotides.

Overview

Disclosed herein are compositions and methods useful for treating a disease or condition such as cancer. Disclosed herein are also treatment regimes for the therapy of various diseases or conditions such as cancer. A treatment regime can comprise administering genetically modified cells, such as tumor infiltrating lymphocytes for therapeutic applications. Effective adoptive cell transfer-based immunotherapies (ACT) can be useful to treat cancer (e.g., metastatic cancer) patients. For example, tumor infiltrating lymphocytes can be modified to disrupt an immune checkpoint gene.

Cells

Compositions disclosed herein can utilize cells. Cells can be primary cells. Cells can be recombinant cells. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. For example, any T cell lines can be used. Alternatively, the cell can be derived from a healthy donor, from a patient diagnosed with cancer, or from a patient diagnosed with an infection. In another embodiment, the cell can be part of a mixed population of cells which present different phenotypic characteristics. A cell can also be obtained from a cell therapy bank. Disrupted cells resistant to an immunosuppressive treatment can be obtained. A desirable cell population can also be selected prior to modification. A selection can include at least one of: magnetic separation, flow cytometric selection, antibiotic selection. The one or more cells can be any blood cells, such as peripheral blood mononuclear cell (PBMC), lymphocytes, monocytes or macrophages. The one or more cells can be any immune cells such as lymphocytes, B cells, or T cells. Cells can also be obtained from whole food, apheresis, or a tumor sample of a subject. A cell can be a tumor infiltrating lymphocytes (TIL). In some cases an apheresis can be a leukapheresis. Leukapheresis can be a procedure in which blood cells are isolated from blood. During a leukapheresis, blood can be removed from a needle in an arm of a subject, circulated through a machine that divides whole blood into red cells, plasma and lymphocytes, and then the plasma and red cells are returned to the subject through a needle in the other arm. In some cases, cells are isolated after an administration of a treatment regime and cellular therapy. For example, an apheresis can be performed in sequence or concurrent with a cellular administration. In some cases, an apheresis is performed prior to and up to about 6 weeks following administration of a cellular product. In some cases, an apheresis is performed −3 weeks, −2 weeks, −1 week, 0, 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, or up to about 10 years after an administration of a cellular product. In some cases, cells acquired by an apheresis can undergo testing for specific lysis, cytokine release, metabolomics studies, bioenergetics studies, intracellular FACs of cytokine production, ELISA-spot assays, and lymphocyte subset analysis. In some cases, samples of cellular products or apheresis products can be cryopreserved for retrospective analysis of infused cell phenotype and function.

A TIL can be isolated from an organ afflicted with a cancer. One or more cells can be isolated from an organ with a cancer that can be a brain, heart, lungs, eye, stomach, pancreas, kidneys, liver, intestines, uterus, bladder, skin, hair, nails, ears, glands, nose, mouth, lips, spleen, gums, teeth, tongue, salivary glands, tonsils, pharynx, esophagus, large intestine, small intestine, rectum, anus, thyroid gland, thymus gland, bones, cartilage, tendons, ligaments, suprarenal capsule, skeletal muscles, smooth muscles, blood vessels, blood, spinal cord, trachea, ureters, urethra, hypothalamus, pituitary, pylorus, adrenal glands, ovaries, oviducts, uterus, vagina, mammary glands, testes, seminal vesicles, penis, lymph, lymph nodes or lymph vessels. One or more TILs can be from a brain, heart, liver, skin, intestine, lung, kidney, eye, small bowel, or pancreas. TILs can be from a pancreas, kidney, eye, liver, small bowel, lung, or heart. TILs can be from a pancreas. The one or more cells can be pancreatic islet cells, for example, pancreatic β cells. In some cases, a TIL can be from a gastrointestinal cancer. A TIL culture can be prepared a number of ways. For example, a tumor can be trimmed from non-cancerous tissue or necrotic areas. A tumor can then be fragmented to about 2-3 mm in length. In some cases, a tumor can be fragmented from about 0.5 mm to about 5 mm in size, from about 1 mm to about 2 mm, from about 2 mm to about 3 mm, from about 3 mm to about 4 mm, or from about 4 mm to about 5 mm. Tumor fragments can then be cultured in vitro utilizing media and a cellular stimulating agent such as a cytokine. In some cases, IL-2 can be utilized to expand TILs from a tumor fragment. A concentration of IL-2 can be about 6000 IU/mL. A concentration of IL-2 can also be about 2000 IU/mL, 3000 IU/mL, 4000 IU/mL, 5000 IU/mL, 6000 IU/mL, 7000 IU/mL, 8000 IU/mL, 9000 IU/mL, or up to about 10000 IU/mL. Once TILs are expanded they can be subject to in vitro assays to determine tumor reactivity. For example, TILs can be evaluated by FACs for CD3, CD4, CD8, and CD58 expression. TILs can also be subjected to cocultured, cytotoxicity, ELISA, or ELISPOT assays. In some cases, TIL cultures can be cryopreserved or undergo a rapid expansion. A cell, such as a TIL, can be isolated from a donor of a stage of development including, but not limited to, fetal, neonatal, young and adult. TILs can be isolated from an adult human. A human from whom cells can be isolated can be under the age of 10, 9, 8, 7, 6, 5, 4, 3, 2, or 1 year(s). For example, cells can be isolated from a human under the age of 6 years. Cells, such as TILs, can also be isolated from a human under the age of 3 years. In some cases, a human donor can be an adult from at least about 18 years of age. In some cases, a blood product may be stored. For example, a cryostore freezing bag may be utilized to store and freeze a blood product.

In some cases, a cell that can be utilized in a cellular therapy or a cell that can be genomically disrupted can be positive or negative for a given factor. In some embodiments, a cell may be a CD3+ cell, CD3− cell, a CD5+ cell, CD5− cell, a CD7+ cell, CD7− cell, a CD14+ cell, CD14− cell, CD8+ cell, a CD8-cell, a CD103+ cell, CD103− cell, CD11b+ cell, CD11b− cell, a BDCA1+ cell, a BDCA1− cell, an L-selectin+ cell, an L-selectin− cell, a CD25+, a CD25− cell, a CD27+, a CD27− cell, a CD28+ cell, CD28-cell, a CD44+ cell, a CD44− cell, a CD56+ cell, a CD56− cell, a CD57+ cell, a CD57− cell, a CD62L+ cell, a CD62L− cell, a CD69+ cell, a CD69− cell, a CD45RO+ cell, a CD45RO− cell, a CD127+ cell, a CD127-cell, a CD132+ cell, a CD132− cell, an IL-7+ cell, an IL-7− cell, an IL-15+ cell, an IL-15− cell, a lectin-like receptor G1 positive cell, a lectin-like receptor G1 negative cell, or a differentiated or de-differentiated cell thereof. The examples of factors expressed by cells is not intended to be limiting, and a person having skill in the art will appreciate that a cell may be positive or negative for any factor known in the art. In some embodiments, a cell may be positive for two or more factors. For example, a cell may be CD4+ and CD8+. In some embodiments, a cell may be negative for two or more factors. For example, a cell may be CD25-, CD44-, and CD69-. In some embodiments, a cell may be positive for one or more factors, and negative for one or more factors. For example, a cell may be CD4+ and CD8-. The selected cells can then be infused into a subject. In some embodiments, the cells may be selected for having or not having one or more given factors (e.g., cells may be separated based on the presence or absence of one or more factors). In some embodiments, the selected cells can also be expanded in vitro. The selected cells can be expanded in vitro prior to infusion. It should be understood that cells used in any of the methods disclosed herein may be a mixture (e.g., two or more different cells) of any of the cells disclosed herein. For example, a method of the present disclosure may comprise cells, and the cells are a mixture of CD4+ cells and CD8+ cells. In another example, a method of the present disclosure may comprise cells, and the cells are a mixture of CD4+ cells and naïve cells. In some cases, a cell can be a stem memory $T_{SCM}$ cell comprised of CD45RO (−), CCR7(+), CD45RA (+), CD62L+(L-selectin), CD27+, CD28+ and IL-7Rα+, stem memory cells can also express CD95, IL-2Rβ, CXCR3, and LFA-1, and show numerous functional attributes distinctive of stem memory cells. Engineered cells can also be central memory $T_{CM}$ cells comprising L-selectin and CCR7, where the central memory cells can secrete, for example, IL-2, but not IFNγ or IL-4. Engineered cells can also be effector memory $T_{EM}$ cells comprising L-selectin or CCR7 and produce, for example, effector cytokines such as IFNγ and IL-4. In some cases a population of cells can be introduced to a subject. For example, a population of cells can be a combination of T cells and NK cells. In other cases, a population can be a combination of naïve cells and effector cells. A population of cells can be TILs.

In particular, T cell populations can be stimulated in vitro such as by contact with an anti-CD3 antibody or antigen-binding fragment thereof, or an anti-CD2 antibody immobilized on a surface, or by contact with a protein kinase C activator (e.g., bryostatin) sometimes in conjunction with a calcium ionophore. For co-stimulation of an accessory molecule on the surface of the T cells, a ligand that binds the accessory molecule can be used. For example, a population of T cells can be contacted with an anti-CD3 antibody and an anti-CD28 antibody, under conditions that can stimulate proliferation of the T cells. In some cases, 4-1BB can be used to stimulate cells. For example, cells can be stimulated with 4-1BB and IL-21 or another cytokine. To stimulate proliferation of either CD4 T cells or CD8 T cells, an anti-CD3 antibody and an anti-CD28 antibody can be used. For example, the agents providing a signal may be in solution or coupled to a surface. The ratio of particles to cells may depend on particle size relative to the target cell. In further embodiments, the cells, such as T cells, can be combined with agent-coated beads, where the beads and the cells can be subsequently separated, and optionally cultured. Each bead can be coated with either anti-CD3 antibody or an anti-CD28 antibody, or in some cases, a combination of the two. In an alternative embodiment, prior to culture, the agent-coated beads and cells are not separated but are cultured together. Cell surface proteins may be ligated by allowing paramagnetic beads to which anti-CD3 and anti-CD28 can be attached (3×28 beads) to contact the T cells. In some cases cells and beads (for example, DYNABEADS® M-450 CD3/CD28 T paramagnetic beads at a ratio of 1:1) are combined in a buffer, for example, phosphate buffered saline (PBS) (e.g., without divalent cations such as, calcium and magnesium). Any cell concentration may be used. The mixture may be cultured for or for about several hours (e.g., about 3 hours) to or to about 14 days or any hourly integer value in between. In another embodiment, the mixture may be cultured for or for about 21 days or for up to or for up to about 21 days. Conditions appropriate for T cell culture can include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, IL-10, IL-21, IL-15, TGF beta, and TNF alpha or any other additives for the growth of cells. Other additives for the growth of cells include, but are not limited to, surfactant, plasmanate, and reducing agents such as N-acetyl-cysteine and 2-mercaptoethanol. Media can include RPMI 1640, A1 M-V, DMEM, MEM, α-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. In some cases, an 865 mL bottle of RPMI may have 100 mL of human serum, 25 mL of Hepes 1M, 10 mL of Penicillin/streptomycin at 10,000 U/mL and 10,000 µg/mL, and 0.2 mL of gentamycin at 50 mg/mL. After addition of additives an RPMI media may be filtered using a 0.2 µm×1 L filter and stored at 4° C. In some embodiments, antibiotics, e.g., penicillin and streptomycin, are included only in experimental cultures but not in cultures of cells that are to be infused into a subject. In some cases, human serum can be thawed in a 37° C. water bath, and then heat inactivated (e.g., at 56° C. for 30 min for 100 mL bottle). The sera can be filtered through a 0.8 µm and 0.45 µm filter prior to addition of medium.

The target cells can be maintained under conditions necessary to support growth; for example, an appropriate temperature (e.g., 37° C.) and atmosphere (e.g., air plus 5% $CO_2$). In some instances, T cells that have been exposed to varied stimulation times may exhibit different characteristics. In some cases, a soluble monospecific tetrameric antibody against human CD3, CD28, CD2, or any combination thereof may be used.

In some cases, cells to undergo disruption can be activated or expanded by co-culturing with tissue or cells. A cell can be an antigen presenting cell. An artificial antigen presenting cells (aAPCs) can express ligands for T cell receptor and costimulatory molecules and can activate and expand T cells for transfer, while improving their potency and function in some cases. An aAPC can be engineered to express any gene for T cell activation. An aAPC can be engineered to express any gene for T cell expansion. An aAPC can be a bead, a cell, a protein, an antibody, a cytokine, or any combination. An aAPC can deliver signals to a cell population that may undergo genomic transplant. For example, an aAPC can deliver a signal 1, signal, 2, signal 3 or any combination. A signal 1 can be an antigen recognition signal. For example, signal 1 can be ligation of a TCR by a peptide-MHC complex or binding of agonistic antibodies directed towards CD3 that can lead to activation of the CD3 signal-transduction complex. Signal 2 can be a co-stimulatory signal. For example, a co-stimulatory signal can be anti-CD28, inducible co-stimulator (ICOS), CD27, and 4-1BB (CD137), which bind to ICOS-L, CD70, and 4-1BBL, respectively.

Signal 3 can be a cytokine signal. A cytokine can be any cytokine. A cytokine can be IL-2, IL-7, IL-12, IL-15, IL-21, or any combination thereof.

In some cases an artificial antigen presenting cell (aAPC) may be used to activate and/or expand a cell population. In some cases, an artificial may not induce allospecificity. An aAPC may not express HLA in some cases. An aAPC may be genetically modified to stably express genes that can be used to activation and/or stimulation. In some cases, a K562 cell may be used for activation. A K562 cell may also be used for expansion. A K562 cell can be a human erythroleukemic cell line. A K562 cell may be engineered to express genes of interest. K562 cells may not endogenously express HLA class I, II, or CD1d molecules but may express ICAM-1 (CD54) and LFA-3 (CD58). K562 may be engineered to deliver a signal 1 to T cells. For example, K562 cells may be engineered to express HLA class I. In some cases, K562 cells may be engineered to express additional molecules such as B7, CD80, CD83, CD86, CD32, CD64, 4-1BBL, anti-CD3, anti-CD3 mAb, anti-CD28, anti-CD28mAb, CD1d, anti-CD2, membrane-bound IL-15, membrane-bound IL-17, membrane-bound IL-21, membrane-bound IL-2, truncated CD19, or any combination. In some cases, an engineered K562 cell can expresses a membranous form of anti-CD3 mAb, clone OKT3, in addition to CD80 and CD83. In some cases, an engineered K562 cell can expresses a membranous form of anti-CD3 mAb, clone OKT3, membranous form of anti-CD28 mAb in addition to CD80 and CD83.

In some cases, restimulation of cells can be performed with antigen and irradiated, histocompatible antigen presenting cells (APCs), such as feeder PBMCs. In some cases, cells can be grown using non-specific mitogens such as PHA and allogenic feeder cells. Feeder PBMCs can be irradiated at 40Gy. Feeder PBMCs can be irradiated from about 10 Gy to about 15 Gy, from about 15 Gy to about 20 Gy, from about 20Gy to about 25 Gy, from about 25 Gy to about 30 Gy, from about 30 Gy to about 35 Gy, from about 35 Gy to about 40 Gy, from about 40 Gy to about 45 Gy, from about 45 Gy to about 50 Gy. In some cases, a control flask of irradiated feeder cells only can be stimulated with anti-CD3 and IL-2.

An aAPC can be a bead. A spherical polystyrene bead can be coated with antibodies against CD3 and CD28 and be used for T cell activation. A bead can be of any size. In some cases, a bead can be or can be about 3 and 6 micrometers. A bead can be or can be about 4.5 micrometers in size. A bead can be utilized at any cell to bead ratio. For example, a 3 to 1 bead to cell ratio at 1 million cells per milliliter can be used. An aAPC can also be a rigid spherical particle, a polystyrene latex microbeads, a magnetic nano- or microparticles, a nanosized quantum dot, a 4, polylactic-coglycolic acid) (PLGA) microsphere, a nonspherical particle, a 5, carbon nanotube bundle, a 6, ellipsoid PLGA micropar-ticle, a 7, nanoworms, a fluidic lipid bilayer-containing system, an 8, 2D-supported lipid bilayer (2D-SLBs), a 9, liposome, a 10, RAFTsomes/microdomain liposome, an 11, SLB particle, or any combination thereof.

In some cases, an aAPC can expand CD4 T cells. For example, an aAPC can be engineered to mimic an antigen processing and presentation pathway of HLA class II-restricted CD4 T cells. A K562 can be engineered to express HLA-D, DP α, DP β chains, Ii, DM α, DM β, CD80, CD83, or any combination thereof. For example, engineered K562 cells can be pulsed with an HLA-restricted peptide in order to expand HLA-restricted antigen-specific CD4 T cells.

In some cases, the use of aAPCs can be combined with exogenously introduced cytokines for T cell activation, expansion, or any combination. Cells can also be expanded in vivo, for example in the subject's blood after administration of genomically transplanted cells into a subject.

In some cases, cells can be scaled up to yields achieved by standard rapid expansion protocols (REP). An average fold expansion of genetically modified TILs can be 1071. In some cases, an average fold expansion can be from 500 to 2000. An average fold expansion of genetically modified TILs can be from 500 to 600, from 600 to 700, from 700 to 800, from 800 to 900, from 900 to 1000, from 1000 to up to 2000 fold. In some cases, an engineered cellular dosage can be from about $1 \times 10^{10}$ knockout TIL for patient infusion.

Cells (e.g., engineered cells or engineered primary T cells or TILs) before, after, and/or during administration can be functional. For example, cells can be functional for at least or at least about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 40, 50, 60, 70, 80, 90, or 100 days after administration. Adoptively transferred cells can be functional for at least or at least about 1, 2, 3, 4, 5, 6, 7, 8, 9, 10, 11, or 12 months after administration. Administered cells can be functional for at least or at least about 1, 2, 3, 4, 5, 6, 7, 8, 9, 10, 15, 20, 25, or 30 years after infusion. In some cases, administered cells can be functional for up to the lifetime of a recipient.

Further, adoptively transferred cells can function at 100% of their normal intended operation. Cells can also function 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of their normal intended operation.

In long-term cultures, a genomically disrupted cell cannot exhibit properties of stimulation-independent growth or transformation. For example, in some cases, a genomically disrupted cell may not expand when cultured without a cytokine, such as IL-2. In some cases, a genomically disrupted cell may not be viable after about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 days after contact with a cytokine such as IL-2.

Cellular compositions described herein can be cryopreserved. A cryopreservation can be performed in, for example, a Cryostor CS10 at 5% DMSO final concentration. A cryopreservation can be at a freeze density from about $7.5 \times 10^7$ cells/mL to about $1.5 \times 10^8$ cells/mL. A freeze density can be from about $1 \times 10^7$ cells/mL, $1.5 \times 10^7$ cells/mL, $2 \times 10^7$ cells/mL, $2.5 \times 10^7$ cells/mL, $3 \times 10^7$ cells/mL, $3.5 \times 10^7$ cells/mL, $4 \times 10^7$ cells/mL, $4.5 \times 10^7$ cells/mL, $5 \times 10^7$ cells/mL, $5.5 \times 10^7$ cells/mL, $6 \times 10^7$ cells/mL, $6.5 \times 10^7$ cells/mL, $7 \times 10^7$ cells/mL, $7.5 \times 10^7$ cells/mL, $8 \times 10^7$ cells/mL, $8.5 \times 10^7$ cells/mL, $9 \times 10^7$ cells/mL, $9.5 \times 10^7$ cells/mL, $1 \times 10^8$ cells/mL, $1.5 \times 10^8$ cells/mL, $2 \times 10^8$ cells/mL, $2.5 \times 10^8$ cells/mL, $3 \times 10^8$ cells/mL, $3.5 \times 10^8$ cells/mL, $4 \times 10^8$ cells/mL, $4.5 \times 10^8$ cells/mL, $5 \times 10^8$ cells/mL, $5.5 \times 10^8$ cells/mL, $6 \times 10^8$ cells/mL, $6.5 \times 10^8$ cells/mL, $7 \times 10^8$ cells/mL, $7.5 \times 10^8$ cells/mL, or up to about $8 \times 10^8$ cells/mL.

For example, in some cases, a TIL can be harvested, washed, and re-suspended in a buffer, such as Cryostor buffer. This preparation can be mixed with an equal volume of Cryostore CS10. In some cases, a cellular composition is thawed prior to an introducing into a subject in need thereof.

Cellular viability can be determined by flow cytometry and trypan blue exclusion. In some cases, a forward scatter and side scatter on a flow cytometer can identify percent viable cells. In other cases, cells can be stained with Annexin V to determine a percent of dead/live cells. Trypan blue exclusion may also be utilized to determine cellular viability with a hemocytometer. In some cases, at least about 50% cells can be viable for administration. In other cases from about 50%, 60%, 70%, 80%, 90%, 95%, or up to about 100% cells can be viable.

Cellular Targets

A cell such as a TIL can target an antigen. A cell can also target an epitope. An antigen can be a tumor cell antigen. An epitope can be a tumor cell epitope. Tumor infiltrating lymphocytes (TIL) can be selected as clonal and/or oligoclonal subpopulations possessing specific reactivity against subject-specific cancer neoantigens. Specific reactivity can be determined using at least one of: tumor whole-exome sequencing and tandem mini-gene/synthetic long peptide screening approach, E. Tran et al., Cancer immunotherapy based on mutation-specific CD4+ T cells in a patient with epithelial cancer. Science 344, 641-645 (2014). A tumor cell epitope may be derived from a wide variety of tumor antigens such as antigens from tumors resulting from mutations (neo antigens or neo epitopes), shared tumor specific antigens, differentiation antigens, and antigens overexpressed in tumors. In some cases, a neoantigen or neoepitope can be identified by 5'RACE and TCR-PCR. Those antigens, for example, may be derived from alpha-actinin-4, ARTC1, BCR-ABL fusion protein (b3a2), B-RAF, CASP-5, CASP-8, beta-catenin, Cdc27, CDK4, CDKN2A, COA-1, dek-can fusion protein, EFTUD2, Elongation factor 2, ETV6-AML1 fusion protein, FLT3-ITD, FN1, GPNMB, LDLR-fucosyltransferase fusion protein, HLA-A2d, HLA-A1 1d, hsp70-2, KIAAO205, MART2, ME1, MUM-lf, MUM-2, MUM-3, neo-PAP, Myosin class I, NFYC, OGT, OS-9, p53, pml-RARalpha fusion protein, PRDXS, PTPRK, K-ras, N-ras, RBAF600, SIRT2, SNRPD1, SYT-SSX1- or -SSX2 fusion protein, TGF-betaRll, triosephosphate isomerase, BAGE-1, GAGE-1, 2, 8, Gage 3, 4, 5, 6, 7, GnTVf, HERV-K-MEL, KK-LC-1, KM-HN-1, LAGE-1, MAGE-A1, MAGE-A2, MAGE-A3, MAGE-A4, MAGE-A6, MAGE-A9, MAGE-A10, MAGE-A12, MAGE-C2, mucink, NA-88, NY-ESO-1/LAGE-2, SAGE, Sp17, SSX-2, SSX-4, TAG-1, TAG-2, TRAG-3, TRP2-INT2g, XAGE-1b, CEA, gp100/Pme117, Kallikrein 4, mammaglobin-A, Melan-A/MART-1, NY-BR-1, OA1, PSA, RAB38/NY-MEL-1, TRP-1/gp75, TRP-2, tyrosinase, adipophilin, AIM-2, ALDH1A1, BCLX (L), BCMA, BING-4, CPSF, cyclin D1, DKK1, ENAH (hMena), EP-CAM, EphA3, EZH2, FGFS, G250/MN/CAIX, HER-2/neu, IL13Ralpha2, intestinal carboxyl esterase, alpha fetoprotein, M-CSFT, MCSP, mdm-2, MMP-2, MUC1, p53, PBF, PRAME, PSMA, RAGE-1, RGSS, RNF43, RU2AS, secernin 1, SOX10, STEAP1, survivin, Telomerase, VEGF, and/or WT1, just to name a few. Tumor-associated antigens may be antigens not normally expressed by the host; they can be mutated, truncated, misfolded, or otherwise abnormal manifestations of molecules normally expressed by the host; they can be identical to molecules normally expressed but expressed at abnormally high levels; or they can be expressed in a context or environment that is abnormal. Tumor-associated antigens may be, for example, proteins or protein fragments, complex carbohydrates, gangliosides, haptens, nucleic acids, other biological molecules or any combinations thereof. In some cases, a target is a neo antigen or neo epitope. For example, a neo antigen can be an E805G mutation in ERBB2IP. Neo antigen and neo epitopes can be identified by whole-exome sequencing in some cases. A neo antigen and neo epitope target can be expressed by a gastrointestinal cancer cell in some cases. A neo antigen and neo epitope can be expressed on an epithelial carcinoma.

An epitope can be a stromal epitope. An epitope can be on the stroma of the tumor microenvironment. The antigen can be a stromal antigen. An antigen can be on the stroma of the tumor microenvironment. Those antigens and those epitopes, for example, can be present on tumor endothelial cells, tumor vasculature, tumor fibroblasts, tumor pericytes, tumor stroma, and/or tumor mesenchymal cells, just to name a few. Those antigens, for example, can comprise CD34, MCSP, FAP, CD31, PCNA, CD117, CD40, MMP4, and/or Tenascin.

Genomic Disruptions

A genomic disruption can include exons or introns. In some cases, a genomic disruption can be of a gene sequence. The disruption of genes can be of any particular gene. It is contemplated that genetic homologues (e.g., any mammalian version of the gene) of the genes within this applications are covered. Some genetic homologues are known in the art, however, in some cases, homologues are unknown. However, homologous genes between mammals can be found by comparing nucleic acid (DNA or RNA) sequences or protein sequences using publically available databases such as NCBI BLAST.

A genomic disruption can improve a function of a cell. For example, a genomic disruption can enhance a cellular cytotoxicity of a target. A genomic disruption can also enhance proliferation or persistence of a cell. For example, a gene that can be disrupted can improve therapeutic potential of cancer immunotherapy. A cell can be engineered to knock out one or more endogenous genes. Endogenous genes that can be knocked out can comprise immune checkpoint genes. An immune checkpoint gene can be stimulatory checkpoint gene or an inhibitory checkpoint gene Immune checkpoint gene locations can be provided using the Genome Reference Consortium Human Build 38 patch release 2 (GRCh38.p2) assembly. A gene to be knocked out can be selected using a database. In some cases, certain endogenous genes are more amendable to genomic engineering. A database can comprise epigenetically permissive target sites. A database can be ENCODE (encyclopedia of DNA Elements) (http://www.genome.gov/10005107) in some cases. A databased can identify regions with open chromatin that can be more permissive to genomic engineering. A gene that can be disrupted can be involved in attenuating TCR signaling, functional avidity, or immunity to cancer. In some cases, a gene to be disrupted is upregulated when a TCR is stimulated. A gene can be involved in inhibiting cellular expansion, functional avidity, or cytokine polyfunctionality. A gene can be involved in negatively regulating cellular cytokine production. For example, a gene can be involved in inhibiting production of effector cytokines, IFN-gamma and/or TNF for example. A gene can also be involved in inhibiting expression of supportive cytokines such as IL-2 after TCR stimulation.

A cell can have one or more disrupted genes. For example, one or more genes whose expression is disrupted can be a checkpoint gene, such as PD-1 or CISH. In some cases, one or more genes whose expression can be disrupted are shown in Table 1. For example, genes that can be disrupted can exhibit a certain identity and/or homology to genes disclosed herein such as in Table 1, Therefore, it is contemplated that a gene that exhibits or exhibits about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% homology (at the nucleic acid or protein level) of Table 1 can be disrupted. It is also contemplated that a gene that exhibits or exhibits about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity (at the nucleic acid or protein level) of Table 1 can be disrupted.

TABLE 1

Checkpoint gene summary

| SEQ ID | Gene Symbol | Abbreviation | Name | NCBI number (GRCh38.p2) *AC010327.8 ** GRCh38.p7 | Original Start | Original Stop | Location in genome |
|---|---|---|---|---|---|---|---|
| 1 | ADORA2A | A2aR; RDC8; ADORA2 | adenosine A2a receptor | 135 | 24423597 | 24442360 | 22q11.23 |
| 2 | CD276 | B7H3; B7-H3; B7RP-2; 4Ig-B7-H3 | CD276 molecule | 80381 | 73684281 | 73714518 | 15q23-q24 |
| 3 | VTCN1 | B7X; B7H4; B7S1; B7-H4; B7h.5; VCTN1; PRO1291 | V-set domain containing T cell activation inhibitor 1 | 79679 | 117143587 | 117270368 | 1p13.1 |
| 4 | BTLA | BTLA1; CD272 | B and T lymphocyte associated | 151888 | 112463966 | 112499702 | 3q13.2 |
| 5 | CTLA4 | GSE; GRD4; ALPS5; CD152; CTLA-4; IDDM12; CELIAC3 | cytotoxic T-lymphocyte-associated protein 4 | 1493 | 203867788 | 203873960 | 2q33 |
| 6 | IDO1 | IDO; INDO; IDO-1 | indoleamine 2,3-dioxygenase 1 | 3620 | 39913809 | 39928790 | 8p12-p11 |
| 7 | KIR3DL1 | KIR; NKB1; NKAT3; NKB1B; NKAT-3; CD158E1; KIR3DL2; KIR3DL1/S1 | killer cell immunoglobulin-like receptor, three domains, long cytoplasmic tail, 1 | 3811 | 54816438 | 54830778 | 19q13.4 |

TABLE 1-continued

Checkpoint gene summary

| SEQ ID | Gene Symbol | Abbreviation | Name | NCBI number (GRCh38.p2) *AC010327.8 ** GRCh38.p7 | Original Start | Original Stop | Location in genome |
|---|---|---|---|---|---|---|---|
| 8 | LAG3 | LAG3; CD223 | lymphocyte-activation gene 3 | 3902 | 6772483 | 6778455 | 12p13.32 |
| 9 | PDCD1 | PD1; PD-1; CD279; SLEB2; hPD-1; hPD-1; hSLE1 | programmed cell death 1 | 5133 | 241849881 | 241858908 | 2q37.3 |
| 10 | HAVCR2 | TIM3; CD366; KIM-3; TIMD3; Tim-3; TIMD-3; HAVcr-2 | hepatitis A virus cellular receptor 2 | 84868 | 157085832 | 157109237 | 5q33.3 |
| 11 | VISTA | C10orf54, differentiation of ESC-1 (Dies1); platelet receptor Gi24 precursor; PD1 homolog (PD1H) B7H5; GI24; B7-H5; SISP1; PP2135 | V-domain immunoglobulin suppressor of T-cell activation | 64115 | 71747556 | 71773580 | 10q22.1 |
| 12 | CD244 | 2B4; 2B4; NAIL; Nmrk; NKR2B4; SLAMF4 | CD244 molecule, natural killer cell receptor 2B4 | 51744 | 160830158 | 160862902 | 1q23.3 |
| 13 | CISH | CIS; G18; SOCS; CIS-1; BACTS2 | cytokine inducible SH2-containing protein | 1154 | 50606454 | 50611831 | 3p21.3 |
| 14 | HPRT1 | HPRT; HGPRT | hypoxanthine phosphoribosyl transferase 1 | 3251 | 134452842 | 134500668 | Xq26.1 |
| 15 | AAV*S1 | AAV | adeno-associated virus integration site 1 | 14 | 7774 | 11429 | 19q13 |
| 16 | CCR5 | CKR5; CCR-5; CD195; CKR-5; CCCKR5; CMKBR5; IDDM22; CC-CKR-5 | chemokine (C-C motif) receptor 5 (gene/pseudogene) | 1234 | 46370142 | 46376206 | 3p21.31 |
| 17 | CD160 | NK1; BY55; NK28 | CD160 molecule | 11126 | 145719433 | 145739288 | 1q21.1 |
| 18 | TIGIT | VSIG9; VSTM3; WUCAM | T-cell immunoreceptor with Ig and ITIM domains | 201633 | 114293986 | 114310288 | 3q13.31 |
| 19 | CD96 | TACTILE | CD96 molecule | 10225 | 111542079 | 111665996 | 3q13.13-q13.2 |
| 20 | CRTAM | CD355 | cytotoxic and regulatory T-cell molecule | 56253 | 122838431 | 122872643 | 11q24.1 |
| 21 | LAIR1 | CD305; LAIR-1 | leukocyte associated immunoglobulin like receptor 1 | 3903 | 54353624 | 54370556 | 19q13.4 |
| 22 | SIGLEC7 | p75; QA79; AIRM1; CD328; CDw328; D-siglec; SIGLEC-7; SIGLECP2; SIGLEC19P; p75/AIRM1 | sialic acid binding Ig like lectin 7 | 27036 | 51142294 | 51153526 | 19q13.3 |
| 23 | SIGLEC9 | CD329; CDw329; FOAP-9; siglec-9; OBBP-LIKE | sialic acid binding Ig like lectin 9 | 27180 | 51124880 | 51141020 | 19q13.41 |
| 24 | TNFRSF10B | DR5; CD262; KILLER; TRICK2; TRICKB; ZTNFR9; TRAILR2; TRICK2A; TRICK2B; TRAIL-R2; KILLER/DR5 | tumor necrosis factor receptor superfamily member 10b | 8795 | 23006383 | 23069187 | 8p22-p21 |

TABLE 1-continued

Checkpoint gene summary

| SEQ ID | Gene Symbol | Abbreviation | Name | NCBI number (GRCh38.p2) *AC010327.8 ** GRCh38.p7 | Original Start | Original Stop | Location in genome |
|---|---|---|---|---|---|---|---|
| 25 | TNFRSF10A | DR4; APO2; CD261; TRAILR1; TRAILR-1 | tumor necrosis factor receptor superfamily member 10a | 8797 | 23191457 | 23225167 | 8p21 |
| 26 | CASP8 | CAP4; MACH; MCH5; FLICE; ALPS2B; Casp-8 | caspase 8 | 841 | 201233443 | 201287711 | 2q33-q34 |
| 27 | CASP10 | MCH4; ALPS2; FLICE2 | caspase 10 | 843 | 201182898 | 201229406 | 2q33-q34 |
| 28 | CASP3 | CPP32; SCA-1; CPP32B | caspase 3 | 836 | 184627696 | 184649475 | 4q34 |
| 29 | CASP6 | MCH2 | caspase 6 | 839 | 109688628 | 109713904 | 4q25 |
| 30 | CASP7 | MCH3; CMH-1; LICE2; CASP-7; ICE-LAP3 | caspase 7 | 840 | 113679162 | 113730909 | 10q25 |
| 31 | FADD | GIG3; MORT1 | Fas associated via death domain | 8772 | 70203163 | 70207402 | 11q13.3 |
| 32 | FAS | APT1; CD95; FAS1; APO-1; FASTM; ALPS1A; TNFRSF6 | Fas cell surface death receptor | 355 | 88969801 | 89017059 | 10q24.1 |
| 33 | TGFBRII | AAT3; FAA3; LDS2; MFS2; RIIC; LDS1B; LDS2B; TAAD2; TGFR-2; TGFbeta-RII | transforming growth factor beta receptor II | 7048 | 30606493 | 30694142 | 3p22 |
| 34 | TGFBR1 | AAT5; ALK5; ESS1; LDS1; MSSE; SKR4; ALK-5; LDS1A; LDS2A; TGFR-1; ACVRLK4; tbetaR-I | transforming growth factor beta receptor I | 7046 | 99104038 | 99154192 | 9q22 |
| 35 | SMAD2 | JV18; MADH2; MADR2; JV18-1; hMAD-2; hSMAD2 | SMAD family member 2 | 4087 | 47833095 | 47931193 | 18q21.1 |
| 36 | SMAD3 | LDS3; LDS1C; MADH3; JV15-2; HSPC193; HsT17436 | SMAD family member 3 | 4088 | 67065627 | 67195195 | 15q22.33 |
| 37 | SMAD4 | JIP; DPC4; MADH4; MYHRS | SMAD family member 4 | 4089 | 51030213 | 51085042 | 18q21.1 |
| 38 | SKI | SGS; SKV | SKI proto-oncogene | 6497 | 2228695 | 2310213 | 1p36.33 |
| 39 | SKIL | SNO; SnoA; SnoI; SnoN | SKI-like proto-oncogene | 6498 | 170357678 | 170396849 | 3q26 |
| 40 | TGIF1 | HPE4; TGIF | TGFB induced factor homeobox 1 | 7050 | 3411927 | 3458411 | 18p11.3 |
| 41 | IL10RA | CD210; IL10R; CD210a; CDW210A; HIL-10R; IL-10R1 | interleukin 10 receptor subunit alpha | 3587 | 117986391 | 118001483 | 11q23 |
| 42 | IL10RB | CRFB4; CRF2-4; D21S58; D21S66; CDW210B; IL-10R2 | interleukin 10 receptor subunit beta | 3588 | 33266360 | 33297234 | 21q22.11 |
| 43 | HMOX2 | HO-2 | heme oxygenase 2 | 3163 | 4474703 | 4510347 | 16p13.3 |
| 44 | IL6R | IL6Q; gp80; CD126; IL6RA; IL6RQ; IL-6RA; IL-6R-1 | interleukin 6 receptor | 3570 | 154405193 | 154469450 | 1q21 |
| 45 | IL6ST | CD130; GP130; CDW130; IL-6RB | interleukin 6 signal transducer | 3572 | 55935095 | 55994993 | 5q11.2 |
| 46 | CSK | CSK | c-src tyrosine kinase | 1445 | 74782084 | 74803198 | 15q24.1 |
| 47 | PAG1 | CBP; PAG | phosphoprotein membrane anchor with glycosphingolipid microdomains 1 | 55824 | 80967810 | 81112068 | 8q21.13 |

TABLE 1-continued

Checkpoint gene summary

| SEQ ID | Gene Symbol | Abbreviation | Name | NCBI number (GRCh38.p2) *AC010327.8 ** GRCh38.p7 | Original Start | Original Stop | Location in genome |
|---|---|---|---|---|---|---|---|
| 48 | SIT1 | SIT1 | signaling threshold regulating transmembrane adaptor 1 | 27240 | 35649298 | 35650950 | 9p13-p12 |
| 49 | FOXP3 | JM2; AIID; IPEX; PIDX; XPID; DIETER | forkhead box P3 | 50943 | 49250436 | 49269727 | Xp11.23 |
| 50 | PRDM1 | BLIMP1; PRDI-BF1 | PR domain 1 | 639 | 106086320 | 106109939 | 6q21 |
| 51 | BATF | SFA2; B-ATF; BATF1; SFA-2 | basic leucine zipper transcription factor, ATF-like | 10538 | 75522441 | 75546992 | 14q24.3 |
| 52 | GUCY1A2 | GC-SA2; GUC1A2 | guanylate cyclase 1, soluble, alpha 2 | 2977 | 106674012 | 107018445 | 11q21-q22 |
| 53 | GUCY1A3 | GUCA3; MYMY6; GC-SA3; GUC1A3; GUCSA3; GUCY1A1 | guanylate cyclase 1, soluble, alpha 3 | 2982 | 155666568 | 155737062 | 4q32.1 |
| 54 | GUCY1B2 | GUCY1B2 | guanylate cyclase 1, soluble, beta 2 (pseudogene) | 2974 | 50994511 | 51066157 | 13q14.3 |
| 55 | GUCY1B3 | GUCB3; GC-SB3; GUC1B3; GUCSB3; GUCY1B1; GC-S-beta-1 | guanylate cyclase 1, soluble, beta 3 | 2983 | 155758973 | 155807642 | 4q31.3-q33 |
| 56 | TRA | IMD7; TCRA; TCRD; TRAalpha; TRAC | T-cell receptor alpha locus | 6955 | 21621904 | 22552132 | 14q11.2 |
| 57 | TRB | TCRB; TRBbeta | T cell receptor beta locus | 6957 | 142299011 | 142813287 | 7q34 |
| 58 | EGLN1 | HPH2; PHD2; SM20; ECYT3; HALAH; HPH-2; HIFPH2; ZMYND6; C1orf12; HIF-PH2 | egl-9 family hypoxia-inducible factor 1 | 54583 | 231363751 | 231425044 | 1q42.1 |
| 59 | EGLN2 | EIT6; PHD1; HPH-1; HPH-3; HIFPH1; HIF-PH1 | egl-9 family hypoxia-inducible factor 2 | 112398 | 40799143 | 40808441 | 19q13.2 |
| 60 | EGLN3 | PHD3; HIFPH3; HIFP4H3 | egl-9 family hypoxia-inducible factor 3 | 112399 | 33924215 | 33951083 | 14q13.1 |
| 61 | PPP1R12C** | p84; p85; LENG3; MBS85 | protein phosphatase 1 regulatory subunit 12C | 54776 | 55090913 | 55117600 | 19q13.42 |

A cell can have one or more suppressed genes. For example, one or more genes whose expression is suppressed can comprise any one of the genes in Table 1 as well as homologous or modified versions thereof. Gene suppression can also be done in a number of ways. For example, gene expression can be suppressed by knock out, altering a promoter of a gene, and/or by administering interfering RNAs. This can be done at an organism level or at a tissue, organ, and/or cellular level. If one or more genes are knocked down in a cell, tissue, and/or organ, the one or more genes can be suppressed by administrating RNA interfering reagents, e.g., siRNA, shRNA, or microRNA. For example, a nucleic acid which can express shRNA can be stably transfected into a cell to knockdown expression. Furthermore, a nucleic acid which can express shRNA can be inserted into the genome of a T cell, thus knocking down a gene within the T cell.

In some instances, a gene that can be disrupted or suppressed can be CISH. A CISH gene can be a member of a cytokine-induced STAT inhibitor (CIS), also known as suppressor of cytokine signaling (SOCS) or STAT-induced STAT inhibitor (SSI), protein family (see e.g., Palmer et al., Cish actively silences TCR signaling in CD8+ T cells to maintain tumor tolerance, The Journal of Experimental Medicine 202(12), 2095-2113 (2015)). A gene can be part of a SOCS family of proteins that can form part of a classical negative feedback system that can regulate cytokine signal transduction. CISH can be involved in negative regulation of cytokines that signal through the JAK-STAT5 pathway such as erythropoietin, prolactin or interleukin 3 (IL-3) receptor. A gene can inhibit STAT5 trans-activation by suppressing its tyrosine phosphorylation. CISH family members are known to be cytokine-inducible negative regulators of cytokine signaling Expression of a gene can be induced by IL2, IL3, GM-CSF or EPO in hematopoietic cells. Proteasome-mediated degradation of a gene protein can be involved in the inactivation of an erythropoietin receptor. In some cases, a gene to be targeted can be expressed in tumor-specific T cells. A gene to be targeted can increase infiltration of an engineered cell into antigen-relevant tumors when disrupted.

Improving the functional avidity of effector T cells can be critical in overcoming inhibitory factors within the tumor microenvironment and eliciting tumor regression. In some cases, Cish (Cytokine-induced SH2 protein), a member of the Suppressor of Cytokine Signaling (SOCS) family, can be induced by T cell receptor (TCR) stimulation in $CD8^+$ T cells, can be expressed in tumor-resident T cells and can inhibit their functional avidity against tumor(s). Genetic deletion of Cish in tumor-specific $CD8^+$ T cells can enhance their expansion, functional avidity and cytokine polyfunctionality, resulting in pronounced and durable regression of established tumors. Cish physically interacts with the critical TCR signaling intermediate, Phospholipase C-$\gamma$1 (PLC-$\gamma$1), targeting it for proteasomal degradation following TCR stimulation. These findings established a novel targetable interaction that regulates the functional avidity of tumor-specific $CD8^+$ T cells and can be manipulated to improve ACT cancer immunotherapy. In some cases, Cish knockout or knockdown may result in an increase in cytokine levels. Increased cytokine levels may comprise increases in IFN-$\gamma$, TNF-$\alpha$, IL-2, or a combination thereof in a supernatant as compared to supernatants of wildtype counterpart cells. In other cases, knockout or knockdown of a gene, such as Cish, can comprise an increase in antigen sensitivity. An increase in antigen sensitivity may be measured by total cytokine expression levels in some cases, an increase in antigen sensitivity may be from 40 to 100 fold. An increase in antigen sensitivity may be from 40 to 50, from 50 to 60, from 60 to 70, from 70 to 80, from 80 to 90, from 90 to 100 fold as compared to control counterpart cells.

In some cases, Cish knockout or knockdown may result in an increase in a maximal amount of cytokine release as measured by IFN-$\gamma$, TNF-$\alpha$ and/or IL-2 levels. In some cases, an ELISA can measure total cytokine levels in a supernatant and may not directly measure cytokine-production on a sub-population or cellular level. To evaluate if different subpopulations or individual T cells may be responsible for an increase in cytokine production, $CD8^+$ T may be selected, stimulated, and co-stained for intracellular IFN-$\gamma$, TNF-$\alpha$ and IL-2 and evaluated with flow cytometry. In some cases, Cish can negatively regulate both total effector cytokine production and polyfunctionality in tumor-specific T cells. The genetic whole-body deletion of Cish can enhance functional avidity and licenses $CD8^+$ T cells into long-lasting tumor killers which may have implications in memory responses to a relapsing tumor.

One or more genes in a T cell can be knocked out or disrupted using any method. For example, knocking out one or more genes can comprise deleting one or more genes from a genome of a T cell. Knocking out can also comprise removing all or a part of a gene sequence from a T cell. It is also contemplated that knocking out can comprise replacing all or a part of a gene in a genome of a T cell with one or more nucleotides. Knocking out one or more genes can also comprise inserting a sequence in one or more genes thereby disrupting expression of the one or more genes. For example, inserting a sequence can generate a stop codon in the middle of one or more genes. Inserting a sequence can also shift the open reading frame of one or more genes. It is also contemplated that any combinations of knockout technology can be combined. For example, tissue specific knockout or cell specific knockout can be combined with inducible technology, creating a tissue specific or cell specific, inducible knockout. Furthermore, other systems such developmental specific promoter, can be used in combination with tissues specific promoters, and/or inducible knockouts.

Knocking out technology can also comprise gene editing. For example, gene editing can be performed using a nuclease, including CRISPR associated proteins (Cas proteins, e.g., Cas9), Zinc finger nuclease (ZFN), Transcription Activator-Like Effector Nuclease (TALEN), and meganucleases. Nucleases can be naturally existing nucleases, genetically modified, and/or recombinant. Gene editing can also be performed using a transposon-based system (e.g. PiggyBac, Sleeping beauty). For example, gene editing can be performed using a transposase.

In some cases, a cell that is engineered or contains a disrupted gene or portion thereof can undergo pre-infusion testing. Pre-infusion testing can include at least one of phenotypic testing, potency testing, microbiological testing, endotoxin testing, viability testing, and tumor cell testing of a culture of engineered cells. A phenotypic testing can comprise detecting a presence of CD3, CD4, CD8, CD56, CD45RA, CD45RO, IL-7 receptor alpha, CD28, to name a few. In some cases, a level of a marker on an engineered cell is over at least about 20%, 30%, 40%, 50%, 60%, 70%, 80%, 90%, 95%, or up to about 100%. TILs can be administered when pre-infusion testing can be at least about 80% CD3 positive for a phenotypic testing.

In some cases, potency testing of TILs can include detecting a level of IFN$\gamma$ upon anti-CD3 stimulation of a TIL culture. In some cases, a level of FN$\gamma$ upon anti-CD3 stimulation of a TIL culture is significantly greater than a comparable control population of cells. In some cases, TILs are administered when a pre-infusion testing yields at least about 200 pg/mL per $10^5$ cells of IFN$\gamma$ upon anti-CD3 stimulation of TILs in a potency test. In some cases, TILs are administered when a pre-infusion testing yields at least about 50 pg/mL per $10^5$ cells, 75 pg/mL per $10^5$ cells, 100 pg/mL per $10^5$ cells, 150 pg/mL per $10^5$ cells, 200 pg/mL per $10^5$ cells, 250 pg/mL per $10^5$ cells, 300 pg/mL per $10^5$ cells, or up to about 350 pg/mL per $10^5$ cells of IFN$\gamma$ upon anti-CD3 stimulation of TILs in a potency test.

In some cases, a population of TILs is tested for the presence of tumor cells in a composition. TILs that can be administered can be negative for tumor cells per at least about 200 TILs examined in a cytopathology testing. In other cases, less than 1% of tumor cells exist per at least about 200 TILs examined in a cytopathology testing. In other cases, less than 2% of tumor cells exist per at least about 200 TILs examined in a cytopathology testing. In other cases, less than 3% of tumor cells exist per at least about 200 TILs examined in a cytopathology testing. In other cases, less than 4% of tumor cells exist per at least about 200 TILs examined in a cytopathology testing. In other cases, less than 5% of tumor cells exist per at least about 200 TILs examined in a cytopathology testing.

CRISPR System

Methods described herein can take advantage of a CRISPR system. There are at least five types of CRISPR systems which all incorporate RNAs and Cas proteins. Types I, III, and IV assemble a multi-Cas protein complex that is capable of cleaving nucleic acids that are complementary to the crRNA. Types I and III both require pre-crRNA processing prior to assembling the processed crRNA into the multi-Cas protein complex. Types II and V CRISPR systems comprise a single Cas protein complexed with at least one guiding RNA.

The general mechanism and recent advances of CRISPR system is discussed in Cong, L. et al., "Multiplex genome engineering using CRISPR systems," Science, 339(6121): 819-823 (2013); Fu, Y. et al., "High-frequency off-target mutagenesis induced by CRISPR-Cas nucleases in human cells," Nature Biotechnology, 31, 822-826 (2013); Chu, V T et al. "Increasing the efficiency of homology-directed repair for CRISPR-Cas9-induced precise gene editing in mammalian cells," Nature Biotechnology 33, 543-548 (2015); Shmakov, S. et al., "Discovery and functional characterization of diverse Class 2 CRISPR-Cas systems," Molecular Cell, 60, 1-13 (2015); Makarova, K S et al., "An updated evolutionary classification of CRISPR-Cas systems,", Nature Reviews Microbiology, 13, 1-15 (2015). Site-specific cleavage of a target DNA occurs at locations determined by both 1) base-pairing complementarity between the guide RNA and the target DNA (also called a protospacer) and 2) a short motif in the target DNA referred to as the protospacer adjacent motif (PAM). For example, an engineered cell can be generated using a CRISPR system, e.g., a type II CRISPR system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to 20 nucleotides of a guide sequence and that have a protospacer-adjacent motif (PAM) following the 20 nucleotides of the target sequence.

In some cases, a CRISPR system may introduce a mutation. A mutation can be an insertion or deletion. For example a CRISPR system may introduce a 1bp insertion comprising at least a portion of CISH. In some cases, manipulation of TIL with a CRISPR system may not have a negative effect on TIL expansion post-electroporation of a CRISPR system. In some cases, to determine whether an observed knockout frequency at the genetic level correlates with loss of protein, the expression of protein, such as CISH protein, after CRISPR knockout can be evaluated. For example, peripheral blood (PB) T-cells and TILs can be re-stimulated at day 14 post-electroporation using plate bound anti-CD3 and soluble anti-CD28 antibody and the loss of protein, for example CISH protein, by flow cytometry and western blot can be assessed. In some cases, CRISPR modified PB T-cells and TILs can be expanded for 14 days and then re-stimulated for 48 hrs. Cells can be collected and extracts analyzed by western blot as CISH is an intracellular protein. Consistent with a high rate of knockout by TiDE analysis of genomic modification, a protein, such as CISH, can be essentially absent or reduced in knockout circulating T-cells and TILs.

I. Cas Protein

A vector can be operably linked to an enzyme-coding sequence encoding a CRISPR enzyme, such as a Cas protein (CRISPR-associated protein). Non-limiting examples of Cas proteins can include Cas1, Cas1B, Cas2, Cas3, Cas4, Cas5, Cas6, Cas7, Cas8, Cas9 (also known as Csn1 or Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Cpf1, c2c1, c2c3, Cas9HiFi, homologues thereof, or modified versions thereof. In some cases a catalytically dead Cas protein can be used, for example a dCas9. An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within or within about 1, 2, 3, 4, 5, 6, 7, 8, 9, 10, 15, 20, 25, 50, 100, 200, 500, or more base pairs from the first or last nucleotide of a target sequence. A vector that encodes a CRISPR enzyme that is mutated with respect to a corresponding wild-type enzyme such that the mutated CRISPR enzyme lacks the ability to cleave one or both strands of a target polynucleotide containing a target sequence can be used. A Cas protein can be a high fidelity Cas protein such as Cas9HiFi. In some cases, a Cas protein can be modified. For example, a Cas protein can be N7-Methyl-Gppp (2'-O-Methyl-A). In some cases, a Cas protein, such as a Cas9 protein, can be sequenced prior to clinical use. For example, a purified in vitro transcription product can be assessed by polyacrylamide gel electrophoresis to verify no other mRNA species exist within a clinical product other than Cas9. Additionally, purified mRNA encoding a Cas protein, such as Cas9, can undergo a validation by reverse-transcription followed by sequencing to verify an identity at a nucleotide level. A Cas sequence can contain a nuclear localization sequence (NLS). A nuclear localization sequence can be from SV40. An NLS can be from at least one of: SV40, nucleoplasmin, importin alpha, C-myc, EGL-13, TUS, BORG, hnRNPA1, Mata2, or PY-NLS. An NLS can be on a C-terminus or an N-terminus of a Cas protein. In some cases, a Cas protein may contain from 1 to 5 NLS sequences. A Cas protein can contain 1, 2, 3, 4, 5, 6, 7, 8, 9, or up to 10 NLS sequences. A Cas protein, such as Cas9 may contain two NLS sequences. A Cas protein may contain a SV40 and nuceloplasmin NLS sequence. A Cas protein may also contain at least one untranslated region.

TABLE 2

*Streptococcus pyogenes* Cas9 (SpCas9)

| SEQ ID | Sequence |
|---|---|
| 62 | ATGGACTATAAGGACCACGACGGAGACTACAAGGATCATG ATATTGATTACAAAGACGATGACGATAAGATGGCCCCAAA GAAGAAGCGGAAGGTCGGTATCCACGGAGTCCCAGCAGCC GACAAGAAGTACAGCATCGGCCTGGACATCGGCACCAACT CTGTGGGCTGGGCCGTGATCACCGACG |

TABLE 3

Modified *Streptococcus pyogenes* Cas9 mRNA

| SEQ ID | Sequence |
|---|---|
| 63 | GGAAATAAGAGAGAAAAGAAGAGTAAGAAGAAATATAAGA GCCACCATGGCCCCAAAGAAGAAGCGGAAGGTCGGTATCC ACGGAGTCCCAGCAGCCGACAAGAAGTACAGCATCGGCCT GGACATCGGCACCAACTCTGTGGGCTGGGCCGTGATCACC GACGAGTACAAGGTGCCCAGCAAGAAATTCAAGGTGCTGG GCAACACCGACCGGCACAGCATCAAGAAGAACCTGATCGG AGCCCTGCTGTTCGACAGCGGCGAAACAGCCGAGGCCACC CGGCTGAAGAGAACCGCCAGAAGAAGATACACCAGACGGA AGAACCGGATCTGCTATCTGCAAGAGATCTTCAGCAACGA GATGGCCAAGGTGGACGACAGCTTCTTCCACAGACTGGAA GAGTCCTTCCTGGTGGAAGAGGACAAGAAGCACGAGAGAC ACCCCATCTTCGGCAACATCGTGGACGAGGTGGCCTACCA CGAGAAGTACCCCACCATCTACCACCTGAGAAAGAAACTG GTGGACAGCACCGACAAGGCCGACCTGAGACTGATCTACC TGGCCCTGGCCCACATGATCAAGTTCAGAGGCCACTTCCT GATCGAGGGCGACCTGAACCCCGACAACAGCAGCGTGGAC AAGCTGTTCATCCAGCTGGTGCAGACCTACAACCAGCTGT TCGAGGAAAACCCCATCAACGCCAGCGGCGTGGACGCCAA GGCTATCCTGTCTGCCAGACTGAGCAAGAGCAGAAGGCTG GAAAATCTGATCGCCCAGCTGCCCGGCGAGAAGAAGAACG |

TABLE 3-continued

Modified *Streptococcus pyogenes* Cas9 mRNA

| SEQ ID | Sequence |
|---|---|
| | GCCTGTTCGGCAACCTGATTGCCCTGAGCCTGGGCCTGAC |
| | CCCCAACTTCAAGAGCAACTTCGACCTGGCCGAGGATGCC |
| | AAAACTGCAGCTGAGCAAGGACACCTACGACGACGACCTGG |
| | ACAACCTGCTGGCCCAGATCGGCGACCAGTACGCCGACCT |
| | GTTCCTGGCCGCCAAGAACCTGTCTGACGCCATCCTGCTG |
| | AGCGACATCCTGAGAGTGAACACCGAGATCACCAAGGCCC |
| | CCCTGAGCGCCTCTATGATCAAGAGATACGACGAGCACCA |
| | CCAGGACCTGACCCTGCTGAAAGCTCTCGTGCGGCAGCAG |
| | CTGCCTGAGAAGTACAAAGAAATCTTCTTCGACCAGAGCA |
| | AGAACGGCTACGCCGGCTACATCGATGGCGGCGCTAGCCA |
| | GGAAGAGTTCTACAAGTTCATCAAGCCCATCCTGGAAAAG |
| | ATGGACGGCACCGAGGAACTGCTCGTGAAGCTGAACAGAG |
| | AGGACCTGCTGAGAAAGCAGAGAACCTTCGACAACGGCAG |
| | CATCCCCCACCAGATCCACCTGGGAGAGCTGCACGCTATC |
| | CTGAGAAGGCAGGAAGATTTTTACCCATTCCTGAAGGACA |
| | ACCGGGAAAAGATCGAGAAGATCCTGACCTTCAGGATCCC |
| | CTACTACGTGGGCCCCCTGGCCAGAGGCAACAGCAGATTC |
| | GCCTGGATGACCAGAAGAGCGAGGAAACCATCACCCCCT |
| | GGAACTTCGAGGAAGTGGTGGACAAGGGCGCCAGCGCCCA |
| | GAGCTTCATCGAGAGAATGACAAACTTCGATAAGAACCTG |
| | CCCAACGAGAAGGTGCTGCCCAAGCACAGCCTGCTGTACG |
| | AGTACTTCACCGTGTACAACGAGCTGACCAAAGTGAAATA |
| | CGTGACCGAGGGAATGAGAAAGCCCGCCTTCCTGAGCGGC |
| | GAGCAGAAAAAGGCCATCGTGGACCTGCTGTTCAAGACCA |
| | ACAGAAAAGTGACCGTGAAGCAGCTGAAAGAGGACTACTT |
| | CAAGAAAATCGAGTGCTTCGACTCCGTGGAAATCTCCGGC |
| | GTGGAAGATAGATTCAACGCCTCCCTGGGCACATACCACG |
| | ATCTGCTGAAAATTATCAAGGACAAGGACTTCCTGGATAA |
| | CGAAGAGAACGAGGACATTCTGGAAGATATCGTGCTGACC |
| | CTGACACTGTTTGAGGACCGCGAGATGATCGAGGAAAGGC |
| | TGAAAACCTACGCTCACCTGTTCGACGACAAAGTGATGAA |
| | GCAGCTGAAGAGAAGGCGGTACACCGGCTGGGGCAGGCTG |
| | AGCAGAAAGCTGATCAACGGCATCAGAGACAAGCAGAGCG |
| | GCAAGACAATCCTGGATTTCCTGAAGTCCGACGGCTTCGC |
| | CAACCGGAACTTCATGCAGCTGATCCACGACGACAGCCTG |
| | ACATTCAAAGAGGACATCCAGAAAGCCCAGGTGTCCGGCC |
| | AGGGCGACTCTCTGCACGAGCATATCGCTAACCTGGCCGG |
| | CAGCCCCGCTATCAAGAAGGGCATCCTGCAGACAGTGAAG |
| | GTGGTGGACGAGCTCGTGAAAGTGATGGGCAGACACAAGC |
| | CCGAGAACATCGTGATCGAGATGGCTAGAGAGAACCAGAC |
| | CACCCAGAAGGGACAGAAGAACTCCCGCGAGAGGATGAAG |
| | AGAATCGAAGAGGGCATCAAAGAGCTGGGCAGCCAGATCC |
| | TGAAAGAACACCCCGTGGAAAACACCCAGCTGCAGAACGA |
| | GAAGCTGTACCTGTACTACCTGCAGAATGGCCGGGATATG |
| | TACGTGGACCAGGAACTGGACATCAACAGACTGTCCGACT |
| | ACGATGTGGACCATATCGTGCCTCAGAGCTTTCTGAAGGA |
| | CGACTCCATCGATAACAAAGTGCTGACTCGGAGCGACAAG |
| | AACAGAGGCAAGAGCGACAACGTGCCCTCCGAAGAGGTCG |
| | TGAAGAAGATGAAGAACTACTGGCGACAGCTGCTGAACGC |
| | CAAGCTGATTACCCAGAGGAAGTTCGATAACCTGACCAAG |
| | GCCGAGAGAGGCGGCCTGAGCGAGCTGGATAAGGCCGGCT |
| | TCATCAAGAGGCAGCTGGTGGAAACCAGACAGATCACAAA |
| | GCACGTGGCACAGATCCTGGACTCCCGGATGAACACTAAG |
| | TACGACGAAAACGATAAGCTGATCCGGGAAGTGAAAGTGA |
| | TCACCCTGAAGTCCAAGCTGGTGTCCGATTTCCGGAAGGA |
| | TTTCCAGTTTTACAAAGTGCGCGAGATCAACAACTACCAC |
| | CACGCCCACGACGCCTACCTGAACGCCGTCGTGGGAACCG |
| | CCCTGATCAAAAAGTACCCTAAGCTGGAAAGCGAGTTCGT |
| | GTACGGCGACTACAAGGTGTACGACGTGCGGAAGATGATC |
| | GCCAAGAGCGAGCAGGAAATCGGCAAGGCTACCGCCAAGT |
| | ACTTCTTCTACAGCAACATCATGAACTTTTTCAAGACCGA |
| | AATCACCCTGGCCAACGGCGAGATCAGAAAGCGCCCTCTG |
| | ATCGAGACAAACGGCGAAACCGGGGAGATCGTGTGGGATA |
| | AGGGCAGAGACTTCGCCACAGTGCGAAAGGTGCTGAGCAT |
| | GCCCCAAGTGAATATCGTGAAAAAGACCGAGGTGCAGACA |
| | GGCGGCTTCAGCAAAGAGTCTATCCTGCCCAAGAGGAACA |
| | GCGACAAGCTGATCGCCAGAAAGAAGGACTGGGACCCCAA |
| | GAAGTACGGCGGCTTCGACAGCCCTACCGTGGCCTACTCT |
| | GTGCTGGTGGTGGCTAAGGTGGAAAAGGGCAAGTCCAAGA |
| | AACTGAAGAGTGTGAAAGAGCTGCTGGGGATCACCATCAT |
| | GGAAAGAGCAGCTTTGAGAAGAACCCTATCGACTTTCTG |
| | GAAGCCAAGGGCTACAAAGAAGTGAAAAAGGACCTGATCA |
| | TCAAGCTGCCTAAGTACTCCCTGTTCGAGCTGGAAAACGG |
| | CAGAAAGAGAATGCTGGCCTCTGCCGGCGAACTGCAGAAG |
| | GGAAACGAGCTGGCCCTGCCTAGCAAATATGTGAACTTCC |
| | TGTACCTGGCCTCCCACTATGAGAAGCTGAAGGGCAGCCC |
| | TGAGGACAACGAACAGAAACAGCTGTTTGTGGAACAGCAT |
| | AAGCACTACCTGGACGAGATCATCGAGCAGATCAGCGAGT |
| | TCTCCAAGAGAGTGATCCTGGCCGACGCCAATCTGGACAA |
| | GGTGCTGTCTGCCTACAACAAGCACAGGGACAAGCCTATC |
| | AGAGAGCAGGCCGAGAATATCATCCACCTGTTCACCCTGA |
| | CAAACCTGGGCGCTCCTGCCGCCTTCAAGTACTTTGACAC |
| | CACCATCGACCGGAAGAGGTACACCAGCACCAAAGAGGTG |
| | CTGGACGCCACCCTGATCCACCAGAGCATCACCGGCCTGT |
| | ACGAGACAAGAATCGACCTGTCTCAGCTGGGAGGCGACAA |
| | GAGACCTGCCGCCACTAAGAAGGCCGGACAGGCCAAAAAG |
| | AAGAAGTGAGCGGCCGCTTAATTAAGCTGCCTTCTGCGGG |
| | GCTTGCCTTCTGGCCATGCCCTTCTTCTCTCCCTTGCACC |
| | TGTACCTCTTGGTCTTTGAATAAAGCCTGAGTAGGAAGAA |
| | AAAAAAAAAAAAAAAAAAAAAAAAAAAAAAAAAAAAAAAA |
| | AAAAAAAAAAAAAAAAAAAAAAAAAAAAAAAAAAAAAAAA |
| | AAAAAAAAAAAAAAAAAAAAAAAAAAAAAAAAAAAA |

Cas9 can refer to a polypeptide with at least or at least about 50%, 60%, 70%, 80%, 90%, 100% sequence identity and/or sequence similarity to a wild type exemplary Cas9 polypeptide (e.g., Cas9 from *S. pyogenes*). Cas9 can refer to a polypeptide with at most or at most about 50%, 60%, 70%, 80%, 90%, 100% sequence identity and/or sequence similarity to a wild type exemplary Cas9 polypeptide (e.g., from *S. pyogenes*). Cas9 can refer to the wild type or a modified form of the Cas9 protein that can comprise an amino acid change such as a deletion, insertion, substitution, variant, mutation, fusion, chimera, or any combination thereof.

A polynucleotide encoding an endonuclease (e.g., a Cas protein such as Cas9) can be codon optimized for expression in particular cells, such as eukaryotic cells. This type of optimization can entail the mutation of foreign-derived (e.g., recombinant) DNA to mimic the codon preferences of the intended host organism or cell while encoding the same protein.

A vector that encodes a CRISPR enzyme comprising one or more nuclear localization sequences (NLSs), such as more than or more than about 1, 2, 3, 4, 5, 6, 7, 8, 9, 10, NLSs can be used. For example, a CRISPR enzyme can comprise more than or more than about 1, 2, 3, 4, 5, 6, 7, 8, 9, 10, NLSs at or near the ammo-terminus, more than or more than about 1, 2, 3, 4, 5, 6, 7, 8, 9, 10, NLSs at or near the carboxyl-terminus, or any combination of these (e.g., one or more NLS at the ammo-terminus and one or more NLS at the carboxyl terminus). When more than one NLS is present, each can be selected independently of others, such that a single NLS can be present in more than one copy and/or in combination with one or more other NLSs present in one or more copies.

An NLS can be monopartite or bipartite. In some cases, a bipartite NLS can have a spacer sequence as opposed to a monopartite NLS. An NLS can be from at least one of: SV40, nucleoplasmin, importin alpha, C-myc, EGL-13, TUS, BORG, hnRNPA1, Mata2, or PY-NLS. An NLS can be located anywhere within the polypeptide chain, e.g., near the N- or C-terminus. For example, the NLS can be within or within about 1, 2, 3, 4, 5, 10, 15, 20, 25, 30, 40, 50 amino acids along a polypeptide chain from the N- or C-terminus. Sometimes the NLS can be within or within about 50 amino acids or more, e.g., 100, 200, 300, 400, 500, 600, 700, 800, 900, or 1000 amino acids from the N- or C-terminus.

An endonuclease can comprise an amino acid sequence having at least or at least about 50%, 60%, 70%, 75%, 80%, 85%, 90%, 95%, 99%, or 100%, amino acid sequence identity to the nuclease domain of a wild type exemplary site-directed polypeptide (e.g., Cas9 from *S. pyogenes*).

While *S. pyogenes* Cas9 (SpCas9), Table 2, is commonly used as a CRISPR endonuclease for genome engineering, it may not be the best endonuclease for every target excision site. For example, the PAM sequence for SpCas9 (5' NGG 3') is abundant throughout the human genome, but a NGG sequence may not be positioned correctly to target a desired gene for modification. In some cases, a different endonuclease may be used to target certain genomic targets. In some cases, synthetic SpCas9-derived variants with non-NGG PAM sequences may be used. Additionally, other Cas9 orthologues from various species have been identified and these "non-SpCas9s" bind a variety of PAM sequences that could also be useful for the present invention. For example, the relatively large size of SpCas9 (approximately 4 kb coding sequence) means that plasmids carrying the SpCas9 cDNA may not be efficiently expressed in a cell. Conversely, the coding sequence for *Staphylococcus aureus* Cas9 (SaCas9) is approximately 1 kilo base shorter than SpCas9, possibly allowing it to be efficiently expressed in a cell Similar to SpCas9, the SaCas9 endonuclease is capable of modifying target genes in mammalian cells in vitro and in mice in vivo.

Alternatives to *S. pyogenes* Cas9 may include RNA-guided endonucleases from the Cpf1 family that display cleavage activity in mammalian cells. Unlike Cas9 nucleases, the result of Cpf1-mediated DNA cleavage is a double-strand break with a short 3' overhang. Cpf1's staggered cleavage pattern may open up the possibility of directional gene transfer, analogous to traditional restriction enzyme cloning, which may increase the efficiency of gene editing. Like the Cas9 variants and orthologues described above, Cpf1 may also expand the number of sites that can be targeted by CRISPR to AT-rich regions or AT-rich genomes that lack the NGG PAM sites favored by SpCas9.

Any functional concentration of Cas protein can be introduced to a cell. For example, 15 micrograms of Cas mRNA can be introduced to a cell. In other cases, a Cas mRNA can be introduced from 0.5 micrograms to 100 micrograms. A Cas mRNA can be introduced from 0.5, 5, 10, 15, 20, 25, 30, 35, 40, 45, 50, 55, 60, 65, 70, 75, 80, 85, 90, 95, or 100 micrograms.

In some cases, a dual nickase approach may be used to introduce a double stranded break or a genomic break. Cas proteins can be mutated at known amino acids within either nuclease domains, thereby deleting activity of one nuclease domain and generating a nickase Cas protein capable of generating a single strand break. A nickase along with two distinct guide RNAs targeting opposite strands may be utilized to generate a DSB within a target site (often referred to as a "double nick" or "dual nickase" CRISPR system). This approach may dramatically increase target specificity, since it is unlikely that two off-target nicks will be generated within close enough proximity to cause a DSB.

A nuclease, such as Cas9, can be tested for identity and potency prior to use. For example, identity and potency can be determined using at least one of spectrophotometric analysis, RNA agarose gel analysis, LC-MS, endotoxin analysis, and sterility testing. In some cases, identity testing can determine an acceptable level for clinical/therapeutic use. For example, an acceptable spectrophotometric analysis result can be 105±10 µL/vial at 1.0±0.1 mg/mL. An acceptable spectrophotometric analysis result can also be from about 90-120±10 µL/vial at 1.0±0.1 mg/mL or from about 90-120±10 µL/vial at about 0.1 to 5.0±0.1 mg/mL.

In some cases, a nuclease, such as Cas9, can have a UV260/280 ratio of about 1.0±0.1. A UV260-280 ratio can be from about 1.0-5.0±0.1.

In some cases, a nuclease, such as Cas9, can have an integrity/size measured by RNA agarose gel analysis. A size of a Cas9 can be about 4500 bases. A size of a Cas9 can be from about 4000 to about 8000 bases. A size of a Cas9 can be from about 4000 to about 5000 bases, from about 5000 to about 6000 bases, from about 6000 to about 7000 bases, from about 7000 to about 8000 bases. In some cases, a bioanalyzer can be utilized to determine a size of a nuclease sequence, such as Cas9. A bioanalyzer can determine a size of a Cas9 sequence that can be from about 4000 to about 5000 bases, from about 5000 to about 6000 bases, from about 6000 to about 7000 bases, from about 7000 to about 8000 bases.

In some cases, an endotoxin level of a nuclease, such as Cas9, can be determined. An endotoxin testing can be a limulus assay. A clinically/therapeutically acceptable level of an endotoxin can be less than 3 EU/mL. A clinically/therapeutically acceptable level of an endotoxin can be less than 10 EU/mL. A clinically/therapeutically acceptable level of an endotoxin can be less than 8 EU/mL. A clinically/therapeutically acceptable level of an endotoxin can be less than 5 EU/mL. A clinically/therapeutically acceptable level of an endotoxin can be less than 4 EU/mL. A clinically/therapeutically acceptable level of an endotoxin can be less than 3 EU/mL. A clinically/therapeutically acceptable level of an endotoxin can be less than 2 EU/mL. A clinically/therapeutically acceptable level of an endotoxin can be less than 1 EU/mL. A clinically/therapeutically acceptable level of an endotoxin can be less than 0.5 EU/mL.

In some cases a nuclease, such as Cas9, can undergo sterility testing. A clinically/therapeutically acceptable level of a sterility testing can be 0 or denoted by no growth on a culture. A clinically/therapeutically acceptable level of a sterility testing can be less than 0.5% growth. A clinically/therapeutically acceptable level of a sterility testing can be less than 1% growth.

In some cases, a nuclease sequence, such as a Cas9 sequence can be sequenced to confirm its identity. For example, an input Cas9 mRNA transcription template can be sequenced at about a 4-fold coverage prior to a production of a Cas9 mRNA lot. A purified in vitro transcription produce can be assessed by polyacrylamide gel electrophoresis (PAGE) to verify that an mRNA is the size expected for Cas9 and no other mRNA species exist within a clinical or therapeutic product. In some cases, a purified mRNA will undergo a validation by reverse transcriptase (RT)-mediated reverse-transcription followed by DNA sequencing to verify identity at the nucleotide level.

In some cases, a potency of nuclease functionality can be tested with a trial run. For example, a Cas9 can be tested for functional potency in primary human T cells derived from three independent donors. Reagent delivery can be performed in the same fashion as for a patient sample. Potency can be determined by sequencing of the target genomic locus and indel frequency may meet or exceed 50% in each donor. In some cases, potency can be determined by sequencing of the target genomic locus and indel frequency may meet or exceed 60% in each donor. In some cases, potency can be determined by sequencing of the target genomic locus and indel frequency may meet or exceed 65% in each donor. In some cases, potency can be determined by sequencing of the target genomic locus and indel frequency may meet or exceed 70% in each donor. In some cases, potency can be determined by sequencing of the target genomic locus and indel frequency may meet or exceed 75% in each donor.

II. Guiding Polynucleic Acid

A guiding polynucleic acid can be DNA or RNA. A guiding polynucleic acid can be single stranded or double stranded. In some cases, a guiding polynucleic acid can contains regions of single stranded areas and double stranded areas. A guiding polynucleic acid can also form secondary structures. As used herein, the term "guide RNA (gRNA)," and its grammatical equivalents can refer to an RNA which can be specific for a target DNA and can form a complex with a Cas protein. A guide RNA can comprise a guide sequence, or spacer sequence, that specifies a target site and guides an RNA/Cas complex to a specified target DNA for cleavage. For example, a guide RNA can target a CRISPR complex to different genes and perform a targeted double strand break. Site-specific cleavage of a target DNA occurs at locations determined by both 1) base-pairing complementarity between a guide RNA and a target DNA (also called a protospacer) and 2) a short motif in a target DNA referred to as a protospacer adjacent motif (PAM). In some cases, gRNAs can be designed using an algorithm which can identify gRNAs located in early exons within commonly expressed transcripts. Candidate gRNAs can be ranked by off-target potential using a scoring system that can take into account: (a) the total number of mismatches between the gRNA sequence and any closely matching genomic sequences; (b) the mismatch position(s) relative to the PAM site which correlate with a negative effect on activity for mismatches falling close to the PAM site; (c) the distance between mismatches to account for the cumulative effect of neighboring mismatches in disrupting guide-DNA interactions; and any combination thereof. In some cases, a greater number of mismatches between a gRNA and a genomic target site can yield a lower potential for CRISPR-mediated cleavage of that site. In some cases, a mismatch position is directly adjacent to a PAM site. In other cases, a mismatch position can be from 1 nucleotide up to 100 kilobases away from a PAM site. Candidate gRNAs comprising mismatches may not be adjacent to a PAM in some cases. In other cases, at least two candidate gRNAs comprising mismatches may bind a genome from 1 nucleotide up to 100 kilobases away from each other. A mismatch can be a substitution of a nucleotide. For example, in some cases a G will be substituted for a T. Mismatches between a gRNA and a genome may allow for reduced fidelity of CRISPR gene editing. In some cases, a positive scoring gRNA can be about 110 nucleotides in length and may contain no mismatches to a complementary genome sequence. In other cases, a positive scoring gRNA can be about 110 nucleotides in length and may contain up to 3 mismatches to a complementary genome sequence. In other cases, a positive scoring gRNA can be about 110 nucleotides in length and may contain up to 20 mismatches to a complementary genome sequence. A guiding polynucleic acid can have at least or at least about 50%, 60%, 65%, 70%, 75%, 80%, 85%, 90%, 95%, 98%, or up to about 100% sequence identity and/or sequence similarity to any of the sequences of Table 4. In some cases, a guiding polynucleic acid can contain internucleotide linkages that can be phosphorothioates. Any number of phosphorothioates can exist. For example from 1 to about 100 phosphorothioates can exist in a guiding polynucleic acid sequence. In some cases from 1 to 10 phosphorothioates are present. In some cases, 0, 1, 2, 3, 4, 5, 6, 7, 8, 9, 10, 11, 12, 13, 14, 15, 16, 17, 18, 19, or 20 phosphorothioates exist in a guiding polynucleic acid sequence.

TABLE 4

Sequence listings for modified gRNAs targeting the PD-1, CTLA-4, AAVS1, or CISH genes.

| SEQ ID | gRNA | Sequence |
|---|---|---|
| 64 | PD-1 gRNA #2 | CCUGCUCGUGGUGACCGAAGGU UUUAGAGCUAGAAAUAGCAAGU UAAAAUAAGGCUAGUCCGUUAU CAACUUGAAAAAGUGGCACCGA GUCGGUGCUUUU |
| 65 | PD-1 gRNA #6 | ACGGAAGCGGCAGUCCUGGCGU UUUAGAGCUAGAAAUAGCAAGU UAAAAUAAGGCUAGUCCGUUAU CAACUUGAAAAAGUGGCACCGA GUCGGUGCUUUU |
| 66 | CTLA4 gRNA #3 | CUAGAUGAUUCCAUCUGCACGU UUUAGAGCUAGAAAUAGCAAGU UAAAAUAAGGCUAGUCCGUUAU CAACUUGAAAAAGUGGCACCGA GUCGGUGCUUUU |
| 67 | CTLA4 gRNA #2 | GUGCGGCAACCUACAUGAUGGU UUUAGAGCUAGAAAUAGCAAGU UAAAAUAAGGCUAGUCCGUUAU CAACUUGAAAAAGUGGCACCGA GUCGGUGCUUUU |
| 68 | CISH gRNA #2 | GGGUUCCAUUACGGCCAGCGGU UUUAGAGCUAGAAAUAGCAAGU UAAAAUAAGGCUAGUCCGUUAU CAACUUGAAAAAGUGGCACCGA GUCGGUGCUUUU |
| 69 | AAVS1 | GUCACCAAUCCUGUCCCUAGGU UUUAGAGCUAGAAAUAGCAAGU UAAAAUAAGGCUAGUCCGUUAU CAACUUGAAAAAGUGGCACCGA GUCGGUGCUUUU |

In some cases, top scoring gRNAs can be designed and selected and an on-target editing efficiency of each can be assessed experimentally in patient derived TIL and peripheral blood-derived T cells. In some cases, an editing efficiency as determined by TiDE analysis can exceed at least about 20%. In other cases, and editing efficiency can be from about 20% to from about 50%, from about 50% to from about 80%, from about 80% to from about 100%. In some cases, editing efficiency as measured by TiDE can be 85% for PD-1 and 90% for CISH. In some cases, a percent indel can be determined in a trial GMP run. For example, a final cellular product can be analyzed for on-target indel formation by Sanger sequencing and TIDE analysis. Genomic DNA can be extracted from about $1 \times 10^6$ cells from both a control and experimental sample and subjected to PCR using primers flanking a gene that has been disrupted, such as CISH. Sanger sequencing chromatogramps can be analyzed using a TIDE software program that can quantify indel frequency and size distribution of indels by comparison of control and knockout samples.

A method disclosed herein also can comprise introducing into a cell or embryo at least one guide RNA or nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-guide RNA (sgRNA) formed by fusion of a portion (e.g., a functional portion) of crRNA and tracrRNA. A guide RNA can also be a dual RNA comprising a crRNA and a tracrRNA. A guide RNA can comprise a crRNA and lack a tracrRNA. Furthermore, a crRNA can hybridize with a target DNA or protospacer sequence.

As discussed above, a guide RNA can be an expression product. For example, a DNA that encodes a guide RNA can be a vector comprising a sequence coding for the guide RNA. A guide RNA can be transferred into a cell or organism by transfecting the cell or organism with an isolated guide RNA or plasmid DNA comprising a sequence coding for the guide RNA and a promoter. A guide RNA can also be transferred into a cell or organism in other way, such as using virus-mediated gene delivery.

A guide RNA can be isolated. For example, a guide RNA can be transfected in the form of an isolated RNA into a cell or organism. A guide RNA can be prepared by in vitro transcription using any in vitro transcription system. A guide RNA can be transferred to a cell in the form of isolated RNA rather than in the form of plasmid comprising encoding sequence for a guide RNA.

A guide RNA can comprise a DNA-targeting segment and a protein binding segment. A DNA-targeting segment (or DNA-targeting sequence, or spacer sequence) comprises a nucleotide sequence that can be complementary to a specific sequence within a target DNA (e.g., a protospacer). A protein-binding segment (or protein-binding sequence) can interact with a site-directed modifying polypeptide, e.g. an RNA-guided endonuclease such as a Cas protein. By "segment" it is meant a segment/section/region of a molecule, e.g., a contiguous stretch of nucleotides in an RNA. A segment can also mean a region/section of a complex such that a segment may comprise regions of more than one molecule. For example, in some cases a protein-binding segment of a DNA-targeting RNA is one RNA molecule and the protein-binding segment therefore comprises a region of that RNA molecule. In other cases, the protein-binding segment of a DNA-targeting RNA comprises two separate molecules that are hybridized along a region of complementarity.

A guide RNA can comprise two separate RNA molecules or a single RNA molecule. An exemplary single molecule guide RNA comprises both a DNA-targeting segment and a protein-binding segment.

An exemplary two-molecule DNA-targeting RNA can comprise a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A first RNA molecule can be a crRNA-like molecule (targeter-RNA), that can comprise a DNA-targeting segment (e.g., spacer) and a stretch of nucleotides that can form one half of a double-stranded RNA (dsRNA) duplex comprising the protein-binding segment of a guide RNA. A second RNA molecule can be a corresponding tracrRNA-like molecule (activator-RNA) that can comprise a stretch of nucleotides that can form the other half of a dsRNA duplex of a protein-binding segment of a guide RNA. In other words, a stretch of nucleotides of a crRNA-like molecule can be complementary to and can hybridize with a stretch of nucleotides of a tracrRNA-like molecule to form a dsRNA duplex of a protein-binding domain of a guide RNA. As such, each crRNA-like molecule can be said to have a corresponding tracrRNA-like molecule. A crRNA-like molecule additionally can provide a single stranded DNA-targeting segment, or spacer sequence. Thus, a crRNA-like and a tracrRNA-like molecule (as a corresponding pair) can hybridize to form a guide RNA. A subject two-molecule guide RNA can comprise any corresponding crRNA and tracrRNA pair.

A DNA-targeting segment or spacer sequence of a guide RNA can be complementary to sequence at a target site in a chromosomal sequence, e.g., protospacer sequence such that the DNA-targeting segment of the guide RNA can base pair with the target site or protospacer. In some cases, a DNA-targeting segment of a guide RNA can comprise from or from about 10 nucleotides to from or from about 25 nucleotides or more. For example, a region of base pairing between a first region of a guide RNA and a target site in a chromosomal sequence can be or can be about 10, 11, 12, 13, 14, 15, 16, 17, 18, 19, 20, 22, 23, 24, 25, or more than 25 nucleotides in length. Sometimes, a first region of a guide RNA can be or can be about 19, 20, or 21 nucleotides in length.

A guide RNA can target a nucleic acid sequence of or of about 20 nucleotides. A target nucleic acid can be less than or less than about 20 nucleotides. A target nucleic acid can be at least or at least about 5, 10, 15, 16, 17, 18, 19, 20, 21, 22, 23, 24, 25, 30 or more nucleotides. A target nucleic acid can be at most or at most about 5, 10, 15, 16, 17, 18, 19, 20, 21, 22, 23, 24, 25, 30 or more nucleotides. A target nucleic acid sequence can be or can be about 20 bases immediately 5' of the first nucleotide of the PAM. A guide RNA can target the nucleic acid sequence. A guiding polynucleic acid, such as a guide RNA, can bind to a genomic sequence with at least or at least about 50%, 60%, 65%, 70%, 75%, 80%, 85%, 90%, 95%, 98%, or up to about 100% sequence identity and/or sequence similarity to any of the sequences of Table 5 or Table 6. In some cases, a guiding polynucleic acid, such as a guide RNA, can bind a genomic region from about 1 basepair to about 20 basepairs away from a PAM. A guide can bind a genomic region from about 1, 2, 3, 4, 5 6, 7, 8, 9, 10, 11, 12, 13, 14, 15, 16, 17, 18, 19, or up to about 20 base pairs away from a PAM.

TABLE 5

Engineered CISH guide RNA (gRNA) target sequences

| SEQ ID | gRNA No. | Exon | Target 5'-3' |
|---|---|---|---|
| 70 | 1 | 2 | TTGCTGGCTGTGGAGCGGAC |
| 71 | 2 | 2 | GACTGGCTTGGGCAGTTCCA |
| 72 | 3 | 2 | TGCTGGGGCCTTCCTCGAGG |
| 73 | 4 | 2 | CCGAAGGTAGGAGAAGGTCT |
| 74 | 5 | 2 | ATGCACAGCAGATCCTCCTC |
| 75 | 6 | 2 | AGAGAGTGAGCCAAAGGTGC |
| 76 | 1 | 3 | GGCATACTCAATGCGTACAT |
| 77 | 2 | 3 | GGGTTCCATTACGGCCAGCG |
| 78 | 3 | 3 | AAGGCTGACCACATCCGGAA |
| 79 | 4 | 3 | TGCCGACTCCAGCTTCCGTC |
| 80 | 5 | 3 | CTGTCAGTGAAAACCACTCG |
| 81 | 6 | 3 | CGTACTAAGAACGTGCCTTC |

Genomic sequences that are targeted by engineered gRNAs are shown in Table 5 and Table 6. FIG. 22 shows modified gRNA targeting the CISH gene.

TABLE 6

AAVS1 gRNA target sequence

| SEQ ID | Gene | gRNA Sequence (5' to 3') |
|---|---|---|
| 82 | AAVS1 | GTCACCAATCCTGTCCCTAG- |

A guide nucleic acid, for example, a guide RNA, can refer to a nucleic acid that can hybridize to another nucleic acid, for example, the target nucleic acid or protospacer in a genome of a cell. A guide nucleic acid can be RNA. A guide nucleic acid can be DNA. The guide nucleic acid can be programmed or designed to bind to a sequence of nucleic acid site-specifically. A guide nucleic acid can comprise a polynucleotide chain and can be called a single guide nucleic acid. A guide nucleic acid can comprise two polynucleotide chains and can be called a double guide nucleic acid.

A guide nucleic acid can comprise one or more modifications to provide a nucleic acid with a new or enhanced feature. A guide nucleic acid can comprise a nucleic acid affinity tag. A guide nucleic acid can comprise synthetic nucleotide, synthetic nucleotide analog, nucleotide derivatives, and/or modified nucleotides.

A guide nucleic acid can comprise a nucleotide sequence (e.g., a spacer), for example, at or near the 5' end or 3' end, that can hybridize to a sequence in a target nucleic acid (e.g., a protospacer). A spacer of a guide nucleic acid can interact with a target nucleic acid in a sequence-specific manner via hybridization (i.e., base pairing). A spacer sequence can hybridize to a target nucleic acid that is located 5' or 3' of a protospacer adjacent motif (PAM). The length of a spacer sequence can be at least or at least about 5, 10, 15, 16, 17, 18, 19, 20, 21, 22, 23, 24, 25, 30 or more nucleotides. The length of a spacer sequence can be at most or at most about 5, 10, 15, 16, 17, 18, 19, 20, 21, 22, 23, 24, 25, 30 or more nucleotides.

A guide RNA can also comprises a dsRNA duplex region that forms a secondary structure. For example, a secondary structure formed by a guide RNA can comprise a stem (or hairpin) and a loop. A length of a loop and a stem can vary. For example, a loop can range from about 3 to about 10 nucleotides in length, and a stem can range from about 6 to about 20 base pairs in length. A stem can comprise one or more bulges of 1 to about 10 nucleotides. The overall length of a second region can range from about 16 to about 60 nucleotides in length. For example, a loop can be or can be about 4 nucleotides in length and a stem can be or can be about 12 base pairs. A dsRNA duplex region can comprise a protein-binding segment that can form a complex with an RNA-binding protein, such as a RNA-guided endonuclease, e.g. Cas protein.

A guide RNA can also comprise a tail region at the 5' or 3' end that can be essentially single-stranded. For example, a tail region is sometimes not complementarity to any chromosomal sequence in a cell of interest and is sometimes not complementarity to the rest of a guide RNA. Further, the length of a tail region can vary. A tail region can be more than or more than about 4 nucleotides in length. For example, the length of a tail region can range from or from about 5 to from or from about 60 nucleotides in length.

A guide RNA can be introduced into a cell or embryo as an RNA molecule. For example, a RNA molecule can be transcribed in vitro and/or can be chemically synthesized. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III).

A DNA molecule encoding a guide RNA can also be linear. A DNA molecule encoding a guide RNA can also be circular. A DNA sequence encoding a guide RNA can also be part of a vector. Some examples of vectors can include plasmid vectors, phagemids, cosmids, artificial/mini-chromosomes, transposons, and viral vectors. For example, a DNA encoding a RNA-guided endonuclease is present in a plasmid vector. Other non-limiting examples of suitable plasmid vectors include pUC, pBR322, pET, pBluescript, and variants thereof. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like.

When both a RNA-guided endonuclease and a guide RNA are introduced into a cell as DNA molecules, each can be part of a separate molecule (e.g., one vector containing fusion protein coding sequence and a second vector containing guide RNA coding sequence) or both can be part of a same molecule (e.g., one vector containing coding (and regulatory) sequence for both a fusion protein and a guide RNA).

A Cas protein, such as a Cas9 protein or any derivative thereof, can be pre-complexed with a guide RNA to form a ribonucleoprotein (RNP) complex. The RNP complex can be introduced into primary immune cells. Introduction of the RNP complex can be timed. The cell can be synchronized with other cells at G1, S, and/or M phases of the cell cycle. The RNP complex can be delivered at a cell phase such that HDR is enhanced. The RNP complex can facilitate homology directed repair.

A guide RNA can also be modified. The modifications can comprise chemical alterations, synthetic modifications, nucleotide additions, and/or nucleotide subtractions. The modifications can also enhance CRISPR genome engineering. A modification can alter chirality of a gRNA. In some cases, chirality may be uniform or stereopure after a modification. A guide RNA can be synthesized. The synthesized guide RNA can enhance CRISPR genome engineering. A guide RNA can also be truncated. Truncation can be used to reduce undesired off-target mutagenesis. The truncation can comprise any number of nucleotide deletions. For example, the truncation can comprise 1, 2, 3, 4, 5, 10, 15, 20, 25, 30, 40, 50 or more nucleotides. A guide RNA can comprise a region of target complementarity of any length. For example, a region of target complementarity can be less than 20 nucleotides in length. A region of target complementarity can be more than 20 nucleotides in length. A region of target complementarity can target from about 5 bp to about 20 bp directly adjacent to a PAM sequence. A region of target complementarity can target about 13 bp directly adjacent to a PAM sequence.

In some cases, a potency of a guiding polynucleic acid can be tested with a trial run. For example, a guiding polynucleic acid can be tested for functional potency in primary human T cells derived from three independent donors. Reagent delivery can be performed in the same fashion as for a patient sample. Potency can be determined by sequencing of the target genomic locus and indel frequency may meet or exceed 50% in each donor. In some cases, potency can be determined by sequencing of the target genomic locus and indel frequency may meet or exceed 60% in each donor. In some cases, potency can be determined by sequencing of the target genomic locus and indel frequency may meet or exceed 65% in each donor. In some cases, potency can be determined by sequencing of the target genomic locus and indel frequency may meet or exceed 70% in each donor. In some cases, potency can be determined by sequencing of the target genomic locus and indel frequency may meet or exceed 75% in each donor.

A CRISPR system can be introduced into a cell or pluarality of cells using any means. In some cases, a CRISPR system may be introduced by electroporation or nucleofection. Electroporation can be performed for example, using the Neon® Transfection System (ThermoFisher Scientific) or the AMAXA® Nucleofector (AMAXA® Biosystems) can also be used for delivery of nucleic acids into a cell. Electroporation parameters may be adjusted to optimize transfection efficiency and/or cell viability. Electroporation devices can have multiple electrical wave form pulse settings such as exponential decay, time constant and square wave. Every cell type has a unique optimal Field Strength (E) that is dependent on the pulse parameters applied (e.g., voltage, capacitance and resistance). Application of optimal field strength causes electropermeabilization through induction of transmembrane voltage, which allows nucleic acids to pass through the cell membrane. In some cases, the electroporation pulse voltage, the electroporation pulse width, number of pulses, cell density, and tip type may be adjusted to optimize transfection efficiency and/or cell viability.

In some cases, a Neon transfection system may be utilized. A Neon system can be a three-component electroporation apparatus comprising a central control module, an electroporation chamber that can be connected to a central control module by a 3-foot-long electrical cord, and a specialized pipette. In some cases, a specialized pipette can be fitted with exchangeable and/or disposable sterile tips. In some cases, an electroporation chamber can be fitted with exchangeable/disposable sterile electroporation cuvettes. In some cases, standard electroporation buffers supplied by a manufacturer of a system, such as a Neon system, can be replaced with GMP qualified solutions and buffers. In some cases, a standard electroporation buffer can be replaced with GMP grade phosphate buffered saline (PBS). A self-diagnostic system check can be performed on a control module prior to initiation of sample electroporation to ensure the Neon system is properly functioning. In some cases, a transfection can be performed in a class 1,000 biosafety cabinet within a class 10,000 clean room in a cGMP facility. Trained medical technologists can use aseptic technique throughout an entire manufacturing process, and the product can be ultimately tested for sterility.

In some cases, electroporation pulse voltage may be varied to optimize transfection efficiency and/or cell viability. In some cases, the electroporation voltage may be less than about 500 volts. In some cases, the electroporation voltage may be at least about 500 volts, at least about 600 volts, at least about 700 volts, at least about 800 volts, at least about 900 volts, at least about 1000 volts, at least about 1100 volts, at least about 1200 volts, at least about 1300 volts, at least about 1400 volts, at least about 1500 volts, at least about 1600 volts, at least about 1700 volts, at least about 1800 volts, at least about 1900 volts, at least about 2000 volts, at least about 2100 volts, at least about 2200 volts, at least about 2300 volts, at least about 2400 volts, at least about 2500 volts, at least about 2600 volts, at least about 2700 volts, at least about 2800 volts, at least about 2900 volts, or at least about 3000 volts. In some cases, the electroporation pulse voltage required for optimal transfection efficiency and/or cell viability may be specific to the cell type. For example, an electroporation voltage of 1900 volts may optimal (e.g., provide the highest viability and/or transfection efficiency) for macrophage cells. In another example, an electroporation voltage of about 1350 volts may optimal (e.g., provide the highest viability and/or transfection efficiency) for Jurkat cells or primary human cells such as T cells. In some cases, a range of electroporation voltages may be optimal for a given cell type. For example, an electroporation voltage between about 1000 volts and about 1300 volts may optimal (e.g., provide the highest viability and/or transfection efficiency) for human 578T cells.

In some cases, electroporation pulse width may be varied to optimize transfection efficiency and/or cell viability. In some cases, the electroporation pulse width may be less than about 5 milliseconds. In some cases, the electroporation width may be at least about 5 milliseconds, at least about 6 milliseconds, at least about 7 milliseconds, at least about 8 milliseconds, at least about 9 milliseconds, at least about 10 milliseconds, at least about 11 milliseconds, at least about 12 milliseconds, at least about 13 milliseconds, at least about 14 milliseconds, at least about 15 milliseconds, at least about 16 milliseconds, at least about 17 milliseconds, at least about 18 milliseconds, at least about 19 milliseconds, at least about 20 milliseconds, at least about 21 milliseconds, at least about 22 milliseconds, at least about 23 milliseconds, at least about 24 milliseconds, at least about 25 milliseconds, at least about 26 milliseconds, at least about 27 milliseconds, at least about 28 milliseconds, at least about 29 milliseconds, at least about 30 milliseconds, at least about 31 milliseconds, at least about 32 milliseconds, at least about 33 milliseconds, at least about 34 milliseconds, at least about 35 milliseconds, at least about 36 milliseconds, at least about 37 milliseconds, at least about 38 milliseconds, at least about 39 milliseconds, at least about 40 milliseconds, at least about 41 milliseconds, at least about 42 milliseconds, at least about 43 milliseconds, at least about 44 milliseconds, at least about 45 milliseconds, at least about 46 milliseconds, at least about 47 milliseconds, at least about 48 milliseconds, at least about 49 milliseconds, or at least about 50 milliseconds. In some cases, the electroporation pulse width required for optimal transfection efficiency and/or cell viability may be specific to the cell type. For example, an electroporation pulse width of 30 milliseconds may optimal (e.g., provide the highest viability and/or transfection efficiency) for macrophage cells. In another example, an electroporation width of about 10 milliseconds may optimal (e.g., provide the highest viability and/or transfection efficiency) for Jurkat cells. In some cases, a range of electroporation widths may be optimal for a given cell type. For example, an electroporation width between about 20 milliseconds and about 30 milliseconds may optimal (e.g., provide the highest viability and/or transfection efficiency) for human 578T cells.

In some cases, the number of electroporation pulses may be varied to optimize transfection efficiency and/or cell viability. In some cases, electroporation may comprise a single pulse. In some cases, electroporation may comprise more than one pulse. In some cases, electroporation may comprise 2 pulses, 3 pulses, 4 pulses, 5 pulses 6 pulses, 7 pulses, 8 pulses, 9 pulses, or 10 or more pulses. In some cases, the number of electroporation pulses required for optimal transfection efficiency and/or cell viability may be specific to the cell type. For example, electroporation with a single pulse may be optimal (e.g., provide the highest viability and/or transfection efficiency) for macrophage cells. In another example, electroporation with a 3 pulses may be optimal (e.g., provide the highest viability and/or transfection efficiency) for primary cells. In some cases, a range of electroporation widths may be optimal for a given cell type. For example, electroporation with between about 1 to about 3 pulses may be optimal (e.g., provide the highest viability and/or transfection efficiency) for human cells. The efficiency of genomic disruption of cells with any of the nucleic acid delivery platforms described herein, for example, nucleofection or electroporation, can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%.

In some cases, a starting cell density for electroporation may be varied to optimize transfection efficiency and/or cell viability. In some cases, the starting cell density for electroporation may be less than about $1 \times 10^5$ cells. In some cases, the starting cell density for electroporation may be at least about $1 \times 10^5$ cells, at least about $2 \times 10^5$ cells, at least about $3 \times 10^5$ cells, at least about $4 \times 10^5$ cells, at least about $5 \times 10^5$ cells, at least about $6 \times 10^5$ cells, at least about $7 \times 10^5$ cells, at least about $8 \times 10^5$ cells, at least about $9 \times 10^5$ cells, at least about $1 \times 10^6$ cells, at least about $1.5 \times 10^6$ cells, at least about $2 \times 10^6$ cells, at least about $2.5 \times 10^6$ cells, at least about $3 \times 10^6$ cells, at least about $3.5 \times 10^6$ cells, at least about $4 \times 10^6$ cells, at least about $4.5 \times 10^6$ cells, at least about $5 \times 10^6$ cells, at least about $5.5 \times 10^6$ cells, at least about $6 \times 10^6$ cells, at least about $6.5 \times 10^6$ cells, at least about $7 \times 10^6$ cells, at least about $7.5 \times 10^6$ cells, at least about $8 \times 10^6$ cells, at least about $8.5 \times 10^6$ cells, at least about $9 \times 10^6$ cells, at least about $9.5 \times 10^6$ cells, at least about $1 \times 10^7$ cells, at least about $1.2 \times 10^7$ cells, at least about $1.4 \times 10^7$ cells, at least about $1.6 \times 10^7$ cells, at least about $1.8 \times 10^7$ cells, at least about $2 \times 10^7$ cells, at least about $2.2 \times 10^7$ cells, at least about $2.4 \times 10^7$ cells, at least about $2.6 \times 10^7$ cells, at least about $2.8 \times 10^7$ cells, at least about $3 \times 10^7$ cells, at least about $3.2 \times 10^7$ cells, at least about $3.4 \times 10^7$ cells, at least about $3.6 \times 10^7$ cells, at least about $3.8 \times 10^7$ cells, at least about $4 \times 10^7$ cells, at least about $4.2 \times 10^7$ cells, at least about $4.4 \times 10^7$ cells, at least about $4.6 \times 10^7$ cells, at least about $4.8 \times 10^7$ cells, or at least about $5 \times 10^7$ cells. In some cases, the starting cell density for electroporation required for optimal transfection efficiency and/or cell viability may be specific to the cell type. For example, a starting cell density for electroporation of $1.5 \times 10^6$ cells may optimal (e.g., provide the highest viability and/or transfection efficiency) for macrophage cells. In another example, a starting cell density for electroporation of $5 \times 10^6$ cells may optimal (e.g., provide the highest viability and/or transfection efficiency) for human cells. In some cases, a range of starting cell densities for electroporation may be optimal for a given cell type. For example, a starting cell density for electroporation between of $5.6 \times 10^6$ and $5 \times 10^7$ cells may optimal (e.g., provide the highest viability and/or transfection efficiency) for human cells such as T cells.

In some cases, a GUIDE-Seq analysis can be performed to determine the specificity of engineered guide RNAs. The general mechanism and protocol of GUIDE-Seq profiling of off-target cleavage by CRISPR system nucleases is discussed in Tsai, S. et al., "GUIDE-Seq enables genome-wide profiling of off-target cleavage by CRISPR system nucleases," Nature, 33: 187-197 (2015). To assess off-target frequencies by next generation sequencing human primary T cells can be transfected with Cas9 mRNA and a guiding RNA, such as anti-CISH gRNA. Genomic DNA can be isolated from transfected cells from about 72 hours post transfection and PCR amplified at potential off-target sites. A potential off-target site can be predicted using the Wellcome Trust Sanger Insisute Genome Editing database (WGE) algorithm. Candidate off-target sites can be chosen based on sequence homology to an on-target site. In some cases, sites with about 4 or less mismatches between a gRNA and a genomic target site can be utilized. For each candidate off-target site, two primer pairs can be designed. PCR amplicons can be obtained from both untreated (control) and Cas9/gRNA-treated cells. PCR amplicons can be pooled. NGS libraries can be prepared using TruSeq Nano DNA library preparation kit (Illumina). Samples can be analyzed on an Illumina HiSeq machine using a 250 bp paired-end workflow. In some cases, from about 40 million mappable NGS reads per gRNA library can be acquired. This can equate to an average number of about 450,000 reads for each candidate off-target site of a gRNA. In some cases, detection of CRISPR-mediated disruption can be at a frequency as low as 1%, 0.9%, 0.8%, 0.7%, 0.6%, 0.5%, 0.4%, 0.3%, 0.2%, or 0.1% at a genomic locus.

Computational predictions can be used to select candidate gRNAs likely to be the safest choice for a targeted gene, such as PD-1 and/or CISH functional disruption. Candidate gRNAs can then tested empirically using a focused approach steered by computational predictions of potential off-target sites. In some cases, an assessment of gRNA off-target safety can employ a next-generation deep sequencing approach to analyze the potential off-target sites predicted by the CRISPR design tool for each gRNA. In some cases, gRNAs can be selected with fewer than 3 mismatches to any sequence in the genome (other than the perfect matching intended target). In some cases, a gRNA can be selected with fewer than 50, 40, 30, 20, 10, 5, 4, 3, 2, or 1 mismatch(es) to any sequence in a genome. In some cases, a computer system or software can be utilized to provide recommendations of candidate gRNAs with predictions of low off-target potential.

In some cases, potential off-target sites can be identified with at least one of: GUIDE-Seq and targeted PCR amplification, and next generation sequencing. In addition, modified cells, such as Cas9/gRNA-treated cells can be subjected to karyotyping to identify any chromosomal re-arrangements or translocations.

A gRNA can be introduced at any functional concentration. For example, a gRNA can be introduced to a cell at 10 micrograms. In other cases, a gRNA can be introduced from 0.5 micrograms to 100 micrograms. A gRNA can be introduced from 0.5, 5, 10, 15, 20, 25, 30, 35, 40, 45, 50, 55, 60, 65, 70, 75, 80, 85, 90, 95, or 100 micrograms.

Disclosed herein is a method of making an engineered TIL cell comprising: introducing at least one guide RNA (gRNA) comprising at least one modification; and introducing at least one endonuclease; wherein the gRNA comprises at least one sequence complementary to at least one endogenous genome. In some cases, a modification is on a 5' end, a 3' end, from a 5' end to a 3' end, a single base modification, a 2'-ribose modification, or any combination thereof. A modification can be selected from a group consisting of base substitutions, insertions, deletions, chemical modifications, physical modifications, stabilization, purification, and any combination thereof.

In some cases, a modification is a chemical modification. A modification can be selected from 5' adenylate, 5' guanosine-triphosphate cap, 5'N7-Methylguanosine-triphosphate cap, 5' triphosphate cap, 3'phosphate, 3'thiophosphate, 5'phosphate, 5'thiophosphate, Cis-Syn thymidine dimer, trimers, C12 spacer, C3 spacer, C6 spacer, dSpacer, PC spacer, rSpacer, Spacer 18, Spacer 9,3'-3' modifications, 5'-5' modifications, abasic, acridine, azobenzene, biotin, biotin BB, biotin TEG, cholesteryl TEG, desthiobiotin TEG, DNP TEG, DNP-X, DOTA, dT-Biotin, dual biotin, PC biotin, psoralen C2, psoralen C6, TINA, 3'DABCYL, black hole quencher 1, black hole quencher 2, DABCYL SE, dT-DABCYL, IRDye QC-1, QSY-21, QSY-35, QSY-7, QSY-9, carboxyl linker, thiol linkers, 2'deoxyribonucleoside analog purine, 2'deoxyribonucleoside analog pyrimidine, ribonucleoside analog, 2'-O-methyl ribonucleoside analog, sugar modified analogs, wobble/universal bases, fluorescent dye label, 2'fluoro RNA, 2'O-methyl RNA, methylphosphonate, phosphodiester DNA, phosphodiester RNA, phosphothioate DNA, phosphorothioate RNA, UNA, pseudouridine-5'-triphosphate, 5-methylcytidine-5'-triphosphate, 2-O-methyl 3phosphorothioate or any combinations thereof.

The polynucleic acids as described herein can be modified. A modification can be made at any location of a polynucleic acid. More than one modification can be made to a single polynucleic acid. A polynucleic acid can undergo quality control after a modification. In some cases, quality control may include PAGE, HPLC, MS, or any combination thereof. A modification can be a substitution, insertion, deletion, chemical modification, physical modification, stabilization, purification, or any combination thereof. A polynucleic acid can also be modified by 5'adenylate, 5' guanosine-triphosphate cap, 5'$N^7$-Methylguanosine-triphosphate cap, 5'triphosphate cap, 3'phosphate, 3'thiophosphate, 5'phosphate, 5'thiophosphate, Cis-Syn thymidine dimer, trimers, C12 spacer, C3 spacer, C6 spacer, dSpacer, PC spacer, rSpacer, Spacer 18, Spacer 9,3'-3' modifications, 5'-5' modifications, abasic, acridine, azobenzene, biotin, biotin BB, biotin TEG, cholesteryl TEG, desthiobiotin TEG, DNP TEG, DNP-X, DOTA, dT-Biotin, dual biotin, PC biotin, psoralen C2, psoralen C6, TINA, 3'DABCYL, black hole quencher 1, black hole quencher 2, DABCYL SE, dT-DABCYL, IRDye QC-1, QSY-21, QSY-35, QSY-7, QSY-9, carboxyl linker, thiol linkers, 2'deoxyribonucleoside analog purine, 2'deoxyribonucleoside analog pyrimidine, ribonucleoside analog, 2'-O-methyl ribonucleoside analog, sugar modified analogs, wobble/universal bases, fluorescent dye label, 2'fluoro RNA, 2'O-methyl RNA, methylphosphonate, phosphodiester DNA, phosphodiester RNA, phosphothioate DNA, phosphorothioate RNA, UNA, pseudouridine-5'-triphosphate, 5-methylcytidine-5'-triphosphate, or any combination thereof. A representative 2'O-methyl RNA modified gRNA is shown in FIG. 22. In some cases, a modification can be permanent. In other cases, a modification can be transient. In some cases, multiple modifications are made to a polynucleic acid. A polynucleic acid modification may alter physio-chemical properties of a nucleotide, such as their conformation, polarity, hydrophobicity, chemical reactivity, base-pairing interactions, or any combination thereof.

A modification can also be a phosphorothioate substitute. In some cases, a natural phosphodiester bond may be susceptible to rapid degradation by cellular nucleases and; a modification of internucleotide linkage using phosphorothioate (PS) bond substitutes can be more stable towards hydrolysis by cellular degradation. A modification can increase stability in a polynucleic acid. A modification can also enhance biological activity. In some cases, a phosphorothioate enhanced RNA polynucleic acid can inhibit RNase A, RNase T1, calf serum nucleases, or any combinations thereof. These properties can allow the use of PS-RNA polynucleic acids to be used in applications where exposure to nucleases is of high probability in vivo or in vitro. For example, phosphorothioate (PS) bonds can be introduced between the last 3-5 nucleotides at the 5'- or 3'-end of a polynucleic acid which can inhibit exonuclease degradation. In some cases, phosphorothioate bonds can be added throughout an entire polynucleic acid to reduce attack by endonucleases.

In some cases, a modification can be screened. Screening can include, but is not limited to, testing for immunogenicity, testing for toxicity, testing for efficiency of transcription, testing for efficiency of translation, or any combination thereof. In some cases, a modification may not be immunogenic. A modification may not be toxic. In some cases, candidate modifications are screened prior to being incorporated into a polynucleic acid. In other cases, polynucleic acids with different modifications are screened to determine the level of immunogenicity, toxicity, efficacy, or any combination of the added modifications. In some cases, a modification is screened for its ability to support reverse transcription of a polynucleic acid. In some cases, a modification is a pseudouridine-5'-triphosphate (see e.g., FIG. 32). In other cases a modification is a 5-methylcytidine-5'-triphosphate (see e.g., FIG. 32). A modification can also include a change in chirality.

Guiding polynucleic acids can be assembled by a variety of methods, e.g., by automated solid-phase synthesis. A polynucleic acid can be constructed using standard solid-phase DNA/RNA synthesis. A polynucleic acid can also be constructed using a synthetic procedure. A polynucleic acid can also be synthesized either manually or in a fully automated fashion. In some cases, a synthetic procedure may comprise 5'-hydroxyl oligonucleotides can be initially transformed into corresponding 5'-H-phosphonate mono esters, subsequently oxidized in the presence of imidazole to activated 5'-phosphorimidazolidates, and finally reacted with pyrophosphate on a solid support. This procedure may include a purification step after the synthesis such as PAGE, HPLC, MS, or any combination thereof.

In some cases, a modification is a 2-O-methyl 3 phosphorothioate addition denoted as "m". A phosphothioate backbone can be denoted as "(ps)." A 2-O-methyl 3 phosphorothioate addition can be performed from 1 base to 150 bases. A 2-O-methyl 3 phosphorothioate addition can be performed from 1 base to 4 bases. A 2-O-methyl 3 phosphorothioate addition can be performed on 2 bases. A 2-O-methyl 3 phosphorothioate addition can be performed on 4 bases. A modification can also be a truncation. A truncation can be a 5 base truncation. In some cases, a modification may be at C terminus and N terminus nucleotides, for example 5' [mG](ps)[mG](ps)[mG](ps) [mU](ps) UC CAU UAC GGC CAG CGG UUU UAG AGC UAG AAA UAG CAA GUU AAA AUA AGG CUA GUC CGU UAU CAA CUU GAA AAA GUG GCA CCG AGU CGG UG[mC](ps)[mU](ps)[mU](ps)[mU](ps) U 3'.

A guiding polynucleic acid can have any frequency of bases. For example a guiding polynucleic acid can have 29 As, 17 Cs, 23 Gs, 23 Us, 3 mGs, 1 mCs, and 4 mUs. A guiding polynucleic acid can have any ratio of nucleotide bases. For example, a guiding polynucleic acid can have a percent adenine of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%. A guiding polynucleic acid can have a percent cytosine of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%. A guiding polynucleic acid can have a percent thymine of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%. A guiding polynucleic acid can have a percent guanine of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%. A guiding polynucleic acid can have a percent uracil of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%. A guiding polynucleic acid can have from about 1 to about 100 nucleotides. A guiding polynucleic acid can have from about 1 to 30 of a single polynucleotide. A guiding polynucleic acid can have from about 1 to 10, 10 to 20, or from 20 to 30 of a single nucleotide.

A guiding polynucleic acid (also referred to as a guide polynucleic acid) can be tested for identity and potency prior to use. For example, identity and potency can be determined using at least one of spectrophotometric analysis, RNA agarose gel analysis, LC-MS, endotoxin analysis, and sterility testing. In some cases, identity testing can determine an acceptable level for clinical/therapeutic use. For example, an acceptable spectrophotometric analysis result can be 14±2 µL/vial at 5.0±0.5 mg/mL. an acceptable spectrophotometric analysis result can also be from about 10-20±2 µL/vial at 5.0±0.5 mg/mL or from about 10-20±2 µL/vial at about 3.0 to 7.0±0.5 mg/mL. An acceptable clinical/therapeutic size of a guiding polynucleic acid can be about 100 bases. A clinical/therapeutic size of a guiding polynucleic acid can be from about 5 bases to about 150 bases. A clinical/therapeutic size of a guiding polynucleic acid can be from about 20 bases to about 150 bases. A clinical/therapeutic size of a guiding polynucleic acid can be from about 40 bases to about 150 bases. A clinical/therapeutic size of a guiding polynucleic acid can be from about 60 bases to about 150 bases. A clinical/therapeutic size of a guiding polynucleic acid can be from about 80 bases to about 150 bases. A clinical/therapeutic size of a guiding polynucleic acid can be from about 100 bases to about 150 bases. A clinical/therapeutic size of a guiding polynucleic acid can be from about 110 bases to about 150 bases. A clinical/therapeutic size of a guiding polynucleic acid can be from about 120 bases to about 150 bases.

In some cases, a mass of a guiding polynucleic acid can be determined. A mass can be determined by LC-MS assay. A mass can be about 32,461.0 amu. A guiding polynucleic acid can have a mass from about 30,000 amu to about 50,000 amu. A guiding polynucleic acid can have a mass from about 30,000 amu to 40,000 amu, from about 40,000 amu to about 50,000 amu. A mass can be of a sodium salt of a guiding polynucleic acid.

In some cases, an endotoxin level of a guiding polynucleic acid can be determined. A clinically/therapeutically acceptable level of an endotoxin can be less than 3 EU/mL. A clinically/therapeutically acceptable level of an endotoxin can be less than 10 EU/mL. A clinically/therapeutically acceptable level of an endotoxin can be less than 8 EU/mL. A clinically/therapeutically acceptable level of an endotoxin can be less than 5 EU/mL. A clinically/therapeutically acceptable level of an endotoxin can be less than 4 EU/mL. A clinically/therapeutically acceptable level of an endotoxin can be less than 3 EU/mL. A clinically/therapeutically acceptable level of an endotoxin can be less than 2 EU/mL. A clinically/therapeutically acceptable level of an endotoxin can be less than 1 EU/mL. A clinically/therapeutically acceptable level of an endotoxin can be less than 0.5 EU/mL.

In some cases a guiding polynucleic acid can go sterility testing. A clinically/therapeutically acceptable level of a sterility testing can be 0 or denoted by no growth on a culture. A clinically/therapeutically acceptable level of a sterility testing can be less than 0.5% growth. A clinically/therapeutically acceptable level of a sterility testing can be less than 1% growth.

Treatment Regimes

Disclosed herein can be cells used in a treatment regime. For example, a subject can receive engineered cells as part of a treatment regime for treatment of a cancer or disease. Treatment regimes can include: surgery, chemotherapy, radiation, immunosuppressive agents, immunostimulatory agents, antifungals, antivirals, antibiotics, or antiemetics, to name a few. In some cases, cellular compositions can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. A surgery can be a tumor resection in some cases. A surgery can be performed to isolate a TIL.

With the instant application in hand, the skilled worker can determine a therapeutically effective amount of cells for administration. In some cases, about $5 \times 10^{10}$ cells are administered to a subject. In some cases, about $5 \times 10^{10}$ cells represent the median amount of cells administered to a subject. In some embodiments, about $5 \times 10^{10}$ cells are necessary to effect a therapeutic response in a subject. In some embodiments, at least about at least about $1 \times 10^6$ cells, at least about $2 \times 10^6$ cells, at least about $3 \times 10^6$ cells, at least about $4 \times 10^6$ cells, at least about $5 \times 10^6$ cells, at least about $6 \times 10^6$ cells, at least about $6 \times 10^6$ cells, at least about $8 \times 10^6$ cells, at least about $9 \times 10^6$ cells, $1 \times 10^7$ cells, at least about $2 \times 10^7$ cells, at least about $3 \times 10^7$ cells, at least about $4 \times 10^7$ cells, at least about $5 \times 10^7$ cells, at least about $6 \times 10^7$ cells, at least about $6 \times 10^7$ cells, at least about $8 \times 10^7$ cells, at least about $9 \times 10^7$ cells, at least about $1 \times 10^8$ cells, at least about $2 \times 10^8$ cells, at least about $3 \times 10^8$ cells, at least about $4 \times 10^8$ cells, at least about $5 \times 10^8$ cells, at least about $6 \times 10^8$ cells, at least about $6 \times 10^8$ cells, at least about $8 \times 10^8$ cells, at least about $9 \times 10^8$ cells, at least about $1 \times 10^9$ cells, at least about $2 \times 10^9$ cells, at least about $3 \times 10^9$ cells, at least about $4 \times 10^9$ cells, at least about $5 \times 10^9$ cells, at least about $6 \times 10^9$ cells, at least about $6 \times 10^9$ cells, at least about $8 \times 10^9$ cells, at least about $9 \times 10^9$ cells, at least about $1 \times 10^{10}$ cells, at least about $2 \times 10^{10}$ cells, at least about $3 \times 10^{10}$ cells, at least about $4 \times 10^{10}$ cells, at least about $5 \times 10^{10}$ cells, at least about $6 \times 10^{10}$ cells, at least about $6 \times 10^{10}$ cells, at least about $8 \times 10^{10}$ cells, at least about $9 \times 10^{10}$ cells, at least about $1 \times 10^{11}$ cells, at least about $2 \times 10^{11}$ cells, at least about $3 \times 10^{11}$ cells, at least about $4 \times 10^{11}$ cells, at least about $5 \times 10^{11}$ cells, at least about $6 \times 10^{11}$ cells, at least about $6 \times 10^{11}$ cells, at least about $8 \times 10^{11}$ cells, at least about $9 \times 10^{11}$ cells, or at least about $1 \times 10^{12}$ cells are administered to a subject. For example, about $5 \times 10^{10}$ cells may be administered to a subject. In another example, starting with $3 \times 10^6$ cells, the cells may be expanded to about $5 \times 10^{10}$ cells and administered to a subject. In some cases, cells are expanded to sufficient numbers for therapy. For example, $5 \times 10^7$ cells can undergo rapid expansion to generate sufficient numbers for therapeutic use. In some cases, sufficient numbers for therapeutic use can be $5 \times 10^{10}$. Any number of cells can be infused for therapeutic use. For example, a patient may be infused with a number of cells between $1 \times 10^6$ to $5 \times 10^{12}$, inclusive. A patient may be infused with as many cells that can be generated for them. In some cases, cells that are infused into a patient are not all engineered. For example, at least 90% of cells that are infused into a patient can be engineered. In other instances, at least 40% of cells that are infused into a patient can be engineered. The amount of cells that are necessary to be therapeutically effective in a patient may vary depending on the viability of the cells, and the efficiency with which the cells have been genetically modified. In some cases, the product (e.g., multiplication) of the viability of cells post genetic modification may correspond to the therapeutic aliquot of cells available for administration to a subject. In some cases, an increase in the viability of cells post genetic modification may correspond to a decrease in the amount of cells that are necessary for administration to be therapeutically effective in a patient.

In some cases, a method can comprise calculating and/or administering to a subject an amount of engineered cells necessary to effect a therapeutic response in the subject. In some embodiments, calculating the amount of engineered cells necessary to effect a therapeutic response comprises determining the viability of the engineered cells. In some embodiments, in order to effect a therapeutic response in a subject, the cells administered to the subject are viable cells. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells are viable cells. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells have had one or more endogenous genes or portion thereof disrupted in a genome of a cell.

In some cases, adoptively transplanted cells can be monitored by quantitative PCR (qPCR). A qPCR assay of adoptively transplanted cells can indicate a level of modified cells that exist in a subject after an introduction. In some cases, adoptively transferred cells can be monitored using flow cytometry. For example a flow cytometry assay may determine a level of 4-1BB vs TCR. In some cases, a single-cell TCR PCR can be performed. Levels of adoptively transferred cells can be identified on day 40 post infusion. Levels of adoptively transferred cells, such as modified cells, can be identified of day 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or up to day 200 post infusion.

I. Immunostimulants

In some cases, an immunostimulant can be introduced to cells or a subject. An immunostimulant can be specific or non-specific. A specific immunostimulant can provide antigenic specificity such as a vaccine or an antigen. A non-specific immunostimulant can augment an immune response or stimulate an immune response. A non-specific immunostimulant can be an adjuvant Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin One or more cytokines can be introduced with cells of the invention. Cytokines can be utilized to boost cytotoxic T lymphocytes (including adoptively transferred tumor-specific cytotoxic T lymphocytes) to expand within a tumor microenvironment. In some cases, IL-2 can be used to facilitate expansion of the cells described herein. Cytokines such as IL-15 can also be employed. Other relevant cytokines in the field of immunotherapy can also be utilized, such as IL-2, IL-7, IL-12, IL-15, IL-21, or any combination thereof. In some cases, IL-2, IL-7, and IL-15 are used to culture cells of the invention. An interleukin can be IL-2, or aldeskeukin Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg. An immunostimulant (e.g., aldesleukin) can be administered from 1 dose to about 14 doses. An immunostimulant (e.g., aldesleukin) can be administered from at least about 1 dose, 2 doses, 3 doses, 4 doses, 5 doses, 6 doses, 7 doses, 8 doses, 9 doses, 10 doses, 11 doses, 12 doses, 13 doses, 14 doses, 15 doses, 16 doses, 17 doses, 18 doses, 19 doses, or up to about 20 doses. In some cases, an immunostimulant such as aldesleukin can be administered from about 1 dose to 3 doses, from 3 doses to 5 doses, from 5 doses, to 8 doses, from 8 doses to 10 doses, from 10 doses to 14 doses, from 14 doses to 20 doses. In some cases, aldeskeukin is administered over 20 doses. In some cases, an immunostimulant, such as aldesleukin, can be administered in sequence or concurrent with a cellular administration. For example, an immunostimulant can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14. In some cases, an immunostimulant, such as aldesleukin, is administered from day 0 to day 4 after administration of a population of cells. In some cases, an immunostimulant (e.g., aldesleukin) is administered over a period of about 10 min, 15 min, 20 min, 30 min, 40 min, 50 min, 1 hour, 2 hours or up to about 3 hours. In some cases, an immunostimulant (e.g., aldesleukin) can be administered from about 24 hours prior to an administration of engineered cell to about 4 days after an administration of engineered cells. An immunostimulant (e.g., aldesleukin) can be administered from day −7, −6, −5, −4, −3, −2, −1, 0, 1, 2, 3, 4, 5, 6, 7, 8, 9, 10, 11, 12, 13, 14, 15, 16, 17, 18, 19, or up to about 20 days after an administration of engineered cells.

Immunostimulants such as aldesleukin can be provided as single-use vials containing 22 million IU (−1.3 mg) IL-2 as a sterile, white to off-white lyophilized cake plus 50 mg mannitol and 0.18 mg sodium dodecyl sulfate, buffered with approximately 0.17 mg monobasic and 0.89 mg dibasic sodium phosphate to a pH of 7.5 (range 7.2 to 7.8). The vial can be reconstituted with 1.2 mL of Sterile Water for Injection, USP, and the resultant concentration is 18 million IU/ml or 1.1 mg/mL. Diluent should be directed against the side of the vial to avoid excess foaming Since vials contain no preservative, reconstituted solution should be used with 24 hours. Reconstituted aldesleukin can be further diluted with 50 mL of 5% Human Serum Albumin (HSA). The HSA should be added to the diluent prior to the addition of RIL-2. Dilutions of the reconstituted solution over a 1000-fold range (i.e., 1 mg/mL to 1 mcg/mL) are acceptable in either glass bottles or polyvinyl chloride bags. Aldesleukin is chemically stable for 48 hours at refrigerated and room temperatures, 2°-30° C. Administration of aldesleukin can be calculated based on total body weight. The final dilution of aldesleukin can be infused over 15 minutes.

In some cases, an immunostimulant is a colony stimulating factor. A colony stimulating factor can be G-CSF (filgrastim). Filgrastim can be stored in 300 mcg/ml and 480 ug/1.6 ml vials. Filgrastim can be administered daily as a subcutaneous injection. A filgrastim administration can be from about 5 mcg/kg/day. A filgrastim administration can be from about 1 mcg/kg/day, a filgrastim administration can be from about 2 mcg/kg/day, a filgrastim administration can be from about 3 mcg/kg/day, a filgrastim administration can be from about 4 mcg/kg/day, a filgrastim administration can be from about 5 mcg/kg/day, a filgrastim administration can be from about 6 mcg/kg/day, a filgrastim administration can be from about 7 mcg/kg/day, a filgrastim administration can be from about 8 mcg/kg/day, a filgrastim administration can be from about 9 mcg/kg/day, a filgrastim administration can be from about 10 mcg/kg/day. In some cases, Filgrastim can be administered at a dose ranging from about 0.5 mcg/kg/day to about 1.0 mcg/kg/day, from about 1.0 mcg/kg/day to 1.5 mcg/kg/day, from about 1.5 mcg/kg/day to about 2.0 mcg/kg/day, from about 2.0 mcg/kg/day to about 3.0 mcg/kg/day, from about 2.5 mcg/kg/day to about 3.5 mcg/kg/day, from about 3.5 mcg/kg/day to about 4.0 mcg/kg/day, from about 4.0 mcg/kg/day to about 4.5 mcg/kg/day. Filgrastim administration can continue daily until neutrophil count is at least about $1.0 \times 10^9$/L×3 days or at least about $5.0 \times 10^9$/L. An immunostimulant such as Filgrastim can be administered from day −7, −6, −5, −4, −3, −2, −1, 0, 1, 2, 3, 4, 5, 6, 7, 8, 9, 10, 11, 12, 13, 14, 15, 16, 17, 18, 19, or up to about 20 days after an administration of engineered cells.

II. Chemotherapeutic Agents

A chemotherapeutic agent or compound can be a chemical compound useful in the treatment of cancer. The chemotherapeutic cancer agents that can be used in combination with the disclosed T cell include, but are not limited to, mitotic inhibitors (*vinca* alkaloids). These include vincristine, vinblastine, vindesine and Navelbine™ (vinorelbine, 5'-noranhydroblastine). In yet other cases, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that can be used in the methods and compositions disclosed herein are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions disclosed herein include antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The disclosed T cell herein can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2) Small molecules, including topoisomerases such as razoxane, a topoisomerase II inhibitor with anti-angiogenic activity, can also be used.

Other anti-cancer agents that can be used in combination with the disclosed engineered cells can include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; avastin; azacitidine; azatepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin;

paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bl; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromely sin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; erythrocyte gene therapy; velaresol; veramine; verdins; verteporfin; vinorelbine; vinxaltine; vitaxin; vorozole; zanoterone; zeniplatin; zilascorb; and zinostatin stimalamer. Any of the aforementioned chemotherapeutics can be administered at a clinically effective dose. A chemotherapeutic can also be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of a population of cells. In some cases, a subject can have a refractory cancer that is unresponsive to a chemotherapeutic.

III. Antifungal Agents

In some cases, an antifungal therapy is administered to a subject receiving engineered cells. Antifungals can be drugs that can kill or prevent the growth of fungi. Targets of antifungal agents can include sterol biosynthesis, DNA biosynthesis, and β-glucan biosynthesis. Antifungals can also be folate synthesis inhibitors or nucleic acid cross-linking agents. A folate synthesis inhibitor can be a sulpha based drug. For example, a folate synthesis inhibitor can be an agent that inhibits a fungal synthesis of folate or a competitive inhibitor. A sulpha based drug, or folate synthesis inhibitor, can be methotrexate or sulfamethaxazole. In some cases, an antifungal can be a nucleic acid cross-linking agent. A cross-linking agent may inhibit a DNA or RNA process in fungi. For example, a cross-linking agent can be 5-fluorocytosine, which can be a fluorinated analog of cytosine. 5-fluorocytosine can inhibit both DNA and RNA synthesis via intracytoplasmic conversion to 5-fluorouracil. Other anti-fungal agents can be griseofulvin. Griseofulvin is an antifungal antibiotic produced by *Penicillium griseofulvum*. Griseofulvin inhibits mitosis in fungi and can be considered a cross linking agent. Additional cross linking agent can be allylamines (naftifine and terbinafine) inhibit ergosterol synthesis at the level of squalene epoxidase; one morpholene derivative (amorolfine) inhibits at a subsequent step in the ergosterol pathway.

In some cases, an antifungal agent can be from a class of polyene, azole, allylamine, or echinocandin. In some embodiments, a polyene antifungal is amphotericin B, candicidin, filipin, hamycin, natamycin, nystatin, or rimocidin. In some cases, an antifungal can be from an azole family. Azole antifungals can inhibit lanosterol 14 α-demethylase. An azole antifungal can be an imidazole such as bifonazole, butoconazole, clotrimazole, econazole, fenticonazole, isoconazole, ketoconazole, luliconazole, miconazole, omoconazole, oxiconazole, sertaconazole, sulcoazole, or tioconazole. An azole antifungal can be a triazole such as albaconazole, efinaconazole, epoxiconazole, fluconazole, isavuvonazole, itraconazole, posaconazole, propiconazole, ravuconazole, terconazole, or voriconazole. In some cases an azole can be a thiazole such as abafungin. An antifungal can be an allylamine such as amorolfin, butenafine, naftifine, or terbinafine. An antifungal can also be an echinocandin such as anidulafungin, caspofungin, or micafungin. Additional agents that can be antifungals can be aurones, benzoic acid, ciclopirox, flucytosine, griseofulvin, haloprogin, tolnaftate, undecylenic acid, cystal violet or balsam of Peru.

A person of skill in the art can appropriately determine which known antifungal medication to apply based on the fungus infecting the individual. In some cases, a subject will receive fluconazole in combination with engineered TILs comprising a genomic knockout of at least a portion of a gene, such as CISH. An anti-fungal therapy can be administered prophalaytically.

Fluconazole can be available in 200 mg tablets. In some cases, fluconazole can be administered as a 50 mg, 100 mg, 150 mg, 200 mg, 250 mg, 300 mg, 350 mg, or up to about 400 mg tablet. For IV administration in subjects who cannot tolerate an oral preparation, fluconazole comes in 2 MG/ML solution for injection. It should be administered at a maximum IV rate of 200 mg/hr. In some cases, an infusion rate can be from about 50 mg/hr to about 500 mg/hr. An infusion rate can also be from about 20 mg/hr to about 30 mg/hr, from about 30 mg/hr to about 40 mg/hr, from about 40 mg/hr to about 50 mg/hr, from about 50 mg/hr to about 60 mg/hr, from about 60 mg/hr to about 70 mg/hr, from about 70 mg/hr to about 80 mg/hr, from about 80 mg/hr to about 90 mg/hr, from about 90 mg/hr to about 100 mg/hr, from about 100 mg/hr to about 120 mg/hr, from about 120 mg/hr to about 140 mg/hr, from about 140 mg/hr to about 160 mg/hr, from about 160 mg/hr to about 180 mg/hr, from about 180 mg/hr to about 200 mg/hr, from about 180 mg/hr to about 220 mg/hr, from about 220 mg/hr to about 240 mg/hr, from about 240 mg/hr to about 275 mg/hr.

Antifungals can be administered at therapeutically effective doses. A therapeutically effective dose is a dose that treats or prevents a fungal infection but that is not effective for treating a cancer. For example an antifungal such as fluconazole can be administered from about 10 mg to about 1000 mg. Fluconazole can be administered from about 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or up to about 1000 mg. Fluconazole can be administered at 400 mg. In some cases, an antifungal administration can be before a cellular therapy, during a cellular therapy or after a cellular therapy has been administered. For example a fluconazole administration can be from about day 0 (day a cellular therapy is introduced into a subject) to about day 4 after administration of a cellular therapy. An antifungal can be administered from about 14 days leading up to a cellular therapy administration to about 14 days after a cellular therapy is completed. An antifungal can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14.

IV. Immunosuppressive Agents

In some cases, a subject may receive an immunosuppressive agent as part of a therapy regime. An immunosuppressive agent can refer to a radiotherapeutic, a biologic, or a chemical agent. In some cases, an immunosuppressive agent can include a chemical agent. For example, a chemical agent can comprise at least one member from the group consisting of: cyclophosphamide, mechlorethamine, chlorambucil, melphalan, ifosfamide, thiotepa, hexamethylmelamine, busulfan, fludarabine, nitrosoureas, platinum, methotrexate, azathioprine, mercaptopurine, procarbazine, dacarbazine, temozolomide, carmustine, lomustine, streptozocin, fluorouracil, dactinomycin, anthracycline, mitomycin C, bleomycin, and mithramycin. A chemical agent can be cyclophosphamide or fludarabine.

Additionally, immunosuppressive agents can include glucocorticoids, cytostatic, antibodies, anti-immunophilins, or any derivatives thereof. A glucocorticoid can suppress an allergic response, inflammation, and autoimmune conditions. Glucocorticoids can be prednisone, dexamethasone, and hydrocortisone Immunosuppressive therapy can comprise any treatment that suppresses the immune system Immunosuppressive therapy can help to alleviate, minimize, or eliminate transplant rejection in a recipient. For example, immunosuppressive therapy can comprise immuno-suppressive drugs. Immunosuppressive drugs that can be used before, during and/or after transplant, but are not limited to, MMF (mycophenolate mofetil (Cellcept)), ATG (anti-thymocyte globulin), anti-CD154 (CD40L), anti-CD40 (2C10, ASKP1240, CCFZ533X2201), alemtuzumab (Campath), anti-CD20 (rituximab), anti-IL-6R antibody (tocilizumab, Actemra), anti-IL-6 antibody (sarilumab, olokizumab), CTLA4-Ig (Abatacept/Orencia), belatacept (LEA29Y), sirolimus (Rapimune), everolimus, tacrolimus (Prograf), daclizumab (Ze-napax), basiliximab (Simulect), infliximab (Remicade), cyclosporin, deoxyspergualin, soluble complement receptor 1, cobra venom factor, compstatin, anti C5 antibody (eculizumab/Soliris), methylprednisolone, FTY720, everolimus, leflunomide, anti-IL-2R-Ab, rapamycin, anti-CXCR3 antibody, anti-ICOS antibody, anti-OX40 antibody, and anti-CD122 antibody. Furthermore, one or more than one immunosuppressive agents/drugs can be used together or sequentially. One or more than one immunosuppressive agents/drugs can be used for induction therapy or for maintenance therapy. The same or different drugs can be used during induction and maintenance stages. In some cases, daclizumab (Zenapax) can be used for induction therapy and tacrolimus (Prograf) and sirolimus (Rapimune) can be used for maintenance therapy. Daclizumab (Zenapax) can also be used for induction therapy and low dose tacrolimus (Prograf) and low dose sirolimus (Rapimune) can be used for maintenance therapy. Immunosuppression can also be achieved using non-drug regimens including, but not limited to, whole body irradiation, thymic irradiation, and full and/or partial splenectomy.

In some cases, a cytostatic agent can be administered for immunosuppression. Cytostatic agents can inhibit cell division. A cytostatic agent can be a purine analog. A cytostatic agent can be an alkylating agent, an antimetabolite such as methotrexate, azathioprine, or mercaptopurine. A cytostatic agent can be at least one of cyclophosphamide, mechlorethamine, chlorambucil, melphalan, ifosfamide, thiotepa, hexamethylmelamine, busulfan, fludarabine, nitrosoureas, platinum, methotrexate, azathioprine, mercaptopurine, procarbazine, dacarbazine, temozolomide, carmustine, lomustine, streptozocin, fluorouracil, dactinomycin, anthracycline, mitomycin C, bleomycin, and mithramycin.

In some cases, an immunosuppressive agent such as fludarabine can be administered as part of a treatment regime. Fludarabine phosphate can be a synthetic purine nucleoside that differs from physiologic nucleosides in that the sugar moiety can be arabinose instead of ribose or deoxyribose. Fludarabine can be a purine antagonist antimetabolite. Fludarabine can be supplied in a 50 mg vial as a fludarabine phosphate powder in the form of a white, lyophilized solid cake. Following reconstitution with 2 mL of sterile water for injection to a concentration of 25 mg/ml, the solution can have a pH of 7.7. The fludarabine powder can be stable for at least 18 months at 2-8° C.; when reconstituted, fludarabine is stable for at least 16 days at room temperature. Because no preservative is present, reconstituted fludarabine will typically be administered within 8 hours. Specialized references should be consulted for specific compatibility information. Fludarabine can be dephosphorylated in serum, transported intracellularly and converted to the nucleotide fludarabine triphosphate; this 2-fluoro-ara-ATP molecule is thought to be required for the drug's cytotoxic effects. Fludarabine inhibits DNA polymerase, ribonucleotide reductase, DNA primase, and may interfere with chain elongation, and RNA and protein synthesis. Fludarabine can be administered as an IV infusion in 100 ml 0.9% sodium chloride, USP over 15 to 30 minutes. The doses will be based on body surface area (BSA). If patient is obese (BMI >35) drug dosage will be calculated using practical weight. In some cases, an immunosuppressive agent such as fludarabine can be administered from about 20 $mg/m^2$ to about 30 $mg/m^2$ of body surface area of a subject. In some cases, an immunosuppressive agent such as fludarabine can be administered from about 5 $mg/m^2$ to about 10 $mg/m^2$ of body surface area of a subject, from about 10 $mg/m^2$ to about 15 $mg/m^2$ of body surface area of a subject, from about 15 $mg/m^2$ to about 20 $mg/m^2$ of body surface area of a subject, from about 20 $mg/m^2$ to about 25 $mg/m^2$ of body surface area of a subject, from about 25 $mg/m^2$ to about 30 $mg/m^2$ of body surface area of a subject, from about 30 $mg/m^2$ to about 40 $mg/m^2$ of body surface area of a subject. In some cases, an immunosuppressive agent such as fludarabine can be administered from about 1 $mg/m^2$, 2 $mg/m^2$, 3 $mg/m^2$, 4 $mg/m^2$, 5 $mg/m^2$, 6 $mg/m^2$, 7 $mg/m^2$, 8 $mg/m^2$, 9 $mg/m^2$, 10 $mg/m^2$, 11 $mg/m^2$, 12 $mg/m^2$, 13 $mg/m^2$, 14 $mg/m^2$, 15 $mg/m^2$, 16 $mg/m^2$, 17 $mg/m^2$, 18 $mg/m^2$, 19 $mg/m^2$, 20 $mg/m^2$, 21 $mg/m^2$, 22 $mg/m^2$, 23 $mg/m^2$, 24 $mg/m^2$, 25 $mg/m^2$, 26 $mg/m^2$, 27 $mg/m^2$, 28 mg/m², 29 mg/m², 30 mg/m², 31 mg/m², 32 mg/m², 33 mg/m², 34 mg/m², 35 mg/m², 36 mg/m², 37 mg/m², 38 mg/m², 39 mg/m², 40 mg/m², 41 mg/m², 42 mg/m², 43 mg/m², 44 mg/m², 45 mg/m², 46 mg/m², 47 mg/m², 48 mg/m², 49 mg/m², 50 mg/m², 51 mg/m², 52 mg/m², 53 mg/m², 54 mg/m², 55 mg/m², 56 mg/m², 57 mg/m², 58 mg/m², 59 mg/m², 60 mg/m², 61 mg/m², 62 mg/m², 63 mg/m², 64 mg/m², 65 mg/m², 66 mg/m², 67 mg/m², 68 mg/m², 69 mg/m², 70 mg/m², 71 mg/m², 72 mg/m², 73 mg/m², 74 mg/m², 75 mg/m², 76 mg/m², 77 mg/m², 78 mg/m², 79 mg/m², 80 mg/m², 81 mg/m², 82 mg/m², 83 mg/m², 84 mg/m², 85 mg/m², 86 mg/m², 87 mg/m², 88 mg/m², 89 mg/m², 90 mg/m², 91 mg/m², 92 mg/m², 93 mg/m², 94 mg/m², 95 mg/m², 96 mg/m², 97 mg/m², 98 mg/m², 99 mg/m², up to about 100 mg/m² of body surface area of a subject. In some cases, an immunosuppressive agent such as fludarabine is at a dose of 25 mg/m² in 100 ml 0.9% sodium chloride, USP and infused over about 15 to about 30 minutes.

In some cases, an immunosuppressive agent such as cyclophosphamide can be administered as part of a treatment regime. Cyclophosphamide can be a nitrogen mustard-derivative alkylating agent. Following conversion to active metabolites in the liver, cyclophosphamide functions as an alkyating agent; the drug also possesses potent immunosuppressive activity. The serum half-life after IV administration ranges from 3-12 hours; the drug and/or its metabolites can be detected in the serum for up to 72 hours after administration. Following reconstitution as directed with sterile water for injection, cyclophosphamide can be stable for 24 hours at room temperature or 6 days when kept at 2-8° C. Cyclophosphamide can be diluted in 250 ml D5W and infused over one hour. The dose will be based on a subject's body weight. If a subject is obese (BMI >35) drug dosage will be calculated using practical weight as described in. In some cases, an immunosuppressive agent such as cyclophosphamide can be administered from about 1 mg/kg to about 3 mg/kg, from about 3 mg/kg to about 5 mg/kg, from about 5 mg/kg to about 10 mg/kg, from about 10 mg/kg to about 20 mg/kg, 20 mg/kg to about 30 mg/kg, from about 30 mg/kg to about 40 mg/kg, from about 40 mg/kg to about 50 mg/kg, from about 50 mg/kg to about 60 mg/kg, from about 60 mg/kg to about 70 mg/kg, from about 70 mg/kg to about 80 mg/kg, from about 80 mg/kg to about 90 mg/kg, from about 90 mg/kg to about 100 mg/kg. In some cases, an immunosuppressive agent such as cyclophosphamide is administered in excess of 50 mg/kg of a subject. In some cases, an immunosuppressive agent such as cyclophosphamide can be administered from about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg/kg, 80 mg/kg, 81 mg/kg, 82 mg/kg, 83 mg/kg, 84 mg/kg, 85 mg/kg, 86 mg/kg, 87 mg/kg, 88 mg/kg, 89 mg/kg, 90 mg/kg, 91 mg/kg, 92 mg/kg, 93 mg/kg, 94 mg/kg, 95 mg/kg, 96 mg/kg, 97 mg/kg, 98 mg/kg, 99 mg/kg, up to about 100 mg/kg of a subject. In some cases, an immunosuppressive agent such as cyclophosphamide can be administered over at least about 1 day to about 3 days, from 3 days to 5 days, from 5 days to 7 days, from 7 days to about 10 days, from 10 days to 14 days, from 14 days to about 20 days. In some cases, cyclophosphamide can be at a dose of about 60 mg/kg and is diluted in 250 ml 5% dextrose in water and infused over one hour.

An immunosuppressive agent can be, for example, a regime of cyclophosphamide and fludarabine. For example, a cyclophosphamide fludarabine regimen can be administered to a subject receiving an engineered cellular therapy. A cyclophosphamide fludarabine regimen can be administered at a regime of 60 mg/kg qd for 2 days and 25 mg/m² qd for 5 days. A chemotherapeutic regime, for example, cyclophosphamide fludarabine, can be administered from 1 hour to 14 days preceding administration of engineered cells of the present invention. A chemotherapy regime can be administered at different doses. For example, a subject may receive a higher initial dose followed by a lower dose. A subject may receive a lower initial dose followed by a higher dose.

In some cases, an immunosuppressive agent can be an antibody. An antibody can be administered at a therapeutically effective dose. An antibody can be a polyclonal antibody or a monoclonal antibody. A polyclonal antibody that can be administered can be an antilymphocyte or antithymocyte antigen. A monoclonal antibody can be an anti-IL-2 receptor antibody, an anti-CD25 antibody, or an anti-CD3 antibody. An anti-CD20 antibody can also be used. B-cell ablative therapy such as agents that react with CD20, e.g., Rituxan can also be used as immunosuppressive agents.

An immunosuppressive can also be an anti-immunophilin Anti-immunophilins can be ciclosporin, tacrolimus, everolimus, or sirolimus. Additional immunosuppressive agents can be interferons such as IFN-beta, opioids, anti-TNF binding agents, mycophenolate, or fingolimod.

Immunosuppressive agents can also refer to radiotherapeutics. Radiotherapy can include radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips. For example, in one embodiment, subjects may undergo standard treatment with high dose chemotherapy followed by peripheral blood stem cell transplantation. In certain embodiments, following the transplant, subjects receive an infusion of the expanded immune cells of the present invention. The dosage of the above treatments to be administered to a patient will vary with the precise nature of the condition being treated and the recipient of the treatment. The scaling of dosages for human administration can be performed according to art-accepted practices, The dose for CAMPATH, for example, will generally be in the range 1 to about 100 mg for an adult patient, usually administered daily for a period between 1 and 30 days, The preferred daily dose is 1 to 10 mg per day although in some instances larger doses of up to 40 mg per day may be used (described in U.S. Pat. No. 6,120,766).

V. Antibiotic Agents

An antibiotic can be administered to a subject as part of a therapeutic regime. An antibiotic can be administered at a therapeutically effective dose. An antibiotic can kill or inhibit growth of bacteria. An antibiotic can be a broad spectrum antibiotic that can target a wide range of bacteria. Broad spectrum antibiotics, either a $3^{rd}$ or $4^{th}$ generation, can be cephalosporin or a quinolone.

An antibiotic can also be a narrow spectrum antibiotic that can target specific types of bacteria. An antibiotic can target a bacterial cell wall such as penicillins and cephalosporins. An antibiotic can target a cellular membrane such as polymyxins. An antibiotic can interfere with essential bacterial enzymes such as antibiotics: rifamycins, lipiarmycins, quinolones, and sulfonamides. An antibiotic can also be a protein synthesis inhibitor such as macrolides, lincosamides, and tetracyclines. An antibiotic can also be a cyclic lipopeptide such as daptomycin, glycylcyclines such as tigecycline, oxazolidiones such as linezolid, and lipiarmycins such as fidaxomicin.

In some cases, an antibiotic can be $1^{st}$ generation, $2^{nd}$ generation, $3^{rd}$ generation, 4th generation, or $5^{th}$ generation. A first generation antibiotic can have a narrow spectrum. Examples of $1^{st}$ generation antibiotics can be penicillins (Penicillin G or Penicillin V), Cephalosporins (Cephazolin, Cephalothin, Cephapirin, Cephalethin, Cephradin, or Cephadroxin). In some cases, an antibiotic can be $2^{nd}$ generation. $2^{nd}$ generation antibiotics can be a penicillin (Amoxicillin or Ampicillin), Cephalosporin (Cefuroxime, Cephamandole, Cephoxitin, Cephaclor, Cephrozil, Loracarbef). In some cases, an antibiotic can be $3^{th}$ generation. A $3^{th}$ generation antibiotic can be penicillin (carbenicillin and ticarcillin) or cephalosporin (Cephixime, Cephtriaxone, Cephotaxime, Cephtizoxime, and Cephtazidime). An antibiotic can also be a $4^{th}$ generation antibiotic. A $4^{th}$ generation antibiotic can be Cephipime. An antibiotic can also be $5^{th}$ generation. $5^{th}$ generation antibiotics can be Cephtaroline or Cephtobiprole.

In some cases, an antibiotic can be a bacterial wall targeting agent, a cell membrane targeting agent, a bacterial enzyme interfering agent, a bactericidal agent, a protein synthesis inhibitor, or a bacteriostatic agent. A bacterial wall targeting agent can be a penicillin derivatives (penams), cephalosporins (cephems), monobactams, and carbapenems. β-Lactam antibiotics are bactericidal or bacteriostatic and act by inhibiting the synthesis of the peptidoglycan layer of bacterial cell walls. In some cases an antibiotic may be a protein synthesis inhibitor. A protein synthesis inhibitor can be ampicillin which acts as an irreversible inhibitor of the enzyme transpeptidase, which is needed by bacteria to make the cell wall. It inhibits the third and final stage of bacterial cell wall synthesis in binary fission, which ultimately leads to cell lysis; therefore, ampicillin is usually bacteriolytic. In some cases, a bactericidal agent can be cephalosporin or quinolone. In other cases, a bacteriostatic agent is trimethoprim, sulfamethoxazole, or pentamidine.

In some cases, an agent for the prevention of PCP pneumonia may be administered. For example, Trimethoprim and Sulfamethoxazole can be administered to prevent pneumonia. A dose of trimethoprim and sulfamethoxazole (TMP/SMX; an exemplary sulfa drug) can be 1 tablet PO daily three times a week, on non-consecutive days, on or after the first dose of chemotherapy and continuing for at least about 6 months and until a CD4 count is greater than 200 on at least 2 consecutive lab studies. In some cases, trimethoprim can be administered at 160 mg. Trimethoprim can be administered from about 100 to about 300 mgs. Trimethoprim can be administered from about 100 mg, 125 mg, 150 mg, 175 mg, 200 mg, 225 mg, 250 mg, 275 mg, or up to about 300 mg. In some cases, sulfamethoxazole is administered at 800 mg. Sulfamethoxazole can be administered from about 500 mg to about 1000 mg. Sulfamethoxazole can be administered from about 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or up to about 1000 mgs. In some cases, a TMP/SMX regime can be administered at a therapeutically effective amount. TMP/SMX can be administered from about 1× to about 10× daily. TMP/SMX can be administered 1×, 2×, 3×, 4×, 5×, 6×, 7×, 8×, 9×, 10×, 11×, 12×, 13×, 14×, 15×, 16×, 17×, 18×, 19×, or up to about 20× daily. In some cases, TMP/SMX can be administered on a weekly basis. For example, TMP/SMX can be administered from 1×, 2×, 3×, 4×, 5×, 6×, or up to about 7× a week. A TMP/SMX regime can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of a cellular therapy, such as TILs.

In some cases, a bacteriostatic agent is administered from about 8 days prior to TILs to at least 4 days after said TILs.

In some cases, a subject that has a sulfa allergy may receive pentamidine. Pentamidine can be administered by aerosol. Pentamidine 300 mg per nebulizer within one week prior to admission and continued monthly until the CD4 count is above 200 on two consecutive follow up lab studies and for at least 6 months post chemotherapy. Pentamidine can be used to prevent the occurrence of PCP infections. It can be supplied in 300 mg vials of lyophilized powder and will be administered via nebulizer. Pentamidine can be administered from about 300 mg to about 500 mgs. In some cases, petamidine can be administered from about 100 mg, 200 mg, 300 mg, 400 mg, 500 mg, 600 mg, 700 mg, or up to about 800 mgs.

In some cases, a bacteriostatic agent, such as an antibiotic can be administered prior to TILs, concurrent with said TILs, or after said TILs. In some cases, a bacteriostatic agent can be administered from about 14 days prior to an administration of said TILs to about 6 months after said administration of said TILs.

VI. Anti-Viral Agents

In some cases, an anti-viral agent may be administered as part of a treatment regime. In some cases, a herpes virus prophylaxis can be administered to a subject as part of a treatment regime. A herpes virus prophylaxis can be valacyclovir (Valtrex). Valtrex can be used orally to prevent the occurrence of herpes virus infections in subjects with positive HSV serology. It can be supplied in 500 mg tablets. Valacyclovir can be administered at a therapeutically effective amount. For example, valacyclovir can be administered from about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, or up to about 700 mg tablets. Valacyclovir can be started the day after the last dose of fludarabine at a dose of 500 mg orally daily if a subject is able to tolerate oral intake. An antiviral therapy can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of a cellular therapy such as TIL therapy.

In some cases, a subject may not be able to take oral medication for the prophylaxis of herpes. In those cases, acyclovir can be administered. Acyclovir can be supplied as a powder for injection in 500 mg/vials. In some cases, acyclovir can be administered at a therapeutically effective amount. Acyclovir can be administered orally from about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, or up to about 700 mgs. Acyclovir can be administered 1×, 2×, 3×, 4×, 5×, 6×, or up to about 7× per day. Acyclovir can be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of a cellular therapy such as TIL therapy. In some cases, acyclovir can be administered intravenously. For example, acyclovir can be administered at 1 mg/kg to about 3 mg/kg, from about 3 mg/kg to about 5 mg/kg, from about 5 mg/kg to about 10 mg/kg, from about 10 mg/kg to about 20 mg/kg, 20 mg/kg to about 30 mg/kg, from about 30 mg/kg to about 40 mg/kg, from about 40 mg/kg to about 50 mg/kg, from about 50 mg/kg to about 60 mg/kg, from about 60 mg/kg to about 70 mg/kg, from about 70 mg/kg to about 80 mg/kg, from about 80 mg/kg to about 90 mg/kg, from about 90 mg/kg to about 100 mg/kg. In some cases, acyclovir is administered in excess of 50 mg/kg. Acyclovir can be reconstituted in 10 mL of sterile water for injection to a concentration of 50 mg/mL. Reconstituted solutions should be used within 12 hours. IV solutions can be diluted to a concentration of 7 mg/mL or less and infused over 1 hour to avoid renal damage.

Disease Parameters

In some cases, a level of disease can be determined in sequence or concurrent with a treatment regime or cellular administration. A level of disease on target lesions can be measured as a Complete Response (CR): Disappearance of all target lesions, Partial Response (PR): At least a 30% decrease in the sum of the longest diameter (LD) of target lesions taking as reference the baseline sum LD, Progression (PD): At least a 20% increase in the sum of LD of target lesions taking as reference the smallest sum LD recorded since the treatment started or the appearance of one or more new lesions, Stable Disease (SD): Neither sufficient shrinkage to qualify for PR nor sufficient increase to qualify for PD taking as references the smallest sum LD. In other cases, a non-target lesion can be measured. A level of disease of a non-target lesion can be Complete Response (CR): Disappearance of all non-target lesions and normalization of tumor marker level, Non-Complete Response: Persistence of one or more non-target lesions, Progression (PD): Appearance of one or more new lesions. Unequivocal progression of existing non-target lesions.

In some cases, a subject that undergoes a treatment regime and cellular administration can be evaluated for best overall response. A best overall response can be the best response recorded from the start of treatment until disease progression/recurrence (taking as reference for progressive disease the smallest measurements recorded since the treatment started). A subject's best response assignment can depend on the achievement of both measurement and confirmation criteria. The time to progression can be measured from the date of randomization.

TABLE 7

| Lesion evaluation | | | |
|---|---|---|---|
| Target Lesions | Non-Target Lesions | New Lesions | Overall Response |
| CR | CR | No | CR |
| CR | Non-CR/Non-PD | No | PR |
| PR | Non-PD | No | PR |

TABLE 7-continued

| Lesion evaluation | | | |
|---|---|---|---|
| Target Lesions | Non-Target Lesions | New Lesions | Overall Response |
| SD | Non-PD | No | SD |
| PD | Any | Yes or No | PD |
| Any | PD | Yes or No | PD |
| Any | Any | Yes | PD |

To be assigned a status of PR or CR, changes in tumor measurements must be confirmed by repeat studies that should be performed at least about 4 weeks after the criteria for response are first met. In the case of SD, follow-up measurements must have met the SD criteria at least once after study entry at a minimum interval of 6-8 weeks. In some cases, a duration of overall response can be measured from the time measurement criteria are met for CR/PR (whichever is first recorded) until the first date that recurrent or progressive disease is objectively documented (taking as reference for progressive disease the smallest measurements recorded since the treatment started). The duration of overall complete response can be measured from the time measurement criteria are first met for CR until the first date that recurrent disease is objectively documented. Stable disease can be measured from the start of the treatment until the criteria for progression are met, taking as reference the smallest measurements recorded since the treatment started.

In some cases, measurable disease can be taken and recorded in metric notation using a ruler or calipers. All baseline evaluations can be performed as closely as possible to the beginning of treatment. A lesion can be considered measurable when it is superficial (e.g., skin nodule and palpable lymph nodes) and over at least about 10 mm in diameter using calipers. In some cases, color photography can be taken.

In other cases, a computerized tomography scan (CT) can or magnetic resonance imaging (MRI) can be taken. A CT can be taken on a slice thickness of 5 mm or less. If CT scans have slice thickness greater than 5 mm, the minimum size for a measurable lesion should be twice the slice thickness. In some cases, an FDG-PET scan can be used. FDG-PET can be used to evaluate new lesions. A negative FDG-PET at baseline, with a positive FDG-PET at follow up is a sign of progressive disease (PD) based on a new lesion. No FDG-PET at baseline and a positive FDG-PET at follow up: if a positive FDG-PET at follow-up corresponds to a new site of disease confirmed by CT, this is PD. If a positive PDG-PET at follow up corresponds to a pre-existing site of disease on CT that may not be progressing on a basis of anatomic imagines, this may not be PD. In some cases, FDG-PET may be used to upgrade a response to a CR in a manner similar to biopsy in cases where a residual radiographic abnormality is thought to represent fibrosis or scarring. A positive FDG-PET scan lesion means one which is FDG avid with an uptake greater than twice that of the surrounding tissue on an attenuation corrected image.

In some cases an evaluation of a lesion can be performed. A complete response (CR) can be a disappearance of all target lesions. Any pathological lymph nodes (target or non-target) may have reduction in short axis to less than 10 mm. A partial response (PR) can be at least a 30% decrease in a sum of the diameters of target lesions, taking as reference the baseline sum of diameters. Progressive disease (PD) can be at least a 20% increase in the sum of the diameters of target lesions, taking as reference the smallest sum. In addition to the relative increase of 20%, the sum must also demonstrate an absolute increase of at least 5 mm. Stable disease (SD) can be neither sufficient shrinkage to quality for PR nor sufficient increase to quality for PD, taking as reference the smallest sum of diameters.

In some cases, non-target lesions can be evaluated. A complete response of a non-target lesion can be a disappearance and normalization of tumor marker level. All lymph nodes must be non-pathological in size (less than 10 mm short axis). If tumor markers are initially above the upper normal limit, they must normalize for a patient to be considered a complete clinical response. Non-CR/Non-PD is persistence of one or more non-target lesions and or maintenance of tumor marker level above the normal limit. Progressive disease can be appearance of one or more new lesions and or unequivocal progression of existing non-target lesions. Unequivocal progression should not normally trump target lesion status.

In some cases, a best overall response can be the best response recorded from the start of treatment until disease progression/recurrence.

Toxicity Criteria

In some cases, toxicity to a treatment regime or cellular administration can be determined. A toxicity determination can encompass toxicity, immunologic effects and anti-tumor efficacy of a treatment regimen. A toxicity study can utilize the CTCAE version 3.0 for toxicity and adverse event reporting. Early toxicities related specifically to the infusion of engineered cells (those which are seen immediately following cell infusion and prior to aldesleukin administration) are generally mild and can include fevers, chills, headache, and malaise. Toxicities which occur following administration of aldesleukin but are thought to be related to engineered cell administration can include immune mediated events such as vitiligo, transient uveitis, hearing loss and vestibular dysfunction. The use of a non-myeloablative regimen prior to cell administration can increase the toxicity of treatment as profound myelosuppression occurs in subjects. In some cases, the standard approach to the administration of high-dose aldesleukin can be to continue dosing until grade 3 or 4 events occur. The most commonly seen grade 4 events are pulmonary and renal impairment, and mental status changes. These toxicities may sometimes require intubation for protection of a subject's airway. In some cases, fatal complications can be possible and it can be appropriate to carry out treatment in the context of life threatening metastatic cancer.

In some cases, a subject treated with a treatment regime or cellular product described herein can experience an adverse event associated with the regime or cellular product. An adverse event can be any reaction, side effect, or untoward event that occurs during the course of the treatment associated with the use of a drug in humans, whether or not the event is considered related to the treatment or clinically significant. In some cases, an adverse event can include events reported by a subject, as well as clinically significant abnormal findings on physical examination or laboratory evaluation. A new illness, symptom, sign or clinically significant laboratory abnormality or worsening of a pre-existing condition or abnormality can be considered an adverse event. All adverse events, including clinically significant abnormal findings on laboratory evaluations, regardless of severity, will be followed until resolution to grade 2 or less with the exception of lymphopenia and alopecia. If an adverse event is not expected to resolve to grade 2 or less a subject may cease therapy.

In some cases, a treatment regime may be administered with toxicity reducing agents. A toxicity reducing agent can be a fever or vomit reducing agent. For example Mesna can be administered to reduce toxicities such as nausea, vomiting, and diarrhea.

Mesna can be a diluted solution (1 to 20 mg/mL) and can be physically and chemically stable for at least 24 hours under refrigeration. Mesna can be chemically stable at room temperature for 48-72 hours in D5W, 48-72 hour in D5W/ 0.45% NaCl, or 24 hours in 0.9% NaCl. Mesna can be diluted to concentrations less than or equal to 20 mg mesna/ml fluid in D5W or 0.9% NaCl and to be administered intravenously as a continuous infusion. If patient is obese (BMI >35) drug dosage will be calculated using practical weight.

In other cases, additional support medications can include Ondansetron hydrochloride. Ondansetron hydrochloride can be used to control nausea and vomiting during the chemotherapy preparative regimen. It can cause headache, dizziness, myalgias, drowsiness, malaise, and weakness. Less common side effects include chest pain, hypotension, pruritis, constipation and urinary retention. In other cases, furosemide can also be administered. Furosemide can be used to enhance urine output during the chemotherapy preparative regimen with cyclophosphamide. Adverse effects include dizziness, vertigo, paresthesias, weakness, orthostatic hypotension, photosensitivity, rash and pruritus.

Methods of Administration

Provided herein can be methods for administering a therapeutic regime to a subject having a condition such as cancer. In some instances, a cellular composition (for example, comprising TILs such as TILs (including autologous TILs) with a CISH disruption) can be provided in a unit dosage form. A cellular composition (for example, comprising TILs (including autologous TILs) such as TILs with a CISH disruption) can be resuspended in solution and administered as an infusion. Provided herein can also be a treatment regime that includes immunostimulants, immunosuppressants, antibiotics, antifungals, antiemetics, chemotherapeutics, radiotherapy, and any combination thereof. A treatment regime that includes any of the above can be lyophilized and reconstituted in an aqueous solution (e.g., saline solution). In some instances, a treatment (for example, a cellular treatment such as TILs, e.g., TILs (including autologous TILs) with a CISH disruption) is administered by a route selected from subcutaneous injection, intramuscular injection, intradermal injection, percutaneous administration, intravenous ("i.v.") administration, intranasal administration, intralymphatic injection, and oral administration. In some instances, a subject is infused with a cellular composition comprising TILs by an intralymphatic microcatheter.

Many drugs can be administered orally as liquids, capsules, tablets, or chewable tablets. Because the oral route is the most convenient and usually the safest and least expensive, it is the one most often used. However, it has limitations because of the way a drug typically moves through the digestive tract. For drugs administered orally, absorption may begin in the mouth and stomach. However, most drugs are usually absorbed from the small intestine. The drug passes through the intestinal wall and travels to the liver before being transported via the bloodstream to its target site. The intestinal wall and liver chemically alter (metabolize) many drugs, decreasing the amount of drug reaching the bloodstream. Consequently, these drugs are often given in smaller doses when injected intravenously to produce the same effect.

For a subcutaneous route, a needle is inserted into fatty tissue just beneath the skin. After a drug is injected, it then moves into small blood vessels (capillaries) and is carried away by the bloodstream. Alternatively, a drug reaches the bloodstream through the lymphatic vessels. The intramuscular route is preferred to the subcutaneous route when larger volumes of a drug product are needed. Because the muscles lie below the skin and fatty tissues, a longer needle is used. Drugs are usually injected into the muscle of the upper arm, thigh, or buttock. How quickly the drug is absorbed into the bloodstream depends, in part, on the blood supply to the muscle: The sparser the blood supply, the longer it takes for the drug to be absorbed. For the intravenous route, a needle is inserted directly into a vein. A solution containing the drug may be given in a single dose or by continuous infusion. For infusion, the solution is moved by gravity (from a collapsible plastic bag) or, more commonly, by an infusion pump through thin flexible tubing to a tube (catheter) inserted in a vein, usually in the forearm. In some cases, cells or therapeutic regimes are administered as infusions. An infusion can take place over a period of time. For example, an infusion can be an administration of a cell or therapeutic regime over a period of about 5 minutes to about 5 hours. An infusion can take place over a period of about 5 min, 10 min, 20 min, 30 min, 40 min, 50 min, 1 hour, 1.5 hours, 2 hours, 2.5 hours, 3 hours, 3.5 hours, 4 hours, 4.5 hours, or up to about 5 hours.

In some embodiments, intravenous administration is used to deliver a precise dose quickly and in a well-controlled manner throughout the body. It is also used for irritating solutions, which would cause pain and damage tissues if given by subcutaneous or intramuscular injection. An intravenous injection can be more difficult to administer than a subcutaneous or intramuscular injection because inserting a needle or catheter into a vein may be difficult, especially if the person is obese. When given intravenously, a drug is delivered immediately to the bloodstream and tends to take effect more quickly than when given by any other route. Consequently, health care practitioners closely monitor people who receive an intravenous injection for signs that the drug is working or is causing undesired side effects. Also, the effect of a drug given by this route tends to last for a shorter time. Therefore, some drugs must be given by continuous infusion to keep their effect constant. For the intrathecal route, a needle is inserted between two vertebrae in the lower spine and into the space around the spinal cord. The drug is then injected into the spinal canal. A small amount of local anesthetic is often used to numb the injection site. This route is used when a drug is needed to produce rapid or local effects on the brain, spinal cord, or the layers of tissue covering them (meninges)—for example, to treat infections of these structures.

Drugs administered by inhalation through the mouth can be atomized into smaller droplets than those administered by the nasal route, so that the drugs can pass through the windpipe (trachea) and into the lungs. How deeply into the lungs they go depends on the size of the droplets. Smaller droplets go deeper, which increases the amount of drug absorbed. Inside the lungs, they are absorbed into the bloodstream. Drugs applied to the skin are usually used for their local effects and thus are most commonly used to treat superficial skin disorders, such as psoriasis, eczema, skin infections (viral, bacterial, and fungal), itching, and dry skin. The drug is mixed with inactive substances. Depending on the consistency of the inactive substances, the formulation may be an ointment, cream, lotion, solution, powder, or gel In some cases, a treatment regime may be dosed according to a body weight of a subject. In subjects who are determined obese (BMI >35) a practical weight may need to be utilized. BMI is calculated by: BMI=weight (kg)/[height (m)]$^2$.

An ideal body weight may be calculated for men as 50 kg+2.3*(number of inches over 60 inches) or for women 45.5 kg+2.3 (number of inches over 60 inches). An adjusted body weight may be calculated for subjects who are more than 20% of their ideal body weight. An adjusted body weight may be the sum of an ideal body weight+(0.4× (Actual body weight−ideal body weight)). In some cases a body surface area may be utilized to calculate a dosage. A body surface area (BSA) may be calculated by: BSA (m2)=√Height (cm)*Weight (kg)/3600.

In some cases, a pharmaceutical composition comprising a cellular therapy can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes.

In some cases, a therapeutic regime can be administered along with a carrier or excipient. Exemplary carriers and excipients can include dextrose, sodium chloride, sucrose, lactose, cellulose, xylitol, sorbitol, malitol, gelatin, PEG, PVP, and any combination thereof.

In some cases, an excipient such as dextrose or sodium chloride can be at a percent from about 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or up to about 15%.

Described herein is a method of treating a disease (e.g., cancer, such as gastrointestinal cancer) in a recipient comprising transplanting to the recipient one or more cells (including organs and/or tissues) comprising engineered cells. Cells prepared by intracellular genomic transplant can be used to treat cancer.

In some embodiments, a method of treating gastrointestinal cancer comprises: a) obtaining tumor infiltrating lymphocytes (TIL) from a tumor sample (e.g., a tumor sample from a subject having gastrointestinal cancer); b) identifying a mutation reactive TIL; and disrupting an endogenous gene or portion thereof with a Cas nuclease in said mutation reactive TIL. In some embodiments, the tumor sample is subjected to sequencing analysis, such as whole exomic sequencing, transcriptome sequencing, or a combination thereof. In some embodiments, the identifying comprises introducing the TIL to antigen presenting cells (APCs) pulsed with peptides comprising the mutation (e.g., from about 15mer mutant peptides up to about 30mer mutant peptides, such as 25mer mutant peptides). In some embodiments, the TIL are contacted with APCs expressing peptides to determine reactivity of TIL. A peptide can comprise a tumor mutation that may be targeted by a TIL. For example, an APC may express a multitude of peptides, some encoding a tumor mutation that may be utilized to identify tumor-reactive TILs. Those TILs that are identified as having tumor reactivity may be isolated or purified and utilized for genomic engineering. In some cases, a tumor-reactive TIL may be genomically engineered with a CRISPR system.

A CRISPR system may be used to knock out an endogenous gene, such as CISH, in a tumor-reactive TIL. A CRISPR system may be used to knock out an endogenous gene, such as PD-1, in a tumor-reactive TIL. In some embodiments, the identifying comprises introducing said TIL to antigen presenting cells (APCs) electroporated with a polynucleic acid comprising a mutation. In some embodiments, the identifying further comprises detecting a cytokine such as IL-2, IFN-gamma, IL-6, degranulation, cellular proliferation, or the like.

EXAMPLES

Example 1: Identify gRNA with Highest Double Strand Break (DSB) Induction at Each Gene Site Design and Construction of Guide RNAs Guide RNAs (gRNAs) were designed to the desired region of a gene. Multiple primers to generate gRNAs (shown in Table 1) were chosen based on the highest ranked values determined by off-target locations. The gRNAs were ordered in oligonucleotide pairs: 5'-CACCG-gRNA sequence-3' and 5'-AAAC-reverse complement gRNA sequence-C-3' (sequences of the oligonucleotide pairs are listed in Table 1).

TABLE 8

Primers used to generate the gRNAs (the sequence CACCG is added to the sense and AAAC to the antisense for cloning purposes).

| SEQ ID | Primer Name | Sequence 5'-3' |
|---|---|---|
| 82 | HPRT gRNA 1 Sense | CACCGCACGTGTGAACCAACCCGCC |
| 83 | HPRT gRNA 1 Anti | AAACGGCGGGTTGGTTCACACGTGC |
| 84 | HPRT gRNA 2 Sense | CACCGAAACAACAGGCCGGGCGGGT |
| 85 | HPRT gRNA 2 Anti | AAACACCCGCCCGGCCTGTTGTTTC |
| 86 | HPRT gRNA 3 Sense | CACCGACAAAAAAATTAGCCGGGTG |
| 87 | HPRT gRNA 3 Anti | AAACCACCCGGCTAATTTTTTTGT |
| 88 | HPRT gRNA 4 Sense | CACCGTAAATTTCTCTGATAGACTA |
| 89 | HPRT gRNA 4 Anti | AAACTAGTCTATCAGAGAAATTTAC |
| 90 | HPRT gRNA 5 Sense | CACCGTGTTTCAATGAGAGCATTAC |
| 91 | HPRT gRNA 5 Anti | AAACGTAATGCTCTCATTGAAACAC |
| 92 | HPRT gRNA 6 Sense | CACCGGTCTCGAACTCCTGAGCTC |
| 93 | HPRT gRNA 6 Anti | AAACGAGCTCAGGAGTTCGAGACC |
| 94 | HPRT CelI For | AGTGAAGTGGCGCATTCTTG |
| 95 | HPRT CelI Rev | CACCCTTTCCAAATCCTCAGC |
| 96 | AAVS1 gRNA 1 Sense | CACCGTGGGGGTTAGACCCAATATC |
| 97 | AAVS1 gRNA 1 Anti | AAACGATATTGGGTCTAACCCCCAC |
| 98 | AAVS1 gRNA 2 Sense | CACCGACCCCACAGTGGGGCACTA |
| 99 | AAVS1 gRNA 2 Anti | AAACTAGTGCCCCACTGTGGGGTC |
| 100 | AAVS1 gRNA 3 Sense | CACCGAGGGCCGGTTAATGTGGCTC |
| 101 | AAVS1 gRNA 3 Anti | AAACGAGCCACATTAACCGGCCCTC |
| 102 | AAVS1 gRNA 4 Sense | CACCGTCACCAATCCTGTCCCTAG |

TABLE 8-continued

Primers used to generate the gRNAs (the sequence CACCG is added to the sense and AAAC to the antisense for cloning purposes).

| SEQ ID | Primer Name | Sequence 5'-3' |
|---|---|---|
| 103 | AAVS1 gRNA 4 Anti | AAACCTAGGGACAGGATTGGTGAC |
| 104 | AAVS1 gRNA 5 Sense | CACCGCCGGCCCTGGGAATATAAGG |
| 105 | AAVS1 gRNA 5 Anti | AAACCCTTATATTCCCAGGGCCGGC |
| 106 | AAVS1 gRNA 6 Sense | CACCGCGGGCCCCTATGTCCACTTC |
| 107 | AAVS1 gRNA 6 Anti | AAACGAAGTGGACATAGGGGCCCGC |
| 108 | AAVS1 CelI For | ACTCCTTTCATTTGGGCAGC |
| 109 | AAVS1 CelI Rev | GGTTCTGGCAAGGAGAGAGA |
| 110 | PD-1 gRNA 1 Sense | CACCGCGGAGAGCTTCGTGCTAAAC |
| 111 | PD-1 gRNA 1 Anti | AAACGTTTAGCACGAAGCTCTCCGC |
| 112 | PD-1 gRNA 2 Sense | CACCGCCTGCTCGTGGTGACCGAAG |
| 113 | PD-1 gRNA 2 Anti | AAACCTTCGGTCACCACGAGCAGGC |
| 114 | PD-1 gRNA 3 Sense | CACCGCAGCAACCAGACGGACAAGC |
| 115 | PD-1 gRNA 3 Anti | AAACGCTTGTCCGTCTGGTTGCTGC |
| 116 | PD-1 gRNA 4 Sense | CACCGAGGCGGCCAGCTTGTCCGTC |
| 117 | PD-1 gRNA 4 Anti | AAACGACGGACAAGCTGGCCGCCTC |
| 118 | PD-1 gRNA 5 Sense | CACCGCGTTGGGCAGTTGTGTGACA |
| 119 | PD-1 gRNA 5 Anti | AAACTGTCACACAACTGCCCAACGC |
| 120 | PD-1 gRNA 6 Sense | CACCGACGGAAGCGGCAGTCCTGGC |
| 121 | PD-1 gRNA 6 Anti | AAACGCCAGGACTGCCGCTTCCGTC |
| 122 | PD-1 CelI For | AGAAGGAAGAGGCTCTGCAG |
| 123 | PD-1 CelI Rev | CTCTTTGATCTGCGCCTTGG |
| 124 | CTLA4 gRNA 1 Sense | CACCGCCGGGTGACAGTGCTTCGGC |
| 125 | CTLA4 gRNA 1 Anti | AAACGCCGAAGCACTGTCACCCGGC |
| 126 | CTLA4 gRNA 2 Sense | CACCGTGCGGCAACCTACATGATG |
| 127 | CTLA4 gRNA 2 Anti | AAACCATCATGTAGGTTGCCGCAC |
| 128 | CTLA4 gRNA 3 Sense | CACCGCTAGATGATTCCATCTGCAC |
| 129 | CTLA4 gRNA 3 Anti | AAACGTGCAGATGGAATCATCTAGC |
| 130 | CTLA4 gRNA 4 Sense | CACCGAGGTTCACTTGATTTCCAC |
| 131 | CTLA4 gRNA 4 Anti | AAACGTGGAAATCAAGTGAACCTC |
| 132 | CTLA4 gRNA 5 Sense | CACCGCCGCACAGACTTCAGTCACC |
| 133 | CTLA4 gRNA 5 Anti | AAACGGTGACTGAAGTCTGTGCGGC |
| 134 | CTLA4 gRNA 6 Sense | CACCGCTGGCGATGCCTCGGCTGC |
| 135 | CTLA4 gRNA 6 Anti | AAACGCAGCCGAGGCATCGCCAGC |
| 136 | CTLA4 CelI For | TGGGGATGAAGCTAGAAGGC |
| 137 | CTLA4 CelI Rev | AATCTGGGTTCCGTTGCCTA |
| 138 | CCR5 gRNA 1 Sense | CACCGACAATGTGTCAACTCTTGAC |
| 139 | CCR5 gRNA 1 Anti | AAACGTCAAGAGTTGACACATTGTC |

TABLE 8-continued

Primers used to generate the gRNAs
(the sequence CACCG is added to the sense and
AAAC to the antisense for cloning purposes).

| SEQ ID | Primer Name | Sequence 5'-3' |
|---|---|---|
| 140 | CCR5 gRNA 2 Sense | CACCGTCATCCTCCTGACAATCGAT |
| 141 | CCR5 gRNA 2 Anti | AAACATCGATTGTCAGGAGGATGAC |
| 142 | CCR5 gRNA 3 Sense | CACCGGTGACAAGTGTGATCACTT |
| 143 | CCR5 gRNA 3 Anti | AAACAAGTGATCACACTTGTCACC |
| 144 | CCR5 gRNA 4 Sense | CACCGACACAGCATGGACGACAGCC |
| 145 | CCR5 gRNA 4 Anti | AAACGGCTGTCGTCCATGCTGTGTC |
| 146 | CCR5 gRNA 5 Sense | CACCGATCTGGTAAAGATGATTCC |
| 147 | CCR5 gRNA 5 Anti | AAACGGAATCATCTTTACCAGATC |
| 148 | CCR5 gRNA 6 Sense | CACCGTTGTATTTCCAAAGTCCCAC |
| 149 | CCR5 gRNA 6 Anti | AAACGTGGGACTTTGGAAATACAAC |
| 150 | CCR5 CelI For | CTCAACCTGGCCATCTCTGA |
| 151 | CCR5 CelI Rev | CCCGAGTAGCAGATGACCAT |

The gRNAs were cloned together using a target sequence cloning protocol. Briefly, the oligonucleotide pairs were phosphorylated and annealed together using T4 PNK (NEB) and 10×T4 Ligation Buffer (NEB) in a thermocycler with the following protocol: 37° C. 30 minutes, 95° C. 5 minutes and then ramped down to 25° C. at 5° C./minute. pENTR1-U6-Stuffer-gRNA vector was digested with FastDigest Bbsl (Fermentas), FastAP (Fermentas) and 10× Fast Digest Buffer were used for the ligation reaction. The digested pENTR1 vector was ligated together with the phosphorylated and annealed oligo duplex (dilution 1:200) from the previous step using T4 DNA Ligase and Buffer (NEB). The ligation was incubated at room temperature for 1 hour and then transformed and subsequently mini-prepped using GeneJET Plasmid Miniprep Kit (Thermo Scientific). The plasmids were sequenced to confirm the proper insertion.

Validation of gRNAs

HEK293T cells were plated out at a density of 1×10^5 cells per well in a 24 well plate. 150 uL of Opti-MEM medium was combined with 1.5 ug of gRNA plasmid, 1.5 ug of Cas9 plasmid. Another 150 uL of Opti-MEM medium was combined with 5 uL of Lipofectamine 2000 Transfection reagent (Invitrogen). The solutions were combined together and incubated for 15 minutes at room temperature. The DNA-lipid complex was added dropwise to wells of the 24 well plate. Cells were incubated for 3 days at 37° C. and genomic DNA was collected using the GeneJET Genomic DNA Purification Kit (Thermo Scientific). Activity of the gRNAs was quantified by a Surveyor Digest, gel electrophoresis, and densitometry (Guschin, D. Y., et al., "A Rapid and General Assay for Monitoring Endogenous Gene Modification," Methods in Molecular Biology, 649: 247-256 (2010)).

Results

The efficiencies of Cas9 in creating double strand break (DSB) with the assistance of different gRNA sequences are listed in Table 9. The percentage numbers in Table 9 indicated the percent of gene modifications in the sample.

TABLE 9

The efficiencies of Cas9/gRNA pair in creating double strand break (DSB) at each target gene site.

|  | HPRT | AAVS1 | CCR5 | PD1 | CTLA4 |
|---|---|---|---|---|---|
| gRNA#1 | 27.85% | 32.99% | 21.47% | 10.83% | 40.96% |
| gRNA#2 | 30.04% | 27.10% | >60% | >60% | 56.10% |
| gRNA#3 | <1% | 39.82% | 55.98% | 37.42% | 39.33% |
| gRNA#4 | <5% | 25.93% | 45.99% | 20.87% | 40.13% |
| gRNA#5 | <1% | 27.55% | 36.07% | 30.60% | 15.90% |
| gRNA#6 | <5% | 39.62% | 33.17% | 25.91% | 36.93% |

DSB were created at all five tested target gene sites. Among them, CCR5, PD1, and CTLA4 provided the highest DSB efficiency. Other target gene sites, including hRosa26, are tested using the same methods described herein.

The percent of double strand break compared to donor control and Cas9 only controls are listed. A three representative target gene sites (i.e., CCR5, PD1, and CTLA4) were tested.

Example 2: GUIDE-Seq Library Preparation

To examine off-target cutting of PD-1 gRNA known as genome-wide, unbiased identification of double-strand breaks (DSBs) is achieved by sequencing or GUIDE-seq. It is a method that uses capture of double-stranded oligonucleotides into DSBs generated by CRISPR/Cas9, followed by next-generation sequencing to determine the location of the genetic modification.

Human T cells were isolated using solid-phase reversible immobilization magnetic beads (Agencourt DNAdvance), were sheared with a Covaris 5200 instrument to an average length of 500 bp, end-repaired, A-tailed, and ligated to half-functional adapters, incorporating a 8-nt random molecular index. Two rounds of nested anchored PCR, with primers complementary to the oligo tag, were used for target enrichment. End Repair Thermocycler Program: 12° C. for 15 min, 37° C. for 15 min; 72° C. for 15 min; hold at 4° C.

Start sites of GUIDE-Seq reads mapped back to the genome enable localization of the DSB to within a few base pairs. The library was quantitated using Kapa Biosy stems kit for Illumina Library Quantification kit, according to manufacturer instruction. Using the mean quantity estimate of number of molecules per uL given by the qPCR run for each sample, the total set of libraries were normalized to 1.2×10'10 molecules, divided by the number of libraries to be pooled together for sequencing. This gave a by molecule input for each sample, and also a by volume input for each sample. Reads were mapped for the on- and off-target sites of the three RGNs directed by truncated gRNAs assessed by GUIDE-Seq. In all cases, the target site sequence has the protospacer sequence to the left and the PAM sequence to the right on the x-axis. The library was denatured and loaded onto the Miseq according to Illumina's standard protocol for sequencing with an Illumina Miseq Reagent Kit V2-300 cycle (2×150 bp paired end).

In a second experiment, GUIDE-Seq analysis of the PD-1 gRNA revealed only one reproducible off-target modification. This site matches the single off-target location detected by the deep sequencing of predicted sites demonstrating a correlation between the two approaches. Thus, the NGS analysis of off-targets is sensitive and comprehensive. The gRNA designs for PD-1 were highly specific with only one detectable off target site which resides in an inert section of the genome and which modification of would not be expected to result in any adverse effects. The gRNA designs for CISH were highly specific with no measurable off-target activity.

Example 3: Genomic Engineering of TIL to Knock Out PD-1, CTLA-4, and CISH

Suitable tumors from eligible stage IIIc-IV cancer patients are resected and cut up into small 3-5 mm$^2$ fragments and placed in culture plates or small culture flasks with growth medium and high-dose (HD) IL-2. The TILs are initially expanded for 3-5 weeks during this "pre-rapid expansion protocol" (pre-REP) phase to at least 50×10$^6$ cells. TILs are electroporated using the Neon Transfection System (100 uL or 10 ul Kit, Invitrogen, Life Technologies). TILS are pelleted and washed once with T buffer. TILs are resuspended at a density of 2×10$^5$ cells in 10 uL of T buffer for 10 ul tip, and 3×10$^6$ cells in 100 ul T buffer for 100 ul tips. TILs are then electroporated at 1400 V, 10 ms, 3 pulses utilizing 15 ug Cas9 mRNA, and 10-50 ug PD-1, CTLA-4, and CISH gRNA-RNA (100 mcl tip). After transfection, TILs are plated at 1000 cells/effectuL in antibiotic free culture media and incubated at 30 C in 5% CO2 for 24 hrs. After 24 hr recovery, TILs can be transferred to antibiotic containing media and cultured at 37° C. in 5% CO2.

The cells are then subjected to a rapid expansion protocol (REP) over two weeks by stimulating the TILs using anti-CD3 in the presence of PBMC feeder cells and IL-2. The expanded TIL (now billions of cells) are washed, pooled, and infused into a patient followed by one or two cycles of HD IL-2 therapy. Before TIL transfer, a patient can be treated with a preparative regimen using cyclophosphamide (Cy) and fludaribine (Flu) that transiently depletes host lymphocytes "making room" for the infused TIL and removing cytokine sinks and regulatory T cells in order to facilitate TIL persistence. Subjects receive an infusion of their own modified TIL cells over 30 minutes and remain in the hospital to be monitored for adverse events until they have recovered from the treatment. FIG. 40A and FIG. 40B show cellular expansion of TIL of two different subjects. FIG. 41A and FIG. 41B show cellular expansion of TIL electroporated with a CRISPR system, and anti-PD-1 guides and cultured with the addition of feeder cells or no addition of feeder cells.

Example 4: gRNA Modification

Design and Construction of Modified Guide RNAs:
Guide RNAs (gRNAs) were designed to the desired region of a gene. Multiple gRNAs (shown in Table 4) were chosen based on the highest ranked values determined by off-target locations. The gRNAs targeting PD-1, CTLA-4, and CISH gene sequences were modified to contain 2-O-Methyl 3phosphorothioate additions, FIG. 22 and FIG. 32.

Example 5: Phase I Clinical Trial of TIL Therapy for Gastrointestinal Cancer

A subject with evaluable gastrointestinal cancer will undergo a resection of tumorous samples. Tumor infiltrating lymphocytes (TIL) will be grown and expanded. Multiple individual fragments or multiple individual cultures of tumor infiltrating lymphocytes will be grown ex vivo. Individual cultures are separately expanded and when a sufficient yield of TIL (approximately 10$^8$ cells) is expanded from each culture, the TIL is cryopreserved and aliquots taken for immunologic testing. An aliquot of the original tumor is subjected to exomic and, when possible, transcriptome sequencing to identify mutations uniquely present in the cancer compared to normal cells of the subject. Aliquots of each cultured TIL preparation are tested for reactivity against identified mutations using in vitro functionality testing. In brief, the subjects's antigen presenting cells are pulsed with 25mer peptides including the mutated peptide in the center flanked by 12 normal amino acids. Alternatively, in vitro transcribed RNA encoding all mutations are electroporated into the patient's antigen presenting cells. Using either or both of these techniques, the previously cryopreserved TIL cultures are then tested for reactivity to identify the exact mutations recognized. The cultures with high degrees of reactivity against individual cancer mutations are then subjected to CRISPR knockout of the CISH gene. Up to five different cultures can be selected for this procedure from each patient. Cultures with demonstrated mutation reactivity are sent to the good manufacturing practices (GMP) Cell Production Facility where CRISPR technology is used to knockout the CISH gene. Knockout of the CISH gene is determined by DNA sequencing based tracking of indels by decomposition (TIDE) analysis. Cell populations with successful knockout of the CISH gene are then rapidly expanded utilizing OKT3 and feeder cells. Cryopreserved lymphocytes are then utilized in patient treatment. In the first part of this clinical trial protocol, a dose escalation is initiated utilizing one subject per group starting at 10$^9$ CISH knockout cells per subject. Individual subjects are treated at half log increments and if any toxicity higher than Grade 2 is seen due to the cell infusion, that group is then expanded to additional patients. The following doses are utilized: 1) 10$^9$ cells 2) 3×10$^9$ cells 3) 10$^{10}$ cells 4) 3×10$^{10}$ cells 5) 3×10$^{10}$ to 2×10$^{11}$ cells. Patients receive a lymphodepleting preparative regimen followed by infusion of engineered cells and high dose IL-2. Patients are evaluated for persistence of the cells as well as for clinical response approximately 4 to 6 weeks following administration of the cell product. Each patient receives only a single course of treatment and patients are followed monthly with lymphocyte and serum collections for immunologic studies.

The safety of the administration of mutation reactive autologous lymphocytes with knockout of the CISH gene in patients with refractory metastatic cancer is evaluated. The response rate of the standard non-myeloablative conditioning regimen mutation reactive TIL with knockout of CISH gene plus high dose IL-2 using lymphocytes in patients with metastatic cancer also is determined as well as the survival and persistence of CISH knockout mutation reactive lymphocytes in subjects with metastatic gastrointestinal cancer.

Example 6: CISH Knock Down in a Murine Model

To explore the role of Cish in CD8$^+$ T cells, CD8$^+$ T cells are isolated from wild type (WT) or Cish$^{-/-}$ pmel-1 mice, stimulated with peptide-pulsed splenocytes from C57BL/6 mice, and examined for proliferation and cytokine production in vitro. Flow cytometric analysis after CD8$^+$ T cell isolation reveals that the CD8$^+$ T cell differentiation state remains unaltered in the steady-state with or without Cish. Enumeration of CD8$^+$ T cells one week after in vitro priming reveals significantly more T cells in the absence of Cish. Evaluation of apoptosis may account for this increased in vitro T cell expansion. Primed T cells are TCR-stimulated and stained with the nuclear stain, 7-AAD and Annexin V, which binds to phosphatidylserine on the cell surface of pre-apoptotic cells.

Example 7: Melanoma Murine Model of Cish-Deficiency

The in vivo functional significance of Cish-deficient CD8+ T cells can be determined by using a pmel-1 melanoma model. Melanoma-specific pmel-1 T cells with or without Cish is adoptively transferred (ACT) into established B16 melanoma-bearing C57BL/6 hosts and evaluated for tumor growth and in vivo persistence by IVIS imaging of fluorescently labelled tumor cells and flow cytometric analysis of transferred engineered cells. The ACT of Cish-deficient pmel-1 T cells, results in a significant and durable regression of large, established tumors as compared to WT T cells. This profound regression also results in improved survival, with the ACT of Cish$^{-/-}$ T cells extending the survival of tumor-bearing mice for greater than 60 days. Serial sampling of treated mice after the ACT of congenically-marked pmel-1 T cells reveals a pronounced expansion and delayed contraction of Cish-deficient T cells compared to T cells obtained from their WT littermates.

Example 8: Melanoma Murine Model of Cish-Deficiency in Rag1$^{-/-}$

Using tumor-bearing hosts lacking an adaptive immune system Cish regulated CD8+ T cell-intrinsic in vivo tumor killing is evaluated. Sub-therapeutic numbers of pmel-1 T cells with or without Cish ($2.5\times10^5$) are adoptively transferred into "empty" Rag1$^{-/-}$ B16 tumor-bearing hosts, with reduced administration of vaccine ($1\times10^7$ PFU) and exogenous IL-2 ($2\times10^4$ IU), and then tumor growth is evaluated. Long-term tumor "maintenance" or regression with the sub-therapeutic administration of tumor-specific Cish-deficient but not the WT CD8 T cells is anticipated, with no progression of palpable tumor masses for greater than 50 days. Whether Cish$^{-/-}$ tumor-specific T cells maintain their increased functional avidity in vivo will be determined. To this end, congenically-marked pmel-1 T cells are ex vivo enriched from splenocytes with magnetic beads seven days after transfer and evaluated for IFN-γ release against peptide-pulsed targets. A significant increase in functional avidity of ex vivo stimulated Cish$^{-/-}$ compared to WT T cells can result. This apparent "maintenance" of enhanced functional avidity can be important when targeting tumors that typically express low levels of antigen. Cish$^{-/-}$ tumor-specific T cells are eliminated even 35 days after ACT by CD8-depletion, followed by tumor growth analysis to evaluate long-term tumor specificity.

Example 9: gRNA Safety Analysis

To assess off-target sites by next-generation deep sequencing, human peripheral blood-derived T cells were electroporated with CRISPR/Cas9 reagents targeting PD-1 or CISH, and genomic DNA was harvested 72-hours post transfection. Each site was amplified by PCR (250 nucleotides surrounding the predicted Cas9 cleavage site) from the pool of targeted T cells and subjected to deep sequencing using an Illumina Hi-Seq machine. This enabled an incredibly deep analysis of sequence reads from the pool of PCR products, with on average 450,000 sequence reads available for detection for each off-target site. Therefore, even off-target modifications with low abundance are readily detectible using this method.

The deep sequencing output of each off-target site from T cells transfected with the CRISPR/Cas9 reagents were compared to T cells left untreated to identify sites, which have undergone CRISPR-mediated modification. For PD-1, only 1 of the 71 candidate sites displayed evidence of an off target modification frequency higher than that observed in untreated control cells (see Table 10) and none of the sites analyzed for CISH showed evidence of a CRISPR-mediated modification (see Table 11). The off-target activity uncovered for the PD-1 gRNA showed a disruption frequency of less than 1% and this site maps to a sequence within the genome, which does not fall within any known coding genes and therefore is unlikely to have any influence on T cell function if modified.

Example 10: Identification and Isolation of Reactive TIL

TILs are isolated from a cancer lesion. ELISPOT assay of 24 individual TIL cultures after co-culture with autologous dendritic cells transfected with an irrelevant tandem minigene (TMG) RNA, or the indicated TMG-MCSP construct encoding the 61 mutations identified by whole-exome and transcriptome sequencing is performed. IFN-γ production as determined by ELISPOT assay, and flow cytometric analysis of 4-1BB or CD28 expression on CD8+ and/or CD4+ T cells of TIL culture after co-culture with dendritic cells (DCs) transfected with an irrelevant TMG RNA or TMG-MCSP, or incubated overnight with the mutated long peptides encoded by TMG-MCSP.

Flow cytometry based TCR-Vβ spectratyping of TIL culture showing reactivity to MCSP is performed. Magnetic bead-based enrichment of the anti-MCSP TCR-Vβ population is performed using TCR-alpha and beta chain sequences from enriched TCR-Vβ population determined by 5' RACE and TCR-PCR.

TABLE 10

Predicted off-target sites for the PD-1 gRNA analyzed by deep sequencing. DNA sequences and their genomic locations are indicated along with the number of mismatches between the genomic site and gRNA. Where sites reside within genes, the gene names are noted. A blank under mutation frequency means there was no detectable frequency greater than observed in the untreated control cells.

| ID | Off target sequence | Mis matches | Genomic location | Gene | Mutation frequency |
|---|---|---|---|---|---|
| 158 | CCTCCTCCTGGTGACCGGAGAGG | 3 | chr17:77041232-77041254 | | |
| 159 | CTTGCTGGTGGTGACAGAAGAGG | 3 | chr16:6995450-6995472 | RBFOX1 | |
| 160 | ACTGCTTGTTGTGACCGATGGGG | 4 | chr6:168617770-168617792 | SMOC2 | |

TABLE 10-continued

Predicted off-target sites for the PD-1 gRNA analyzed by deep sequencing. DNA sequences and their genomic locations are indicated along with the number of mismatches between the genomic site and gRNA. Where sites reside within genes, the gene names are noted. A blank under mutation frequency means there was no detectable frequency greater than observed in the untreated control cells.

| ID | Off target sequence | Mismatches | Genomic location | Gene | Mutation frequency |
|---|---|---|---|---|---|
| 161 | CCAGCACATGGTGACCAAAGGAG | 4 | chr6:3146908-3146930 | BPHL | |
| 162 | CCTGCTTGTGGTGACCTAATAAG | 3 | chr5:144090947-144090969 | | |
| 163 | CCAGGTGGTGGTGAGCGAAGAGG | 4 | chr18:75064030-75064052 | ZNF407 | |
| 164 | CCTAATCGTGGTCACCGAAAGAG | 4 | chr3:35529500-35529522 | | |
| 165 | CCTGCTGGTGGTGACCTATGAGG | 3 | chr6:148164881-148164903 | | |
| 166 | CCTGCTACTGGTGTCCGAAGTGG | 3 | chr4:63174604-63174626 | | |
| 167 | GCAGCTCGAGGTGACGGAAGAGG | 4 | chrY:7092092-7092114 | | |
| 168 | CATGCTCCTAGTGACAGAAGGGG | 4 | chr2:174733509-174733531 | | |
| 169 | CCCGCTGGTGGGAACCGAAGGAG | 4 | chr17:40648598-40648620 | | |
| 170 | CCTGGGCGTAGTGAGCGAAGCGG | 4 | chr17:79841725-79841747 | | |
| 171 | CCTGGCCGCGGTGACCGAGGCGG | 4 | chr19:36215042-36215064 | ZNF146, ZNF565 | |
| 172 | CCTGCCCAAGGTTACCGAAGTGG | 4 | chr2:144324103-144324125 | GTDC1 | |
| 173 | CCTGCTCCAGTTGACCAAAGAGG | 4 | chr15:29622634-29622656 | | |
| 174 | ACTGCACGTGGTGAACCAAGAGG | 4 | chr19:11426472-11426494 | CCDC151 | |
| 175 | GCTGCCCATGGTGACAGAAGGGG | 4 | chr13:26920698-26920720 | | 0.8% |
| 176 | ACTGCTGGTGGTGAACGAAAGGG | 4 | chr6:136920831-136920853 | | |
| 177 | GCTGCTAGTGGTGACGGAAAGAG | 4 | chrX:56147227-56147249 | | |
| 178 | TCTGCTATTGGTGTCCGAAGTGG | 4 | chr11:23650922-23650944 | | |
| 179 | CGAGCTCGTGGTTACAGAAGGGG | 4 | chr7:98230892-98230914 | TECPR1 | |
| 180 | CCAGCTCGTCGGGACAGAAGAGG | 4 | chr1:1295498-1295520 | ACAP3 | |
| 181 | CCACCTCGGGGTGGCCGAAGCGG | 4 | chr1:6428267-6428289 | ESPN | |
| 182 | CCAGCTAGTGTTGACTGAAGGGG | 4 | chr17:45123452-45123474 | PLCD3 | |
| 183 | CCTGGCTGTGGTGACAGAAGGGG | 4 | chrX:7445082-7445104 | | |
| 184 | CCTGCACGTGATGACCTAACAGG | 4 | chr15:68344743-68344765 | ITGA11 | |
| 185 | CCTGCTCGTGCTGTCCGCAGCAG | 3 | chr17:14206970-14206992 | COX10 | |
| 186 | CCTGCTGGTGGTGACGGCAGCAG | 3 | chr6:40571706-40571728 | LRFN2 | |
| 187 | GCTGCTGGTGGTGCCCGATGGGG | 4 | chr7:135152893-135152915 | TMEM140 | |
| 188 | CCTGCTCGTGGTGATATGAGGGG | 4 | chr20:32138893-32138915 | TM9SF4 | |
| 189 | CCAGCTGGTGGTGACTCAAGGAG | 4 | chr2:227246997-227247019 | COL4A3 | |
| 190 | CCTTCTCGTGGAGACAGATGAGG | 4 | chr16:31360121-31360143 | ITGAX | |
| 191 | CCTTCTCGTGGTGCCTGGAGTGG | 4 | chr17:75077493-75077515 | | |
| 192 | CCTTCTCATGGTGGCGGAAGGAG | 4 | chr20:12304659-12304681 | | |
| 193 | CCTTCTCATGGTGACAGTAGAGG | 4 | chr10:15505067-15505089 | | |
| 194 | CCTGGTCGTGTTGAGTGAAGGGG | 4 | chr22:44286292-44286314 | KIAA1644 | |

TABLE 10-continued

Predicted off-target sites for the PD-1 gRNA analyzed by deep sequencing. DNA sequences and their genomic locations are indicated along with the number of mismatches between the genomic site and gRNA. Where sites reside within genes, the gene names are noted. A blank under mutation frequency means there was no detectable frequency greater than observed in the untreated control cells.

| ID | Off target sequence | Mis matches | Genomic location | Gene | Mutation frequency |
|---|---|---|---|---|---|
| 195 | CCTGGTAGTGGTGACCACAGTGG | 4 | chr14:93411523-93411545 | UNC79 | |
| 196 | CCTGGTGGTGGTGACCATAGAGG | 4 | chr17:52593937-52593959 | | |
| 197 | CCTGCCCGTGGTAATCGAACCGG | 4 | chr16:55091717-55091739 | | |
| 198 | CCTGCCCGTGGTGAACGCTGTGG | 4 | chr1:11838633-11838655 | CLCN6 | |
| 199 | CCTGCACGTGGTGACAGCATGGG | 4 | chr15:29685533-29685555 | | |
| 200 | CCTGCGTGTGGAGGCCGAAGGGG | 4 | chr20:62333572-62333594 | LAMA5 | |
| 201 | CCTGCCGGTGGTGACCTATGTGG | 4 | chr11:45161912-45161934 | PRDM11 | |
| 202 | CCTGCTGGTGCTGCCTGAAGGGG | 4 | chr10:70197667-70197689 | | |
| 203 | CCTGCTGGTGCTGGCCGATGGGG | 4 | chr13:28923534-28923556 | | |
| 204 | CCTGCTAGTGGAAACCGCAGGGG | 4 | chr16:85775103-85775125 | | |
| 205 | CCTGCTGGTGGTACCAGAAGAGG | 4 | chr16:69413041-69413063 | | |
| 206 | CCTGCTGGTGGTACCAGAAGAGG | 4 | chr22:38687937-38687959 | JOSD1 | |
| 207 | CCTGCTGGTGGTGGCAGCAGTGG | 4 | chr10:117265710-117265732 | SLC18A2 | |
| 208 | CCTGCTAGTGGTGGCAGTAGTGG | 4 | chr12:125804661-125804683 | | |
| 209 | CCTGCTTATGGGGACTGAAGGGG | 4 | chr10:103671399-103671421 | SH3PXD2A | |
| 210 | CCTGCTTCTGGTGTCAGAAGTGG | 4 | chr9:32579566-32579588 | | |
| 211 | CCTGCTGCTGGTGGCCGACGTGG | 4 | chr11:1017425-1017447 | MUC6 | |
| 212 | CCTGCTGTTGGTGACTCAAGGAG | 4 | chr11:129696156-129696178 | | |
| 213 | CCTGCTGTTGGTGACTCAAGGAG | 4 | chr9:33720172-33720194 | | |
| 214 | CCTGCTTGGGCTGACCGTAGGGG | 4 | chr6:31860468-31860490 | NEU1 | |
| 215 | CCTGCTAGGGGAGACAGAAGAGG | 4 | chr19:27868452-27868474 | | |
| 216 | CCTGCTCCTGCTGCACGAAGTGG | 4 | chr11:7884410-7884432 | | |
| 217 | CCTGCTCTTGGGGACTGAATTGG | 4 | chrX:89186332-89186354 | | |
| 218 | CCTGCTCCTGGTTCCCAAAGAGG | 4 | chr4:102987791-102987813 | SLC9B1 | |
| 219 | CCTGCTCTTGGTCACTGCAGAGG | 4 | chr11:1977982-1978004 | | |
| 220 | CCTGCTCCTGGTGCAAGAAGGGG | 4 | chrX:115722874-115722896 | | |
| 221 | CCTGCTCCTGGTGCAAGAAGGGG | 4 | chrX:115840863-115840885 | | |
| 222 | CCTGCTCTTGGTGGAAGAAGTGG | 4 | chr14:56244618-56244640 | PELI2 | |
| 223 | CCTGCTCCTGGTGTGGGAAGAGG | 4 | chr7:157720635-157720657 | PTPRN2 | |
| 224 | CCTGCTCTTGGTGAACACAGGAG | 4 | chr2:74250861-74250883 | SLC4A5 | |
| 225 | CCTGCTCAAGGAGACAGAAGTGG | 4 | chr22:32997494-32997516 | SYN3 | |
| 226 | CCTGCTCCAGGTGAATGAAGAGG | 4 | chr15:95449375-95449397 | | |
| 227 | CCTGCTCTGGGTGACGGAGGGAG | 4 | chr16:89293161-89293183 | ANKRD11 | |
| 228 | CCTGCTCGCGGTGGGCTAAGGGG | 4 | chr5:10250461-10250483 | CCT5 | |

TABLE 11 predicted off-target sites for the CISH gRNA analyzed by deep sequencing. DNA sequences and their genomic locations are indicated along with the number of mismatches between the genomic site and gRNA. Where sites reside within genes, the gene names are noted. A blank under mutation frequency means there was no detectable frequency greater than observed in the untreated control cells and 'TBD' denotes a site that requires follow-up sequencing.

| ID | Off target sequence | Mis matches | Genomic location | Gene | Mutation frequency |
|---|---|---|---|---|---|
| 229 | CAGTTCCATTACCGCCAGCGGGG | 3 | chr11:72372913-72372935 | | |
| 230 | GGTTTCCATTCCTGCCAGCGGGG | 3 | chr2:65436495-65436517 | | |
| 231 | GTGTCCCGTTACGGCCAGCTCGG | 4 | chr17:28521552-28521574 | | |
| 232 | AGCTTCCCTTAGGGCCAGCGAAG | 4 | chr9:134261588-134261610 | | |
| 233 | GGGGTCCCTAAGGGCCAGCGAGG | 4 | chr1:109980531-109980553 | | |
| 234 | GCGTCGCACTACGGCCAGCGAGG | 4 | chr21:44899646-44899668 | | |
| 235 | GCGTGCCACTACGGCCAGCTAAG | 4 | chr6:44184900-44184922 | | |
| 236 | GGGTCCCCATAGGGCCAGCGAGG | 4 | chr19:51490678-51490700 | | |
| 237 | GGCTCCCATTGCAGCCAGCGTGG | 4 | chr10:2405356-2405378 | | |
| 238 | TTGTTCCATTATGGCCAGAGAAG | 4 | chr13:69635293-69635315 | | |
| 239 | TTGTTCCATTATGGCCAGAGAAG | 4 | chr2:161519910-161519932 | | |
| 240 | GGATACCAATACGGCCAACGAGG | 4 | chr20:59259210-59259232 | | |
| 241 | GGTTTCCTTTACTGCCGGCGAGG | 4 | chr15:59996211-59996233 | | |
| 242 | GGGTGCCAGTGGGGCCAGCGAGG | 4 | chr12:111198693-111198715 | | |
| 243 | GGGTTCCTTCAGGGCCAGAGAGG | 4 | chr19:50418174-50418196 | | |
| 244 | GGGCTCCATCACAGCCAGCAGGG | 4 | chr6:160117643-160117665 | | |
| 245 | AGGTTCCAGTTCGGCCAGTGAAG | 4 | chr2:68053890-68053912 | | |
| 246 | GTGTTCCATTCCGGCCCGCCAGG | 4 | chr13:98047590-98047612 | | |
| 247 | GGCTTCCAATAAGGCCAACGAGG | 4 | chr2:85513577-85513599 | | |
| 248 | GGGTTCCAGTGTGGCCAGCAAGG | 4 | chr15:30985934-30985956 | | |
| 249 | GGGTTCCTTTTCTGCCAGCTTGG | 4 | chr3:153163818-153163840 | RAP2B | |
| 250 | GGGTTCCTTTTCTGCCAGCTTGG | 4 | chr19:56218323-56218345 | | TBD |
| 251 | GGGTTCCTTTTCTGCCAGCTTGG | 4 | chr19:56233892-56233914 | | |
| 252 | GGGTTCCTTTAGGGCCAGGATGG | 4 | chr1:23956834-23956856 | | |
| 253 | GGGTTCTATTCCAGCCAGCTTGG | 4 | chr4:25743884-25743906 | | |
| 254 | GGGTTTCAGTAAGGCCAGGGTGG | 4 | chrX:102018328-102018350 | | |
| 255 | GGGCCCCATTACAGCCATCGTGG | 4 | chr12:130872701-130872723 | | |
| 256 | GGGGTCCATGACAGACAGCGTGG | 4 | chr8:62633692-62633714 | | |
| 257 | GGGGTCCATTCCCGCCAGAGTGG | 4 | chr7:2382393-2382415 | | |
| 258 | GGGTTACATCAAGGCCACCGAGG | 4 | chr22:20208799-20208821 | | |
| 259 | GGGTTCAATTACGGAAAGGGAGG | 4 | chr8:133296918-133296940 | NDRG1 | |
| 260 | GGGTTCCACTCCTTCCAGCGAGG | 4 | chr14:24036459-24036481 | DHRS4L1 | TBD |
| 261 | GGGTTCCATTATGACAAGCATGG | 4 | chr3:120731615-120731637 | | |
| 262 | GGGTTCCATTCTGGCAAGGGTGG | 4 | chr16:73686902-73686924 | | |

TABLE 11-continued predicted off-target sites for the CISH gRNA analyzed
by deep sequencing. DNA sequences and their genomic locations
are indicated along with the number of mismatches between the
genomic site and gRNA. Where sites reside within genes,
the gene names are noted. A blank under mutation frequency
means there was no detectable frequency greater than observed
in the untreated control cells and 'TBD' denotes a site that
requires follow-up sequencing.

| ID | Off target sequence | Mis matches | Genomic location | Gene | Mutation frequency |
|---|---|---|---|---|---|
| 263 | GGGTTCCATTGCTGGCAGAGTGG | 4 | chr1:67494513-67494535 | | |
| 264 | GGGTTCCATGAAGGCCAAAGGGG | 4 | chr1:92108114-92108136 | | |
| 265 | GGGTTCCAATCCGGCCACTGTGG | 4 | chr11:3217536-3217558 | | |
| 266 | GGGTTCCACTACTGCCTGCTTGG | 4 | chr1:159529114-159529136 | | |
| 267 | GGGTTCCGTTCCGGCCACTGGGG | 4 | chr19:32230844-32230866 | | |
| 268 | GGGTTTCATTGGAGCCAGCGTGG | 4 | chr16:66480442-66480464 | | |
| 269 | GGGTTTCATTACGCTCAGCTAAG | 4 | chr16:8173059-8173081 | | |
| 270 | GGGTTACCTTACGACCTGCGTGG | 4 | chr1:121422833-121422855 | | |
| 271 | GGGCTCCATTCCGGCCATGGTGG | 4 | chr16:55487566-55487588 | | |

Example 10: A Phase I/II Trial in Patients with Metastatic Cancer of the Adoptive Transfer of Tumor-Infiltrating Lymphocytes in which the Gene Encoding CISH was Inactivated Using the CRISPR/Cas 9 System Objectives:

Primary objectives are 1) to determine the safety of the administration of mutation reactive autologous lymphocytes with knockout of the CISH gene in patients with refractory metastatic cancer; and 2) to determine the response rate of the standard non-myeloablative conditioning regimen plus administration of mutation reactive TIL with knockout of the CISH gene plus high dose IL-2 in patients with metastatic cancer. A secondary objective is to evaluate the survival and persistence of CISH knockout mutation-reactive lymphocytes in patients with metastatic cancer.

Eligibility

Subjects with an age greater than or equal to 18 and less than or equal to 70 years are eligible. Subjects have evaluable metastatic cancer refractory to standard chemotherapy, metastatic cancer lesions suitable for surgical resection for the preparation of TIL, no contraindications to high-dose aldesleukin administration, and no concurrent major medical illnesses or any form of immunodeficiency Inclusion Criteria Inclusion criteria include measurable cancer melanoma with at least one lesion that is resectable for TIL generation, plus one other lesion that can be measured and confirmation of diagnosis of metastatic cancer. Patients with three or fewer brain metastases that are less than 1 cm in diameter and that are asymptomatic are eligible. Lesions that have been treated with stereotactic radiosurgery must be clinically stable for 1 month after treatment for the patient to be eligible. Patients with surgically resected brain metastases are eligible. Progressive disease following at least one first line standard therapy: six weeks must have elapsed from the time of any of these prior antibody therapies that could effect an anti-cancer immune response, at the time the patient receives the preparative regimen to allow antibody levels to decline. Patients who have previously received ipilimumab and have documented GI toxicity must have a normal colonoscopy with normal colonic biopsies. Patients are greater than or equal to 18 years of age and less than or equal to 70 years of age, and have a clinical performance status of ECOG 0 or 1. Patients have a life expectancy of greater than three months. Patients of both genders must be willing to practice birth control from the time of enrollment on this study and for up to four months after treatment.

Serology

Patients are seronegative for HIV antibody. Patients who are HIV seropositive can have decreased immune-competence and thus are less responsive to the experimental treatment and more susceptible to its toxicities. Patients are seronegative for hepatitis B antigen, and seronegative for hepatitis C antibody. If hepatitis C antibody test is positive, then patient must be tested for the presence of antigen by RT-PCR and be HCV RNA negative. Women of child-bearing potential must have a negative pregnancy test.

Hematology

Absolute neutrophil count greater than 1000/mm$^3$ without the support of filgrastim, WBC≥3000/mm$^3$, Platelet count ≥100,000/mm$^3$, Hemoglobin >8.0 g/dl Chemistry Patients have serum ALT/AST ≤to 2.5 times the upper limit of normal, Serum Creatinine ≤to 1.6 mg/dl, and total bilirubin ≤to 1.5 mg/dl, except in patients with Gilbert's Syndrome who must have a total bilirubin less than 3.0 mg/dl. More than four weeks have elapsed since any prior systemic therapy at the time the patient receives the preparative regimen, and patients' toxicities have recovered to a grade 1 or less (except for toxicities such as alopecia or vitiligo). Patients have progressive disease after prior treatment. Patients may have undergone minor surgical procedures within the past 3 weeks, as long as all toxicities have recovered to grade 1 or less. Six weeks have elapsed from the time of any antibody therapy that could effect an anti-cancer immune response, including anti-CTLA4 antibody therapy, at the time the patient receives the preparative regimen to allow antibody levels to decline.

Exclusion Criteria

Excluded are women of child-bearing potential who are pregnant or breastfeeding, or have any form of primary immunodeficiency (such as Severe Combined Immunodeficiency Disease). Excluded are patients with concurrent opportunistic infections. Excluded are patients with active systemic infections (e.g., requiring anti-infective treatment), coagulation disorders or other active major medical illnesses of the cardiovascular, respiratory or immune system, as evidenced by a positive stress thallium or comparable test, myocardial infarction, cardiac arrhythmias, obstructive or restrictive pulmonary disease. Excluded are patients on concurrent systemic steroid therapy, with a history of severe immediate hypersensitivity reaction to cyclophosphamide or fludarabine, or a history of coronary revascularization or ischemic symptoms. Patients have a documented LVEF of less than or equal to 45%; testing is required in patients with: age >65 years old, clinically significant atrial and or ventricular arrhythmias including but not limited to: atrial fibrillation, ventricular tachycardia, second or third degree heart block.

Screening Evaluation

Within 4 Weeks Prior to Starting the Chemotherapy Regimen:

Complete history and physical examination, including weight, ECOG, and vital signs, and eye exam noting in detail the exact size and location of any lesions that exist is taken. (Note: patient history may be obtained within 8 weeks), Chest x-ray, EKG, Baseline CT of the chest, abdomen and pelvis, and brain MRI to evaluate the status of disease. Additional scans and x-rays are performed if clinically indicated based on patients' signs and symptoms. Pulmonary Function Testing for patients with a prolonged history of cigarette smoking (20 pack/year of smoking within the past 2 years) or symptoms of respiratory dysfunction. (Note: are performed within 8 weeks of treatments). Cardiac Evaluation (stress thallium, echocardiogram, MUGA, etc.) for patients who are greater than or equal to age 60, or who have a history of ischemic heart disease, chest pain, or clinically significant atrial and/or ventricular arrhythmias including but not limited to: atrial fibrillation, ventricular tachycardia, heart block. Patients with a LVEF of less than or equal to 45% will not be eligible. Patients under the age of 60 who present with cardiac risk factors may undergo cardiac evaluation as noted above (e.g., diabetes, hypertension, and obesity.) (Note: may be performed within 8 weeks of treatment). HIV antibody titer and HbsAG determination, and anti HCV (may be performed within 3 months of chemotherapy start date.) Anti CMV antibody titer, HSV serology, and EBV panel. (Note, may be performed within 3 months of chemotherapy start date; patients who are known to be positive for any of the above do not need to be retested.)

Within 14 Days Prior to Starting the Chemotherapy Regimen:

Baseline blood tests, Chem 20: (Sodium (Na), Potassium (K), Chloride (C1), Total $CO^2$ (bicarbonate), Creatinine, Glucose, Urea nitrogen (BUN), Albumin, Calcium total, Magnesiumtotal (Mg), Inorganic Phosphorus, Alkaline Phosphatase, ALT/GPT, AST/GOT, Total Bilirubin, Direct Bilirubin, LD, Total Protein, Total CK, Uric Acid), Thyroid panel, CBC with differential and platelet count, PT/PTT, Urinalysis and culture, if indicated Within 7 Days Prior to Starting the Chemotherapy Regimen:

β-HCG pregnancy test (serum or urine) on all women of child-bearing potential, ECOG performance status of 0 or 1

Study Design

Patients with evaluable metastatic cancer undergo resection of tumor. Lymphocytes from the tumor (TIL) are grown and expanded according to the procedure shown in FIG. 42. Multiple individual fragments or multiple individual cultures of tumor infiltrating lymphocytes are grown. Individual cultures are separately expanded and when a sufficient yield of TIL (approximately $10^8$ cells) is expanded from each culture, the TIL are cryopreserved and aliquots taken for immunologic testing. An aliquot of the original tumor is subjected to exomic and, when possible, transcriptome sequencing to identify mutations uniquely present in the cancer compared to normal cells. Aliquots of each cultured TIL preparation is tested for reactivity against these mutations using the approaches previously described. In brief, the patient's antigen presenting cells are pulsed with 25mer peptides including the mutated peptide in the center flanked by 12 normal amino acids. Alternatively, in vitro transcribed RNA encoding all mutations are electroporated into the patient's antigen presenting cells. Using either or both of these techniques the previously cryopreserved TIL cultures are tested for reactivity against individual cancer mutations are subjected to CRISPR knockout of the CISH gene. Up to five different cultures are selected for this procedure from each patient.

Cultures with demonstrated mutation reactivity are sent to a GMP Cell Production Facility where CRISPR technology is used to knockout the CISH gene under cGMP conditions. Knockout of the CISH gene is determined by DNA sequencing based tracking of indels by decomposition (TIDE) analysis. Cell populations with successful knockout of the CISH gene are then rapidly expanded utilizing OKT3 and feeder cells. Cryopreserved lymphocytes are used in patient treatment.

In the first part of this protocol a dose escalation is initiated utilizing one patient per group starting at $10^9$ CISH knockout cells per patient. Individual patients are treated at half log increments and if any toxicity higher than Grade 2 is seen, that group is expanded to additional patients. Thus the following doses are utilized: $10^9$ cells, $3\times10^9$ cells, $10^{10}$ cells, $3\times10^{10}$ cells, and 3 to $10\times10^{10}$ cells.

Patients receive a lymphodepleting preparative regimen followed by infusion of the cells and high dose aldesleukin. Patients are evaluated for persistence of the cells as well as for clinical response approximately 4-6 weeks following administration of the cell product. Each patient receives only a single course of treatment and patients are followed monthly with lymphocyte and serum collections for immunologic studies Drug Administration Preparative Regimen with Cyclophosphamide and Fludarabine:

Times are offered as examples and may be changed as long as a similar time relationship between administrations of the drugs is maintained Study medication start times for drugs given once daily should be given within 2 hours of the scheduled time. All other medications should be given+/− one hour of the scheduled time; the length of administration is all+/−15 minutes. Administration of diuretics, electrolyte replacement, and hydration and monitoring of electrolytes should all be performed as clinically indicated—the doses and times noted below are offered only as examples. Infusions may be slowed or delayed as medically indicated.

DAYS −7 and −6

6 AM Hydrate: Begin hydration with 0.9% Sodium Chloride Injection containing 10 meq/L of potassium chloride at 2.6 ml/kg/hr (starting 11 hours pre-cyclophosphamide and continue hydration until 24 hours after last cyclophosphamide infusion). At any time during the preparative regimen, if urine output <1.5 ml/kg/hr or if body weight >2 kg over pre-cyclophosphamide value, furosemide 10-20 mg IV can be administered. Serum potassium should be monitored and treated as indicated following administration of furosemide.

4 PM: Ondansetron (0.15 mg/kg/dose [rounded to the nearest even mg dose between 8 mg and 16 mg based on patient weight] IV every 8 hours×3 days) is given for nausea.

5 PM: Cyclophosphamide 60 mg/kg/day×2 days IV in 250 ml D5W with Mesna 15 mg/kg/day×2 days over 1 hr. If patient is obese (BMI >35) drug dosage is calculated using practical weight.

10 pm: Begin mesna infusion at 3 mg/kg/hour intravenously diluted in a suitable diluent (see pharmaceutical section) over 23 hours after each cyclophosphamide dose. If patient is obese (BMI >35) drug dosage is calculated using practical weight.

DAYS −7 to −3

Fludarabine 25 mg/m$^2$/day IVPB daily over 30 minutes for 5 days. If patient is obese (BMI >35) drug dosage is calculated using practical weight as described in Appendix 2. (The fludarabine is started approximately 1-2 hours after the cyclophosphamide and mesna on Days −7 and −6).

Day 0 (Two to Four Days after the Last Dose of Fludarabine):

Autologous TIL infusion is administered intravenously over 20 to 30 minutes via non-filtered tubing, gently agitating the bag during infusion to prevent cell clumping.

Aldesleukin as described below. Day 1-4 (Day 0 is the day of cell infusion):

Aldesleukin as described below. Beginning on day 1 or 2, filgrastim may be administered subcutaneously at a dose of 5 mcg/kg/day (not to exceed 300 mcg/day). Filgrastim administration continues daily until neutrophil count >1.0× $10^9$/L×3 days or >5.0×$10^9$/L.

up to 24 hours may elapse between doses depending on patient tolerance. Aldesleukin dosing is stopped if toxicities are not sufficiently recovered with supportive measures within 24 hours of the last dose of aldesleukin Doses are delayed or stopped if patients reach Grade 3 or 4 toxicity due to aldesleukin except for the reversible Grade 3 toxicities common to aldesleukin such as diarrhea, nausea, vomiting, hypotension, skin changes, anorexia, mucositis, dysphagia, or constitutional symptoms and laboratory changes as detailed in Appendix 3. Toxicities are managed. If these toxicities can be easily reversed within 24 hours by supportive measures then additional doses are given.

Prior to Starting the Preparative Regimen

Apheresis as indicated. Within 14 days prior to starting the preparative regimen, patients have a complete blood count, electrolytes, BUN, creatinine, liver function tests, TBNK, and serum chemistries performed. If any results are beyond the criteria established for eligibility, the patient does not proceed until the abnormalities can be resolved.

During the Preparative Regimen: DAILY

Complete Blood Count, Chem 20 equivalent: Sodium (Na), Potassium (K), Chloride (Cl), Total CO2 (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin, Direct Bilirubin, LD, Total Protein, Total CK, Uric Acid, Urinalysis.

After Cell Infusion

Vital signs are monitored hourly (+/−15 minutes) for four hours and then routinely (every 4-6 hours) unless otherwise clinically indicated. Once total lymphocyte count is greater than 200/mm$^3$, TBNK for peripheral blood CD4 count is drawn weekly (while the patient is hospitalized).

During Hospitalization Every 1-2 Days

A review of systems and physical exam as clinically indicated, CBC, Chem 20 equivalent: Sodium (Na), Potassium (K), Chloride (Cl), Total CO2 (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin,

TABLE 12

Treatment Timeline and administered medicaments

| Therapy | Day | | | | | | | | | | | |
|---|---|---|---|---|---|---|---|---|---|---|---|---|
|  | −7 | −6 | −5 | −4 | −3 | −2 | −1 | 0 | 1 | 2 | 3 | 4 |
| Cyclophosphamide (60 mg/kg) | X | X | | | | | | | | | | |
| Fludarabine (25 mg/m$^2$) | | X | X | X | X | X | | | | | | |
| TIL | | | | | | | | X[1] | | | | |
| Aldesleukin | | | | | | | | X[2] | X | X | X | X |
| Filgrastim[3] (5 mcg/kg/day) | | | | | | | | | X | X | X | X |
| TMP/SMX[4] 160 mg/800 mg (example) | X | X | X | X | X | X | X | X | X | X | X | X |
| Fluconazole[5] (400 mg po) | | | | | | | | X | X | X | X | X |
| Valacyclovir po or Acyclovir IV[6] | | | | | | | | X | X | X | X | X |

[1]Two to four days after the last dose of fludarabine
[2]Initiate within 24 hours after cell infusion
[3]Continue until neutrophils count > 1 x $10^9$/L for 3 consecutive days or >5 x $10^9$/L.
[4]The TMP/SMX schedule should be adjusted to QD three times per week (Monday, Wednesday, Friday) and continue for at least six months and until CD4 > 200 x 2
[5]Continue until ANC > 1000/mm$^3$ [6] In patients positive for HSV continue until CD4 > 200 x 2

Aldesleukin: Intravenous Administration

Aldesleukin is administered at a dose of 720,000 IU/kg (based on total body weight) as an intravenous bolus over a 15 minute period beginning within 24 hours of cell infusion and continuing for up to 5 days (maximum 15 doses). Doses are preferentially administered every eight hours; however, Direct Bilirubin, LD, Total Protein, Total CK, Uric Acid, Other tests are performed as clinically indicated.

Post Study Evaluation (Follow-Up)

All patients return to the hospital for evaluation 6 weeks (+/−2 weeks) following administration of the cell product. At each scheduled evaluation patients undergo: Physical examination, Chem 20 equivalent: Sodium (Na), Potassium (K), Chloride (Cl), Total CO2 (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin, Direct Bilirubin, LD, Total Protein, Total CK, Uric Acid, Complete blood count, Thyroid panel as clinically indicated, TBNK, until CD4>200×2, Toxicity assessment, including a review of systems. CT of the chest, abdomen and pelvis as clinically indicated. If clinically indicated, other scans or x-rays may be performed, e.g. brain MRI, bone scan. A 5 liter apheresis may be performed at the first follow up visit, if the patient is unable to undergo apheresis, approximately 96 ml of blood may be obtained. Subsequently, approximately 60 ml of blood is obtained at follow up visits for at least 3 months. Peripheral blood mononuclear cells are cryopreserved so that immunologic testing may be performed.

Infection Prophylaxis

*Pneumocystis Jirovecii* Pneumonia

All patients receive the fixed combination of trimethoprim and sulfamethoxazole [SMX] as double strength (DS) tab (DS tabs=TMP 160 mg/tab, and SMX 800 mg/tab) P.O. daily three times a week on non-consecutive days, beginning between days −5 and −8. Pentamidine is substituted for TMP/SMX-DS in patients with sulfa allergies. It is administered aerosolized at 300 mg per nebulizer within one week of chemotherapy start date.

Herpes Virus Prophylaxis

Patients with positive HSV serology are given valacyclovir orally at a dose of 500 mg daily the day after chemotherapy ends, or acyclovir, 250 mg/m$^2$ IV q 12 hrs if the patient is not able to take medication by. Reversible renal insufficiency has been reported with IV but not oral acyclovir. Neurologic toxicity including delirium, tremors, coma, acute psychiatric disturbances, and abnormal EEGs have been reported with higher doses of acyclovir. Should this occur, a dosage adjustment is made or the drug is discontinued. Acyclovir is not used concomitantly with other nucleoside analogs which interfere with DNA synthesis, e.g. ganciclovir. In renal disease, the dose is adjusted as per product labeling. Prophylaxis for *Pneumocystis* and Herpes will continue for 6 months post chemotherapy. If the CD4 count is less than 200 at 6 months post chemotherapy, prophylaxis will continue until the CD4 count is greater than 200 for 2 consecutive measures.

Fungal Prophylaxis (Fluconazole)

Patients start Fluconazole 400 mg p.o. the day after chemotherapy concludes and continue until the absolute neutrophil count is greater than 1000/mm$^3$. The drug may be given IV at a dose of 400 mg in 0.9% sodium chloride USP daily in patients unable to take it orally.

Empiric Antibiotics

Patients start on broad-spectrum antibiotics, either a 3$^{rd}$ or 4$^{th}$ generation cephalosporin or a quinolone for fever of 38.3° C. once or two temperatures of 38.0° C. or above at least one hour apart, and an ANC <500/mm$^3$. Infectious disease consultation is obtained for all patients with unexplained fever or any infectious complications.

Blood Product Support

Using daily CBC's as a guide, the patient receives platelets and packed red blood cells (PRBC's) as needed. All blood products are irradiated. Leukocyte filters are utilized for all blood and platelet transfusions to decrease sensitization to transfused WBC's and decrease the risk of CMV infection.

Other Concomitant Medications to Control Side Effects

Concomitant medications to control side effects of therapy may be given. Meperidine (25-50 mg) is given intravenously if severe chilling develops. Other supportive therapy is given as required and may include acetaminophen (650 mg q4h), indomethacin (50-75 mg q6h) and ranitidine (150 mg g12h). If patients require steroid therapy they are taken off treatment. Patients who require transfusions will receive irradiated blood products. Ondansetron 0.15 mg/kg/dose IV every 8 hours is administered for nausea and vomiting. Additional antiemetics are administered as needed for nausea and vomiting uncontrolled by ondansetron. Antibiotic coverage for central venous catheters may be provided at the discretion of the investigator.

Tumor Biopsies

Biopsies of tumor tissue or lymph node may be performed but are not required during the course of therapy. Studies may evaluate the antigen expression by the tumor and to evaluate the reactivity of lymphocytes grown from these biopsies. Biopsies may be performed at baseline, after the course of therapy, and in the event of response. These biopsies are only be performed if minimal morbidity is expected based on the procedure performed and the granulocyte and platelet count. Biopsies are only be allowed if the biopsy does not require more than 1 day in the hospital Immunological Testing:

Apheresis may be performed prior to and 6 weeks (+/−2 weeks) following the administration of the cell product. At other time points, patient peripheral blood lymphocytes (PBL) are obtained from whole blood by purification using centrifugation on a Ficoll cushion. Aliquots of these PBMC are cryopreserved for immunological monitoring of cell function. A variety of tests including evaluation of specific lysis and cytokine release, metabolomic and bioenergetic studies (using Seahorse), intracellular FACS of cytokine production, ELISA-spot assays, and lymphocyte subset analysis may be used to evaluate the immunological correlates of treatment. In general, differences of 2 to 3 fold in these assays are indicative of true biologic differences. Samples of all infused cell products are cryopreserved, and extensive retrospective analysis of infused cell phenotype and function are performed to attempt to find in vitro characteristics of the infused cells which correlate with in vivo antitumor activity. Analyses of TIL samples will include evaluation of the activity, specificity, and telomere length of the infused TIL. Blood and tissue specimens collected in the course of this research project may be banked and used in the future to investigate new scientific questions.

Aldesleukin (Interleukin-2, Proleukin, Recombinant Human Interleukin 2)

Formulation/Reconstitution: Aldesleukin is provided as single-use vials containing 22 million IU (1.3 mg) IL-2 as a sterile, white to off-white lyophilized cake plus 50 mg mannitol and 0.18 mg sodium dodecyl sulfate, buffered with approximately 0.17 mg monobasic and 0.89 mg dibasic sodium phosphate to a pH of 7.5 (range 7.2 to 7.8). The vial is reconstituted with 1.2 mL of Sterile Water for Injection, USP, and the resultant concentration is 18 million IU/ml or 1.1 mg/mL. Diluent should be directed against the side of the vial to avoid excess foaming. Swirl contents gently until completely dissolved. Do not shake. Since vials contain no preservative, reconstituted solution should be used with 24 hours.

Dilution/Stability: Reconstituted aldesleukin should be further diluted with 50 mL of 5% Human Serum Albumin (HSA). The HSA is added to the diluent prior to the addition of RIL-2. Dilutions of the reconstituted solution over a 1000-fold range (i.e., 1 mg/mL to 1 mcg/mL) are acceptable in either glass bottles or polyvinyl chloride bags. Aldesleukin is chemically stable for 48 hours at refrigerated and room temperatures, 2°-30° C.

Administration: The dosage is calculated based on total body weight. The final dilution of aldesleukin is infused over 15 minutes. Aldesleukin is administered as an inpatient.

Fludarabine

Administration: Fludarabine is administered as an IV infusion in 100 ml 0.9% sodium chloride, USP over 15 to 30 minutes. The doses are based on body surface area (BSA). If patient is obese (BMI >35) drug dosage is calculated using practical weight.

Cyclophosphamide

Administration: cyclophosphamide is diluted in 250 ml D5W and infused over one hour. The dose is based on the patient's body weight. If patient is obese (BMI >35) drug dosage is calculated using practical weight Mesna (Sodium 2-Mercaptoethanesulfonate, Mesnum, Mesnex, NSC-113891)

Administration: Dilute to concentrations less than or equal to 20 mg mesna/ml fluid in D5W or 0.9% NaCl and to be administered intravenously as a continuous infusion. If patient is obese (BMI >35) drug dosage is calculated using practical weight as described in Appendix 2. Toxicities include nausea, vomiting and diarrhea.

Filgrastim (Granulocyte Colony-Stimulating Factor, G-CSF, Filgrastim, Neupogen)

Filgrastim is obtained commercially and is supplied in 300 ug/ml and 480 ug/1.6 ml vials. Filgrastim should be refrigerated and not allowed. Filgrastim is given as a daily subcutaneous injection.

Example 14: GMP Process Validation

A consideration for clinical translation of a CRISPR/Cas9 system is the capacity to scale up production of knockout TILs to the yields achieved by standard rapid expansion protocols (REP). Utilizing a modified REP strategy, following electroporation of CRISPR/Cas9 reagents an average fold expansion of 1071 across 3 independent cGMP process validation runs was achieved (Table 13 and FIG. 43A, FIG. 43B, FIG. 43C, and FIG. 44). As the capacity to initiate multiple REP simultaneously is now possible, this system will consistently produce cell yields in excess of $1 \times 10^{10}$ knockout TIL for patient infusion. Cyropreservation is also achievable, Table 14.

TABLE 14

Cyropreservation achieved during cGMP process validation

| Freeze density | #/140 ml bag | % cell recovery 4 hours post thaw | % Viable 4 hours post thaw |
|---|---|---|---|
| 7.5e7/ml | 1.05e10 | 89% | 82% |
| 1.5e8/ml | 2.1e10 | 90% | 81% |

Example 11: Detection of Genomic Disruption at the Protein Level

To determine whether observed knockout frequencies at the genetic level correlate with loss of protein, the expression of PD-1 and CISH protein after CRISPR/Cas9 knockout was assessed. Peripheral blood (PB) T-cells and TILs were re-stimulated at day 14 post-electroporation using plate bound anti-CD3 and soluble anti-CD28 antibody and assessed the loss of PD-1 and CISH protein by flow cytometry and western blot, respectively. As shown in FIG. 48, PD-1 protein is lost in >90% of PB T-cells and TILs at day 14. These data confirm that knockout cells have lost target protein expression after modification, and importantly, demonstrate that knockout cells are retained, expand after modification, and are viable, FIG. 46.

Figure 45:
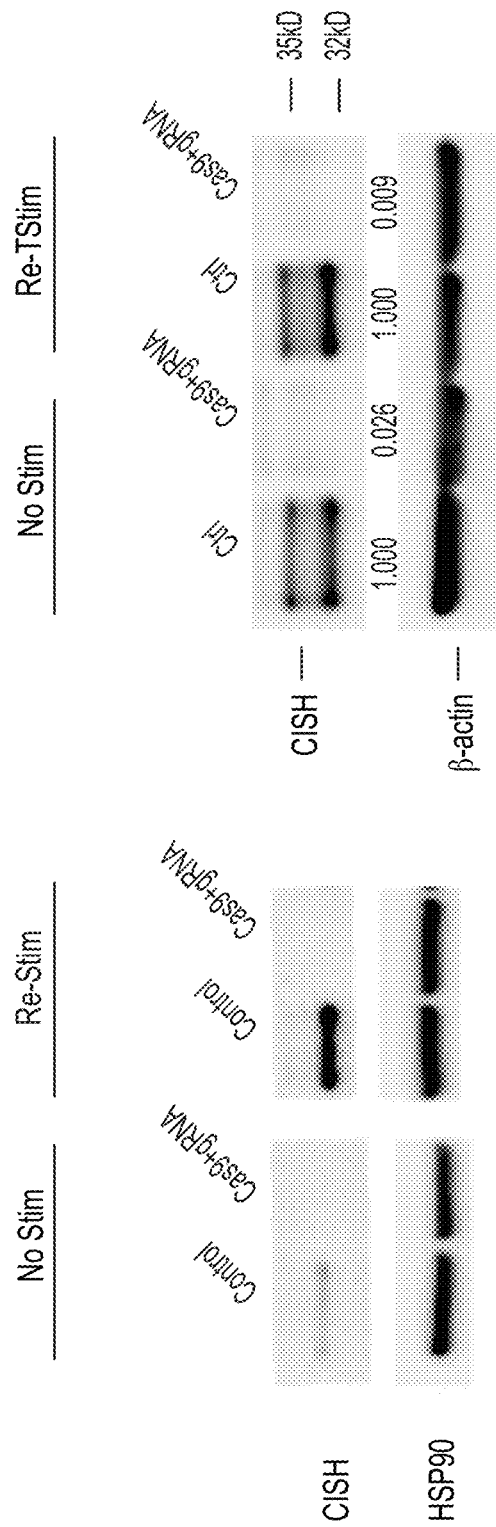

The same strategy was employed to determine the degree of CISH knockout at the protein level. CRISPR/Cas9 modified PB T-cells and TILs were expanded for 14 days and then re-stimulated for 48 hrs. Cells were subsequently collected and extracts analyzed by western blot as CISH is an intracellular protein. Consistent with the high rate of knockout by TiDE analysis of genomic modification, CISH protein was essentially absent in knockout PB T-cells and TILs (FIG. 45). These data demonstrate that this strategy for CRISPR/Cas9 based gene disruption in primary human T-cells and TILs results in targeted gene knockout with high efficiency.

Example 12: Simplified Presentation of Incredibly Complex Evaluations (SPICE) Analysis In addition to the maintenance of high cell viability and proliferation after CRISPR/Cas9 editing, whether knockout T-cells retain effector function upon activation was also sought to be determined. Using intracellular staining and flow cytometry coupled with Simplified Presentation of Incredibly Complex Evaluations (SPICE) analysis, knockout T-cells were demonstrated to maintain cytokine polyfunctionality upon re-stimulation. This indicated that the effector function of PB T-cells and TILs following CRISPR/Cas9-mediated gene editing is preserved (FIG. 47A and FIG. 47B).

TABLE 13

Cell yields achieved during cGMP process validation

| Expt | #/vi al | #Post-thaw | #Post-thaw Viability | #Post-rest | Post-rest Viability | #post-stim | Post-stim Viability | #modified (Starting # for REP) | #Control-D7 (FoldX) | KO-D7 (FoldX) | Control-D14 (FoldX) | KO-D14 (FoldX) |
|---|---|---|---|---|---|---|---|---|---|---|---|---|
| PV1 | 2e7 | 1.16e7 | 69% | 6.81e6 | 52% | 1.01e6 | 99% | KO: 4e5 CON: 4e5 | 1.21e8 (269) | 5.7e7 (130) | 1.09e9 (2620) | 4.48e8 (1028) |
| PV2 | 4e7 | 3.7e7 | 74% | 2.68e7 | 85% | 3.97e7 | 97% | KO: 5e6 CON: 5e5 | 2.9e7 (59) | 1.9e8 (38) | 4.5e8 (900) | 3.5e9 (701) |
| PV3 | 4e7 | 4.4e7 | 87% | 4.4e7 | 87% | 2.4e7 | 97% | KO: 5e6 CON: 5e5 | 4.7e7 (93) | 2.64e8 (53) | 7.53e8 (1507) | 7.42e9 (1484) |

Example 13: Growth Kinetics of Good Manufacturing Practices TIL with and without IL-2

Tumor infiltrating lymphocytes used in good manufacturing practices runs were selected as oligoclonal subpopulations possessing specific reactivity against patient-specific cancer neoantigens using tumor whole-exome sequencing and tendem mini-gene/synthetic long peptide screening. In long-term cultures, cell expansion was observed in the presence of IL-2 (FIG. 50A). Growth experiments in the absence of IL-2 at day 7 after IL-2 withdrawal, FIG. 50B. Without IL-2, cell number and viability decreased and by day 7 there were only a few viable cells remaining (FIG. 50B).

Example 14: Off-Target Frequency Detection by GUIDE-Seq

To assess off-target frequencies by GUIDE-Seq, $3\times10^6$ human PBL derived T cells were electroporated using the Neon Transfection system, 100 µL tip, with 8 pmol or 16 pmol double stranded oligonucleotide (dsODN) (5' GTT-TAATTGAGTTGTCATATGTTAATAACGGTAT-3') in the presence or absence of 15 µg Cas9 mRNA and 10 µg of CISH gRNA, FIG. 52. Genomic DNA was harvested 72 hours after transfection and the integration frequency of the dsODN at the CISH target site was assessed by PCR and Sanger sequencing followed by TiDE analysis. Genomic DNA was sheared to an average length of 500 bp using Covartis S2 sonicator (Covartis). The sheared DNA was purified using Agencourt AMPure XP bead purification kit (Beckman Coulter) before conversion of any cohesive DNA ends to blunt 5'phosphorylated ends using the Anza DNA End Repair Kit (Thermo Fisher). Barcoded sequencing adapters were then ligated to the genomic fragments using PCR to generate the final libraries ready for NGS analysis.

Example 15: Cytogenetic Analysis of CISH Disrupted TIL

Cytogenetic analysis was performed on CISH knockout mutation reactive TIL produced during GMP manufacturing process qualification runs. TIL were stimulated using anti-CD3 and anti-CD28 antibodies followed by electroporation-based delivery of Cas9 mRNA (15 µg) and CISH gRNA (10 µs) using the Neon electroporation system. After electroporation, CISH disrupted mutation reactive TIL underwent a REP in the presence of irradiated feeders for 14 days, at which time a sample was analyzed for cytogenetics. Cytogenetic analysis was performed on 5 samples: PQ1 CISH KO mutation reactive TIL, PQ2 CISH KO mutation reactive TIL, PQ3 pre-treatment, PQ3 CISH KO mutation reactive TIL, and PQ3 control.

A 13.0 mL suspension culture of TIL underwent a 2.0 hr. colcemid treatment, cells were harvested and 20 metaphases were completely analyzed by G-banding at a 400 band level resolution. Additional 30 metaphases were screened for a translocation between chromosomes 4 and 9.

Cytogenomics Results Indicated that:

PQ 3 Control: 46, XX and 46, XX. Findings indicate a normal female karyotype. No translocations were observed.

TABLE 15

| PQ3 Cytogenetics Summary | |
| --- | --- |
| Number of Metaphase cells Analyzed | 20 |
| Number of Metaphase cells Screened | 30 |
| Number of Metaphase cells Karyotyped | 2 |

PQ 3 Pretreatment: 46, XX and 46, XX, t (4; 9) (q31.3; q13) [9]/46, XX. 9 of the 21 metaphase cells analyzed had a reciprogral translocation between the long arm of a chromosome 4 at band 4q31.3 and the long arm of a chromosome 9 at band 9q13. Each of the remaining 12 metaphases had a 46, XX karyotype with two normal #4 and #9 chromosomes.

TABLE 16

| PQ3 Pretreatment Summary | |
| --- | --- |
| Number of Metaphase cells Analyzed | 21 |
| Number of Metaphase cells Screened | 0 |
| Number of Metaphase cells Karyotyped | 4 |

PQ1 Mutation reactive TIL: 46, XX. 45, X,-X, add(1) (p13),der(14)t(1;14)(p13;p11.1),+21, i(21)(q10). 45, X,-X, add (1) (p13), −7, +11, der (14) t (1; 14) (p13; p11.1). 43, X, dic(x; 12) (q21; p13), −17, −19, der (21; 22) (q10; q10), +22. 46, X, Del(x) (q21). 45,XX,-7, −18, +r/46, XX,del(8)(p12), +14, i(14)(q10). Six of the 23 metaphase cells analyzed had numerical and or structural chromosomal abnormalities. All except one of these cells had three or more abnormalities that preferentially involved the X chromosome (4 cells) and rearrangements of the short arms of the acrocentric chromosomes (13, 14, 15, 21, 22). Only two of these six cells shared the same abnormalities, meeting the criteria for the clone.

TABLE 17

| PQ1 mutation reactive TIL | |
| --- | --- |
| Number of Metaphase cells Analyzed | 23 |
| Number of Metaphase cells Screened | 0 |
| Number of Metaphase cells Karyotyped | 4 |

PQ2 Mutation reactive TIL: 46, XX. 45, XX der (15; 22) (q10; q10). One of the 50 metaphase cells analyzed had a translocation between chromosome 15 and a chromosome 22.

TABLE 18

| PQ2 Mutation reactive TIL | |
| --- | --- |
| Number of Metaphase cells Analyzed | 20 |
| Number of Metaphase cells Screened | 30 |
| Number of Metaphase cells Karyotyped | 2 |

PQ 3 Mutation Reactive TIL: 46, XX. 46, XX, t (4; 9) (q31.3; q13). 46, XX, Del (7) (p11.2). Eight of the 20 metaphase cells analyzed had a reciprocal translocation between the long arm of a chromosome 4 at band 4q31.3 and the long arm of a chromosome 9 at band 9q13. One additional cell had a deletion of the short arm of chromosome 7 that was interpreted as a nonclonal event, likely representing a random chromosomal break.

TABLE 19

| PQ 3 Mutation Reactive TIL | |
| --- | --- |
| Number of Metaphase cells Analyzed | 20 |
| Number of Metaphase cells Screened | 0 |
| Number of Metaphase cells Karyotyped | 4 |

What is claimed is:

1. A method of treating cancer in a human subject in need thereof, comprising:
   (a) administering a lymphodepleting preparative regimen that comprises an immunosuppressant in an amount sufficient to result in lymphodepletion in said human subject;
   (b) administering a pharmaceutical composition that comprises an antifungal agent in an amount sufficient to inhibit a fungal infection in said human subject; and
   (c) administering a pharmaceutical composition that comprises a plurality of tumor infiltrating lymphocytes (TILs), wherein said TILs comprise CD4+ T cells, wherein said CD4+ T cells comprise a genomic disruption of at least a portion of a cytokine inducible SH2-containing protein (CISH) gene, and wherein said genomic disruption suppresses or eliminates expression of a CISH protein encoded by said CISH gene thereby treating said cancer.

2. The method of claim 1, further comprising administering a pharmaceutical composition that comprises an antibiotic in an amount sufficient to inhibit a bacterial infection in said human subject.

3. The method of claim 2, wherein said antibiotic is cephalosporin, quinolone, penicillin, rifamycin, lipiarmycin, sulfonamide, macrolide, lincosamide, tetracycline, daptomycin, glycylcycline, tigecycline, oxazolidione, linezolid, lipiarmycins, fidaxomicin, cephazolin,cephalothin, cephapirin, cephalethin, cephradin, cephadroxin, amoxicillin, ampicillin, cefuroxime, cephamandole, cephoxitin, cephaclor, cephrozil, loracarbef, carbenicillin, ticarcillin, cephixime, cephtriaxone, cephotaxime, cephtizoxime, cephtazidime, cephipime, cephtaroline, cephtobiprole, trimethoprim, sulfamethoxazole, or pentamidine.

4. The method of claim 2, wherein said pharmaceutical composition that comprises an antibiotic comprises trimethoprim, sulfamethoxazole, or both trimethoprim and sulfamethoxazole.

5. The method of claim 1, wherein said immunosuppressant is cyclophosphamide, fludarabine, mechlorethamine, chlorambucil, melphalan, ifosfamide, thiotepa, hexamethylmelamine, busulfan, nitrosoureas, platinum, methotrexate, azathioprine, mercaptopurine, procarbazine, dacarbazine, temozolomide, carmustine, lomustine, streptozocin, fluorouracil, dactinomycin, anthracycline, mitomycin C, bleomycin, mithramycin, mycophenolate mofetil, rapamycin, cyclosporin, deoxyspergualin, soluble complement receptor 1, cobra venom factor, compstatin, methylprednisolone, leflunomide anti-thymocyte globulin antibody, anti-CD154 antibody, anti-CD40 antibody, anti-CD20 antibody, anti-IL-6R antibody, anti-IL-6 antibody, anti-IL-2R antibody, anti-CXCR3 antibody, anti-ICOS antibody, anti-OX40 antibody, or an anti-CD122 antibody, anti-C5 antibody, abatacept, belatacept, sirolimus, everolimus, tacrolimus, daclizumab, basiliximab, infliximab, eculizumab, rituximab, alemtuzumab, tocilizumab, sarilumab, or olokizumab.

6. The method of claim 1, wherein said antifungal agent is an azole, polyene, allylamine, or echinocandin.

7. The method of claim 1, further comprising administering a pharmaceutical composition that comprises an immunostimulant.

8. The method of claim 7, wherein said immunostimulant is IL-2, IL-7, IL-12, IL-15, IL-21, or G-CSF, or any combination thereof.

9. The method of claim 7, wherein said immunostimulant is aldesluekin.

10. The method of claim 1, further comprising administering a pharmaceutical composition that comprises an infection prophylaxis agent.

11. The method of claim 10, wherein said infection prophylaxis agent is a herpes virus prophylactic agent.

12. The method of claim 11, wherein said herpes virus prophylactic agent is valacyclovir or acyclovir.

13. The method of claim 1, wherein said immunosuppressant is cyclophosphamide.

14. The method of claim 13, wherein said cyclophosphamide is administered to said subject at a dose from 50 mg per kg body weight of said subject to 80 mg per kg body weight of said subject.

15. The method of claim 1, wherein said immunosuppressant is fludarabine.

16. The method of claim 15, wherein said fludarabine is administered to said subject at a dose from 20 mg/m$^2$ to 30 mg/m$^2$.

17. The method of claim 1, wherein said preparative regimen comprises two immunosuppressants.

18. The method of claim 17, wherein said two immunosuppressants are administered to said subject simultaneously or sequentially.

19. The method of claim 1, wherein said antifungal is fluconazole, bifonazole, butoconazole, clotrimazole, econazole, fenticonazole, isoconazole, ketoconazole, luliconazole, miconazole, omoconazole, oxiconazole, sertaconazole, sulcoazole, tioconazole, albaconazole, efinaconazole, epoxiconazole, isavuvonazole, itraconazole, posaconazole, propiconazole, ravuconazole, terconazole, voriconazole, abafungin, amorolfin, butenafine, naftifine, terbinafine, anidulafungin, caspofungin, micafungin, aurones, benzoic acid, ciclopirox, flucytosine, griseofulvin, haloprogin, tolnaftate, undecylenic acid, cystal violet, or balsam of Peru.

20. The method of claim 19, wherein said antifungal is fluconazole.

21. The method of claim 1, wherein said cancer is gastrointestinal cancer, breast cancer, lymphoma, or prostate cancer.

22. The method of claim 1, wherein said plurality of tumor infiltrating lymphocytes (TILs) are allogeneic to said human subject.

23. The method of claim 1, wherein said plurality of tumor infiltrating lymphocytes (TILs) are autologous to said human subject.

24. The method of claim 1, wherein said immunosuppressant is administered to said subject for 1 to 2 days, 1 to 3 days, 1 to 5 days, 3 to 5 days, 5 to 7 days, 7 to 10 days, 10 to 14 days, or 14 to 20 days.

25. The method of claim 1, wherein said immunosuppressant is administered to said subject from 14 days to 24 hours, 10 days to 24 hours, or 7 days to 24 hours, before said administering of said pharmaceutical composition comprising said plurality of TILs to said subject.

26. The method of claim 1, wherein said disruption is in exon 2 or exon 3 of said CISH gene.

27. The method of claim 1, wherein said plurality of TILs further comprises CD8+ T cells that comprise said genomic disruption of said CISH gene, wherein said genomic disruption suppresses or eliminates expression of said CISH protein encoded by said CISH gene.

28. A method of treating cancer in a human subject in need thereof, comprising:
   a) i) administering a pharmaceutical composition that comprises cyclophosphamide in an amount sufficient to reduce an immune response in said human subject and administering a pharmaceutical composition that comprises fludarabine in an amount sufficient to reduce an immune response in said human subject; or ii) administering a pharmaceutical composition that comprises cyclophosphamide and fludarabine in an amount sufficient to reduce an immune response in said human subject;
   b) administering a pharmaceutical composition that comprises fluconazole in an amount sufficient to inhibit a fungal infection in said human subject; and
   c) administering a pharmaceutical composition that comprises a plurality of tumor infiltrating lymphocytes (TILs), wherein said TILs comprise CD4+ T cells, wherein said CD4+ T cells comprise a genomic disruption of at least a portion of a cytokine inducible SH2-containing protein (CISH) gene, and wherein said genomic disruption suppresses or eliminates expression of a CISH protein encoded by said CISH gene, thereby treating said cancer.

29. The method of claim 28, further comprising administering a pharmaceutical composition that comprises trimethoprim and sulfamethoxazole in an amount sufficient to inhibit a bacterial or fungal infection in said human subject.

30. The method of claim 28, wherein said cancer is gastrointestinal cancer, breast cancer, lymphoma, or prostate cancer.

31. The method of claim 28, wherein said plurality of tumor infiltrating lymphocytes (TILs) are allogeneic to said human subject.

32. The method of claim 28, wherein said plurality of tumor infiltrating lymphocytes (TILs) are autologous to said human subject.

33. The method of claim 28, wherein said disruption is in exon 2 or exon 3 of said CISH gene.

* * * * *